US008426420B2

(12) United States Patent
Nazaré et al.

(10) Patent No.: US 8,426,420 B2
(45) Date of Patent: Apr. 23, 2013

(54) HETEROCYCLIC PYRAZOLE-CARBOXAMIDESAS P2Y12 ANTAGONISTS

(75) Inventors: Marc Nazaré, Frankfurt am Main (DE); Gernot Zech, Frankfurt am Main (DE); Melitta Just, Langen (DE); Tilo Weiss, Frankfurt am Main (DE); Gerhard Hessler, Frankfurt am Main (DE); Markus Kohlmann, Frankfurt am Main (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 12/817,873

(22) Filed: Jun. 17, 2010

(65) Prior Publication Data

US 2011/0021537 A1 Jan. 27, 2011

Related U.S. Application Data

(63) Continuation of application No. PCT/EP2008/010572, filed on Dec. 12, 2008.

(30) Foreign Application Priority Data

Dec. 26, 2007 (EP) .................... 07291627

(51) Int. Cl.
*A61K 31/496* (2006.01)
*A61K 31/454* (2006.01)
*C07D 401/12* (2006.01)
*C07D 401/14* (2006.01)
*C07D 403/12* (2006.01)
*C07D 405/14* (2006.01)
*C07D 413/14* (2006.01)
*C07D 417/14* (2006.01)

(52) U.S. Cl.
USPC ............ 514/253.09; 514/254.02; 514/254.03; 514/254.05; 514/254.07; 514/326; 544/364; 544/366; 544/367; 544/369; 544/370; 544/371; 546/211

(58) Field of Classification Search .................. None
See application file for complete search history.

(56) References Cited

U.S. PATENT DOCUMENTS 6,043,265 A    3/2000   Murugesanet et al.

FOREIGN PATENT DOCUMENTS

| EP | 1698626 A1 | 9/2006 |
|---|---|---|
| WO | WO98/37075 A1 | 8/1998 |
| WO | WO98/57951 A1 | 12/1998 |
| WO | WO00/01389 A1 | 1/2000 |
| WO | WO00/59506 A1 | 10/2000 |
| WO | WO00/76970 A2 | 12/2000 |
| WO | WO01/40231 A1 | 6/2001 |
| WO | WO01/47919 A1 | 7/2001 |
| WO | WO02/44145 A1 | 6/2002 |
| WO | WO02/098856 A2 | 12/2002 |
| WO | WO03/026652 A1 | 4/2003 |
| WO | WO2005/000281 A2 | 1/2005 |
| WO | WO2005/002574 A1 | 1/2005 |

OTHER PUBLICATIONS

European Search Report dated Jun. 23, 2008 issued in EP 07 29 1627.
Gachet, Christian et al., "Purinoceptors on blood platelets: further pharmacological and clinical evidence to suggest the presence of two ADP receptors," British Journal of Haematology (1995), vol. 91, pp. 434-444.
Butler, Donald E. et al., "New General Methods for the Substitution of 5-Chloropyrazoles. The Synthesis of 1,3-Dialkyl-5-chloropyrazol-4-yl Aryl Ketones and New 1,3-Dialkyl-2-pyrazolin-5-ones," Journal of Organic Chemistry (1971), vol. 36, No. 17, pp. 2542-2547.
Hughes, D.L. et al., "A Mechanstc Sudy of he Mitsunobu Eserification Reaction," Jounal of the American Chemical Society (1988), vol. 110, pp. 6487-6491.

(Continued)

*Primary Examiner* — Emily Bernhardt
(74) *Attorney, Agent, or Firm* — Scully, Scott, Murphy & Presser, P.C.

(57) ABSTRACT

The present invention relates to compounds of the formula I, (I)

wherein
R1; R2; Z; A; B; D; Q; J; V; G and M have the meanings indicated in the claims. The compounds of the formula I are valuable pharmacologically active compounds. They exhibit a strong anti-aggregating effect on platelets and thus an anti-thrombotic effect and are suitable, e.g., for the therapy and prophylaxis of cardio-vascular disorders like thromboembolic diseases or restenoses. They are reversible antagonists of the platelet ADP receptor P2Y12, and can in general be applied in conditions in which an undesired activation of the platelet ADP receptor P2Y12 is present or for the cure or prevention of which an inhibition of the platelet ADP receptor P2Y12 is intended. The invention furthermore relates to processes for the preparation of compounds of the formula I, their use, in particular as active ingredients in pharmaceuticals, and pharmaceutical preparations comprising them.

3 Claims, No Drawings

OTHER PUBLICATIONS

Mills, David C.B., "ADP Receptors on Platelets," Thrombosis and Haemostasis (1996), vol. 76, pp. 835-856.

Camp, David et al. "Mechanism of the Mitsunobu Esterification Reaction. 1. The Involvement of Phosphoranes and Oxyphosphonium Salts," Journal of Organic Chemistry (1989), vol. 54, pp. 3045-3049.

Crich, David et al., "Some Observations on the Mechanism of the Mitsunobu Reaction," Journal of Organic Chemistry (1989), vol. 54, pp. 257-259.

Bundgaard, Hans, "Design of prodrugs: Bioreversible derivatives for various functional groups and chemical entities," Elsevier (1985), pp. 1-92.

Nichols, David E. et al., "1-(2,5-Dimethoxy-4-(trifluoromethyl)phenyl)-2-aminopropane: A Potent Serotonin 5-HT2A/2C Agonist," Journal of Medicinal Chemistry (1994), vol. 37, pp. 4346-4351.

Chan, Dominic M.T. et al., "New N- and O-Arylations wth Phenylboronic Acids and Cupric Acetate," Tetrahedron Letters (1998), vol. 39, pp. 2933-2936.

Elnagdi, Mohamed Hilmy et al., "Recent Developments in the Synthesis of Pyrazole Derivatives," Heterocycles (1985), vol. 23, No. 12, pp. 3121-3153.

Qing, Feng-Ling et al., "First synthesis of ortho-trifluoromethylated aryl triflates," Journal of the Chemical Society, Perkin Trans. 1 (1997), pp. 3053-3057.

Fleisher, David et al., "Improved oral drug delivery: solubility limitations overcome by the use of prodrugs," Advanced Drug Delivery Reviews (1996),vol. 19, pp. 115-130.

Foti, Francesco et al., "First Synthesis of a Bromonitrilimine. Direct Formation of 3-Bromopyrazole Derivatives," Tetrahedron Letters (1999), vol. 40, pp. 2605-2606.

Bundgaard, Hans, "Novel chemical approaches in prodrug design," Drugs of the Future (1991), vol. 16, No. 5, pp. 443-458.

Haque, Tasir S. et al., "Parallel Synthesis of Potent, Pyrazole-Based Inhibitors of *Helicobacter pylori* Dihydroorotate Dehydrogenase," Journal of Medicinal Chemistry (2002), vol. 45, pp. 4669-4678.

Huang, Ying R. et al. "Regioselective Synthesis of 1,3,5-Triaryl-4-alkylpyrazoles: Novel Ligands for the Estrogen Receptor," Organic Letters (2000), vol. 2, No. 18, pp. 2833-2836.

Elguero, Jose, "Pyrazoles," Comprehensive Heterocyclic Chemistry II (1996), vol. 3, pp. 1-75.

Testa, Bernard et al., "Hydrolysis in Drug and Prodrug Metabolism: Chemistry, Biochemistry, and Enzymology," Wiley VCH (2003), pp. 1-9.

Hartwig, John F., "Ubergangsmetall-katalysierte Synthese von Arylaminen und Arylethern aus Arylhalogeniden und-triflaten: Anwendungen und Reaktionsmechanismus," Angewandte Chemie (1998), vol. 110, pp. 2154-2177.

Herbert, J.M. et al., "Inhibitory Effect of Clopidogrel on Platelet Adhesion and Intimal Proliferation After Arterial Injury in Rabbits," Arteriosclerosis and Thrombosis (1993), vol. 13, pp. 1171-1179.

Herbert, J.M. et al., "Clopidogrel, A Novel Antiplatelet and Antithrombotic Agent," Cardiovascular Drug Reviews (1993), vol. 11, No. 2, pp. 180-198.

Maffrand, J.P. et al., "ADP Plays a Key Role in Thrombogenesis in Rats," Thrombosis and Haemostasis (1988), vol. 59, pp. 225-230.

Pelletier, Jeffrey C. et al., "Mitsunobu reaction modifications allowing product isolation without chromatography: application to a small parallel library," Tetrahedron Letters (2000), vol. 41, pp. 797-800.

Jeon, Dong Ju et al., "Synthesis of New 4-Benzoyl-5-hydroxy-3-Trifluoromethylpyrazole Derivatives via [1,3] Rearrangements of Benzoyl Group Using tert—Butyllithium," Synthetic Communications (1998), vol. 28, pp. 2159-2166.

Folts, J.D. et al., "Platelet aggregation in partially obstructed vessels and its elimination with aspirin", Circulation (1976), vol. 54, pp. 365-370.

Wolfe, John P. et al., "Simple, Efficient Catalyst System for the Palladium-Catalyzed Amination of Aryl Chlorides, Bromides, and Triflates," Journal of Organic Chemistry (2000), vol. 65, pp. 1158-1174.

Jones, R.G. et al, "vic-Dicarboxylic Acid Derivatives of Pyrazole, Isoxazole, and Pyrimidine," Journal of Organic Chemistry (1955), vol. 20, pp. 1342-1347.

Makino, Kenzi et al., "Selective Fluorination of Ethyl 1-Methylpyrazole-4-carboxylates with Poly(Hydrogen Fluoride)-Amine Complex under Electrolytic Anodic Oxidation," Journal of Fluorine Chemistry (1988), vol. 39, pp. 435-440.

Huisgen, Rolf et al., "Diazocarbonyl Compounds and 1-Diethylaminopropyne," Journal of the American Chemical Society (1979), vol. 101, pp. 3647-3648.

Kudo, Noriaki et al., "Synthesis and Herbicidal Activity of 1,5-Diarylpyrazole Derivatives," Chemical and Pharmaceutical Bulletin (1999), vol. 47, pp. 857-868.

Ochi, Hisao et al., "Synthesis of 2-Substituted 2,6-Dihydro-3-hydroxy-7H-pyrazolo[4,3-d]pyrimidin-7-ones," Chemical and Pharmaceutical Bulletin (1983), vol. 31, pp. 1228-1234.

Heinisch, Gottfried et al., "Pyridazines, 71. A Novel Type of 1,2-Diazine—> 1,2-Diazole Ring Contraction," Heterocycles (1994), vol. 38, No. 9, pp. 2081-2089.

Beller, Matthias et al., "Transition Metals for Organic Synthesis," Wiley-VCH (1998), vol. 1, pp. 1-13.

Netherton, Matthew R. et al., "Palladium-Catalyzed Cross-Coupling Reactions of Unactivated Alkyl Electrophiles with Organometallic Compounds," Topics in Organometallic Chemistry (2005), vol. 14, pp. 85-108.

Takasaki, Jun et al., "Molecular Cloning of the Platelet P2TAC ADP Receptor: Pharmacological Comparison with Another ADP Receptor, the P2Y1 Receptor," Molecular Pharmacology (2001), vol. 60, pp. 432-439.

Greene, T.W., "Protective Groups in Organic Chemistry," Wiley, New York (1991), Kapitel 5, p. 261-263.

Disraeli, Benjamin, "Protecting Groups: An Overview" (1994), pp. 2-17.

Padwa, Albert et al., "Reaction of Hydrazonyl Chlorides and Carboalkoxymethylene Triphenylphosphoranes to Give 5-Alkoxy Substituted Pyrazoles," Journal of Heterocyclic Chemistry (1987), vol. 24, pp. 1225-1227.

Smith, Michael B. et al., "March's Advanced Organic Chemistry: Reactions, Mechanisms, and Structure," Wiley, New York (2001), pp. 506-516.

Smith, Michael B. et al., "March's Advanced Organic Chemistry: Reactions, Mechanisms, and Structure," Wiley, New York (2001), pp. 935-936.

Smith, Michael B. et al., "March's Advanced Organic Chemistry: Reactions, Mechanisms, and Structure," Wiley, New York (2001), pp. 704-707.

Smith, Michael B. et al., "March's Advanced Organic Chemistry: Reactions, Mechanisms, and Structure," Wiley, New York (2001), pp. 1179-1180.

Tsuji, Jiro, "Palladium Reagents and Catalysts," Wiley (1996), pp. 1-12.

Washizuka, Ken-Ichi et al., "Novel generation of azomethine imines from alpha-silylnitrosamines by 1,4-silatropic shift and their cycloaddition," Tetrahedron Letters (1999), vol. 40, pp. 8849-8853.

Gardner, Derek V. et al., "A Versatile Approach to Analogues of the Cannabinoid-like Anti-emetic Nonabine (BRL 4664)," Journal of Heterocyclic Chemistry (1984), vol. 21, pp. 121-127.

Sakamoto, Takao et al., "Palladium-catalyzed cyanation of aryl and heteroaryl iodides with copper(I) cyanide," Journal of the Chemical Society Perkin Trans. 1 (1999), pp. 2323-2326.

Umemoto, Teruo et al., "Power and Structure-Variable Fluorinating Agents, The N-Fluoropyridinium Salt System," Journal of the American Chemical Society (1990), vol. 112, pp. 8563-8575.

Urata, Hisao et al., "A Novel and Convenient Method for Trifluoromethylation of Organic Halides Using CF3SiR'3/KF/Cu(I) System," Tetrahedron Letters (1991), vol. 32, pp. 91-94.

Kang, Suk-ku et al., "Copper-catalyzed N-Arylation of Aryl Iodides with Benzamides or Nitrogen Heterocycles in the Presence of Ethylenediamine," Synlett (2002), vol. 3, pp. 427-430.

Klapars, Artis et al., "A General and Efficient Copper Catalyst for the Amidation of Aryl Halides and the N-Arylation of Nitrogen Heterocycles," Journal of the American Chemical Society (2001), vol. 123, pp. 7727-7729.

Sauer, Daryl R. et al., "The Synthesis of 3(5)-[(2-Hydroxyethoxy)methyl]pyrazole-5(3)-carboxamide, an Acyclic Analogue of 4-Deoxypyrazofurin," Journal of Organic Chemistry (1990), vol. 55, pp. 5535-5538.

Kwong, Fuk Yee et al., "Copper-Catalyzed Coupling of Alkylamines and Aryl Iodides: An Efficient System Even in an Air Atmosphere," Organic Letters (2002), vol. 4, No. 4, pp. 581-584.

Rodriguez-Franco, Maria Isabel et al., "A mild and efficient method for the regioselective iodination of pyrazoles," Tetrahedron Letters (2001), vol. 42, pp. 863-865.

Humphries, R.G. et al., "Pharmacological profile of the novel P2T-purinoceptor antagonist, FPL 67085 in vitro and in the anaesthetized rat in vivo," British Journal of Pharmacology (1995), vol. 115, pp. 1110-1116.

Storer, Richard et al., "The Synthesis and Antiviral Activity of 4-Fluoro-1-B-D-Ribofuranosyl-1H-Pyrazole-3-Carboxamide," Nucleotides & Nucleotides (1999), vol. 18, pp. 203-216.

Su, De-Bao et al., "Methyl Chlorodifluoroacetate a Convenient Trifluoromethylating Agent," Tetrahedron Letters (1991), vol. 32, pp. 7689-7690.

Pilling, Garry M. et al., "The Synthesis of 1H-Pyrazol-4-OLS From 2-(2-Alkylidenehydrazino) Acetic Acids," Tetrahedron Letters (1988), vol. 29, No. 12, pp. 1341-1342.

Pawlas, Jan et al., "Synthesis of 1-Hydroxy-Substituted Pyrazolo[3,4-c]- and Pyrazolo[4,3-c]quinolines and—isoquinolines from 4- and 5-Aryl-Substituted 1-Benzyloxypyrazoles," Journal of Organic Chemistry (2000), vol. 65, pp. 9001-9006.

Lam, Patrick Y.S. et al., "New Aryl/Heteroaryl C-N Bond Cross-coupling Reactions via Arylboronic Acid/Cupric Acetate Arylation," Tetrahedron Letters (1998), vol. 39, pp. 2941-2944.

Andre, Patrick et al., "P2Y12 regulates platelet adhesion/activation, thrombus growth, and thrombus stability in injured arteries," Journal of Clinical Investigation (2003), vol. 112, pp. 398-406.

Patel, Himatkumar V. et al., "Concise and Efficient Synthesis of 1H-Pyrazoles: Reaction of [Hydroxy(tosyloxy)iodo] benzene with Ethyl 2,3-Dioxobutanoate-2-arylhydrazones," Synthetic Communications (1991), vol. 21, pp. 1583-1588.

Nagai, Toshikazu et al., "Recent Progress in the Preparation and Synthetic Uses of the Reactions of 3H-Pyrazoles. A Review," Organic Preparations and Procedures Int. (1993), vol. 25, pp. 403-435.

Mitsunobu, Oyo, "The Use of Diethyl Azodicarboxylate and Triphenylphosphine in Synthesis and Transformation of Natural Products," Synthesis (1981), pp. 1-28.

Martins, Marcos A.P. et al., "One-Pot Synthesis of 3(5)-Ethoxycarbonylpyrazoles," Synthesis (1995), vol. 12, pp. 1491-1492.

Mustard, J. Fraser et al., "[1] Isolation of Human Platelets from Plasma by Centrifugation and Washing," Methods in Enzymology (1989), vol. 169, pp. 3-11.

XP002485258, Chemical Abstracts, Columbus, OH. May 12, 2007.

Sucrow, Wolfgang et al., "Stable Pyrazolium Betaines by Addition of 1,1-Dialkyl-hydrazines to Acetylenecarboxylic Esters," Angewandte Chemie International Edition (1975), vol. 14, No. 8, pp. 560-561.

Littke, Adam F. et al., "Paladium-Catalyzed Coupling Reactions of Aryl Chlorides," Angewandte Chemie International Edition (2002), vol. 41, pp. 4176-4211.

Muci, Alex R. et al., "Practical Palladium Catalysts for C-N and C-O Bond Formation," Topic in Current Chemistry (2002), vol. 219, pp. 131-209.

Tunoori, Ashok Rao et al., "Polymer-Bound Triphenylphosphine as Traceless Reagent for Mitsunobu Reactions in Combinatorial Chemistry: Synthesis of Aryl Ethers from Phenols and Alcohols," Tetrahedron Letters (1998), vol. 39, pp. 8751-8754.

Booker-Milburn, Kevin I., "A Convenient Method for the Synthesis of C-5 Substituted 1-Tosylpyrazoles," Synlett (1992), pp. 327-328.

Bravo, Pierfrancesco et al., "An Efficient Entry to Perfluoroalkyl Substituted Azoles Starting from B-Perfluoroalkyl-B-dicarbonyl Compounds," Tetrahedron (1994), vol. 50, No. 29, pp. 8827-8836.

Yang, Bryant H. et al., "Palladium-catalyzed amination of aryl halides and sulfonates," Journal of Organometallic Chemistry (1999), vol. 576, pp. 125-146.

Gachet, Christian, "ADP Receptors of Platelets and their Inhibition," Journal of Thrombosis and Haemostasis (2001), vol. 86, pp. 222-232.

Diederich, Francois et al., "Metal-catalyzed Cross-coupling Reactions," Wiley-VCH (1998) Full Book, pp. 1-497 (Table of Contents and Author and Subject Index provided).

Farina, Francisco et al., "1,3-Dipolar Cycloadditions with Methyl 4-Oxo- and 4-Hydroxy-2-Butynoates. Synthesis of Functionalized Pyrazoles and Triazoles," Heterocycles (1989), vol. 29, No. 5, pp. 967-974.

Diederichsen, Ulf et al., "Side chain homologation of alanyl peptide nucleic acids: pairing selectivity and stacking," Organic and Biomolecular Chemistry (2005), vol. 3, pp. 1058-1066.

Holzer, Wolfgang et al., "N1-Substituted 3,5-Dimethoxy-4-halogeno-1H-pyrazoles: Synthesis and NMR Study," Journal of Heterocyclic Chemistry (1995), vol. 32, pp. 1351-1354.

Makino, Kenzi et al., "Synthesis of Pyrazoles and Condensed Pyrazoles," Journal of Heterocyclic Chemistry (1999), vol. 36, pp. 321-332.

Makino, Kenzi et al., "Synthesis of Pyrazoles," Journal of Heterocyclic Chemistry (1998), vol. 35, pp. 489-497.

Dangelmaier, Carol et al., "Potentiation of Thromboxane A2-induced Platelet Secretion by Gi Signaling through the Phosphoinositide-3 Kinase Pathway," Journal of Thrombosis and Haemostasis (2001), vol. 85, pp. 341-348.

Savi, P. et al., "Identification and Biological Activity of the Active Metabolite of Clopidogrel," Thrombosis and Haemostasis (2000), vol. 84, pp. 891-896.

Morimoto, Katsushi et al., "Synthesis of Halosulfuron-methyl via Selective Chlorination at 3- and/or 5-Position of Pyrazole-4-carboxylates," Journal of Heterocyclic Chemistry (1997), vol. 34, pp. 537-540.

Baldoli, C. et al., "A Novel Synthesis of 5-Chloro-3-methoxycarbonyl-1-arylpyrazoles from Arylazomethylenetriphenylphosphoranes," Journal of Heterocyclic Chemistry (1989), vol. 26, pp. 241-244.

Ashton, Wallace T., "A Regioselective Route to 3-Alkyl-1-aryl-1H-pyrazole-5-carboxylates: Synthetic Studies and Structural Assignments," Journal of Heterocyclic Chemistry (1993), vol. 30, pp. 307-311.

HETEROCYCLIC PYRAZOLE-CARBOXAMIDESAS P2Y12 ANTAGONISTS

FIELD OF THE INVENTION

The present invention relates to compounds of the formula I,

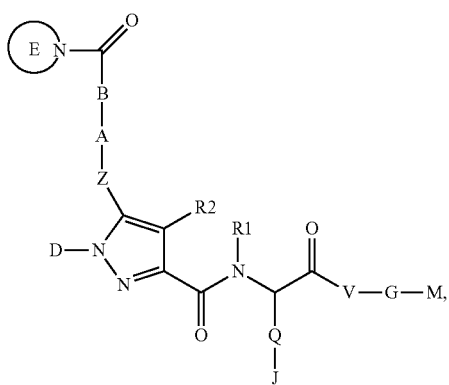

wherein
R1; R2; Z; A; B; D; Q; J; V; G and M have the meanings indicated below. The compounds of the formula I are valuable pharmacologically active compounds. They exhibit a strong anti-aggregating effect on platelets and thus an anti-thrombotic effect and are suitable e.g. for the therapy and prophylaxis of cardio-vascular disorders like thromboembolic diseases or restenoses. They are reversible antagonists of the platelet ADP receptor P2Y12, and can in general be applied in conditions in which an undesired activation of the platelet ADP receptor P2Y12 is present or for the cure or prevention of which an inhibition of the platelet ADP receptor P2Y12 is intended. The invention furthermore relates to processes for the preparation of compounds of the formula I, their use, in particular as active ingredients in pharmaceuticals, and pharmaceutical preparations comprising them.

BACKGROUND OF THE INVENTION

In the industrialized world thrombotic complications are one of the major causes of death. Examples of conditions associated with pathological thrombus formation include deep vein thrombosis, venous and arterial thromboembolism, thrombophlebitis, coronary and cerebral arterial thrombosis, cerebral embolism, renal embolism and pulmonary embolism, disseminated intravascular coagulation, transient ischemic attacks, strokes, acute myocardial infarction, unstable angina, chronic stable angina, peripheral vascular disease, preeclampsia/eclampsia, and thrombotic cytopenic purpura. Also during or following invasive procedures, including insertion of endovascular devices and protheses, carotid endarterectomy, angioplasty, CABG (coronary artery bypass graft) surgery, vascular graft surgery, and stent placements, thrombotic and restenotic complications could occur.

Platelet adhesion and aggregation play a critical role in these intravascular thrombotic events. Platelets can be activated by mediators released from circulating cells and damaged endothelial cells lining the vessel or by exposed subendothelial matrix molecules such as collagen, or by thrombin, which is formed in the coagulation cascade.

Furthermore platelets can be activated under conditions of high shear blood flow in diseased vessels. Following activation, platelets, which normally circulate freely in the vasculature, and other cells, accumulate at the site of a vessel injury to form a thrombus and recruit more platelets to the developing thrombus. During this process, thrombi can grow to a sufficient size to partly or completely block arterial blood vessels.

In veins thrombi can also form in areas of stasis or slow blood flow. These venous thrombi can create emboli that travel through the circulatory system, as they easily detach portions of themselves. These traveling emboli can block other vessels, such as pulmonary or coronary arteries, which can result in the above-mentioned pathological outcomes such as pulmonary or coronary embolism.

In summary, for venous thrombi, morbidity and mortality arise primarily after embolization or distant blockade of vessels, whereas arterial thrombi cause serious pathological conditions by local blockade.

It was demonstrated that ADP (adenosine 5'-diphosphate) is an important mediator of platelet activation and aggregation. It plays a key role in the initiation and progression of arterial thrombus formation (Maffrand, et al, Thromb Haemostas (1988); 59: 225-230; Herbert, et al, Arterioscl Thromb (1993), 13: 1171-1179).

Upon activation by various agents, such as collagen and thrombin, ADP is released from blood platelets in the vasculature, as well as from damaged blood cells, endothelium or tissues. The ADP-induced platelet aggregation is triggered by its binding to two specific G protein-coupled receptors expressed on the plasma membrane of human platelets: $P2Y_1$, and $P2Y_{12}$. ADP binding to these receptors induces inhibition of adenylyl cyclase and modulation of intracellular signaling pathways such as influx and mobilization of intracellular $Ca^{2+}$, activation of phosphoinositide-3 kinase (PI3K), shape change, secretion of other mediators, and platelet aggregation (Dangelmaier, et al. Thromb. Haemost. (2001), 85: 341-348). Activation by ADP results in the recruitment of more platelets and stabilization of existing platelet aggregates. Activation of the $P2Y_1$ receptor leads to calcium mobilization from intracellular stores, platelet shape change and initiation of aggregation.

Activation of the P2Y12 receptor (also referred to as HORK3, P2RY12, SP1999, P2TAC, P2T or P2YAC) by ADP, leads to inhibition of adenylyl cyclase and activation of PI3K. Activation of P2Y12 is required for platelet secretion and stabilization of platelet aggregates (Gachet, Thromb. Haemost. (2001), 86, 222-232; Andre, et al., J. Clin. Invest., (2003), 112, 398-406).

There are several reports about directly or indirectly acting synthetic inhibitors of ADP-dependent platelet aggregation, which show antithrombotic activity.

The orally active thienopyridines, ticlopidine and clopidogrel, react covalently with the P2Y12 receptor and lead to an irreversible platelet inhibition in vivo. They also inhibit binding of radiolabeled ADP receptor agonist 2-methylthioadenosine 5'-diphosphate to platelets, and other ADP-dependent events (Savi, et al., Thromb Haemost. (2000), 84: 891-896).

In WO 02/098856 piperazine derivatives are disclosed, which are active as platelet adenosine diphosphate receptor antagonists. In EP 1698626 pyrazole derivatives are disclosed, which are active in platelet coagulation inhibition.

Houille et al. (WO 2005/000281 and WO 2005/002574) disclose pyrazolidinedione derivatives, useful as antithrombotic agents via inhibition of the platelet ADP receptor.

However, besides being effective P2Y12 antagonists, which antagonize the effect of endogenous ADP on its platelet ADP receptor, it is desirable that such antagonists also have further advantageous properties, for instance stability in plasma and liver and selectivity versus other receptors whose agonism or antagonism is not intended. There is an ongoing need for further low molecular weight P2Y12 antagonist, which are effective and have the above advantages as well.

The present invention satisfies the above needs by providing novel compounds of the formula I, which exhibit better P2Y12 antagonistic activity and are favorable agents with high bioavailability.

DESCRIPTION OF THE INVENTION

Thus, the present invention relates to compounds of formula I,

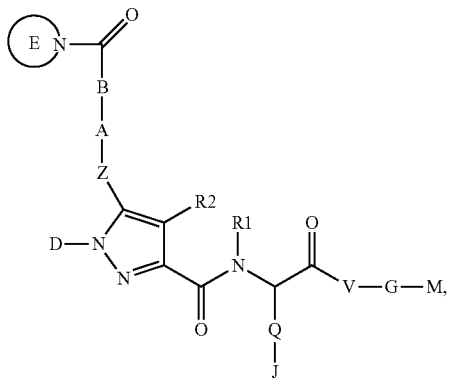

(I)

wherein

E is 3- to 10-membered heterocyclic residue, containing one nitrogen atom and up to 0, 1, 2, or 3 additional heteroatoms chosen from nitrogen, sulfur or oxygen, wherein said heterocyclic residue is monocyclic, bicyclic or a spiro-heterocycle and is bond by its nitrogen atom to the carbonyl carbon atom and wherein said heterocyclic residue is unsubstituted or mono-, di- or trisubstituted independently of one another by R3, D is 1) 3- to 15-membered heterocyclic residue, containing 1, 2, or 3 heteroatoms chosen from nitrogen, sulfur or oxygen, wherein said heterocyclic residue is monocyclic or bicyclic and wherein said heterocyclic residue is unsubstituted or substituted 1, 2, 3, 4, 5 or 6 times by R4,
2) —$(C_6-C_{14})$-aryl, wherein aryl is unsubstituted or substituted 1, 2, 3, 4, 5 or 6 times by R4,
3) —$(C_3-C_8)$-cycloalkyl, wherein cycloalkyl is unsubstituted or substituted 1, 2, 3, 4, 5 or 6 times by R4, or
4) —$(C_1-C_6)$-alkyl, wherein alkyl is unsubstituted or substituted 1, 2, 3, 4, 5 or 6 times by R4, Q is 1) a covalent bond,
2) —$(C_2-C_{10})$-alkenylene-,
3) —$(C_2-C_{10})$-alkynylene-,
4) —$(C_0-C_4)$-alkylene-CH(OH)—$(C_0-C_4)$-alkylene-,
5) —$(C_0-C_4)$-alkylene-O—$(C_0-C_4)$-alkylene-,
6) —$(C_0-C_4)$-alkylene-O—C(O)—N(R10)-$(C_0-C_4)$-alkylene-,
7) —$(C_0-C_4)$-alkylene-C(O)—$(C_0-C_4)$-alkylene-,
8) —$(C_0-C_4)$-alkylene-C(O)—O—$(C_0-C_4)$-alkylene-,
9) —$(C_0-C_4)$-alkylene-C(O)—N(R10)-,
10) —$(C_0-C_4)$-alkylene-N(R10)-$(C_0-C_4)$-alkylene-,
11) —$(C_0-C_4)$-alkylene-N(R10)-C(O)—$(C_0-C_4)$-alkylene-,
12) —$(C_0-C_4)$-alkylene-N(R10)-C(O)—O—$(C_0-C_4)$-alkylene-,
13) —$(C_0-C_4)$-alkylene-N(R10)-C(O)—N(R10)-$(C_0-C_4)$-alkylene-,
14) —$(C_0-C_4)$-alkylene-N(R10)-$SO_2$—$(C_0-C_4)$-alkylene-,
15) —$(C_0-C_4)$-alkylene-N(R10)-$SO_2$—NR10-$(C_0-C_4)$-alkylene-,
16) —$(C_0-C_4)$-alkylene-S—$(C_0-C_4)$-alkylene-,
17) —$(C_0-C_4)$-alkylene-S(O)—$(C_0-C_4)$-alkylene-,
18) —$(C_0-C_4)$-alkylene-$SO_2$—$(C_0-C_4)$-alkylene-,
19) —$(C_0-C_4)$-alkylene-$SO_2$—N(R10)-$(C_0-C_4)$-alkylene-,
20) —$(C_0-C_4)$-alkylene-$(C_3-C_8)$-cycloalkyl-$(C_0-C_4)$-alkylene-,
21) —$(C_0-C_4)$-alkylene-phenyl, or
22) —$(C_0-C_4)$-alkylene-heterocyclyl-$(C_0-C_4)$-alkylene-, wherein heterocyclyl is mono or bicyclic and contains 3 to 15 ring carbon atoms and wherein one or more of the ring carbon atoms are replaced by 1, 2, 3 or 4 heteroatoms chosen from nitrogen, sulfur or oxygen, and wherein said heterocyclyl is unsubstituted or mono-, di- or trisubstituted independently of one another by R14; and wherein the alkyl residues are unsubstituted and wherein said heterocyclyl is unsubstituted or mono-, di- or trisubstituted independently of one another by R14; and wherein the alkyl residues are unsubstituted or mono-, di- or trisubstituted independently of one another by halogen, —$NH_2$, —OH; or —$(C_3-C_6)$-cycloalkyl, wherein cycloalkyl is unsubstituted or mono-, di- or trisubstituted independently of one another by halogen, —$NH_2$ or —OH;

J is 1) hydrogen atom,
2) —$(C_1-C_6)$-alkyl, wherein alkyl is unsubstituted or mono-, di- or trisubstituted independently of one another by R13,
3) —$(C_0-C_4)$-alkylene-O—$CH_2$—$(C_1-C_3)$-fluoroalkylene-$CH_2$—O—$(C_1-C_4)$-alkyl,
4) —$(C_0-C_4)$-alkylene-C(O)—R11,
5) —$(C_0-C_4)$-alkylene-C(O)—O—R11,
6) —$(C_0-C_4)$-alkylene-C(O)—O—$(C_1-C_4)$-alkylene-O—C(O)—R17, wherein —$(C_1-C_4)$-alkylene is unsubstituted or mono-, di- or trisubstituted independently of one another by R15,
7) —$(C_0-C_4)$-alkylene-C(O)—O—$(C_1-C_4)$-alkylene-O—C(O)—O—R17, wherein —$(C_1-C_4)$-alkylene is unsubstituted or mono-, di- or trisubstituted independently of one another by R15,
8) —$(C_0-C_4)$-alkylene-C(O)—N(R11)-R13
9) —$(C_0-C_4)$-alkylene-N(R11)-R13,
10) —$(C_0-C_4)$-alkylene-N(R10)-$SO_2$—R10,
11) —$(C_0-C_4)$-alkylene-S—R10,
12) —$(C_0-C_4)$-alkylene-$SO_s$—R11, wherein s is 1 or 2,
13) —$(C_0-C_4)$-alkylene-$SO_t$—N(R11)-R12, wherein t is 1 or 2,
14) —$(C_0-C_4)$-alkylene-$SO_w$—N(R11)-R13, wherein w is 1 or 2,
15) —$(C_0-C_4)$-alkylene-R22,
16) —$(C_0-C_4)$-alkylene-$(C_3-C_8)$-cycloalkyl, wherein cycloalkyl is unsubstituted or mono-, di- or trisubstituted independently of one another by R13,
17) —$(C_0-C_4)$-alkylene-$(C_6-C_{14})$-aryl, wherein aryl is unsubstituted or mono-, di- or trisubstituted independently of one another by R13, or 18) —($C_0$-$C_4$)-alkylene-($C_3$-$C_{15}$)-heterocyclyl, wherein heterocyclyl is un-substituted or mono-, di- or trisubstituted independently of one another by R13, Z is 1) —($C_0$-$C_8$)-alkylene-,
2) —($C_2$-$C_{10}$)-alkenyl-,
3) —($C_2$-$C_{10}$)-alkynyl-,
4) —($C_0$-$C_4$)-alkylene-O—($C_0$-$C_4$)-alkylene-,
5) —($C_0$-$C_4$)-alkylene-O—($C_0$-$C_4$)-alkylene-C(O)—N(R10)-($C_0$-$C_4$)-alkylene-,
6) —($C_0$-$C_4$)-alkylene-C(O)—($C_0$-$C_4$)-alkylene-,
7) —($C_0$-$C_4$)-alkylene-N(R10)-($C_0$-$C_4$)-alkylene-,
8) —($C_0$-$C_4$)-alkylene-N(R10)-C(O)—($C_0$-$C_4$)-alkylene-,
9) —($C_0$-$C_4$)-alkylene-N(R10)-C(O)—O—($C_0$-$C_4$)-alkylene-,
10) —($C_0$-$C_4$)-alkylene-N(R10)-C(O)—N(R10)-($C_0$-$C_4$)-alkylene-,
11) —($C_0$-$C_4$)-alkylene-N(R10)-$SO_2$—($C_0$-$C_4$)-alkylene-,
12) —($C_0$-$C_4$)-alkylene-N(R10)-$SO_2$—N(R10)-($C_0$-$C_4$)-alkylene-,
13) —($C_0$-$C_4$)-alkylene-S—($C_0$-$C_4$)-alkylene-,
14) —($C_0$-$C_4$)-alkylene-S(O)—($C_0$-$C_4$)-alkylene-,
15) —($C_0$-$C_4$)-alkylene-$SO_2$—($C_0$-$C_4$)-alkylene-,
16) —($C_0$-$C_4$)-alkylene-$SO_2$—N(R10)-($C_0$-$C_4$)-alkylene-, or
17) —($C_0$-$C_4$)-alkylene-($C_3$-$C_8$)-cycloalkyl-($C_0$-$C_4$)-alkylene-, A is a covalent bond, —($C_3$-$C_8$)-alkylene, —($C_3$-$C_8$)-cycloalkylene or —($C_0$-$C_4$)-alkylene-heterocyclyl-($C_0$-$C_4$)-alkylene-, wherein heterocyclyl is mono or bicyclic and contains 3 to 15 ring carbon atoms and wherein one or more of the ring carbon atoms are replaced by 1, 2, 3 or 4 heteroatoms chosen from nitrogen, sulfur or oxygen, B is 1) a covalent bond,
2) —($C_2$-$C_{10}$)-alkenyl-,
3) —($C_2$-$C_{10}$)-alkynyl-,
4) —($C_0$-$C_4$)-alkylene-CH(OH)—($C_0$-$C_4$)-alkylene-,
5) —($C_0$-$C_4$)-alkylene-O—($C_0$-$C_4$)-alkylene-,
6) —($C_0$-$C_4$)-alkylene-O—C(O)—N(R10)-($C_0$-$C_4$)-alkylene-,
7) —($C_0$-$C_4$)-alkylene-C(O)—($C_0$-$C_4$)-alkylene-,
8) —($C_0$-$C_4$)-alkylene-C(O)—O—($C_0$-$C_4$)-alkylene-,
9) —($C_0$-$C_4$)-alkylene-C(O)—N(R10)-,
10) —($C_0$-$C_4$)-alkylene-N(R10)-($C_0$-$C_4$)-alkylene-,
11) —($C_0$-$C_4$)-alkylene-N(R10)-C(O)—($C_0$-$C_4$)-alkylene-,
12) —($C_0$-$C_4$)-alkylene-N(R10)-C(O)—O—($C_0$-$C_4$)-alkylene-,
13) —($C_0$-$C_4$)-alkylene-N(R10)-C(O)—N(R10)-($C_0$-$C_4$)-alkylene-,
14) —($C_0$-$C_4$)-alkylene-N(R10)-$SO_2$—($C_0$-$C_4$)-alkylene-,
15) —($C_0$-$C_4$)-alkylene-N(R10)-$SO_2$—N(R10)-($C_0$-$C_4$)-alkylene-,
16) —($C_0$-$C_4$)-alkylene-S—($C_0$-$C_4$)-alkylene-,
17) —($C_0$-$C_4$)-alkylene-S(O)—($C_0$-$C_4$)-alkylene-,
18) —($C_0$-$C_4$)-alkylene-$SO_2$—($C_0$-$C_4$)-alkylene-,
19) —($C_0$-$C_4$)-alkylene-$SO_2$—N(R10)-($C_0$-$C_4$)-alkylene-,
20) —($C_0$-$C_4$)-alkylene-($C_3$-$C_8$)-cycloalkyl-($C_0$-$C_4$)-alkylene-, or
21) —($C_0$-$C_4$)-alkylene-heterocyclyl-($C_0$-$C_4$)-alkylene-, wherein heterocyclyl is mono or bicyclic and contains 3 to 15 ring carbon atoms and wherein one or more of the ring carbon atoms are replaced by 1, 2, 3 or 4 heteroatoms chosen from nitrogen, sulfur or oxygen, and wherein heterocyclyl is unsubstituted or mono-, di- or trisubstituted independently of one another by R14, and wherein the alkyl residues are unsubstituted or mono-, di- or trisubstituted independently of one another by halogen, —$NH_2$, —OH; or —($C_3$-$C_6$)-cycloalkyl, wherein cycloalkyl is unsubstituted or mono-, di- or trisubstituted independently of one another by halogen, —$NH_2$ or —OH;

V is a monocyclic or bicyclic 3- to 15-membered heterocyclyl, wherein heterocyclyl is unsubstituted or mono-, di- or trisubstituted independently of one another by R14, G is 1) a covalent bond,
2) —($C_2$-$C_{10}$)-alkenyl-,
3) —($C_2$-$C_{10}$)-alkynyl-,
4) —($C_0$-$C_4$)-alkylene-CH(OH)—($C_0$-$C_4$)-alkylene-,
5) —($C_0$-$C_4$)-alkylene-O—($C_0$-$C_4$)-alkylene-,
6) —($C_0$-$C_4$)-alkylene-O—C(O)—N(R10)-($C_0$-$C_4$)-alkylene-,
7) —($C_0$-$C_4$)-alkylene-C(O)—($C_0$-$C_4$)-alkylene-,
8) —($C_0$-$C_4$)-alkylene-C(O)—O—($C_0$-$C_4$)-alkylene-,
9) —($C_0$-$C_4$)-alkylene-C(O)—N(R10)-,
10) —($C_0$-$C_4$)-alkylene-N(R10)-($C_0$-$C_4$)-alkylene-,
11) —($C_0$-$C_4$)-alkylene-N(R10)-C(O)—($C_0$-$C_4$)-alkylene-,
12) —($C_0$-$C_4$)-alkylene-N(R10)-C(O)—O—($C_0$-$C_4$)-alkylene-,
13) —($C_0$-$C_4$)-alkylene-N(R10)-C(O)—N(R10)-($C_0$-$C_4$)-alkylene-,
14) —($C_0$-$C_4$)-alkylene-N(R10)-$SO_2$—($C_0$-$C_4$)-alkylene-,
15) —($C_0$-$C_4$)-alkylene-N(R10)-$SO_2$—N(R10)-($C_0$-$C_4$)-alkylene-,
16) —($C_0$-$C_4$)-alkylene-S—($C_0$-$C_4$)-alkylene-,
17) —($C_0$-$C_4$)-alkylene-S(O)—($C_0$-$C_4$)-alkylene-,
18) —($C_0$-$C_4$)-alkylene-$SO_2$—($C_0$-$C_4$)-alkylene-,
19) —($C_0$-$C_4$)-alkylene-$SO_2$—N(R10)-($C_0$-$C_4$)-alkylene-,
20) —($C_0$-$C_4$)-alkylene-($C_3$-$C_8$)-cycloalkyl-($C_0$-$C_4$)-alkylene-, or
21) —($C_0$-$C_4$)-alkylene-heterocyclyl-($C_0$-$C_4$)-alkylene-, wherein heterocyclyl is mono or bicyclic and contains 3 to 15 ring carbon atoms and wherein one or more of the ring carbon atoms are replaced by 1, 2, 3 or 4 heteroatoms chosen from nitrogen, sulfur or oxygen, wherein heterocyclyl is unsubstituted or mono-, di- or trisubstituted independently of one another by R14; and wherein the alkyl residues are unsubstituted or mono-, di- or trisubstituted independently of one another by halogen, —$NH_2$, —OH or —($C_3$-$C_6$)-cycloalkyl, wherein cycloalkyl is unsubstituted or mono-, di- or trisubstituted independently of one another by halogen, —$NH_2$ or —OH, M is 1) hydrogen atom,
2) —($C_1$-$C_8$)-alkyl, wherein alkyl is unsubstituted or mono-, di- or trisubstituted independently of one another by R14,
3) —($C_1$-$C_8$)-alkylen-N(R10)$_2$,
4) —C(O)—O—R12,
5) —C(O)—N(R11)-R12,
6) —($C_3$-$C_8$)-cycloalkyl, wherein said cycloalkyl is unsubstituted or mono-, di- or trisubstituted independently of one another by R14,
7) —($C_6$-$C_{14}$)-aryl, wherein aryl is unsubstituted or mono-, di- or trisubstituted independently of one another by R14, or
8) a monocyclic or bicyclic 3- to 15-membered heterocyclyl, wherein heterocyclyl is as defined above and is unsubstituted or mono-, di- or trisubstituted independently of one another by R14, R1 is hydrogen atom or —$(C_1$-$C_4)$-alkyl, wherein alkyl is unsubstituted or mono-, di or trisubstituted independently of one another by R13, —$(C_1$-$C_3)$-alkylene-C(O)—NH—R10 or —$(C_1$-$C_3)$-alkylene-C(O)—O—R10, R2 is 1) hydrogen atom,
  2) —$(C_1$-$C_6)$-alkyl, wherein alkyl is unsubstituted or mono-, di- or trisubstituted independently of one another by R13,
  3) —$(C_0$-$C_4)$-alkylene-O—R10,
  4) halogen,
  5) —$(C_1$-$C_3)$-fluoroalkyl, or
  6) phenyl, wherein phenyl is unsubstituted or mono-, di- or trisubstituted independently of one another by R13, if two —OR10 residues are attached to adjacent atoms they can form together with the atoms which they are attached to a 5- or 6-membered ring, which is unsubstituted or substituted one, two, three or four times by R13, if two —$(C_1$-$C_6)$-alkyl residues are attached to adjacent atoms they can form together with the atoms which they are attached to a 5- or 6-membered cycloalkyl ring, which is unsubstituted or substituted one, two, three or four times by R13, R3 is 1) hydrogen atom,
  2) halogen,
  3) —$(C_1$-$C_6)$-alkyl, wherein alkyl is unsubstituted or mono-, di- or trisubstituted independently of one another by R13,
  4) =O,
  5) —$(C_1$-$C_3)$-fluoroalkyl,
  6) —$(C_0$-$C_4)$-alkylene-O—R19, wherein R19 is
    a) hydrogen atom,
    b) —$(C_1$-$C_4)$-alkyl, wherein alkyl is unsubstituted or mono-, di- or trisubstituted independently of one another by R13,
    c) —$(C_3$-$C_8)$-cycloalkyl, wherein alkyl is unsubstituted or mono-, di- or trisubstituted independently of one another by R13,
    d) phenyl, wherein phenyl is unsubstituted or mono-, di- or trisubstituted independently of one another by R13,
    e) —$CF_3$, or
    f) —$CHF_2$,
  7) —$NO_2$,
  8) —CN,
  9) —$(C_0$-$C_4)$-alkylene-O—$CH_2$—$(C_1$-$C_3)$-fluoroalkylene-$CH_2$—O—$(C_1$-$C_4)$-alkyl,
  10) —$(C_0$-$C_4)$-alkylene-C(O)—R11,
  11) —$(C_0$-$C_4)$-alkylene-C(O)—O—R11,
  12) —$(C_0$-$C_4)$-alkylene-C(O)—O—$(C_1$-$C_4)$-alkylene-O—C(O)—R17, wherein —$(C_1$-$C_4)$-alkylene is unsubstituted or mono-, di- or trisubstituted independently of one another by R15,
  13) —$(C_0$-$C_4)$-alkylene-C(O)—O—$(C_1$-$C_4)$-alkylene-O—C(O)—O—R17, wherein —$(C_1$-$C_4)$-alkylene is unsubstituted or mono-, di- or trisubstituted independently of one another by R15,
  14) —$(C_0$-$C_4)$-alkylene-C(O)—N(R11)-R12,
  15) —$(C_0$-$C_4)$-alkylene-C(O)—N(R11)-R13,
  16) —$(C_0$-$C_4)$-alkylene-C(O)—N[$(C_0$-$C_4)$-alkylene]-R13, wherein alkyl and cycloalkyl are unsubstituted or mono-, di- or trisubstituted independently of one another by R13,
  17) —$(C_0$-$C_4)$-alkylene-C(O)—N[$(C_0$-$C_4)$-alkylene-$(C_3$-$C_8)$-cycloalkyl]-R13, wherein alkyl and cycloalkyl is unsubstituted or mono-, di- or trisubstituted independently of one another by R13,
  18) —$(C_0$-$C_4)$-alkylene-N(R11)-R12,
  19) —$(C_0$-$C_4)$-alkylene-N(R11)-R13,
  20) —$(C_0$-$C_4)$-alkylene-N(R10)-$SO_2$—R10,
  21) —$(C_0$-$C_4)$-alkylene-S—R10,
  22) —$(C_0$-$C_4)$-alkylene-$SO_s$—R11, wherein s is 1 or 2,
  23) —$(C_0$-$C_4)$-alkylene-$SO_t$—N(R11)-R12, wherein t is 1 or 2,
  24) —$(C_0$-$C_4)$-alkylene-$SO_w$—N(R11)-R13, wherein w is 1 or 2,
  25) —$(C_0$-$C_4)$-alkylene-$SO_u$—$(C_0$-$C_4)$-alkylene-C(O)—O—R10, wherein u is 1 or 2,
  26) —$(C_0$-$C_4)$-alkylene-$(C_3$-$C_8)$-cycloalkyl, wherein cycloalkyl is unsubstituted or mono-, di- or trisubstituted independently of one another by R13,
  27) —$(C_0$-$C_4)$-alkylene-$(C_6$-$C_{14})$-aryl, wherein aryl is unsubstituted or mono-, di- or trisubstituted independently of one another by R13,
  28) —$(C_0$-$C_4)$-alkylene-$(C_3$-$C_{15})$-heterocyclyl, wherein heterocyclyl is un-substituted or mono-, di- or trisubstituted independently of one another by R13,
  29) —$(C_0$-$C_4)$-alkylene-O—$(C_0$-$C_4)$-alkylene-$(C_6$-$C_{14})$-aryl, wherein aryl is unsubstituted or mono-, di- or trisubstituted independently of one another by R13,
  30) —$(C_0$-$C_4)$-alkylene-O—$(C_0$-$C_4)$-alkylene-$(C_3$-$C_{15})$-heterocyclyl, wherein heterocyclyl is un-substituted or mono-, di- or trisubstituted independently of one another by R13,
  31) —$(C_0$-$C_4)$-alkylene-N(R13)—$(C_0$-$C_4)$-alkylene-$(C_6$-$C_{14})$-aryl, wherein aryl is unsubstituted or mono-, di- or trisubstituted independently of one another by R13, or
  32) —$(C_0$-$C_4)$-alkylene-N(R13)—$(C_0$-$C_4)$-alkylene-$(C_3$-$C_{15})$-heterocyclyl, wherein heterocyclyl is un-substituted or mono-, di- or trisubstituted independently of one another by R13, R4 is 1) hydrogen atom,
  2) —$(C_1$-$C_6)$-alkyl, wherein alkyl is unsubstituted or mono-, di- or trisubstituted independently of one another by R13,
  3) —$(C_0$-$C_4)$-alkylene-O—R10,
  4) halogen,
  5) —$(C_1$-$C_3)$-fluoroalkyl,
  6) phenyl, wherein phenyl is unsubstituted or mono-, di- or trisubstituted independently of one another by R13, or
  7) —$(C_0$-$C_4)$-alkylene-R13, R10 and R20 are independently of one another hydrogen atom, —$(C_1$-$C_4)$-alkyl, —$(C_1$-$C_4)$-alkyl-OH, —$(C_0$-$C_4)$-alkylene-O—$(C_1$-$C_4)$-alkyl or —$(C_1$-$C_3)$-fluoroalkyl, R11 and R12 are independently of one another identical or different and are
  1) hydrogen atom,
  2) —$(C_1$-$C_6)$-alkyl, wherein alkyl is unsubstituted or mono-, di- or trisubstituted independently of one another by R13,
  3) —O—R17,
  4) —$SO_t$—R10, wherein t is 1 or 2,
  5) —$(C_1$-$C_3)$-fluoroalkyl,
  6) —$(C_0$-$C_6)$-alkylene-$(C_3$-$C_8)$-cycloalkyl, wherein alkylene and cycloalkyl independently from one another are unsubstituted or mono-, di- or trisubstituted independently of one another by R13,
  7) —$(C_0$-$C_6)$-alkylene-$(C_6$-$C_{14})$-aryl, wherein alkylene and aryl independently from one another are unsubstituted or mono-, di- or trisubstituted by R13, or
  8) —$(C_0$-$C_6)$-alkylene-$(C_3$-$C_{15})$-heterocyclyl, wherein alkylene and heterocyclyl independently from one another are unsubstituted or mono-, di- or trisubstituted by R13, or R11 and R12 form together with the nitrogen atom to which they are attached a 4-, 5-, 6-, 7- or 8-membered monocyclic heterocyclic ring which in addition to the nitrogen atom can contain one or two identical or different ring heteroatoms chosen from oxygen, sulfur and nitrogen, and wherein said ring is unsubstituted or substituted depending on the number of ring atoms one, two, three or four times by R13, R13 is halogen, —$NO_2$, —CN, =O, —OH, —$CF_3$, —C(O)—O—R10, —C(O)—N(R10)-R20, —N(R10)-R20, —($C_3$-$C_8$)-cycloalkyl, —($C_2$-$C_{10}$)-alkenyl-, —($C_2$-$C_{10}$)-alkynyl-, —O—$CF_3$, —Si—$(CH_3)_3$, —($C_0$-$C_4$)-alkylene-O—R10, —N(R10)-S(O)$_u$—R10, wherein u is 1 or 2, —$SO_r$—R10, wherein r is 1 or 2, —S(O)$_v$—N(R10)-R20, wherein v is 1 or 2, —S—R10, —C(O)—R10, —($C_1$-$C_8$)-alkyl, —($C_1$-$C_8$)-alkoxy, phenyl, phenyloxy-, —($C_1$-$C_8$)-alkoxy-phenyl, —($C_0$-$C_4$)-alkylene-C(O)—O—C(R15, R16)-O—C(O)—R17, —NH—C(O)—NH—R10, —($C_0$-$C_4$)-alkylene-C(O)—O—C(R15, R16)-O—C(O)—O—R17, —O—R15, —($C_1$-$C_3$)-fluoroalkyl, —NH—C(O)—O—R10, or —($C_0$-$C_4$)-alkylene-R22, R14 is halogen, —OH, =O, —($C_1$-$C_8$)-alkyl, —($C_1$-$C_4$)-alkoxy, —$NO_2$, —CN, —$NH_2$, —S—R18, —($C_1$-$C_4$)-alkylene-C(O)—OH, —C(O)—O—($C_1$-$C_4$)-alkyl, —($C_1$-$C_4$)-alkylene-C(O)—$NH_2$, —($C_0$-$C_8$)-alkylene-$SO_2$—($C_1$-$C_4$)-alkyl, —($C_0$-$C_8$)-alkylene-$SO_2$—($C_1$-$C_3$)-fluoroalkyl, —($C_0$-$C_8$)-alkylene-$SO_2$—N(R18)-R21, —($C_1$-$C_4$)-alkylene-C(O)—NH—($C_1$-$C_8$)-alkyl, —($C_1$-$C_4$)-alkylene-C(O)—N—[($C_1$-$C_8$)-alkyl]$_2$, —N(R18)-C(O)—NH—($C_1$-$C_8$)-alkyl, —N(R18)-C(O)—NH—[($C_1$-$C_8$)-alkyl]$_2$, —($C_2$-$C_{10}$)-alkenyl, or —($C_2$-$C_{10}$)-alkynyl, wherein R18 and R21 are independently from each other hydrogen atom, —($C_1$-$C_3$)-fluoroalkyl or —($C_1$-$C_6$)-alkyl, R15 and R16 are independently of one another hydrogen atom, —($C_1$-$C_6$)-alkyl, or together with the carbon atom to which they are bonded form a —($C_3$-$C_6$)-cycloalkyl, which is unsubstituted or mono, di- or trisubstituted by R10, R17 is hydrogen atom, —($C_1$-$C_6$)-alkyl, —($C_1$-$C_6$)-alkyl-OH, —($C_1$-$C_6$)-alkylene-O—($C_1$-$C_6$)-alkyl, —($C_1$-$C_6$)-alkylene-O—($C_1$-$C_6$)-alkylene-($C_3$-$C_8$)-cycloalkyl, or —($C_0$-$C_6$)-alkylene-($C_3$-$C_8$)-cycloalkyl, wherein said cycloalkyl ring is unsubstituted or substituted one, two or three times by —OH, —O—($C_1$-$C_4$)-alkyl or R10, and R22 is a residue from the following list:

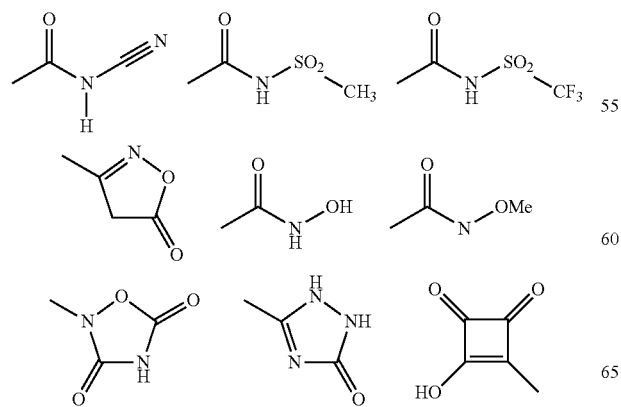

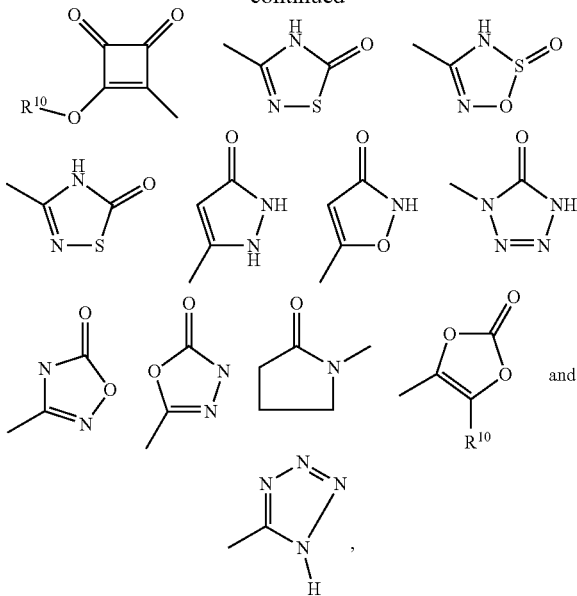

wherein Me is methyl,
in all its stereoisomeric forms and mixtures thereof in any ratio, and its physiologically tolerable salts.

2) The present invention also relates to compounds of the formula I, wherein

E is 3- to 10-membered heterocyclic residue selected from aza-bicycloheptane, aza-bicyclohexane, aza-bicyclooctane, aza-spiroheptane, aza-spirohexane, aza-spirooctane, aza-spiropentane, azepane, azepine, azetidine, aziridine, decahydro-quinoline, diaza-bicyclohexane, diaza-bicycloheptane, 2,5-Diaza-bicyclo[2.2.1]heptane, 1,2-diazapane, diaza-spirohexane, diaza-spirooctane, diaza-spiropentane, diaza-spiroheptane, 1,3-diazepane, 1,4-diazepane, 1,2-diazepine, 1,3-diazepine, 1,4-diazepine, dihydroazepine, 2,3-dihydro-1H-indole, 3,4-dihydro-1H-isoquinoline, 6,7-dihydro-4H-isoxazolo[4,5-c]pyridine, dihydro-pyridazine, dihydro-oxazepine, 4,6-dihydro-4H-pyrrolo[3,4-d]thiazole, 6,7-dihydro-4H-thiazolo[5,4-c]pyridine, 4,7-dihydro-5H-thieno[2,3-c]pyridine, dioxazole, hexahydro-pyridazine, hexahydro-cyclopenta[c]pyrroline, imidazoline, imidazolidine, isoquinoline, isothiazolidine, isothiazoline, isoxazoline, isoxazolidine, ketopiperazine, morpholine, octahydro-cyclopenta[c]pyrrole, 1,4-oxazepane, 1,2-oxa-thiepane, oxazepine, 1,2-oxazine, 1,3-oxazine, 1,4-oxazine, oxazolidine, piperazine, piperidine, pyrazine, pyrazoline, pyrazolidine, pyridazine, pyrrolidine, pyrrolidinone, pyrroline, tetrahydro-azepine, 1,2,3,4-tetrahydro-isoquinoline, 4,5,6,7-tetrahydro-isoxazolo[4,5-c]pyridine, 1,2,3,4-tetrahydropyrazine, 4,5,6,7-tetrahydro-1H-pyrazolo[4,3-c]pyridine, tetrahydro-pyridazine, tetrahydropyridine, 4,5,6,6a-tetrahydro-3aH-pyrrolo[3,4-d]isoxazole, 1,2,3,4-tetrahydro-quinoline, 4,5,6,7-tetrahydro-thieno[2,3-c]pyridine, 1,4,6,7-tetrahydro-thiazolo[5,4-c]pyridine, 4,5,6,7-tetrahydro-thieno[3,2-c]pyridine, tetrazine, tetrazole, thiadiazine, 1,2-thiazine, 1,3-thiazine, 1,4-thiazine, 1,3-thiazole, thiazolidine, thiazoline, thietan, thiomorpholine, triaza-spirooctane, triazepane, 1,2,4-triazinane and 1,3,5-triazinane, wherein said heterocyclic residue is bond by its nitrogen atom to the carbonyl carbon atom and wherein said heterocyclic residue is unsubstituted or mono-, di- or trisubstituted independently of one another by R3, D is 1) 3- to 15-membered heterocyclic residue selected from acridinyl, azabenzimidazolyl, aza-bicycloheptanyl, aza-bicyclohexanyl, aza-bicyclooctanyl, 8-aza-bicyclo[3.2.1]octanyl, azaspirodecanyl, aza-spiroheptanyl, aza-spirohexanyl, aza-spirooctanyl, aza-spiropentanyl, azepinyl, azetidinyl, aziridinyl, benzofuranyl, benzoimidazolyl, benzoisothiazolyl, benzoisoxazolyl, benzotetrazolyl, benzothiazolyl, benzothiofuranyl, benzothiophenyl, benzotriazolyl, benzoxazolyl, carbazolyl, 4aH-carbazolyl, carbolinyl, chromanyl, chromenyl, cinnolinyl, decahydroquinolinyl, diaza-bicyclohexanyl, diaza-bicycloheptanyl, 2,5-Diaza-bicyclo[2.2.1]heptanyl, 1,2-diazapanyl, diaza-spirohexanyl, diaza-spirooctanyl, diaza-spiropentanyl, diaza-spiroheptanyl, 1,3-diazepanyl, 1,4-diazepanyl, 1,2-diazepinyl, 1,3-diazepinyl, 1,4-diazepinyl, dihydroazepinyl, dihydrofuro[2,3-b]tetrahydrofuranyl, 2,3-dihydro-1H-indolyl, 3,4-dihydro-1H-isoquinolinyl, 6,7-dihydro-4H-isoxazolo[4,5-c]pyridinyl, dihydro-pyridazinyl, dihydro-oxazepinyl, 4,5-dihydrooxazolinyl, 4,6-dihydro-4H-pyrrolo[3,4-d]thiazolyl, 6,7-dihydro-4H-thiazolo[5,4-c]pyridinyl, 4,7-dihydro-5H-thieno[2,3-c]pyridinyl, dioxazolyl, dioxazinyl, 1,3-dioxolanyl, 1,3-dioxolenyl, 3,3-dioxo[1,3,4]oxathiazinyl, 6H-1,5,2-dithiazinyl, furanyl, furazanyl, hexahydro-pyridazine, hexahydro-cyclopenta[c]pyrroline, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydro-cyclopenta[c]pyrrolyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 1H-pyrrolopyridinyl, 2H-pyrrolyl, pyrrolyl, quinazolinyl, quinolinyl, 4H-quinolizinyl, quinoxalinyl, quinuclidinyl, tetrahydrofuranyl, 1,2,3,4-tetrahydro-isoquinolinyl, 4,5,6,7-tetrahydro-isoxazolo[4,5-c]pyridinyl, tetrahydropyranyl, 1,2,3,4-tetrahydropyrazinyl, 4,5,6,7-tetrahydro-1H-pyrazolo[4,3-c]pyridinyl, tetrahydro-pyridazinyl, tetrahydro-pyridinyl, 4,5,6,6a-tetrahydro-3aH-pyrrolo[3,4-d]isoxazolyl, 1,2,3,4-tetrahydro-quinolinyl, 4,5,6,7-tetrahydro-thieno[2,3-c]pyridinyl, 1,4,6,7-tetrahydro-thiazolo[5,4-c]pyridinyl, 4,5,6,7-tetrahydro-thieno[3,2-c]pyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, triaza-spirooctanyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl, and xanthenyl, wherein said heterocyclic residue is unsubstituted or substituted 1, 2, 3, 4, 5 or 6 times by R4,
2) —($C_6$-$C_{14}$)-aryl, wherein aryl is selected from phenyl, naphthyl, biphenylyl, indanyl, anthryl or fluorenyl, wherein said aryl residue is unsubstituted or substituted 1, 2, 3, 4, 5 or 6 times by R4,
3) —($C_3$-$C_8$)-cycloalkyl, wherein cycloalkyl is unsubstituted or substituted 1, 2, 3, 4, 5 or 6 times by R4, or
4) —($C_1$-$C_6$)-alkyl, wherein alkyl is unsubstituted or substituted 1, 2, 3, 4, 5 or 6 times by R4, Q is 1) a covalent bond,
2) —($C_2$-$C_{10}$)-alkenylene-,
3) —($C_2$-$C_{10}$)-alkynylene-,
4) —($C_0$-$C_4$)-alkylene-CH(OH)—($C_0$-$C_4$)-alkylene-,
5) —($C_0$-$C_4$)-alkylene-O—($C_0$-$C_4$)-alkylene-,
6) —($C_0$-$C_4$)-alkylene-O—C(O)—N(R10)-($C_0$-$C_4$)-alkylene-,
7) —($C_0$-$C_4$)-alkylene-C(O)—($C_0$-$C_4$)-alkylene-,
8) —($C_0$-$C_4$)-alkylene-C(O)—O—($C_0$-$C_4$)-alkylene-,
9) —($C_0$-$C_4$)-alkylene-C(O)—N(R10)-,
10) —($C_0$-$C_4$)-alkylene-N(R10)-($C_0$-$C_4$)-alkylene-,
11) —($C_0$-$C_4$)-alkylene-N(R10)-C(O)—($C_0$-$C_4$)-alkylene-,
12) —($C_0$-$C_4$)-alkylene-N(R10)-C(O)—O—($C_0$-$C_4$)-alkylene-,
13) —($C_0$-$C_4$)-alkylene-N(R10)-C(O)—N(R10)-($C_0$-$C_4$)-alkylene-,
14) —($C_0$-$C_4$)-alkylene-N(R10)-$SO_2$—($C_0$-$C_4$)-alkylene-,
15) —($C_0$-$C_4$)-alkylene-N(R10)-$SO_2$—NR10-($C_0$-$C_4$)-alkylene-,
16) —($C_0$-$C_4$)-alkylene-S—($C_0$-$C_4$)-alkylene-,
17) —($C_0$-$C_4$)-alkylene-S(O)—($C_0$-$C_4$)-alkylene-,
18) —($C_0$-$C_4$)-alkylene-$SO_2$—($C_0$-$C_4$)-alkylene-,
19) —($C_0$-$C_4$)-alkylene-$SO_2$—N(R10)-($C_0$-$C_4$)-alkylene-,
20) —($C_0$-$C_4$)-alkylene-($C_3$-$C_8$)-cycloalkyl-($C_0$-$C_4$)-alkylene-,
21) —($C_0$-$C_4$)-alkylene-phenyl, or
22) —($C_0$-$C_4$)-alkylene-($C_3$-$C_{15}$)-heterocyclyl-($C_0$-$C_4$)-alkylene-, wherein said heterocyclyl is as defined above and is unsubstituted or mono-, di- or tri-substituted independently of one another by R14; and wherein the alkyl residues are unsubstituted and wherein said heterocyclyl is unsubstituted or mono-, di- or trisubstituted independently of one another by R14; and wherein the alkyl residues are unsubstituted or mono-, di- or trisubstituted independently of one another by halogen, —$NH_2$, —OH; or —($C_3$-$C_6$)-cycloalkyl, wherein cycloalkyl is unsubstituted or mono-, di- or trisubstituted independently of one another by halogen, —$NH_2$ or —OH;

J is 1) hydrogen atom,
2) —($C_1$-$C_6$)-alkyl, wherein alkyl is unsubstituted or mono-, di- or trisubstituted independently of one another by R13,
3) —($C_0$-$C_4$)-alkylene-O—$CH_2$—($C_1$-$C_3$)-fluoroalkylene-$CH_2$—O—($C_1$-$C_4$)-alkyl,
4) —($C_0$-$C_4$)-alkylene-C(O)—R11,
5) —($C_0$-$C_4$)-alkylene-C(O)—O—R11,
6) —($C_0$-$C_4$)-alkylene-C(O)—O—($C_1$-$C_4$)-alkylene-O—C(O)—R17, wherein —($C_1$-$C_4$)-alkylene is unsubstituted or mono-, di- or trisubstituted independently of one another by R15,
7) —($C_0$-$C_4$)-alkylene-C(O)—O—($C_1$-$C_4$)-alkylene-O—C(O)—O—R17, wherein —($C_1$-$C_4$)-alkylene is unsubstituted or mono-, di- or trisubstituted independently of one another by R15,
8) —($C_0$-$C_4$)-alkylene-C(O)—N(R11)-R13
9) —($C_0$-$C_4$)-alkylene-N(R11)-R13,
10) —($C_0$-$C_4$)-alkylene-N(R10)-$SO_2$—R10,
11) —($C_0$-$C_4$)-alkylene-S—R10, 12) —($C_0$-$C_4$)-alkylene-$SO_s$—R11, wherein s is 1 or 2,
13) —($C_0$-$C_4$)-alkylene-$SO_t$—N(R11)-R12, wherein t is 1 or 2,
14) —($C_0$-$C_4$)-alkylene-$SO_w$—N(R11)-R13, wherein w is 1 or 2,
15) —($C_0$-$C_4$)-alkylene-($C_3$-$C_8$)-cycloalkyl, wherein cycloalkyl is unsubstituted or mono-, di- or trisubstituted independently of one another by R13,
16) —($C_0$-$C_4$)-alkylene-($C_6$-$C_{14}$)-aryl, wherein aryl is as defined above and is unsubstituted or mono-, di- or trisubstituted independently of one another by R13, or
17) —($C_0$-$C_4$)-alkylene-($C_3$-$C_{15}$)-heterocyclyl, wherein heterocyclyl is as defined above and is unsubstituted or mono-, di- or trisubstituted independently of one another by R13, Z is 1) —($C_0$-$C_8$)-alkylene-,
2) —($C_2$-$C_{10}$)-alkenyl-,
3) —($C_2$-$C_{10}$)-alkynyl-,
4) —($C_0$-$C_4$)-alkylene-O—($C_0$-$C_4$)-alkylene-,
5) —($C_0$-$C_4$)-alkylene-O—($C_0$-$C_4$)-alkylene-C(O)—N(R10)-($C_0$-$C_4$)-alkylene-,
6) —($C_0$-$C_4$)-alkylene-C(O)—($C_0$-$C_4$)-alkylene-,
7) —($C_0$-$C_4$)-alkylene-N(R10)-($C_0$-$C_4$)-alkylene-,
8) —($C_0$-$C_4$)-alkylene-N(R10)-C(O)—($C_0$-$C_4$)-alkylene-,
9) —($C_0$-$C_4$)-alkylene-N(R10)-C(O)—O—($C_0$-$C_4$)-alkylene-,
10) —($C_0$-$C_4$)-alkylene-N(R10)-C(O)—N(R10)-($C_0$-$C_4$)-alkylene-,
11) —($C_0$-$C_4$)-alkylene-N(R10)-$SO_2$—($C_0$-$C_4$)-alkylene-,
12) —($C_0$-$C_4$)-alkylene-N(R10)-$SO_2$—N(R10)-($C_0$-$C_4$)-alkylene-,
13) —($C_0$-$C_4$)-alkylene-S—($C_0$-$C_4$)-alkylene-,
14) —($C_0$-$C_4$)-alkylene-S(O)—($C_0$-$C_4$)-alkylene-,
15) —($C_0$-$C_4$)-alkylene-$SO_2$—($C_0$-$C_4$)-alkylene-,
16) —($C_0$-$C_4$)-alkylene-$SO_2$—N(R10)-($C_0$-$C_4$)-alkylene-, or
17) —($C_0$-$C_4$)-alkylene-($C_3$-$C_8$)-cycloalkyl-($C_0$-$C_4$)-alkylene-, A is a covalent bond, —($C_3$-$C_8$)-alkylene, —($C_3$-$C_8$)-cycloalkylene or —($C_0$-$C_4$)-alkylene-heterocyclyl-($C_0$-$C_4$)-alkylene-, wherein heterocyclyl is as defined above, B is 1) a covalent bond,
2) —($C_2$-$C_{10}$)-alkenyl-,
3) —($C_2$-$C_{10}$)-alkynyl-,
4) —($C_0$-$C_4$)-alkylene-CH(OH)—($C_0$-$C_4$)-alkylene-,
5) —($C_0$-$C_4$)-alkylene-O—($C_0$-$C_4$)-alkylene-,
6) —($C_0$-$C_4$)-alkylene-O—C(O)—N(R10)-($C_0$-$C_4$)-alkylene-,
7) —($C_0$-$C_4$)-alkylene-C(O)—($C_0$-$C_4$)-alkylene-,
8) —($C_0$-$C_4$)-alkylene-C(O)—O—($C_0$-$C_4$)-alkylene-,
9) —($C_0$-$C_4$)-alkylene-C(O)—N(R10)-,
10) —($C_0$-$C_4$)-alkylene-N(R10)-($C_0$-$C_4$)-alkylene-,
11) —($C_0$-$C_4$)-alkylene-N(R10)-C(O)—($C_0$-$C_4$)-alkylene-,
12) —($C_0$-$C_4$)-alkylene-N(R10)-C(O)—O—($C_0$-$C_4$)-alkylene-,
13) —($C_0$-$C_4$)-alkylene-N(R10)-C(O)—N(R10)-($C_0$-$C_4$)-alkylene-,
14) —($C_0$-$C_4$)-alkylene-N(R10)-$SO_2$—($C_0$-$C_4$)-alkylene-,
15) —($C_0$-$C_4$)-alkylene-N(R10)-$SO_2$—N(R10)-($C_0$-$C_4$)-alkylene-,
16) —($C_0$-$C_4$)-alkylene-S—($C_0$-$C_4$)-alkylene-,
17) —($C_0$-$C_4$)-alkylene-S(O)—($C_0$-$C_4$)-alkylene-,
18) —($C_0$-$C_4$)-alkylene-$SO_2$—($C_0$-$C_4$)-alkylene-,
19) —($C_0$-$C_4$)-alkylene-$SO_2$—N(R10)-($C_0$-$C_4$)-alkylene-,
20) —($C_0$-$C_4$)-alkylene-($C_3$-$C_8$)-cycloalkyl-($C_0$-$C_4$)-alkylene-, or
21) —($C_0$-$C_4$)-alkylene-heterocyclyl-($C_0$-$C_4$)-alkylene-, wherein heterocyclyl is as defined above and is unsubstituted or mono-, di- or trisubstituted independently of one another by R14, and wherein the alkyl residues are unsubstituted or mono-, di- or trisubstituted independently of one another by halogen, —$NH_2$, —OH; or —($C_3$-$C_6$)-cycloalkyl, wherein cycloalkyl is unsubstituted or mono-, di- or trisubstituted independently of one another by halogen, —$NH_2$ or —OH;

V is a monocyclic or bicyclic 3- to 15-membered heterocyclyl, wherein heterocyclyl is as defined above and is unsubstituted or mono-, di- or trisubstituted independently of one another by R14, G is 1) a covalent bond,
2) —($C_2$-$C_{10}$)-alkenyl-,
3) —($C_2$-$C_{10}$)-alkynyl-,
4) —($C_0$-$C_4$)-alkylene-CH(OH)—($C_0$-$C_4$)-alkylene-,
5) —($C_0$-$C_4$)-alkylene-O—($C_0$-$C_4$)-alkylene-,
6) —($C_0$-$C_4$)-alkylene-O—C(O)—N(R10)-($C_0$-$C_4$)-alkylene-,
7) —($C_0$-$C_4$)-alkylene-C(O)—($C_0$-$C_4$)-alkylene-,
8) —($C_0$-$C_4$)-alkylene-C(O)—O—($C_0$-$C_4$)-alkylene-,
9) —($C_0$-$C_4$)-alkylene-C(O)—N(R10)-($C_0$-$C_4$)-alkylene-,
10) —($C_0$-$C_4$)-alkylene-N(R10)-($C_0$-$C_4$)-alkylene-,
11) —($C_0$-$C_4$)-alkylene-N(R10)-C(O)—($C_0$-$C_4$)-alkylene-,
12) —($C_0$-$C_4$)-alkylene-N(R10)-C(O)—O—($C_0$-$C_4$)-alkylene-,
13) —($C_0$-$C_4$)-alkylene-N(R10)-C(O)—N(R10)-($C_0$-$C_4$)-alkylene-,
14) —($C_0$-$C_4$)-alkylene-N(R10)-$SO_2$—($C_0$-$C_4$)-alkylene-,
15) —($C_0$-$C_4$)-alkylene-N(R10)-$SO_2$—N(R10)-($C_0$-$C_4$)-alkylene-,
16) —($C_0$-$C_4$)-alkylene-S—($C_0$-$C_4$)-alkylene-,
17) —($C_0$-$C_4$)-alkylene-S(O)—($C_0$-$C_4$)-alkylene-,
18) —($C_0$-$C_4$)-alkylene-$SO_2$—($C_0$-$C_4$)-alkylene-,
19) —($C_0$-$C_4$)-alkylene-$SO_2$—N(R10)-($C_0$-$C_4$)-alkylene-,
20) —($C_0$-$C_4$)-alkylene-($C_3$-$C_8$)-cycloalkyl-($C_0$-$C_4$)-alkylene-, or
21) —($C_0$-$C_4$)-alkylene-heterocyclyl-($C_0$-$C_4$)-alkylene-, wherein heterocyclyl is as defined above and is unsubstituted or mono-, di- or trisubstituted independently of one another by R14; and wherein the alkyl residues are unsubstituted or mono-, di- or trisubstituted independently of one another by halogen, —$NH_2$, —OH or —($C_3$-$C_6$)-cycloalkyl, wherein cycloalkyl is unsubstituted or mono-, di- or trisubstituted independently of one another by halogen, —$NH_2$ or —OH, M is 1) hydrogen atom,
2) —($C_1$-$C_8$)-alkyl, wherein alkyl is unsubstituted or mono-, di- or trisubstituted independently of one another by R14,
3) —($C_1$-$C_8$)-alkylen-N(R10)$_2$,
4) —C(O)—O—R12,
5) —C(O)—N(R11)-R12,
6) —($C_3$-$C_8$)-cycloalkyl, wherein said cycloalkyl is unsubstituted or mono-, di- or trisubstituted independently of one another by R14,
7) —($C_6$-$C_{14}$)-aryl, wherein aryl is unsubstituted or mono-, di- or trisubstituted independently of one another by R14, or 8) a monocyclic or bicyclic 3- to 15-membered heterocyclyl, wherein heterocyclyl is as defined above and is unsubstituted or mono-, di- or trisubstituted independently of one another by R14, R1 is hydrogen atom or —($C_1$-$C_4$)-alkyl, wherein alkyl is unsubstituted or mono-, di- or trisubstituted independently of one another by R13, —($C_1$-$C_3$)-alkylene-C(O)—NH—R10 or —($C_1$-$C_3$)-alkylene-C(O)—O—R10, R2 is 1) hydrogen atom,
2) —($C_1$-$C_6$)-alkyl, wherein alkyl is unsubstituted or mono-, di- or trisubstituted independently of one another by R13,
3) —($C_0$-$C_4$)-alkylene-O—R10,
4) halogen,
5) —($C_1$-$C_3$)-fluoroalkyl, or
6) phenyl, wherein phenyl is unsubstituted or mono-, di- or trisubstituted independently of one another by R13, if two —OR10 residues are attached to adjacent atoms they can form together with the atoms which they are attached to a 5- or 6-membered ring, which is unsubstituted or substituted one, two, three or four times by R13, if two —($C_1$-$C_6$)-alkyl residues are attached to adjacent atoms they can form together with the atoms which they are attached to a 5- or 6-membered cycloalkyl ring, which is unsubstituted or substituted one, two, three or four times by R13, R3 is 1) hydrogen atom,
2) halogen,
3) —($C_1$-$C_6$)-alkyl, wherein alkyl is unsubstituted or mono-, di- or trisubstituted independently of one another by R13,
4) =O,
5) —($C_1$-$C_3$)-fluoroalkyl,
6) —($C_0$-$C_4$)-alkylene-O—R19, wherein R19 is
   a) hydrogen atom,
   b) —($C_1$-$C_4$)-alkyl, wherein alkyl is unsubstituted or mono-, di- or trisubstituted independently of one another by R13,
   c) —($C_3$-$C_8$)-cycloalkyl, wherein alkyl is unsubstituted or mono-, di- or trisubstituted independently of one another by R13,
   d) phenyl, wherein phenyl is unsubstituted or mono-, di- or trisubstituted independently of one another by R13,
   e) —$CF_3$, or
   f) —$CHF_2$,
7) —$NO_2$,
8) —CN,
9) -($C_0$-$C_4$)-alkylene-O—$CH_2$—($C_1$-$C_3$)-fluoroalkylene-$CH_2$—O—($C_1$-$C_4$)-alkyl,
10) —($C_0$-$C_4$)-alkylene-C(O)—R11,
11) —($C_0$-$C_4$)-alkylene-C(O)—O—R11,
12) —($C_0$-$C_4$)-alkylene-C(O)—O—($C_1$-$C_4$)-alkylene-O—C(O)—R17, wherein —($C_1$-$C_4$)-alkylene is unsubstituted or mono-, di- or trisubstituted independently of one another by R15,
13) —($C_0$-$C_4$)-alkylene-C(O)—O—($C_1$-$C_4$)-alkylene-O—C(O)—O—R17, wherein —($C_1$-$C_4$)-alkylene is unsubstituted or mono-, di- or trisubstituted independently of one another by R15,
14) —($C_0$-$C_4$)-alkylene-C(O)—N(R11)-R12,
15) —($C_0$-$C_4$)-alkylene-C(O)—N(R11)-R13,
16) —($C_0$-$C_4$)-alkylene-C(O)—N[($C_0$-$C_4$)-alkylene]-R13, wherein alkyl and cycloalkyl are unsubstituted or mono-, di- or trisubstituted independently of one another by R13,
17) —($C_0$-$C_4$)-alkylene-C(O)—N[($C_0$-$C_4$)-alkylene-($C_3$-$C_8$)-cycloalkyl]-R13, wherein alkyl and cycloalkyl is unsubstituted or mono-, di- or trisubstituted independently of one another by R13,
18) —($C_0$-$C_4$)-alkylene-N(R11)-R12,
19) —($C_0$-$C_4$)-alkylene-N(R11)-R13,
20) —($C_0$-$C_4$)-alkylene-N(R10)-$SO_2$—R10,
21) —($C_0$-$C_4$)-alkylene-S—R10,
22) —($C_0$-$C_4$)-alkylene-$SO_s$—R11, wherein s is 1 or 2,
23) —($C_0$-$C_4$)-alkylene-$SO_t$—N(R11)-R12, wherein t is 1 or 2,
24) -($C_0$-$C_4$)-alkylene-$SO_w$—N(R11)-R13, wherein w is 1 or 2,
25) —($C_0$-$C_4$)-alkylene-$SO_u$—($C_0$-$C_4$)-alkylene-C(O)—O—R10, wherein u is 1 or 2,
26) —($C_0$-$C_4$)-alkylene-($C_3$-$C_8$)-cycloalkyl, wherein cycloalkyl is unsubstituted or mono-, di- or trisubstituted independently of one another by R13,
27) —($C_0$-$C_4$)-alkylene-($C_6$-$C_{14}$)-aryl, wherein aryl is as defined above and is unsubstituted or mono-, di- or trisubstituted independently of one another by R13,
28) —($C_0$-$C_4$)-alkylene-($C_3$-$C_{15}$)-heterocyclyl, wherein heterocyclyl is as defined above and is unsubstituted or mono-, di- or trisubstituted independently of one another by R13,
29) —($C_0$-$C_4$)-alkylene-O—($C_0$-$C_4$)-alkylene-($C_6$-$C_{14}$)-aryl, wherein aryl is as defined above and is unsubstituted or mono-, di- or trisubstituted independently of one another by R13,
30) —($C_0$-$C_4$)-alkylene-O—($C_0$-$C_4$)-alkylene-($C_3$-$C_{15}$)-heterocyclyl, wherein heterocyclyl is as defined above and is unsubstituted or mono-, di- or trisubstituted independently of one another by R13,
31) —($C_0$-$C_4$)-alkylene-N(R13)-($C_0$-$C_4$)-alkylene-($C_6$-$C_{14}$)-aryl, wherein aryl is as defined above and is unsubstituted or mono-, di- or trisubstituted independently of one another by R13, or
32) —($C_0$-$C_4$)-alkylene-N(R13)-($C_0$-$C_4$)-alkylene-($C_3$-$C_{15}$)-heterocyclyl, wherein heterocyclyl is as defined above and is unsubstituted or mono-, di- or trisubstituted independently of one another by R13, R4 is 1) hydrogen atom,
2) —($C_1$-$C_6$)-alkyl, wherein alkyl is unsubstituted or mono-, di- or trisubstituted independently of one another by R13,
3) —($C_0$-$C_4$)-alkylene-O—R10,
4) halogen,
5) —($C_1$-$C_3$)-fluoroalkyl,
6) phenyl, wherein phenyl is unsubstituted or mono-, di- or trisubstituted independently of one another by R13, or
7) —($C_0$-$C_4$)-alkylene-R13, R10 is hydrogen atom, —($C_1$-$C_4$)-alkyl, —($C_1$-$C_4$)-alkyl-OH, —($C_0$-$C_4$)-alkylene-O—($C_1$-$C_4$)-alkyl or —($C_1$-$C_3$)-fluoroalkyl, R11 and R12 are independently of one another identical or different and are
1) hydrogen atom,
2) —($C_1$-$C_6$)-alkyl, wherein alkyl is unsubstituted or mono-, di- or trisubstituted independently of one another by R13,
3) —O—R17,
4) —$SO_t$—R10, wherein t is 1 or 2,
5) —($C_1$-$C_3$)-fluoroalkyl,
6) —($C_0$-$C_6$)-alkylene-($C_3$-$C_8$)-cycloalkyl, wherein alkylene and cycloalkyl independently from one another are unsubstituted or mono-, di- or trisubstituted independently of one another by R13, 7) —(C$_0$-C$_6$)-alkylene-(C$_6$-C$_{14}$)-aryl, wherein alkylene and aryl independently from one another are unsubstituted or mono-, di- or trisubstituted by R13, or 8) —(C$_0$-C$_6$)-alkylene-(C$_3$-C$_{15}$)-heterocyclyl, wherein alkylene and heterocyclyl independently from one another are unsubstituted or mono-, di- or trisubstituted by R13, or R11 and R12 form together with the nitrogen atom to which they are attached a heterocyclic ring selected from aza-bicycloheptane, aza-bicyclohexane, aza-spiroheptane, aza-spirohexane, aza-spirooctane, aza-spiropentane, azepane, azepine, azetidine, diaza-bicycloheptane, diaza-bicyclohexane, diaza-spiroheptane, diaza-spirohexane, diaza-spiropentane, diaza-spirooctane 1,2-diazapane, 1,3-diazepane, 1,4-diazepane, 1,2-diazepine, 1,3-diazepine, 1,4-diazepine, dihydroazepine, dihydro-oxazepine, dihydro-pyridazine, dioxazole, hexahydro-pyridazine, imidazoline, imidazolidine, isothiazolidine, isothiazoline, isoxazoline, isoxazolidine, ketopiperazine, morpholine, 1,4-oxazepane, 1,2-oxa-thiepane, oxazepine, 1,2-oxazine, 1,3-oxazine, 1,4-oxazine, piperazine, piperidine, pyrazine, pyrazoline, pyrazolidine, pyridazine, pyrrolidine, pyrrolidinone, pyrroline, tetrahydro-azepine, 1,2,3,4-tetrahydro-pyrazine, tetrahydropyridine, tetrazine, tetrazole, thiadiazine, 1,2-thiazine, 1,3-thiazine, 1,4-thiazine, 1,3-thiazole, thiazolidine, thiazoline, thietan, thiomorpholine, triazepane, 1,2,4-triazinane and 1,3,5-triazinane, and wherein said ring is unsubstituted or substituted depending on the number of ring atoms one, two, three or four times by R13, R13 is halogen, —NO$_2$, —CN, =O, —OH, —CF$_3$, —C(O)—O—R10, —C(O)—N(R10)-R20, —N(R10)-R20, —(C$_3$-C$_8$)-cycloalkyl, —(C$_2$-C$_{10}$)-alkenyl-, —(C$_2$-C$_{10}$)-alkynyl-, —O—CF$_3$, —Si—(CH$_3$)$_3$, —(C$_0$-C$_4$)-alkylene-O—R10, —N(R10)-S(O)$_u$—R10, wherein u is 1 or 2, —SO$_r$—R10, wherein r is 1 or 2, —S(O)$_v$—N(R10)-R20, wherein v is 1 or 2, —S—R10, —C(O)—R10, —(C$_1$-C$_8$)-alkyl, —(C$_1$-C$_8$)-alkoxy, phenyl, phenyloxy-, —(C$_1$-C$_8$)-alkoxy-phenyl, —(C$_0$-C$_4$)-alkylene-C(O)—O—C(R15, R16)-O—C(O)—R17, —NH—C(O)—NH—R10, —(C$_0$-C$_4$)-alkylene-C(O)—O—C(R15, R16)-O—C(O)—O—R17, —O—R15, —(C$_1$-C$_3$)-fluoroalkyl, or —NH—C(O)—O—R10, R14 is halogen, —OH, =O, —(C$_1$-C$_8$)-alkyl, —(C$_1$-C$_4$)-alkoxy, —NO$_2$, —CN, —NH$_2$, —S—R18, —(C$_1$-C$_4$)-alkylene-C(O)—OH, —C(O)—O—(C$_1$-C$_4$)-alkyl, —(C$_1$-C$_4$)-alkylene-C(O)—NH$_2$, —(C$_0$-C$_8$)-alkylene-SO$_2$—(C$_1$-C$_4$)-alkyl, —(C$_0$-C$_8$)-alkylene-SO$_2$—(C$_1$-C$_3$)-fluoroalkyl, —(C$_0$-C$_8$)-alkylene-SO$_2$—N(R18)-R21, —(C$_1$-C$_4$)-alkylene-C(O)—NH—(C$_1$-C$_8$)-alkyl, —(C$_1$-C$_4$)-alkylene-C(O)—N—[(C$_1$-C$_8$)-alkyl]$_2$, —N(R18)-C(O)—NH—(C$_1$-C$_8$)-alkyl, —N(R18)-C(O)—NH—[(C$_1$-C$_8$)-alkyl]$_2$, —(C$_2$-C$_{10}$)-alkenyl, or —(C$_2$-C$_{10}$)-alkynyl, wherein R18 and R21 are independently from each other hydrogen atom, —(C$_1$-C$_3$)-fluoroalkyl or —(C$_1$-C$_6$)-alkyl, R15 and R16 are independently of one another hydrogen atom, —(C$_1$-C$_6$)-alkyl, or together with the carbon atom to which they are bonded form a —(C$_3$-C$_6$)-cycloalkyl, which is unsubstituted or mono, di- or trisubstituted by R10, R17 is hydrogen atom, —(C$_1$-C$_6$)-alkyl, —(C$_1$-C$_6$)-alkyl-OH, —(C$_1$-C$_6$)-alkylene-O—(C$_1$-C$_6$)-alkyl, —(C$_1$-C$_6$)-alkylene-O—(C$_1$-C$_6$)-alkylene-(C$_3$-C$_8$)-cycloalkyl, or —(C$_0$-C$_6$)-alkylene-(C$_3$-C$_8$)-cycloalkyl, wherein said cycloalkyl ring is unsubstituted or substituted one, two or three times by —OH, —O—(C$_1$-C$_4$)-alkyl or R10, and R20 is hydrogen atom, —(C$_1$-C$_4$)-alkyl, —(C$_1$-C$_4$)-alkyl-OH, —(C$_0$-C$_4$)-alkylene-O—(C$_1$-C$_4$)-alkyl or —(C$_1$-C$_3$)-fluoroalkyl, in all its stereoisomeric forms and mixtures thereof in any ratio, and its physiologically tolerable salts.

3) The present invention also relates to compounds of the formula I, wherein

E is 3- to 10-membered heterocyclic residue selected from aza-bicyclohexane, aza-bicyclooctane, azetidine, aziridine, decahydro-quinoline, 2,5-diaza-bicyclo[2.2.1]heptane, 1,4-diazepane, 2,3-dihydro-1H-indole, 4,6-dihydro-4H-pyrrolo[3,4-d]thiazole, imidazolidine, morpholine, octahydro-cyclopenta[c]pyrrole, oxazolidine, piperazine, piperidine, pyrazolidine, pyrrolidine, 1,2,3,4-tetrahydro-isoquinoline, 4,5,6,7-tetrahydro-isoxazolo[4,5-c]pyridine, 4,5,6,7-tetrahydro-1H-pyrazolo[4,3-c]pyridine, 4,5,6,6a-tetrahydro-3aH-pyrrolo[3,4-d]isoxazole, 1,2,3,4-tetrahydro-quinoline, 4,5,6,7-tetrahydro-thieno[2,3-c]pyridine, 4,5,6,7-tetrahydro-thieno[3,2-c]pyridine, 4,5,6,7-tetrahydro-thiazolo[5,4-c]pyridine, 1,3,8-triaza-spiro[4.5]decane or triaza-spirooctane, wherein said heterocyclic residue is bond by its nitrogen atom to the carbonyl carbon atom and wherein said heterocyclic residue is unsubstituted or mono-, di- or trisubstituted independently of one another by R3, D is 1) 3- to 15-membered heterocyclic residue selected from acridinyl, azabenzimidazolyl, aza-bicycloheptanyl, aza-bicyclohexanyl, aza-bicyclooctanyl, 8-aza-bicyclo[3.2.1]octanyl, azaspirodecanyl, aza-spiroheptanyl, aza-spirohexanyl, aza-spirooctanyl, aza-spiropentanyl, azepinyl, azetidinyl, aziridinyl, benzofuranyl, benzoimidazolyl, benzoisothiazolyl, benzoisoxazolyl, benzotetrazolyl, benzothiazolyl, benzothiofuranyl, benzothiophenyl, benzotriazolyl, benzoxazolyl, carbazolyl, 4aH-carbazolyl, carbolinyl, chromanyl, chromenyl, cinnolinyl, decahydro-quinolinyl, diaza-bicyclohexanyl, diaza-bicycloheptanyl, 2,5-Diaza-bicyclo[2.2.1]heptanyl, 1,2-diazapanyl, diaza-spirohexanyl, diaza-spirooctanyl, diaza-spiropentanyl, diaza-spiroheptanyl, 1,3-diazepanyl, 1,4-diazepanyl, 1,2-diazepinyl, 1,3-diazepinyl, 1,4-diazepinyl, dihydroazepinyl, dihydrofuro[2,3-b]-tetrahydrofuranyl, 2,3-dihydro-1H-indolyl, 3,4-dihydro-1H-isoquinolinyl, 6,7-dihydro-4H-isoxazolo[4,5-c]pyridinyl, dihydro-pyridazinyl, dihydro-oxazepinyl, 4,5-dihydrooxazolinyl, 4,6-dihydro-4H-pyrrolo[3,4-d]thiazolyl, 6,7-dihydro-4H-thiazolo[5,4-c]pyridinyl, 4,7-dihydro-5H-thieno[2,3-c]pyridinyl, dioxazolyl, dioxazinyl, 1,3-dioxolanyl, 1,3-dioxolenyl, 3,3-dioxo[1,3,4]oxathiazinyl, 6H-1,5,2-dithiazinyl, furanyl, furazanyl, hexahydro-pyridazine, hexahydro-cyclopenta[c]pyrroline, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydro-cyclopenta[c]pyrrolyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 1H-pyrrolopyridinyl, 2H-pyrrolyl, pyrrolyl, quinazolinyl, quinolinyl, 4H-quinolizinyl, quinoxalinyl, quinuclidinyl, tetrahydrofuranyl, 1,2,3,4-tetrahydro-isoquinolinyl, 4,5,6,7-tetrahydro-isoxazolo[4,5-c]pyridinyl, tetrahydropyranyl, 1,2,3,4-tetrahydropyrazinyl, 4,5,6,7-tetrahydro-1H-pyrazolo[4,3-c]pyridinyl, tetrahydro-pyridazinyl, tetrahydro-pyridinyl, 4,5,6,6a-tetrahydro-3aH-pyrrolo[3,4-d]isoxazolyl, 1,2,3,4-tetrahydro-quinolinyl, 4,5,6,7-tetrahydro-thieno[2,3-c]pyridinyl, 1,4,6,7-tetrahydro-thiazolo[5,4-c]pyridinyl, 4,5,6,7-tetrahydro-thieno[3,2-c]pyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, triaza-spirooctanyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl, and xanthenyl, wherein said heterocyclic residue is unsubstituted or substituted 1, 2, 3, 4, 5 or 6 times by R4,
2) phenyl, wherein phenyl is unsubstituted or substituted 1, 2 or 3 times by R4,
3) —($C_3$-$C_6$)-cycloalkyl, wherein cycloalkyl is unsubstituted or substituted 1, 2 or 3 times by R4, or
4) —($C_1$-$C_4$)-alkyl, wherein alkyl is unsubstituted or substituted 1, 2 or 3 times by R4, Q is 1) a covalent bond,
2) —($C_0$-$C_4$)-alkylene-O—,
3) —($C_0$-$C_4$)-alkylene-C(O)—O—($C_0$-$C_4$)-alkylene-,
4) —($C_0$-$C_4$)-alkylene-NH—C(O)—($C_0$-$C_2$)-alkylene-,
5) —($C_0$-$C_4$)-alkylene-NH—C(O)—O—($C_0$-$C_2$)-alkylene-,
6) —($C_0$-$C_4$)-alkylene-NH—$SO_2$—($C_0$-$C_2$)-alkylene-, or
7) —($C_3$-$C_{15}$)-heterocyclyl-, wherein said heterocyclyl is selected from azetidinyl, furanyl, imidazolyl, indolyl, isoxazolyl, oxadiazolyl, oxazolyl, piperazinyl, piperidinyl, pyrrolidinyl, tetrazolyl or thienyl, and is unsubstituted or mono-, di- or tri-substituted independently of one another by R14;

J is 1) hydrogen atom,
2) —($C_1$-$C_6$)-alkyl, wherein alkyl is unsubstituted or mono-, di- or trisubstituted independently of one another by R13,
3) —($C_0$-$C_4$)-alkylene-C(O)—O—R11, or
4) —($C_0$-$C_4$)-alkylene-phenyl, wherein phenyl is unsubstituted or mono-, di- or trisubstituted independently of one another by R13, Z-A-B together with the carbonyl carbon atom form a residue selected from —O—$CH_2$—C(O)—, —O—CH($CH_3$)—C(O)— or —O—C($CH_3$)$_2$—C(O)—, wherein said residue is bond via oxygen atom to pyrazole residue and by the carbonyl carbon atom to the nitrogen atom of E, V is heterocyclyl selected from azetidinyl, furanyl, imidazolyl, indolyl, isoxazolyl, oxadiazolyl, oxazolyl, piperazinyl, piperidinyl, pyrrolidinyl, tetrazolyl or thienyl, and is unsubstituted or mono- or di-substituted independently of one another by R14, G is 1) a covalent bond,
2) —($C_0$-$C_2$)-alkylene-C(O)—,
3) —($C_0$-$C_2$)-alkylene-C(O)—O—($C_0$-$C_4$)-alkylene-, or
4) —($C_0$-$C_2$)-alkylene-N(R10)-C(O)—O—($C_0$-$C_4$)-alkylene-, M is 1) hydrogen atom,
2) —($C_1$-$C_4$)-alkyl, wherein alkyl is unsubstituted or mono-, di- or trisubstituted independently of one another by R14,
3) —($C_3$-$C_6$)-cycloalkyl, wherein said cycloalkyl is unsubstituted or mono-, di- or trisubstituted independently of one another by R14, or
4) -phenyl, wherein phenyl is unsubstituted or mono-, di- or trisubstituted independently of one another by R14, R1 is hydrogen atom,
R2 is hydrogen atom
R3 is 1) hydrogen atom,
2) halogen,
3) —($C_1$-$C_6$)-alkyl, wherein alkyl is unsubstituted or mono-, di- or trisubstituted independently of one another by R13,
4) =O,
5) —($C_1$-$C_3$)-fluoroalkyl,
6) —($C_0$-$C_4$)-alkylene-O—R19, wherein R19 is
  a) hydrogen atom,
  b) —($C_1$-$C_4$)-alkyl, wherein alkyl is unsubstituted or mono-, di- or trisubstituted independently of one another by R13,
  c) —($C_3$-$C_8$)-cycloalkyl, wherein alkyl is unsubstituted or mono-, di- or trisubstituted independently of one another by R13,
  d) phenyl, wherein phenyl is unsubstituted or mono-, di- or trisubstituted independently of one another by R13,
  e) —$CF_3$, or
  f) —$CHF_2$,
7) —($C_0$-$C_4$)-alkylene-C(O)—R11,
8) —($C_0$-$C_4$)-alkylene-C(O)—O—R11,
9) —($C_0$-$C_4$)-alkylene-C(O)—N(R11)-R12,
10) —($C_0$-$C_4$)-alkylene-C(O)—N(R11)-R13,
11) —($C_0$-$C_4$)-alkylene-N(R11)-R13,
12) —($C_0$-$C_4$)-alkylene-$SO_s$—R11, wherein s is 1 or 2,
13) —($C_0$-$C_4$)-alkylene-phenyl, wherein phenyl is unsubstituted or mono-, di- or trisubstituted independently of one another by R13, or
14) -($C_0$-$C_4$)-alkylene-($C_3$-$C_{15}$)-heterocyclyl, wherein heterocyclyl is as defined above and is unsubstituted or mono-, di- or trisubstituted independently of one another by R13, R4 is hydrogen atom or halogen,
R10 is hydrogen atom or —($C_1$-$C_4$)-alkyl,
R11 and R12 are independently of one another identical or different and are
1) hydrogen atom,
2) —($C_1$-$C_4$)-alkyl, wherein alkyl is unsubstituted or mono- or disubstituted independently of one another by R13,
3) —($C_1$-$C_3$)-fluoroalkyl,
4) —($C_0$-$C_6$)-alkylene-($C_3$-$C_8$)-cycloalkyl, wherein alkylene and cycloalkyl independently from one another are unsubstituted or mono-, di- or trisubstituted independently of one another by R13, or
R11 and R12 form together with the nitrogen atom to which they are attached a heterocyclic ring selected from azetidine, piperidine, or pyrrolidine, and wherein said ring is unsubstituted or substituted depending on the number of ring atoms one, two, three or four times by R13, R13 is halogen, —OH, —($C_3$-$C_6$)-cycloalkyl, —S—R10, —C(O)—R10, —($C_1$-$C_6$)-alkyl, —($C_1$-$C_6$)-alkoxy or —($C_1$-$C_3$)-fluoroalkyl, and R14 is halogen, —($C_1$-$C_6$)-alkyl or —($C_1$-$C_4$)-alkoxy, in all its stereoisomeric forms and mixtures thereof in any ratio, and its physiologically tolerable salts.

4) The present invention also relates to compounds of the formula I, wherein
E is 3- to 10-membered heterocyclic residue selected from azetidine, piperazine, piperidine or pyrrolidine, wherein said heterocyclic residue is bond by its nitrogen atom to the carbonyl carbon atom and wherein said heterocyclic residue is unsubstituted or mono- or disubstituted independently of one another by R3,
D is phenyl, wherein phenyl is unsubstituted or substituted 1 or 2 times by R4,
Q is 1) a covalent bond,
   2) —$(C_0\text{-}C_4)$-alkylene-O—,
   3) —$(C_0\text{-}C_4)$-alkylene-C(O)—O—$(C_0\text{-}C_4)$-alkylene-,
   4) —$(C_0\text{-}C_4)$-alkylene-NH—C(O)—$(C_0\text{-}C_2)$-alkylene-,
   5) —$(C_0\text{-}C_4)$-alkylene-NH—C(O)—O—$(C_0\text{-}C_2)$-alkylene-,
   6) —$(C_0\text{-}C_4)$-alkylene-NH—$SO_2$—$(C_0\text{-}C_2)$-alkylene- or
   7) —$(C_3\text{-}C_{15})$-heterocyclyl-, wherein said heterocyclyl is selected from azetidinyl, furanyl, imidazolyl, indolyl, isoxazolyl, oxadiazolyl, oxazolyl, piperazinyl, piperidinyl, pyrrolidinyl, tetrazolyl or thienyl, and is unsubstituted or mono-, di- or trisubstituted independently of one another by R14;
J is 1) hydrogen atom,
   2) —$(C_1\text{-}C_6)$-alkyl, wherein alkyl is unsubstituted or mono-, di- or trisubstituted independently of one another by R13,
   3) —$(C_0\text{-}C_4)$-alkylene-C(O)—O—R11, or
   4) —$(C_0\text{-}C_4)$-alkylene-phenyl, wherein phenyl is unsubstituted or mono-, di- or trisubstituted independently of one another by R13,
Z-A-B together with the carbonyl carbon atom form a residue selected from —O—$CH_2$—C(O)—, —O—CH($CH_3$)—C(O)— or —O—C($CH_3$)$_2$—C(O)—, wherein said residue is bond via oxygen atom to pyrazole residue and by the carbonyl carbon atom to the nitrogen atom of E,
V is heterocyclyl selected from azetidinyl, piperazinyl, piperidinyl or pyrrolidinyl, and is unsubstituted or mono- or di-substituted independently of one another by R14,
G is 1) a covalent bond,
   2) —$(C_0\text{-}C_2)$-alkylene-C(O)—,
   3) —$(C_0\text{-}C_2)$-alkylene-C(O)—O—$(C_0\text{-}C_4)$-alkylene-, or
   4) —$(C_0\text{-}C_2)$-alkylene-N(R10)-C(O)—O—$(C_0\text{-}C_4)$-alkylene-,
M is 1) hydrogen atom,
   2) —$(C_1\text{-}C_4)$-alkyl, wherein alkyl is unsubstituted or mono-, di- or trisubstituted independently of one another by R14,
   3) —$(C_3\text{-}C_6)$-cycloalkyl, wherein said cycloalkyl is unsubstituted or mono-, di- or trisubstituted independently of one another by R14, or
   4)-phenyl, wherein phenyl is unsubstituted or mono-, di- or trisubstituted independently of one another by R14,
R1 and R2 are each hydrogen atom,
R3 is 1) hydrogen atom,
   2) halogen,
   3) —$(C_1\text{-}C_6)$-alkyl, wherein alkyl is unsubstituted or mono-, di- or trisubstituted independently of one another by R13,
   4) =O,
   5) —$(C_1\text{-}C_3)$-fluoroalkyl,
   6) —$(C_0\text{-}C_4)$-alkylene-OH,
   7) —$(C_0\text{-}C_4)$-alkylene-C(O)—R11,
   8) —$(C_0\text{-}C_4)$-alkylene-C(O)—O—R11,
   9) —$(C_0\text{-}C_4)$-alkylene-C(O)—N(R11)-R12,
   10) —$(C_0\text{-}C_4)$-alkylene-C(O)—N(R11)-R13,
   11) —$(C_0\text{-}C_4)$-alkylene-N(R11)-R13,
   12) —$(C_0\text{-}C_4)$-alkylene-$SO_s$—R11, wherein s is 1 or 2,
   13) —$(C_0\text{-}C_4)$-alkylene-phenyl, wherein phenyl is unsubstituted or mono-, di- or trisubstituted independently of one another by R13, or
   14) —$(C_0\text{-}C_4)$-alkylene-$(C_3\text{-}C_{15})$-heterocyclyl, wherein heterocyclyl is as defined above and is unsubstituted or mono-, di- or trisubstituted independently of one another by R13,
R4 is hydrogen atom or halogen,
R10 is hydrogen atom or —$(C_1\text{-}C_4)$-alkyl,
R11 and R12 are independently of one another identical or different and are
   1) hydrogen atom,
   2) —$(C_1\text{-}C_4)$-alkyl, wherein alkyl is unsubstituted or mono- or disubstituted independently of one another by R13,
   3) —$(C_1\text{-}C_3)$-fluoroalkyl,
   4) —$(C_0\text{-}C_6)$-alkylene-$(C_3\text{-}C_8)$-cycloalkyl, wherein alkylene and cycloalkyl independently from one another are unsubstituted or mono-, di- or trisubstituted independently of one another by R13, or
R11 and R12 form together with the nitrogen atom to which they are attached a heterocyclic ring selected from azetidine, piperidine or pyrrolidine, and wherein said ring is unsubstituted or substituted depending on the number of ring atoms one, two, three or four times by R13,
R13 is halogen, —OH, —$(C_3\text{-}C_6)$-cycloalkyl, —S—R10, —C(O)—R10, —$(C_1\text{-}C_6)$-alkyl, —$(C_1\text{-}C_6)$-alkoxy or —$(C_1\text{-}C_3)$-fluoroalkyl, and
R14 is —$(C_1\text{-}C_4)$-alkyl or —$(C_1\text{-}C_4)$-alkoxy,
in all its stereoisomeric forms and mixtures thereof in any ratio, and its physiologically tolerable salts.
5) The present invention also relates to compounds of the formula I, wherein
E is a heterocyclic residue selected from aza-bicyclohexane, aza-bicyclooctane, azetidine, aziridine, decahydro-quinoline, 2,5-diaza-bicyclo[2.2.1]heptane, 1,4-diazepane, 2,3-dihydro-1H-indole, 4,6-dihydro-4H-pyrrolo[3,4-d]thiazole, imidazolidine, morpholine, octahydro-cyclopenta[c]pyrrole, oxazolidine, piperazine, piperidine, pyrazolidine, pyrrolidine, 1,2,3,4-tetrahydro-isoquinoline, 4,5,6,7-tetrahydro-isoxazolo[4,5-c]pyridine, 4,5,6,7-tetrahydro-1H-pyrazolo[4,3-c]pyridine, 4,5,6,6a-tetrahydro-3aH-pyrrolo[3,4-d]isoxazole, 1,2,3,4-tetrahydro-quinoline, 4,5,6,7-tetrahydro-thieno[2,3-c]pyridine, 4,5,6,7-tetrahydro-thieno[3,2-c]pyridine, 4,5,6,7-tetrahydro-thiazolo[5,4-c]pyridine, 1,3,8-triaza-spiro[4.5]decane or triaza-spirooctane, wherein said heterocyclic residue is unsubstituted or mono-, di- or trisubstituted independently of one another by R3,
D is phenyl, wherein phenyl is unsubstituted or substituted 1 or 2 times by R4,
Q is 1) —$(C_0\text{-}C_4)$-alkylene-C(O)—N(R10)-,
   2) —$(C_1\text{-}C_3)$-alkylene-C(O)—O—,
   3) —$(C_1\text{-}C_3)$-alkylene-O— or
   4) —$(C_1\text{-}C_3)$-alkylene-$SO_2$—,
J is 1) hydrogen atom,
   2) —$(C_1\text{-}C_6)$-alkyl,
   3) —$(C_0\text{-}C_2)$-alkylene-phenyl,
   4) —$(C_0\text{-}C_2)$-alkylene-indanyl,
   5) —$(C_0\text{-}C_2)$-alkylene-$(C_3\text{-}C_6)$-cycloalkyl, or
   6) —$(C_0\text{-}C_4)$-alkylene-morpholinyl,
Z-A-B together with the carbonyl carbon atom form a residue selected from —O—$CH_2$—C(O)—, —O—CH($CH_3$)—C(O)— or —O—C($CH_3$)$_2$—C(O)—, wherein said residue is bond via oxygen atom to pyrazole residue and by the carbonyl carbon atom to the nitrogen atom of E, V is piperazinyl,
G and M together form a —C(O)—O—($C_2$-$C_4$)-alkyl, or
G is a direct bond and M is a phenyl residue,
R1 is a hydrogen atom,
R2 is independently of one another selected from
1) hydrogen atom,
2) —($C_1$-$C_6$)-alkyl, wherein alkyl is unsubstituted or mono-, di- or trisubstituted independently of one another by R13,
3) —($C_0$-$C_4$)-alkylene-O—R10,
4) halogen,
5) —($C_1$-$C_3$)-fluoroalkyl, or
6) phenyl, wherein phenyl is unsubstituted or mono-, di- or trisubstituted independently of one another by R13, or
if two —OR10 residues are attached to adjacent atoms they can form together with the atoms which they are attached to a 5- or 6-membered ring, which is unsubstituted or substituted one, two, three or four times by R13,
if two —($C_1$-$C_6$)-alkyl residues are attached to adjacent atoms they can form together with the atoms which they are attached to a 5- or 6-membered cycloalkyl ring, which is unsubstituted or substituted one, two, three or four times by R13,
R3 is 1) hydrogen atom,
2) Cl, F or Br,
3) —($C_1$-$C_4$)-alkyl,
4) =O,
5) —($C_1$-$C_3$)-fluoroalkyl,
6) —($C_0$-$C_2$)-alkylene-OH,
7) —($C_0$-$C_2$)-alkylene-O—($C_1$-$C_4$)-alkyl,
8) —CN,
9) —C(O)—($C_1$-$C_4$)-alkyl,
10) —($C_0$-$C_2$)-alkylene-C(O)—O—R11,
11) —($C_0$-$C_2$)-alkylene-C(O)—N(R11)-R12,
12) —($C_0$-$C_2$)-alkylene-C(O)—N(R11)-R13,
13) —N(R11)-R12,
14) —N(R11)-R13,
15) —NH—C(O)—R10,
16) —$SO_2$—($C_1$-$C_4$)-alkyl,
17) —$SO_2$—($C_1$-$C_2$)-alkylene-C(O)—O—($C_1$-$C_4$)-alkyl,
18) —($C_3$-$C_6$)-cycloalkyl,
19) phenyl or
20) —($C_0$-$C_4$)-alkylene-($C_3$-$C_{15}$)-heterocyclyl, wherein —($C_3$-$C_{15}$)-heterocyclyl is selected from azetidinyl, benzimidazolyl, furanyl, morpholinyl, piperidinyl, pyridyl, pyrrolidinyl, tetrahydrofuranyl, 1H-tetrazolyl or thiazolyl,
R4 is independently of one another selected from
1) hydrogen atom,
2) —($C_1$-$C_6$)-alkyl, wherein alkyl is unsubstituted or mono-, di- or trisubstituted independently of one another by R13,
3) —($C_0$-$C_4$)-alkylene-O—R10,
4) halogen,
5) —($C_1$-$C_3$)-fluoroalkyl,
6) phenyl, wherein phenyl is unsubstituted or mono-, di- or trisubstituted independently of one another by R13, or
7) —($C_0$-$C_4$)-alkylene-R13,
R10 is hydrogen atom or —($C_1$-$C_4$)-alkyl,
R11 and R12 are independently of one another identical or different and are
1) hydrogen atom,
2) —($C_1$-$C_4$)-alkyl,
3) —($C_1$-$C_3$)-fluoroalkyl or
4) —($C_0$-$C_4$)-alkylene-($C_3$-$C_6$)-cycloalkyl, or R11 and R12 together with the nitrogen atom to which they are bonded form a 4- to 8-membered monocyclic heterocyclic ring selected from azetidine, piperidine, pyrrolidine or morpholine,
R13 is F, Cl, Br, =O, —OH, —$CF_3$, —C(O)—O—R10, —($C_3$-$C_6$)-cycloalkyl, —C(O)—R10, phenyl, —($C_0$-$C_4$)-alkylene-O—R10 or —($C_1$-$C_4$)-alkyl,
in all its stereoisomeric forms and mixtures thereof in any ratio, and its physiologically tolerable salts.
6) The present invention also relates to compounds of the formula I, wherein
E is a heterocyclic residue selected from aza-bicyclohexane, aza-bicyclooctane, azetidine, aziridine, decahydro-quinoline, 2,5-diaza-bicyclo[2.2.1]heptane, 1,4-diazepane, 2,3-dihydro-1H-indole, 4,6-dihydro-4H-pyrrolo[3,4-d]thiazole, imidazolidine, morpholine, octahydro-cyclopenta[c]pyrrole, oxazolidine, piperazine, piperidine, pyrazolidine, pyrrolidine, 1,2,3,4-tetrahydro-isoquinoline, 4,5,6,7-tetrahydro-isoxazolo[4,5-c]pyridine, 4,5,6,7-tetrahydro-1H-pyrazolo[4,3-c]pyridine, 4,5,6,6a-tetrahydro-3aH-pyrrolo[3,4-d]isoxazole, 1,2,3,4-tetrahydro-quinoline, 4,5,6,7-tetrahydro-thieno[2,3-c]pyridine, 4,5,6,7-tetrahydro-thieno[3,2-c]pyridine, 4,5,6,7-tetrahydro-thiazolo[5,4-c]pyridine, 1,3,8-triaza-spiro[4.5]decane or triaza-spirooctane, wherein said heterocyclic residue is unsubstituted or mono-, di- or trisubstituted independently of one another by R3,
D is phenyl, wherein phenyl is unsubstituted or substituted 1 or 2 times by R4,
Q is 1) a covalent bond,
2) —($C_0$-$C_4$)-alkylene-N(R10)-C(O)—,
3) —($C_0$-$C_4$)-alkylene-C(O)—N(R10)-,
4) —($C_1$-$C_3$)-alkylene-C(O)—O—,
5) —($C_1$-$C_4$)-alkylene-O— or
6) —($C_1$-$C_3$)-alkylene-$SO_2$—,
J is 1) hydrogen atom,
2) —($C_1$-$C_6$)-alkyl, wherein alkyl is unsubstituted or mono-, di- or trisubstituted independently of one another by R13,
3) —($C_0$-$C_4$)-alkylene-C(O)—R11—,
4) —($C_0$-$C_4$)-alkylene-N(R10)-$SO_2$—R10,
5) —($C_0$-$C_2$)-alkylene-phenyl,
6) —($C_0$-$C_2$)-alkylene-indanyl,
7) —($C_0$-$C_2$)-alkylene-($C_3$-$C_6$)-cycloalkyl, wherein cycloalkyl is un-substituted or mono- or disubstituted independently of one another by R13, or
8) —($C_0$-$C_2$)-alkylene-($C_3$-$C_{15}$)-heterocyclyl, wherein heterocyclyl is a residue selected from tetrahydrofuran, morpholine or oxetan and is unsubstituted or monosubstituted by R13,
Z-A-B together with the carbonyl carbon atom form a residue selected from —O—$CH_2$—C(O)—, —O—CH($CH_3$)—C(O)— or —O—C($CH_3$)$_2$—C(O)—, wherein said residue is bond via oxygen atom to pyrazole residue and by the carbonyl carbon atom to the nitrogen atom of E,
V is piperazinyl,
G is 1) a covalent bond,
2) —($C_0$-$C_4$)-alkylene-C(O)—($C_0$-$C_4$)-alkylene-,
3) —($C_0$-$C_4$)-alkylene-C(O)—O—($C_0$-$C_4$)-alkylene-,
4) —($C_0$-$C_4$)-alkylene-C(O)—N(R10)-($C_0$-$C_4$)-alkylene-, or
5) —($C_0$-$C_4$)-alkylene-($C_3$-$C_8$)-cycloalkyl-($C_0$-$C_4$)-alkylene-,
M is 1) hydrogen atom,
2) —($C_1$-$C_4$)-alkyl, wherein alkyl is unsubstituted or mono-, di- or trisubstituted independently of one another by R14, 3) —($C_3$-$C_8$)-cycloalkyl, wherein said cycloalkyl is unsubstituted or monosubstituted by R14,
4) phenyl, wherein phenyl is unsubstituted or monosubstituted by R14, or
5) pyrrolidine, R1 is a hydrogen atom, R2 is independently of one another selected from
1) hydrogen atom,
2) —($C_1$-$C_6$)-alkyl, wherein alkyl is unsubstituted or mono-, di- or trisubstituted independently of one another by R13,
3) —($C_0$-$C_4$)-alkylene-O—R10,
4) halogen,
5) —($C_1$-$C_3$)-fluoroalkyl, or
6) phenyl, wherein phenyl is unsubstituted or mono-, di- or trisubstituted independently of one another by R13, or
if two —OR10 residues are attached to adjacent atoms they can form together with the atoms which they are attached to a 5- or 6-membered ring, which is unsubstituted or substituted one, two, three or four times by R13,
if two —($C_1$-$C_6$)-alkyl residues are attached to adjacent atoms they can form together with the atoms which they are attached to a 5- or 6-membered cycloalkyl ring, which is unsubstituted or substituted one, two, three or four times by R13, R3 is 1) hydrogen atom,
2) Cl, F or Br,
3) —($C_1$-$C_4$)-alkyl,
4) =O,
5) —($C_1$-$C_3$)-fluoroalkyl,
6) —($C_0$-$C_2$)-alkylene-OH,
7) —($C_0$-$C_2$)-alkylene-O—($C_1$-$C_4$)-alkyl,
8) —CN,
9) —C(O)—($C_1$-$C_4$)-alkyl,
10) —($C_0$-$C_2$)-alkylene-C(O)—O—R11,
11) —($C_0$-$C_2$)-alkylene-C(O)—N(R11)-R12,
12) —($C_0$-$C_2$)-alkylene-C(O)—N(R11)-R13,
13) —N(R11)-R12,
14) —N(R11)-R13,
15) —NH—C(O)—R10,
16) —$SO_2$—($C_1$-$C_4$)-alkyl,
17) —$SO_2$—($C_1$-$C_2$)-alkylene-C(O)—O—($C_1$-$C_4$)-alkyl,
18) —($C_3$-$C_6$)-cycloalkyl,
19) phenyl or
20) —($C_0$-$C_4$)-alkylene-($C_3$-$C_{15}$)-heterocyclyl, wherein —($C_3$-$C_{15}$)-heterocyclyl is selected from azetidinyl, benzimidazolyl, furanyl, morpholinyl, [1,2,4]-oxadiazolyl, piperidinyl, pyridyl, pyrrolidinyl, tetrahydrofuranyl, 1H-tetrazolyl or thiazolyl, and wherein —($C_3$-$C_{15}$)-heterocyclyl is unsubstituted or monosubstituted by R13, R4 is 1) hydrogen atom,
2) —($C_1$-$C_6$)-alkyl, wherein alkyl is unsubstituted or mono-, di- or trisubstituted independently of one another by R13,
3) —($C_0$-$C_4$)-alkylene-O—R10,
4) halogen,
5) —($C_1$-$C_3$)-fluoroalkyl,
6) phenyl, wherein phenyl is unsubstituted or mono-, di- or trisubstituted independently of one another by R13, or
7) —($C_0$-$C_4$)-alkylene-R13, R10 is hydrogen atom, —($C_1$-$C_3$)-fluoroalkyl or —($C_1$-$C_4$)-alkyl, R11 and R12 are independently of one another identical or different and are
1) hydrogen atom,
2) —($C_1$-$C_4$)-alkyl,
3) —($C_1$-$C_3$)-fluoroalkyl or
4) —($C_0$-$C_4$)-alkylene-($C_3$-$C_6$)-cycloalkyl, or R11 and R12 together with the nitrogen atom to which they are bonded form a 4- to 8-membered monocyclic heterocyclic ring selected from azetidine, piperidine, pyrrolidine or morpholine, and R13 is F, Cl, Br, =O, —OH, —$CF_3$, —C(O)—O—R10, —($C_3$-$C_6$)-cycloalkyl, —C(O)—R10, phenyl, —($C_0$-$C_4$)-alkylene-O—R10 or —($C_1$-$C_4$)-alkyl, and R14 is F, Cl, Br, or —($C_1$-$C_4$)-alkoxy, in all its stereoisomeric forms and mixtures thereof in any ratio, and its physiologically tolerable salts.

As used herein, the term alkyl is a hydrocarbon residue, which can be linear, e.g. straight-chain, or branched. Examples of "—($C_1$-$C_8$)-alkyl" or "—($C_1$-$C_8$)-alkylene" are alkyl residues containing 1, 2, 3, 4, 5, 6, 7 or 8 carbon atoms are methyl, methylene, ethyl, ethylene, propyl, propylene, butyl, butylene, pentyl, pentylene, hexyl, hexylene, heptyl or octyl, the n-isomers of all these residues, isopropyl, isobutyl, 1-methylbutyl, isopentyl, neopentyl, 2,2-dimethylbutyl, 2-methylpentyl, 3-methylpentyl, isohexyl, secondary-butyl, tertiary-butyl, tertiary-pentyl, secondary-butyl. The terms "—($C_0$-$C_8$)-alkyl" or "—($C_0$-$C_8$)-alkylene" are each hydrocarbon residues containing 1, 2, 3, 4, 5, 6, 7 or 8 carbon atoms as defined for —($C_1$-$C_8$)-alkyl or —($C_1$-$C_8$)-alkylene and the terms "—$C_0$-alkyl" or "—$C_0$-alkylene" are understood as meaning each a covalent bond.

The terms "—($C_2$-$C_{10}$)-alkenyl" or "—($C_2$-$C_{10}$)-alkenylene" are understood as meaning alkyl residues containing 2, 3, 4, 5, 6, 7, 8, 9 or 10 carbon atoms are, wherein said alkyl residues depending on the chain length contain 1, 2 or 3 double bonds. Examples of such residues are residues such as vinyl, 1-propenyl, 2-propenyl (=allyl), 2-butenyl, 3-butenyl, 2-methyl-2-butenyl, 3-methyl-2-butenyl, 5-hexenyl or 1,3-pentadienyl.

The terms "—($C_2$-$C_{10}$)-alkynyl" or "—($C_2$-$C_{10}$)-alkynylene" are understood as meaning alkyl residues containing 2, 3, 4, 5, 6, 7, 8, 9 or 10 carbon atoms are, wherein said alkyl residues depending on the chain length contain 1, 2 or 3 triple bonds, such as ethynyl, 1-propynyl, 2-propynyl (=propargyl) or 2-butynyl.

The term "—($C_3$-$C_8$)-cycloalkyl" is understood as meaning cycloalkyl residues containing 3, 4, 5, 6, 7 or 8 ring carbon atoms like cyclopropyl, cyclobutyl, cyclopentyl, cyclohexyl, cyloheptyl or cyclooctyl.

The terms "6- to 14-membered aryl" or "—($C_6$-$C_{14}$)-aryl" are understood as meaning a mono- or bicyclic-aromatic hydrocarbon radicals containing from 6 to 14 carbon atoms in the ring. Examples are phenyl, naphthyl, for example 1-naphthyl and 2-naphthyl, biphenylyl, for example 2-biphenylyl, 3-biphenylyl and 4-biphenylyl, indanyl, anthryl or fluorenyl. Biphenylyl radicals, naphthyl radicals and, in particular, phenyl radicals are preferred aryl radicals.

The term "a 3- to 7-membered cyclic residue, containing up to 1, 2, 3 or 4 heteroatoms" refer to structures of heterocycles which are compounds such as azepine, azetidine, aziridine, azirine, 1,4 diazepane, 1,2-diazepine, 1,3-diazepine, 1,4-diazepine, diaziridine, diazirine, dihydroimidazolone, dioxazole, dioxazine, dioxole, 1,3-dioxolene, 1,3-dioxolane, furan, imidazole, imidazoline, imidazolidine, imidazolidinone, isothiazole, isothiazolidine, isothiazoline, isoxazole, isoxazoline, isoxazolidine, morpholine, 1,2-oxa-thiepane, 1,2-oxathiolane, 1,4-oxazepane, 1,2-oxazine, 1,3-oxazine, 1,4-oxazine, oxazolone, oxazole, [1,3,4]oxathiazinane 3,3-dioxide, oxaziridine, oxazolidinone, oxetan, oxirane, piperazine, piperidine, pyran, pyrazine, pyrazole, pyrazoline, pyrazolidine, pyridazine, pyridine, pyridinone, pyrimidine, pyrimidine-2,4-dione, pyrrole, pyrrolidine, pyrrolidinone, pyrroline, tetrahydrofuran, tetrahydropyran, tetrahydropyridine, tetrazine, tetrazole, thiadiazine thiadiazole, 1,2-thiazine, 1,3-thiazine, 1,4-thiazine, 1,3-thiazole, thiazole, thiazolidine, thiazoline, thienyl, thietan, thiomorpholine, thiomorpholine 1,1-dioxide thiopyran, 1,2,3-triazine, 1,2,4-triazine, 1,3,5-triazine, 1,2,3-triazole or 1,2,4-triazole.

The terms "mono- or bicyclic 3- to 15-membered heterocyclyl" or "—$(C_3-C_{15})$-heterocyclyl" refer to heterocycles wherein one or more of the 3 to 15 ring carbon atoms are replaced by heteroatoms such as nitrogen, oxygen or sulfur such as acridinyl, azabenzimidazolyl, aza-bicycloheptanyl, aza-bicyclohexanyl, aza-bicyclooctanyl, 8-aza-bicyclo[3.2.1]octanyl, azaspirodecanyl, aza-spiroheptanyl, aza-spirohexanyl, aza-spirooctanyl, aza-spiropentanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydro-quinolinyl, diaza-bicyclohexanyl, diaza-bicycloheptanyl, 2,5-Diaza-bicyclo[2.2.1]heptanyl, 1,2-diazapanyl, diaza-spirohexanyl, diaza-spirooctanyl, diaza-spiropentanyl, diaza-spiroheptanyl, 1,3-diazepanyl, 1,4-diazepanyl, 1,2-diazepinyl, 1,3-diazepinyl, 1,4-diazepinyl, dihydroazepinyl, dihydrofuro[2,3-b]-tetrahydrofuranyl, 2,3-dihydro-1H-indolyl, 3,4-dihydro-1H-isoquinolinyl, 6,7-dihydro-4H-isoxazolo[4,5-c]pyridinyl, dihydro-pyridazinyl, dihydro-oxazepinyl, 4,5-dihydrooxazolinyl, 4,6-dihydro-4H-pyrrolo[3,4-d]thiazolyl, 6,7-dihydro-4H-thiazolo[5,4-c]pyridinyl, 4,7-dihydro-5H-thieno[2,3-c]pyridinyl, dioxazolyl, dioxazinyl, 1,3-dioxolanyl, 1,3-dioxolenyl, 3,3-dioxo[1,3,4]oxathiazinyl, 6H-1,5,2-dithiazinyl, furanyl, furazanyl, hexahydro-pyridazine, hexahydro-cyclopenta[c]pyrroline, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydro-cyclopenta[c]pyrrolyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, oxazepinyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 1H-pyrrolopyridinyl, 2H-pyrrolyl, pyrrolyl, quinazolinyl, quinolinyl, 4H-quinolizinyl, quinoxalinyl, quinuclidinyl, tetrahydrofuranyl, 1,2,3,4-tetrahydro-isoquinolinyl, 4,5,6,7-tetrahydro-isoxazolo[4,5-c]pyridinyl, tetrahydropyranyl, 1,2,3,4-tetrahydropyrazinyl , 4,5,6,7-tetrahydro-1H-pyrazolo[4,3-c]pyridinyl, tetrahydro-pyridazinyl, tetrahydro-pyridinyl, 4,5,6,6a-tetrahydro-3aH-pyrrolo[3,4-d]isoxazolyl, 1,2,3,4-tetrahydro-quinolinyl, 4,5,6,7-tetrahydro-thieno[2,3-c]pyridinyl, 1,4,6,7-tetrahydro-thiazolo[5,4-c]pyridinyl, 4,5,6,7-tetrahydro-thieno[3,2-c]pyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, triaza-spirooctanyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl, and xanthenyl.

The term "E is 3- to 10-membered heterocyclic residue, containing one nitrogen atom and up to 0, 1, 2, or 3 additional heteroatoms chosen from nitrogen, sulfur or oxygen, wherein said heterocyclic residue is monocyclic, bicyclic or a spiro-heterocycle" refers to structures of heterocycles which are compounds such as aza-bicycloheptane, aza-bicyclohexane, aza-bicyclooctane, aza-spiroheptane, aza-spirohexane, aza-spirooctane, aza-spiropentane, azepane, azepine, azetidine, aziridine, decahydro-quinoline, diaza-bicyclohexane, diaza-bicycloheptane, 2,5-Diaza-bicyclo[2.2.1]heptane, 1,2-diazapane, diaza-spirohexane, diaza-spirooctane, diaza-spiropentane, diaza-spiroheptane, 1,3-diazepane, 1,4-diazepane, 1,2-diazepine, 1,3-diazepine, 1,4-diazepine, dihydroazepine, 2,3-dihydro-1H-indole, 3,4-dihydro-1H-isoquinoline, 6,7-dihydro-4H-isoxazolo[4,5-c]pyridine, dihydro-pyridazine, dihydro-oxazepine, 4,6-dihydro-4H-pyrrolo[3,4-d]thiazole, 6,7-dihydro-4H-thiazolo[5,4-c]pyridine, 4,7-dihydro-5H-thieno[2,3-c]pyridine, dioxazole, hexahydro-pyridazine, hexahydro-cyclopenta[c]pyrroline, imidazoline, imidazolidine, isoquinoline, isothiazolidine, isothiazoline, isoxazoline, isoxazolidine, ketopiperazine, morpholine, octahydro-cyclopenta[c]pyrrole, 1,4-oxazepane, oxazepine, 1,2-oxathiepane, 1,2-oxazine, 1,3-oxazine, 1,4-oxazine, oxazolidine, piperazine, piperidine, pyrazine, pyrazoline, pyrazolidine, pyridazine, pyrrolidine, pyrrolidinone, pyrroline, tetrahydropyridine, tetrahydro-azepine, 1,2,3,4-tetrahydro-isoquinoline, 4,5,6,7-tetrahydro-isoxazolo[4,5-c]pyridine, 1,2,3,4-tetrahydropyrazine, 4,5,6,7-tetrahydro-1H-pyrazolo[4,3-c]pyridine, tetrahydro-pyridazine, 4,5,6,6a-tetrahydro-3aH-pyrrolo[3,4-d]isoxazole, 1,2,3,4-tetrahydro-quinoline, 4,5,6,7-tetrahydro-thieno[2,3-c]pyridine, 1,4,6,7-tetrahydrothiazolo[5,4-c]pyridine, 4,5,6,7-tetrahydro-thieno[3,2-c]pyridine, tetrazine, tetrazole, thiadiazine, 1,2-thiazine, 1,3-thiazine, 1,4-thiazine, 1,3-thiazole, thiazolidine, thiazoline, thietan, thiomorpholine, triaza-spirooctane, triazepane, 1,2,4-triazinane and 1,3,5-triazinane.

The term "R11 and R12 together with the nitrogen atom to which they are bonded can form a 4- to 8-membered monocyclic heterocyclic ring which in addition to the nitrogen atom can contain one or two identical or different ring heteroatoms chosen from oxygen, sulfur and nitrogen" refer to structures of heterocycles which are compounds such as aza-bicycloheptane, aza-bicyclohexane, aza-spiroheptane, aza-spirohexane, aza-spirooctane, aza-spiropentane, azepane, azepine, azetidine, diaza-bicycloheptane, diaza-bicyclohexane, diaza-spiroheptane, diaza-spirohexane, diaza-spiropentane, diaza-spirooctane 1,2-diazapane, 1,3-diazepane, 1,4-diazepane, 1,2-diazepine, 1,3-diazepine, 1,4-diazepine, dihydroazepine, dihydro-oxazepine, dihydro-pyridazine, dioxazole, hexahydro-pyridazine, imidazoline, imidazolidine, isothiazolidine, isothiazoline, isoxazoline, isoxazolidine, ketopiperazine, morpholine, 1,4-oxazepane, 1,2-oxathiepane, oxazepine, 1,2-oxazine, 1,3-oxazine, 1,4-oxazine, piperazine, piperidine, pyrazine, pyrazoline, pyrazolidine, pyridazine, pyrrolidine, pyrrolidinone, pyrroline, tetrahydroazepine, 1,2,3,4-tetrahydropyrazine, tetrahydropyridine, tetrazine, tetrazole, thiadiazine, 1,2-thiazine, 1,3-thiazine, 1,4-thiazine, 1,3-thiazole, thiazolidine, thiazoline, thietan, thiomorpholine, triazepane, 1,2,4-triazinane and 1,3,5-triazinane.

The term "—$(C_1-C_3)$-fluoroalkyl" is a partial or totally fluorinated alkyl-residue consisting of 1 to 3 carbon atoms, which are residues such as —$CF_3$, —$CHF_2$, —$CH_2F$, —$CHF$—$CF_3$, —$CHF$—$CHF_2$, —$CHF$—$CH_2F$, —$CH_2$—

$CF_3$, —$CH_2$—$CHF_2$, —$CH_2$—$CH_2F$, —$CF_2$—$CF_3$, —$CF_2$—$CHF_2$, —$CF_2$—$CH_2F$, —$CH_2$—$CHF$—$CF_3$, —$CH_2$—$CHF$—$CHF_2$, —$CH_2$—$CHF$—$CH_2F$, —$CH_2$—$CH_2$—$CF_3$, —$CH_2$—$CH_2$—$CHF_2$, —$CH_2$—$CH_2$—$CH_2F$, —$CH_2$—$CF_2$—$CF_3$, —$CH_2$—$CF_2$—$CHF_2$, —$CH_2$—$CF_2$—$CH_2F$, —$CHF$—$CHF$—$CF_3$, —$CHF$—$CHF$—$CHF_2$, —$CHF$—$CHF$—$CH_2F$, —$CHF$—$CH_2$—$CF_3$, —$CHF$—$CH_2$—$CHF_2$, —$CHF$—$CH_2$—$CH_2F$, —$CHF$—$CF_2$—$CF_3$, —$CHF$—$CF_2$—$CHF_2$, —$CHF$—$CF_2$—$CH_2F$, —$CF_2$—$CHF$—$CF_3$, —$CF_2$—$CHF$—$CHF_2$, —$CF_2$—$CHF$—$CH_2F$, —$CF_2$—$CH_2$—$CF_3$, —$CF_2$—$CH_2$—$CHF_2$, —$CF_2$—$CH_2$—$CH_2F$, —$CF_2$—$CF_2$—$CF_3$, —$CF_2$—$CF_2$—$CHF_2$ or —$CF_2$—$CF_2$—$CH_2F$.

The term "—($C_1$-$C_3$)-fluoroalkylene" is a partial or totally fluorinated alkylene-residue, residue consisting of 1 to 3 carbon atoms, which can be derived from residues such as —$CF_2$—, —$CHF$—, —$CHF$—$CHF_2$—, —$CHF$—$CHF$—, —$CH_2$—$CF_2$—, —$CH_2$—$CHF$—, —$CF_2$—$CF_2$—, —$CF_2$—$CHF$—, —$CH_2$—$CHF$—$CF_2$—, —$CH_2$—$CHF$—$CHF$—, —$CH_2$—$CH_2$—$CF_2$—, —$CH_2$—$CH_2$—$CHF$, —$CH_2$—$CF_2$—$CF_2$—, —$CH_2$—$CF_2$—$CHF$—, —$CHF$—$CHF$—$CF_2$—, —$CHF$—$CHF$—$CHF$—, —$CHF$—$CH_2$—$CF_2$—, —$CHF$—$CH_2$—$CHF$—, —$CHF$—$CF_2$—$CF_2$—, —$CHF$—$CF_2$—$CHF$—, —$CF_2$—$CHF$—$CF_2$—, —$CF_2$—$CHF$—$CHF$—, —$CF_2$—$CH_2$—$CF_2$—, —$CF_2$—$CH_2$—$CHF$—, —$CF_2$—$CF_2$—$CF_2$—, or —$CF_2$—$CF_2$—$CHF$.

The term "if two —($C_1$-$C_6$)-alkyl residues are attached to adjacent atoms they can form together with the atoms which they are attached to a 5- or 6-membered cycloalkyl ring" refers to residues such as cyclopentyl and cyclohexyl.

The term "if two —$OR10$ residues are attached to adjacent atoms they can form together with the atoms which they are attached to a 5- or 6-membered ring" refers to structures such as 1,3-dioxole ring and 2,3-dihydro-[1,4]dioxine ring.

The term "Z-A-B together with the carbonyl carbon atom form a residue selected from —O—$CH_2$—C(O)—, —O—$CH(CH_3)$—C(O)— or —O—$C(CH_3)_2$—C(O)—, wherein said residue is bond via oxygen atom to pyrazole residue and by the carbonyl carbon atom to the nitrogen atom of E" refers to the following substructure of formula I:

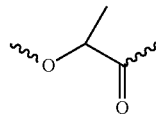

The term —O—$CH_2$—C(O)— is a residue with the following structural formula:

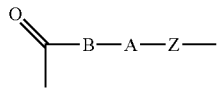

wherein the oxygen atom has a covalent bond with the pyrazole residue and the carbonyl carbon atom has a covalent bond with the nitrogen atom of the residue E.

The term —O—$CH(CH_3)$—C(O)— is a residue with the following structural formula:

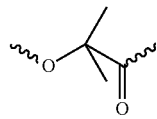

wherein the oxygen atom has a covalent bond with the pyrazole residue and the carbonyl carbon atom has a covalent bond with the nitrogen atom of the residue E.

The term —O—$C(CH_3)_2$—C(O)— is a residue with the following structural formula:

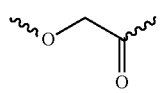

wherein the oxygen atom has a covalent bond with the pyrazole residue and the carbonyl carbon atom has a covalent bond with the nitrogen atom of the residue E.

Halogen is fluorine, chlorine, bromine or iodine.

Optically active carbon atoms present in the compounds of the formula I can independently of each other have R configuration or S configuration. The compounds of the formula I can be present in the form of pure enantiomers or pure diastereomers or in the form of mixtures of enantiomers and/or diastereomers, for example in the form of racemates. The present invention relates to pure enantiomers and mixtures of enantiomers as well as to pure diastereomers and mixtures of diastereomers. The invention comprises mixtures of two or of more than two stereoisomers of the formula I, and it comprises all ratios of the stereoisomers in the mixtures. In case the compounds of the formula I can be present as E isomers or Z isomers (or cis isomers or trans isomers) the invention relates both to pure E isomers and pure Z isomers and to E/Z mixtures in all ratios. The invention also comprises all tautomeric forms of the compounds of the formula I.

Diastereomers, including E/Z isomers, can be separated into the individual isomers, for example, by chromatography. Racemates can be separated into the two enantiomers by customary methods, for example by chromatography on chiral phases or by resolution, for example by crystallization of diastereomeric salts obtained with optically active acids or bases. Stereochemically uniform compounds of the formula I can also be obtained by employing stereochemically uniform starting materials or by using stereoselective reactions.

Physiologically tolerable salts of the compounds of formula I are nontoxic salts that are physiologically acceptable, in particular pharmaceutically utilizable salts. Such salts of compounds of the formula I containing acidic groups, for example a carboxyl group COOH, are for example alkali metal salts or alkaline earth metal salts such as sodium salts, potassium salts, magnesium salts and calcium salts, and also salts with physiologically tolerable quaternary ammonium ions such as tetramethylammonium or tetraethylammonium, and acid addition salts with ammonia and physiologically tolerable organic amines, such as methylamine, dimethylamine, trimethylamine, ethylamine, triethylamine, ethanolamine or tris-(2-hydroxyethyl)amine. Basic groups contained in the compounds of the formula I, for example amino groups or guanidino groups, form acid addition salts, for example with inorganic acids such as hydrochloric acid, hydrobromic acid, sulfuric acid, nitric acid or phosphoric acid, or with organic carboxylic acids and sulfonic acids such as formic acid, acetic acid, oxalic acid, citric acid, lactic acid, malic acid, succinic acid, malonic acid, benzoic acid, maleic acid, fumaric acid, tartaric acid, methanesulfonic acid or p-toluenesulfonic acid. Compounds of the formula I, which simultaneously contain a basic group and an acidic group, for example a guanidino group and a carboxyl group, can also be present as zwitterions (betaines) which are likewise included in the present invention.

Salts of compounds of the formula I can be obtained by customary methods known to those skilled in the art, for example by combining a compound of the formula I with an inorganic or organic acid or base in a solvent or dispersant, or from other salts by cation exchange or anion exchange. The present invention also includes all salts of the compounds of the formula I which, because of low physiologically tolerability, are not directly suitable for use in pharmaceuticals but are suitable, for example, as intermediates for carrying out further chemical modifications of the compounds of the formula I or as starting materials for the preparation of physiologically tolerable salts.

The present invention furthermore includes all solvates of compounds of the formula I, for example hydrates or adducts with alcohols.

The invention also includes derivatives and modifications of the compounds of the formula I, for example prodrugs, protected forms and other physiologically tolerable derivatives, as well as active metabolites of the compounds of the formula I. The invention relates in particular to prodrugs and protected forms of the compounds of the formula I, which can be converted into compounds of the formula I under physiological conditions. Suitable prodrugs for the compounds of the formula I, i.e. chemically modified derivatives of the compounds of the formula I having properties which are improved in a desired manner, for example with respect to solubility, bioavailability or duration of action, are known to those skilled in the art. More detailed information relating to prodrugs is found in standard literature like, for example, Design of Prodrugs, H. Bundgaard (ed.), Elsevier, 1985; Fleisher et al., Advanced Drug Delivery Reviews 19 (1996) 115-130; or H. Bundgaard, Drugs of the Future 16 (1991) 443; or Hydrolysis in Drug and Prodrug Metabolism, B. Testa, J. M. Mayer, Wiley-VCH, 2003, which are all incorporated herein by reference. Suitable prodrugs for the compounds of the formula I are especially acyl prodrugs and carbamate prodrugs of acylatable nitrogen-containing groups such as amino groups and the guanidino group and also ester prodrugs and amide prodrugs of carboxylic acid groups which may be present in compounds of the formula I. In the acyl prodrugs and carbamate prodrugs one or more, for example one or two, hydrogen atoms on nitrogen atoms in such groups are replaced with an acyl group or a carbamate, preferably a —($C_1$-$C_6$)-alkyloxycarbonyl group. Suitable acyl groups and carbamate groups for acyl prodrugs and carbamate prodrugs are, for example, the groups $R^{p1}$—CO— and $R^{p2}$O—CO—, in which $R^{p1}$ is hydrogen, ($C_1$-$C_{18}$)-alkyl, ($C_3$-$C_8$)-cycloalkyl, ($C_3$-$C_8$)-cycloalkyl-($C_1$-$C_4$)-alkyl-, ($C_6$-$C_{14}$)-aryl, het-, ($C_6$-$C_{14}$)-aryl-($C_1$-$C_4$)-alkyl- or het-($C_1$-$C_4$)-alkyl- and in which $R^{p2}$ has the meanings indicated for $R^{p2}$ with the exception of hydrogen.

Also with respect to all preferred compounds of the formula I all their stereoisomeric forms and mixtures thereof in any ratio and their physiologically acceptable salts explicitly are a subject of the present invention, as well as are their prodrugs. Similarly, also in all preferred compounds of the formula I, all residues that are present more than one time in the molecule are independent of each other and can be identical or different.

The compounds of the formula I can be prepared by utilizing procedures and techniques, which per se are well known and appreciated by one of ordinary skill in the art. Starting materials or building blocks for use in the general synthetic procedures that can be applied in the preparation of the compounds of formula I are readily available to one of ordinary skill in the art. In many cases they are commercially available or have been described in the literature. Otherwise they can be prepared from readily available precursor compounds analogously to procedures described in the literature, or by procedures or analogously to procedures described in this application.

In general, compounds of the formula I can be prepared, for example in the course of a convergent synthesis, by linking two or more fragments which can be derived retrosynthetically from the formula I. More specifically, suitably substituted starting pyrazole derivatives are employed as building blocks in the preparation of the compounds of formula I. If not commercially available, such pyrazole derivatives can be prepared according to the well-known standard procedures for the formation of the pyrazole ring system. By choosing suitable precursor molecules, these pyrazole syntheses allow the introduction of a variety of substituents into the various positions of the pyrazole system, which can be chemically modified in order to finally arrive at the molecule of the formula I having the desired substituent pattern. As one of the comprehensive reviews in which numerous details and literature references on the chemistry of pyrazole and on synthetic procedures for their preparation can be found J. Eiguero in "Comprehensive Heterocyclic Chemistry II"; Eds. A. Katritzky, Ch. Rees, E. Scriven; Elsevier 1996, Vol. 3; K. Kirschke in Houben-Weyl, "Methoden der Organischen Chemie" (Methods of Organic Chemistry), Georg Thieme Verlag, Stuttgart, Germany 1994, Vol. E8b Hetarene; T. Nagai et al. Org. Prep. Proced. Int. (1993), 25, 403; M. Elnagdi et al. Heterocycles (1985) 23, 3121; K. Makino et al. J. Heterocycl. Chem. (1998) 35, 489; K. Makino et al. J. Heteterocycl. Chem. (1999) 36, 321.

If starting pyrazole derivatives are not commercially available and have to be synthesized this can be done, for example, according to the well-known pyrazole syntheses mentioned above. In the following procedures of particular interest for the embodiment of this invention are listed and referenced briefly, however, they are standard procedures comprehensively discussed in the literature, and are well known to one skilled in the art. Although not always shown explicitly, in certain cases positional isomers will occur during the synthesis of the below mentioned reactions. Nevertheless such mixtures of positional isomers, can be separated by modern separation techniques like, for example, preparative HPLC.

1) N. Kudo et al. Chem. Pharm. Bull. (1999) 47, 857.

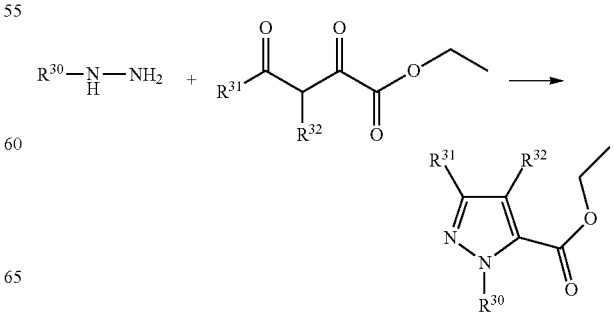

2) A. Padwa, J. Heterocycl. Chem. (1987) 24, 1225.
5) M. A. Martins et al., Synthesis (1995) 12, 1491.
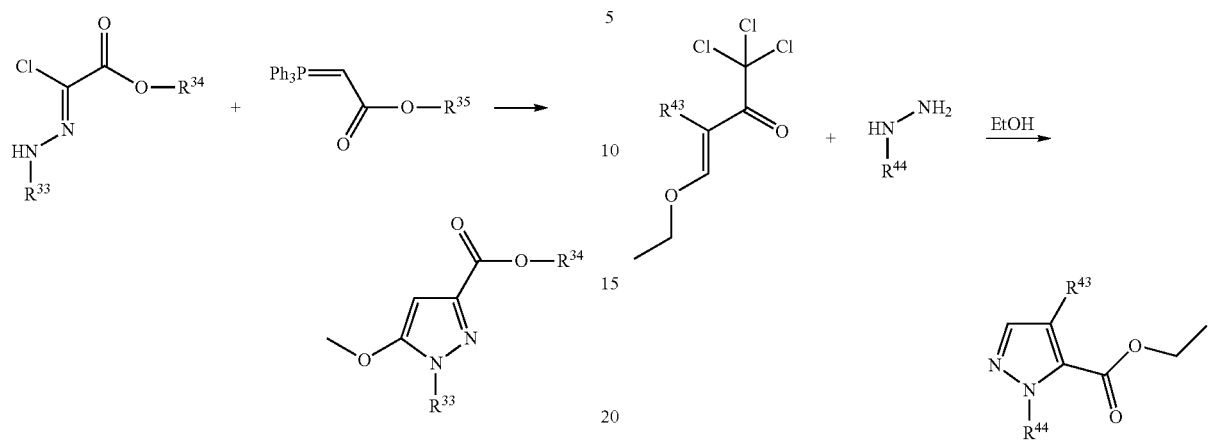
3) N. K. Markova et al., Zh. Org. Khim. (1983) 19, 2281.
6) R. G. Jones et al., J. Org. Chem. (1955) 20, 1342.
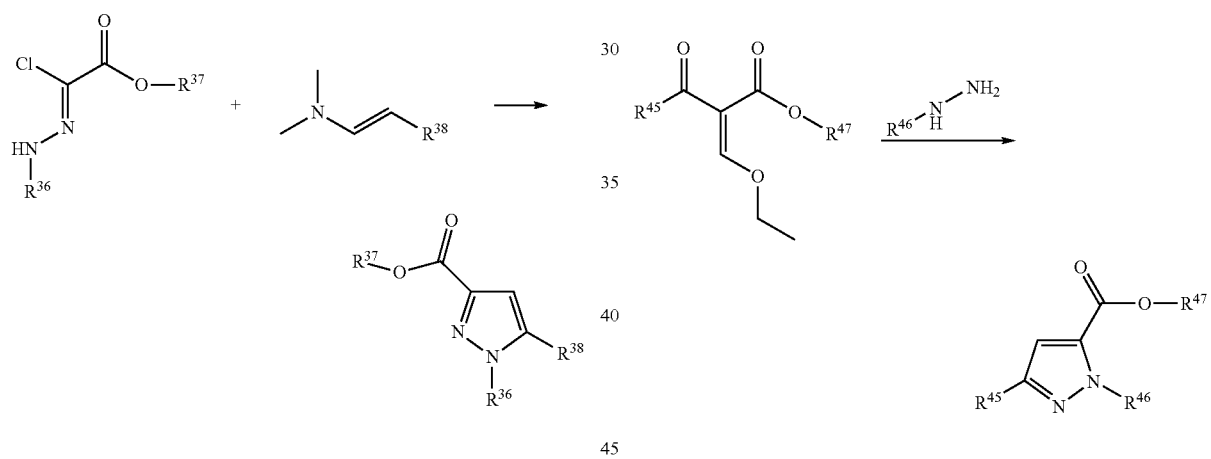
4) P. Bravo et al., Tetrahedron (1994) 50, 8827.
7) W. T. Ashton et al., J. Heterocycl. Chem. (1993) 30, 307.
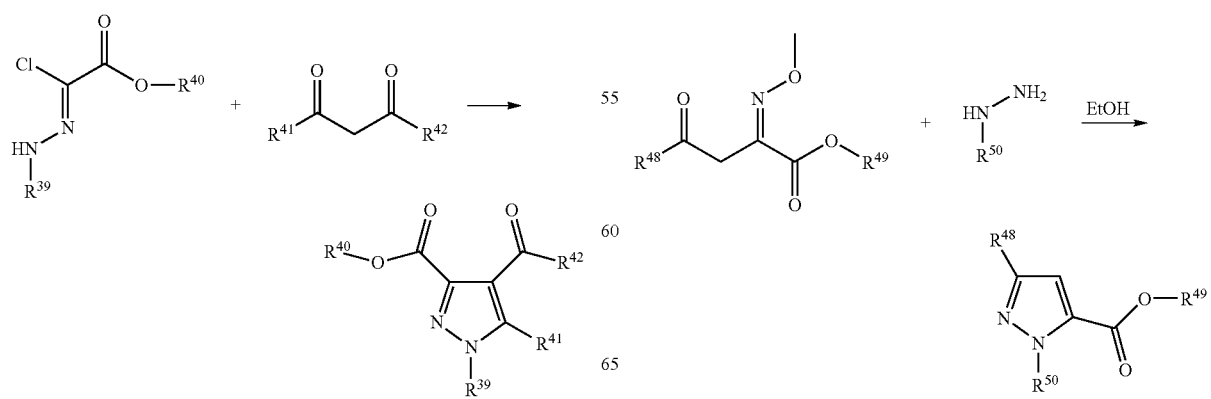

8) K. I. Bookermilburn, Synlett, (1992) 327.
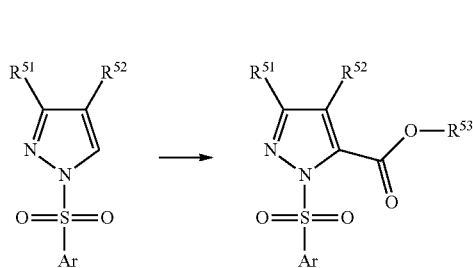
9) F. Farina et al., Heterocycles (1989) 29, 967.
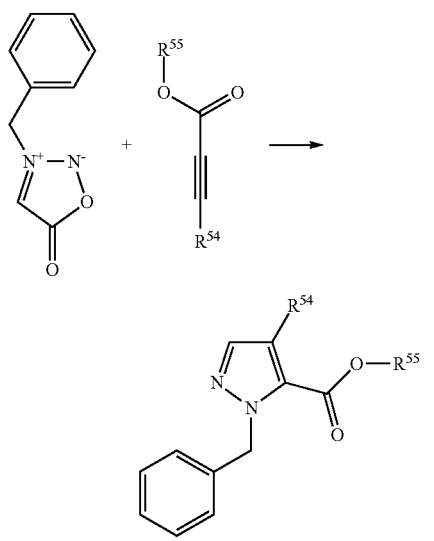
10) T. Hague et al., J. Med. Chem. (2002) 4669.
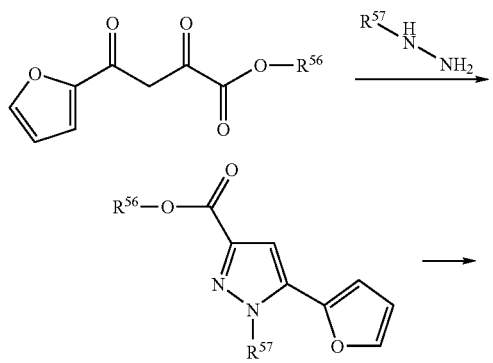
11) H. V. Patel, Synth. Commun. (1991) 21, 1583.
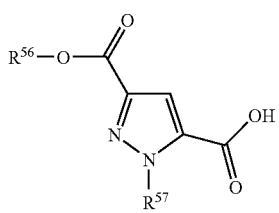
12) F. Farina et al., Heterocycles (1989) 29, 967.
13) R. Huisgen et al., J. Am. Chem. Soc. (1979) 101, 3647.
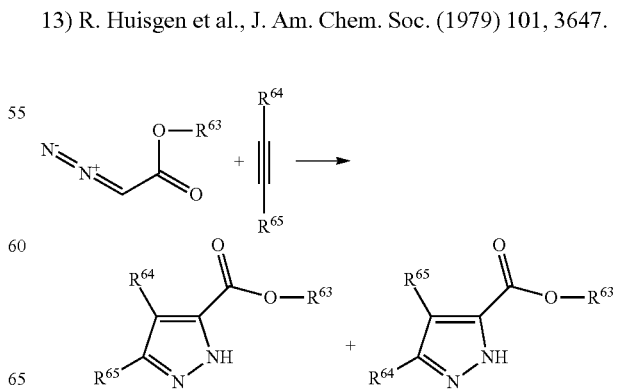

14) W. Sucrow et al., Angew. Chem., Int. Ed. (1975) 14, 560.
18) K. Washizuka et al., Tetrahedron Lett. (1999) 40, 8849.
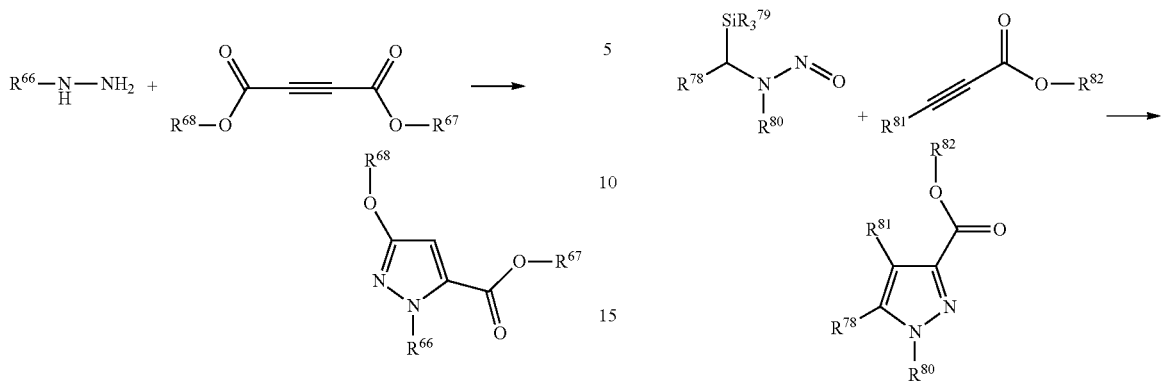
15) C. Baldoli et al., J. Heterocycl. Chem. (1989), 26, 241.
19) F. Foti et al., Tetrahedron Lett. (1999) 40, 2605.
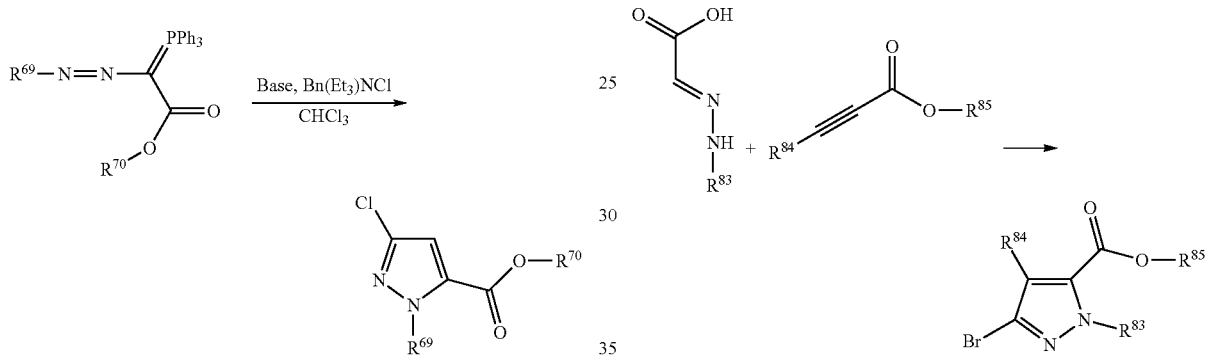
16) G. M. Pilling et al., Tetrahedron Lett. (1988) 29, 1341.
20) M. Martins et al., Synthesis (2003) 15, 2353.
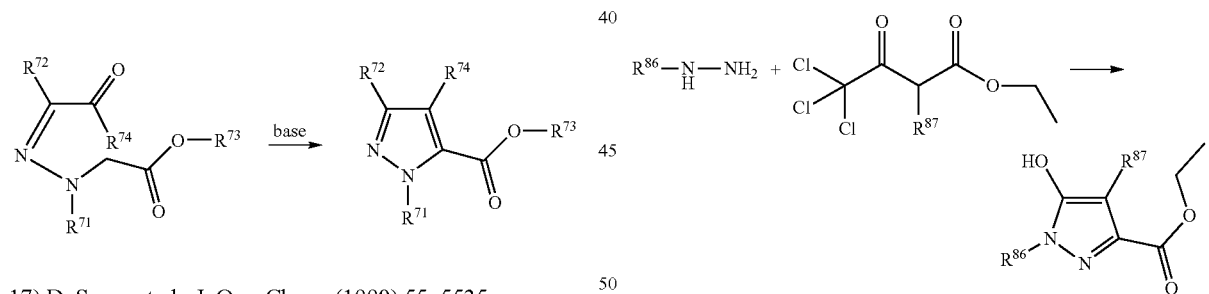
17) D. Sauer et al., J. Org. Chem. (1990) 55, 5535.
21) J. Nef, Liebigs Ann. Chem. (1893) 276, 231.
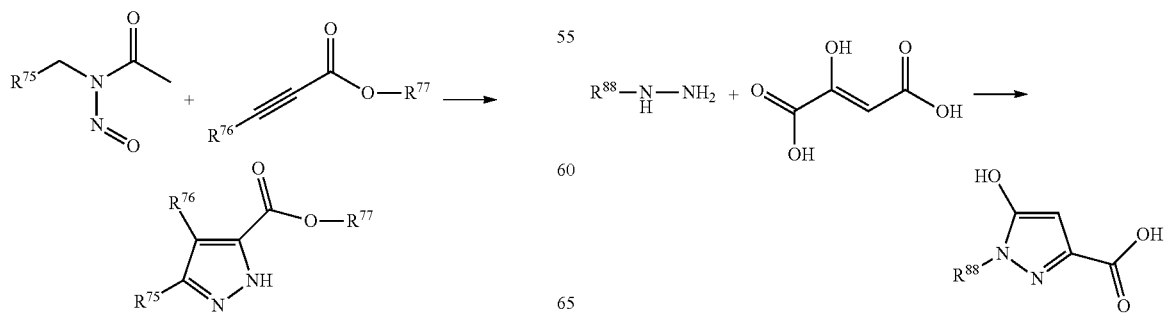

22) Leighton, J. Am. Chem. Soc. (1898) 20, 677.

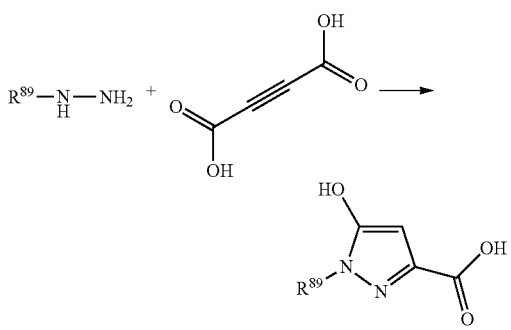

23) H. Ochi et al., Chem. Pham. Bull. (1983) 31, 1228.

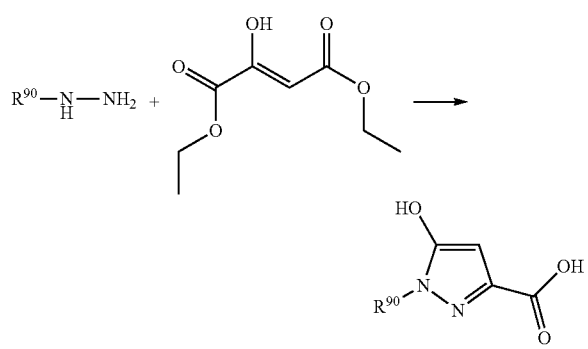

Depending on the substituents in the starting materials, in certain pyrazole syntheses mixtures of positional isomers may be obtained, which, however, can be separated by modern separation techniques like, for example, preparative HPLC.

Further, in order to obtain the desired substituents at the pyrazole ring system in the formula I, the functional groups introduced into the ring system during the pyrazole synthesis can be chemically modified. Especially the substituents present on the pyrazole ring system can be modified by a variety of reactions and thus the desired residues can be obtained. For example, a pyrazole carrying a hydrogen atom in the 4-position can also be obtained by saponification and subsequent decarboxylation of pyrazole carrying an ester group in the relevant position. In addition, carboxylic acid groups and acetic acid groups in the 3-position, the 4-position and the 5-position can be converted into their homologues by usual reactions for chain elongation of carboxylic acids. Halogen atoms can be introduced into the 3-position, the 4-position and the 5-position, for example according to procedures like the following described in the literature. For the fluorination of pyrazoles N-fluoro-2,4,6-trimethylpyridinium triflate is the reagent of choice (T. Umemoto, S. Fukami, G. Tomizawa, K. Harasawa, K. Kawada, K. Tomita, J. Am. Chem. Soc. (1990) 112, 8563 see also K. Manko et al., J. Fluorine Chem. (1988) 39, 435; R. Storer et al. Nucleosides Nucleotides (1999) 18; 203). However, other suitable fluorinating reagents may also be employed where appropriate. The chlorination, bromination, or iodination of pyrazoles can be accomplished by the reaction with elemental halogens or by the use of NCS, NBS or NIS and many other reagents well known to those skilled in the art. In addition suitable procedures are for example reported by M. Rodriguez-Franco et al., Tetrahedron Lett. (2001) 42, 863; J. Pawlas et al., J. Org. Chem. (2000) 65, 9001; Y. Huang et al., Org Lett (2000) 2, 2833; W. Holzer et al., J. Heterocycl. Chem. (1995) 32, 1351; N. Kudo et al., Chem. Pharm. Bull. (1999) 47, 857; G. Auzzi et al., Farmaco, Ed Sci (1979) 34, 743; K. Morimoto et al., J. Heterocycl. Chem. (1997) 34, 537; D. Jeon et al., Synth. Commun. (1998) 28, 2159.

Depending on the reaction conditions, reagent, stochiometry and substitution pattern the halogen is introduced in the 3-position and/or 4-position and/or 5-position. By selective halogen/metal exchange or metalation by selective hydrogen/metal exchange and subsequent reaction with a wide range of electrophiles various substituents can be introduced at the heterocyclic nucleus. (M. R. Grimmett, Heterocycles (1994) 37, 2087; V. D. Gardner et al., J. Heterocycl. Chem. (1984), 21, 121; D. Butler et al., J. Org. Chem. (1971) 36, 2542). Among others the corresponding pyrazolones can be useful precursors for the introduction of halogen atoms. For example a 1H-pyrazol-3-ol can be converted to 5-chloro-1H-pyrazole by using for example phosphorous oxychloride. The 5-bromo-1H-pyrazole can be obtained from 1H-pyrazol-3-ol by similar standard procedures using phosphorous oxybromide, phosphorous tribromide or phosphorous pentabromide.

Halogens, hydroxy groups (via the triflate or nonaflate) or primary amines (via the diazonium salt) or after interconversion to the corresponding stannane, or boronic acid—present in the pyrazole structure can be converted into a variety of other functional groups like for example —CN, —CF$_3$, —C$_2$F$_5$, ethers, acids, amides, amines, alkyl- or aryl-groups mediated by means of transition metals, such as palladium or nickel catalysts or copper salts and reagents for example referred to below (F. Diederich, P. Stang, Metal-catalyzed Cross-coupling Reactions, Wiley-VCH, 1998; or M. Beller, C. Bolm, Transition Metals for Organic Synthesis, Wiley-VCH, 1998; J. Tsuji, Palladium Reagents and Catalysts, Wiley, 1996; J. Hartwig, Angew. Chem. 1998, 110, 2154; B. Yang, S. Buchwald, J. Organomet. Chem. 1999, 576, 125; T. Sakamoto, K. Ohsawa, J. Chem. Soc. Perkin Trans 1, 1999, 2323; D. Nichols, S. Frescas, D. Marona-Lewicka, X. Huang, B. Roth, G. Gudelsky, J. Nash, J. Med. Chem, 1994, 37, 4347; P. Lam, C. Clark, S. Saubern, J. Adams, M. Winters, D. Chan, A. Combs, Tetrahedron Lett., 1998, 39, 2941; D. Chan, K. Monaco, R. Wang, M. Winters, Tetrahedron Lett. 1998, 39, 2933; V. Farina, V. Krishnamurthy, W. Scott, The Stille Reaction, Wiley, 1994; F. Qing et al. J. Chem. Soc. Perkin Trans. 11997, 3053; S. Buchwald et al. J. Am. Chem. Soc. 2001, 123, 7727; S. Kang et al. Synlett 2002, 3, 427; S. Buchwald et al. Organic Lett. 2002, 4, 581; T. Fuchikami et al. Tetrahedron Lett. 1991, 32, 91; Q. Chen et al. Tetrahedron Lett. 1991, 32, 7689; M. R. Netherton, G. C. Fu, Topics in Organometallic Chemistry 2005, 14, 85-108; A. F. Littke, G. F. Fu, Angew. Chem. Int. Ed. 2002, 41, 4176-4211; A. R. Muci, S. L. Buchwald, Topics in Current Chemistry 2002, 219, 131-209.

For example, nitro groups can be reduced to amino groups with various reducing agents, such as sulfides, dithionites, complex hydrides or by catalytic hydrogenation. A reduction of a nitro group may also be carried out at a later stage of the synthesis of a compound of the formula I, and a reduction of a nitro group to an amino group may also occur simultaneously with a reaction performed on another functional group, for example when reacting a group like a cyano group with hydrogen sulfide or when hydrogenating a group. In order to introduce these residues, amino groups can then be modified according to standard procedures for alkylation, for example by reaction with (substituted) alkyl halogenides or by reductive amination of carbonyl compounds, according to standard procedures for acylation, for example by reaction with activated carboxylic acid derivatives such as acid chlorides, anhydrides, activated esters or others or by reaction with carboxylic acids in the presence of an activating agent, or according to standard procedures for sulfonylation, for example by reaction with sulfonyl chlorides.

Ester groups present in the pyrazole nucleus can be hydrolyzed to the corresponding carboxylic acids, which after activation can then be reacted with amines or alcohols under standard conditions. Furthermore these ester or acid groups can be reduced to the corresponding alcohols by many standard procedures. Ether groups present at the pyrazole, for example benzyloxy groups or other easily cleavable ether groups, can be cleaved to give hydroxy groups which then can be reacted with a variety of agents, for example etherification agents or activating agents allowing replacement of the hydroxy group by other groups. Sulfur-containing groups can be reacted analogously.

During the course of the synthesis in order to modify the groups $R^{100}$ or $R^{102}$ attached to the pyrazole ring system by application of parallel synthesis methodology, beside a variety of reactions, palladium, nickel or copper catalysis can be extremely useful. Such reactions are described for example in F. Diederich, P. Stang, Metal-catalyzed Cross-coupling Reactions, Wiley-VCH, 1998; or M. Beller, C. Bolm, Transition Metals for Organic Synthesis, Wiley-VCH, 1998; J. Tsuji, Palladium Reagents and Catalysts, Wiley, 1996; J. Hartwig, Angew. Chem. 1998, 110, 2154; B. Yang, S. Buchwald, J. Organomet. Chem. 1999, 576, 125; P. Lam, C. Clark, S. Saubern, J. Adams, M. Winters, D. Chan, A. Combs, Tetrahedron Lett. 1998, 39, 2941; D. Chan, K. Monaco, R. Wang, M. Winters, Tetrahedron Lett. 1998, 39, 2933; J. Wolfe, H. Tomori, J. Sadight, J. Yin, S. Buchwald, J. Org. Chem. 2000, 65, 1158; V. Farina, V. Krishnamurthy, W. Scott, The Stille Reaction, Wiley, 1994; S. Buchwald et al., J. Am. Chem. Soc. 2001, 123, 7727; S. Kang et al., Synlett 2002, 3, 427; S. Buchwald et al., Org. Lett. 2002, 4, 581.

The previously-mentioned reactions for the conversion of functional groups are furthermore, in general, extensively described in textbooks of organic chemistry like M. Smith, J. March, March's Advanced Organic Chemistry, Wiley-VCH, 2001 and in treatises like Houben-Weyl, "Methoden der Organischen Chemie" (Methods of Organic Chemistry), Georg Thieme Verlag, Stuttgart, Germany, or "Organic Reactions", John Wiley & Sons, New York, or R. C. Larock, "Comprehensive Organic Transformations", Wiley-VCH, $2^{nd}$ ed (1999), B. Trost, I. Fleming (eds.) Comprehensive Organic Synthesis, Pergamon, 1991; A. Katritzky, C. Rees, E. Scriven Comprehensive Heterocyclic Chemistry II, Elsevier Science, 1996) in which details on the reactions and primary source literature can be found. Due to the fact that in the present case the functional groups are attached to a pyrazole ring it may in certain cases become necessary to specifically adapt reaction conditions or to choose specific reagents from a variety of reagents that can in principle be employed in a conversion reaction, or otherwise to take specific measures for achieving a desired conversion, for example to use protection group techniques. However, finding suitable reaction variants and reaction conditions in such cases does not cause any problems for one skilled in the art. The structural elements present in the residues at the 5-position of the pyrazole ring in the compounds of the formula I and in the $COR^{102}$ group present in the 3-position of the pyrazole ring can be introduced into the starting pyrazole derivative using the methods outlined above by consecutive reaction steps using parallel synthesis methodologies like those outlined below using procedures which per se are well known to one skilled in the art.

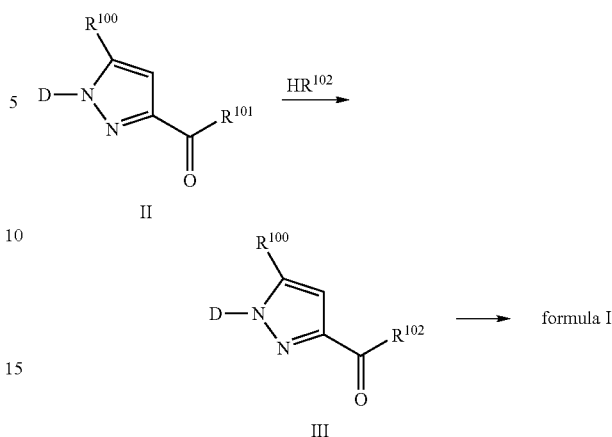

The residues $R^{102}$ can be introduced in compounds of the formula II, for example, by condensing a corresponding carboxylic acid of the formula II with a compound of the formula $HR^{102}$, whereby $HR^{102}$ is an amine of the formula IV, to give a compound of the formula III.

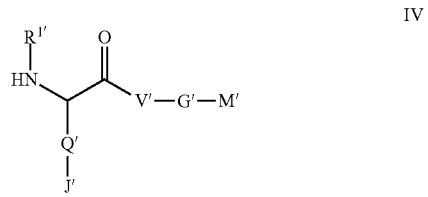

The compound of the formula III thus obtained can already contain the desired final groups, i.e. the groups $R^{102}$ and $R^{100}$ can be the groups of the formulae V and VI, respectively, as defined in formula I, or optionally in the compound of the formula III thus obtained the residue $R^{102}$ or the residues $R^{102}$ and $R^{100}$ are subsequently converted into the residues of the formulae V and VI, respectively, to give the desired compound of the formula I.

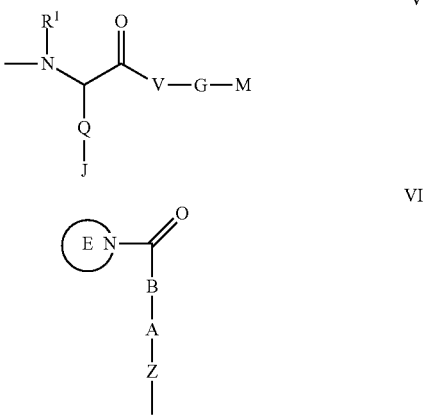

Thus, the residues $R^{102}$ and the residues V', G', Q', J' and M' contained in formula IV can have the denotations of residues of the formula V, respectively, given above or in addition in the residues of the formula IV functional groups can also be present in the form of groups that can subsequently be transformed into the final groups of the formula V, i.e. functional groups can be present in the form of precursor groups or of derivatives, for example in protected form. In the course of the preparation of the compounds of the formula I it can generally be advantageous or necessary to introduce functional groups which reduce or prevent undesired reactions or side reactions in the respective synthesis steps, in the form of precursor groups which are later converted into the desired functional groups, or to temporarily block functional groups by a protective group strategy suited to the synthesis problem. Such strategies are well known to those skilled in the art (see, for example, Greene and Wuts, Protective Groups in Organic Synthesis, Wiley, 1991, or P. Kocienski, Protecting Groups, Thieme 1994). Examples of precursor groups are cyano groups and nitro groups. The cyano group can, in a later step, be transformed into carboxylic acid derivatives or by reduction into aminomethyl groups. Nitro groups may be transformed by reduction like catalytic hydrogenation into amino groups. Protective groups can also have the meaning of a solid phase, and cleavage from the solid phase stands for the removal of the protective group. The use of such techniques is known to those skilled in the art (Burgess K (Ed.) Solid Phase Organic Synthesis, New York, Wiley, 2000). For example, a phenolic hydroxy group can be attached to a trityl-polystyrene resin, which serves as a protecting group, and the molecule is cleaved from this resin by treatment with TFA or other acids at a later stage of the synthesis.

The residue $R^{100}$ in the compounds of the formulae II and III can denote the group of formula VI as defined above which finally is to be present in the desired target molecule of the formula I, or it can denote a group which can subsequently be transformed into the group of formula VI, for example a precursor group or a derivative of the group of formula VI in which functional groups are present in protected form, or $R^{100}$ can denote a hydrogen, a oxygen atom, or a nitrogen, or a sulfur atom or a protective group masking the aforementioned atoms of the pyrazole ring.

The residue $R^{101}$ in the compounds of the formula II which can be identical or different, can be, for example, hydroxy or $(C_1-C_4)$-alkoxy, i.e., the groups $COR^{101}$ present in the compounds of the formula II can be, for example, the free carboxylic acids or esters thereof like alkyl esters as can be the groups $COR^{102}$ in the compounds of the formula III. The groups $COR^{101}$ can also be any other activated derivative of a carboxylic acid which allows amide formation with a compound of the formula $HR^{102}$. The group $COR^{101}$ can be, for example, an acid chloride, an activated ester like a substituted phenyl ester or thioester, an azolide like an imidazolide, an azide or a mixed anhydride, for example a mixed anhydride with a carbonic acid ester or with a sulfonic acid. These derivatives can all be prepared from the carboxylic acid by standard procedures and can be reacted with an amine of the formula $HR^{102}$ under standard conditions. A carboxylic acid group COOH representing $COR^{101}$ in a compound of the formula II can be obtained, for example by standard hydrolysis procedures, from an ester group introduced into the pyrazole system during a pyrazole synthesis.

Compounds of the formula I in which a group $COR^{102}$ is an amide group can be prepared from amines and compounds of the formula II in which $COR^{101}$ is a carboxylic acid group or an ester or thioester thereof by common amination reactions. Especially for the preparation of amides the compounds of the formula II in which $COR^{101}$ is a carboxylic acid group can be condensed under standard conditions with compounds of the formula $HR^{102}$ which are amines by means of common coupling reagents used in peptide synthesis. Such coupling reagents are, for example, carbodiimides like dicyclohexylcarbodiimide (DCC) or diisopropylcarbodiimide, carbonyldiazoles like carbonyldiimidazole (CDI) and similar reagents, propylphosphonic anhydride, O-((cyano-(ethoxycarbonyl)-methylene)amino)-N,N,N',N'-tetramethyluronium tetrafluoroborate (TOTU), diethylphosphoryl cyanide (DEPC) or bis-(2-oxo-3-oxazolidinyl)-phosphoryl chloride (BOP-Cl), O-(benzotriazol-1-yl)-1,1,3,3-tetramethyluronium hexafluorophosphate (HBTU), O-(7-azabenzotriazol-1-yl)-1,1,3,3-tetramethyluronium hexafluorophosphate (HATU), bromo-tris-pyrrolidino-phosphonium hexafluorophosphate (Pybrop) and many others.

The activation of the carboxylic acid function may also favourably be carried out, for example, by conversion of the carboxylic acid group into the pentafluorophenyl ester using dicyclohexylcarbodiimide and pentafluorophenol or by using reagents like pentafluorophenyl trifluoroacetate, tert-butyl pentafluorophenyl carbonate, bis(pentafluorophenyl)carbonate, 2,3,4,5,6-pentafluorophenyl 4-methylbenzenesulfonate, pentafluorophenol-tetramethyluronium hexafluorophosphate, octafluoroacetophenone. The activation of the carboxylic function by conversion to other phenylesters like for example 4-nitro-phenyl esters or 2-nitro-phenyl esters can be also effective. The activation and the subsequent reaction with a group of the formula IX are usually carried out in the presence of an inert solvent or diluent, for example DCM, chloroform, THF, diethyl ether, n-heptane, n-hexane, n-pentane, cyclohexane, diisopropyl ether, methyl tBu ether, acetonitrile, DMF, DMA, NMP, DMSO, dioxane, toluene, benzene, ethyl acetate or a mixture of these solvents, if appropriate with addition of a base such as, for example, potassium tert-butoxide or tributylamine or triethylamine or diisopropylethylamine or N-ethylmorpholine.

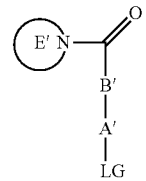

VII

If the residue of the formula VI present in a pyrazole of the formula I or the residue $R^{100}$ present in a pyrazole of the formula II or formula III, or a residue in which functional groups within the residue of the formula VI or $R^{100}$ are present in protected form or in the form of a precursor group, have not already been introduced during a preceding step, for example during a synthesis of the pyrazole nucleus, these residues can, for example, be introduced into the 5-position of the pyrazole system by standard alkylation procedures well-known to one skilled in the art. The starting pyrazole derivative that is to be employed in such a reaction carries an oxygen, or a nitrogen, or a sulfur atom in the 5-position. Alkylation of the aforementioned atom can, for example, be performed under standard conditions, preferably in the presence of a base like $K_2CO_3$, $Cs_2CO_3$, NaH or KO$^t$Bu, using an alkylating compound of the formula VII or of the formula $R^{100}$-LG, wherein the atom in the group A' of the formula VII or in the group $R^{100}$ bonded to the group LG in this case is an aliphatic carbon atom of an alkyl moiety and LG is a leaving group, for example halogen like chlorine, bromine or iodine, or a sulfonyloxy group like tosyloxy, mesyloxy or trifluormethylsulfonyloxy. These standard procedures are for example described in treatises like M. Smith, J. March, March's Advanced Organic Chemistry, Wiley-VCH, 2001; Houben-Weyl, "Methoden der Organischen Chemie" (Methods of Organic Chemistry), Georg Thieme Verlag, Stuttgart, Germany, or "Organic Reactions", John Wiley & Sons, New York, or R. C. Larock, "Comprehensive Organic Transformations", Wiley-VCH, 2$^{nd}$ ed (1999), B. Trost, I. Fleming (eds.) Comprehensive Organic Synthesis, Pergamon, 1991. LG may, for example, also be a hydroxy group which, in order to achieve the alkylation reaction, is activated under the well-known conditions of the Mitsunobu procedure (O. Mitsunobu, Synthesis 1981, 1) or by further modified procedures (A. Tunoori, D. Dutta, G. Gunda, *Tetrahedron Lett.* 39 (1998) 8751; J. Pelletier, S. Kincaid, Tetrahedron Lett. 41 (2000) 797; D. L. Hughes, R. A. Reamer, J. J. Bergan, E. J. J. Grabowski, J. Am. Chem. Soc. 110 (1998) 6487; D. J. Camp, I. D. Jenkins, J. Org. Chem. 54 (1989) 3045; D. Crich, H. Dyker, R. J. Harris, J. Org. Chem. 54 (1989) 257) of even greater use.

The residue of the formula VI present in a pyrazole of the formula I or the residue $R^{100}$ present in a pyrazole of the formula II, or a residue in which functional groups within the residue of the formula VI or $R^{100}$ are present in protected form or in the form of a precursor group, can be for example introduced into the 5-position of the pyrazole system by conventional literature procedures for the amination, etherification or thioetherification of pyrazoles well-known to those skilled in the art. The appropriately substituted pyrazole useful for these reactions carries a leaving group in the 5-position of the pyrazole like for example halogen, triflate, nonaflate, tosylate, azide, or a diazonium salt. Preferably the reaction is carried out in the presence of a base like $K_2CO_3$, $Cs_2CO_3$, NaH or KO$^t$Bu. The desired transformation can also be accomplished with halogens, hydroxy groups (via the triflate or nonaflate) or primary amines (via the diazonium salt) or after interconversion to the corresponding stannane, or boronic acid—present in the 5-position of pyrazole structure—can be converted into a variety of other functional groups like for example —CN, —$CF_3$, —$C_2F_5$, ethers, acids, amides, amines, alkyl- or aryl-groups mediated by means of transition metals, such as palladium or nickel catalysts or copper salts and reagents for example referred to below (F. Diederich, P. Stang, Metal-catalyzed Cross-coupling Reactions, Wiley-VCH, 1998; or M. Beller, C. Bolm, Transition Metals for Organic Synthesis, Wiley-VCH, 1998; J. Tsuji, Palladium Reagents and Catalysts, Wiley, 1996; J. Hartwig, Angew. Chem. 1998, 110, 2154; B. Yang, S. Buchwald, J. Organomet. Chem. 1999, 576, 125; T. Sakamoto, K. Ohsawa, J. Chem. Soc. Perkin Trans 1, 1999, 2323; D. Nichols, S. Frescas, D. Marona-Lewicka, X. Huang, B. Roth, G. Gudelsky, J. Nash, J. Med. Chem., 1994, 37, 4347; P. Lam, C. Clark, S. Saubern, J. Adams, M. Winters, D. Chan, A. Combs, Tetrahedron Lett., 1998, 39, 2941; D. Chan, K. Monaco, R. Wang, M. Winters, Tetrahedron Lett. 1998, 39, 2933; V. Farina, V. Krishnamurthy, W. Scott, The Stille Reaction, Wiley, 1994; F. Qing et al. J. Chem. Soc. Perkin Trans. 1 1997, 3053; S. Buchwald et al. J. Am. Chem. Soc. 2001, 123, 7727; S. Kang et al. Synlett 2002, 3, 427; S. Buchwald et al. Organic Lett. 2002, 4, 581; T. Fuchikami et al. Tetrahedron Lett. 1991, 32, 91; Q. Chen et al. Tetrahedron Lett. 1991, 32, 7689; M. R. Netherton, G. C. Fu, Topics in Organometallic Chemistry 2005, 14, 85-108.). A. F. Littke, G. F. Fu, Angew. Chem. Int. Ed. 2002, 41, 4176-4211; A. R. Muci, S. L. Buchwald, Topics in Current Chemistry 2002, 219, 131-209.

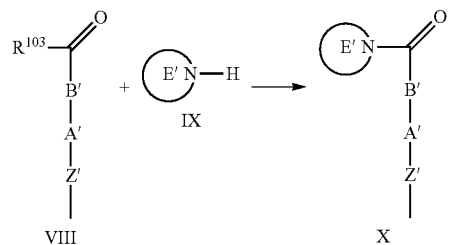

The residues $R^{103}$ in the compounds of the formula VIII which can be identical or different, can be, for example, hydroxy or ($C_1$-$C_4$)-alkoxy, i.e., the groups present in the residues of the formula VIII can be, for example, the free carboxylic acid group or esters thereof like alkyl esters. These groups can also be any other activated derivative of a carboxylic acid group which allows amide bond formation with a compound of the formula IX. The group $COR^{103}$ can be, for example, an acyl chloride, an activated ester like a substituted phenyl ester, an azolide like an imidazolide, an acyl azide or a mixed anhydride, for example a mixed anhydride with a carbonic acid ester or with a sulfonic acid. These derivatives can all be prepared from the carboxylic acid group by standard procedures and can be reacted with an amine of the formula IX under standard conditions. Such coupling reagents are, for example, carbodiimides like dicyclohexylcarbodiimide (DCC) or diisopropylcarbodiimide, carbonyldiazoles like carbonyldiimidazole (CDI) and similar reagents, propylphosphonic anhydride, O-((cyano-(ethoxycarbonyl)-methylene)amino)-N,N,N',N'-tetramethyluronium tetrafluoroborate (TOTU), diethylphosphoryl cyanide (DEPC) or bis-(2-oxo-3-oxazolidinyl)-phosphoryl chloride (BOP-Cl) and many others. O-(benzotriazol-1-yl)-1,1,3,3-tetramethyluronium hexafluorophosphate (HBTU), O-(7-azabenzotriazol-1-yl)-1,1,3,3-tetramethyluronium hexafluorophosphate (HATU), bromo-tris-pyrrolidino-phosphonium hexafluorophosphate (Pybrop). The activation of the carboxylic acid function may also favourably be carried out, for example, by conversion of the carboxylic acid group into the pentafluorophenyl ester using dicyclohexylcarbodiimide and pentafluorophenol or by using reagents like pentafluorophenyl trifluoroacetate, tert-butyl pentafluorophenyl carbonate, bis(pentafluorophenyl)carbonate, 2,3,4,5,6-pentafluorophenyl 4-methylbenzenesulfonate, pentafluorophenol-tetramethyluronium hexafluorophosphate, octafluoroacetophenone. The activation of the carboxylic function by conversion to other phenylesters like for example 4-nitro-phenyl esters or 2-nitro-phenyl esters can be also effective. The activation and the subsequent reaction with the compound of the formula IX are usually carried in the presence of an inert solvent or diluent, for example DCM, chloroform, THF, diethyl ether, n-heptane, n-hexane, n-pentane, cyclohexane, diisopropyl ether, methyl tBu ether, acetonitrile, DMF, DMA, NMP, DMSO, dioxane, toluene, benzene, ethyl acetate or a mixture of these solvents, if appropriate with addition of a base such as, for example, potassium tert-butoxide or tributylamine or triethylamine or diisopropylethylamine or N-ethylmorpholine. A carboxylic acid group —COOH representing $COR^{103}$ in a residue of the formula VIII can be obtained, for example, from an ester group introduced into the pyrazole system during a pyrazole synthesis by standard deprotection procedures like hydrolysis or hydrogenation. For the formation of an amide bond with residues of the formula VIII in which $COR^{103}$ is a carboxylic acid group it can be condensed under standard conditions with compounds of the formula IX which are amines by means of common coupling reagents used in peptide synthesis.

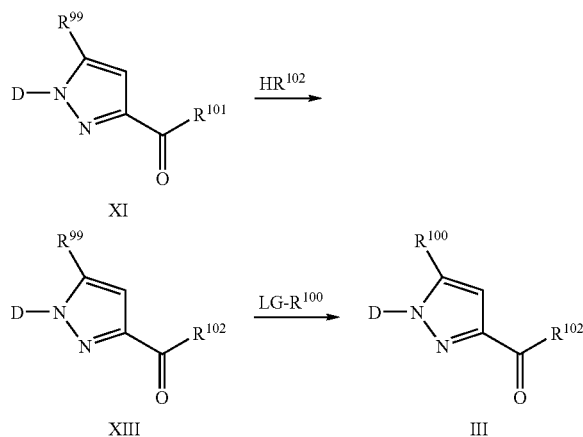

The residues of the formulae VII, VIII, IX and X thus obtained can already contain the desired final groups, i.e. the groups E', Z', A', B', V', G' and M' can be the groups of the formulae V and VI as defined in the formula I, or optionally in the compound of the formula III thus obtained subsequently the residue or the residues $R^{102}$ and $R^{100}$ are converted into the residues of the formulae V and VI, respectively, to give the desired compound of the formula I. Thus, the residues of the formulae VII, VIII, IX and X contained therein can have the denotations of residues of the formulae V and VI, respectively, given above or in addition in the residues of the formulae VII, VIII, IX and X can also be present in the form of groups that can subsequently be transformed into the final groups of the formulae V and VI, i.e. functional groups can be present in the form of precursor groups or of derivatives, for example in protected form. In the course of the preparation of the compounds of the formula I it can generally be advantageous or necessary to introduce functional groups which reduce or prevent undesired reactions or side reactions in the respective synthesis step, in the form of precursor groups which are later converted into the desired functional groups, or to temporarily block functional groups by a protective group strategy suited to the synthesis problem. Such strategies are well known to those skilled in the art (see, for example, Greene and Wuts, Protective Groups in Organic Synthesis, Wiley, 1991, or P. Kocienski, Protecting Groups, Thieme 1994). Protective groups can also have the meaning of a solid phase, and cleavage from the solid phase stands for the removal of the protective group. The use of such techniques is known to those skilled in the art (Burgess K (Ed.) Solid Phase Organic Synthesis, New York, Wiley, 2000).

During the above-mentioned transformations positional isomers may occur, nevertheless these mixtures of positional isomers can be separated by modern separation techniques like, for example, preparative HPLC.

The compounds of the present invention are platelet ADP P2Y12 receptor antagonists, which anatagonize the platelet aggregating effect of the activation of the platelet ADP P2Y12 receptors. In particular, they are highly active antagonists of the P2Y12 receptor. They are specific platelet ADP receptor antagonists inasmuch as they do not substantially inhibit or promote the activity of other receptors whose activiation or inhibition is not desired. The activity of the compounds of the formula I can be determined, for example, in the assays described below or in other in vitro, ex vivo or in vivo assays known to those skilled in the art. For example, the ability of the compounds to bind to the P2Y12 receptor may be measured by methods similar to those described in Gachet, C. et al., Br. J. Haemotol. (1995), 91, 434-444 and Mills, D. C., Thromb. Haemost (1996), 76, 835-856, and by the assay described below. With respect to P2Y12 binding affinity, a preferred embodiment of the invention comprises compounds which have an IC50<1 mM for P2Y12 binding affinity as determined in the assay described, and which preferably do not substantially influence the activity of other receptors involved in platelet aggregation and fibrinolysis whose inhibition or activation is not desired (using the same concentration of the antagonist). The ability of the compounds to inhibit ADP-induced aggregation of platelets may be measured by methods similar to those described in R. G. Humphries et al., Br. J. Pharm. (1995), Vol. 115, pp. 1110-1116 and J. F. Mustard et al. Methods in Enzymology, Vol. 169, p. 3 and by the method described below. The ability of the compounds to inhibit thrombus formation in vivo or ex vivo may be measured by methods similar to those described in J. M. Herbert et al., Cardiovasc. Drug Rev. (1993), 11, 180-198 or J. D. Folts et al., Circulation (1976), 54, 365. The results of these assays clearly demonstrate that the compounds of the invention are functional antagonists of the platelet adenosine diphosphate receptor and are therefore useful for inhibiting platelet aggregation and thrombus formation.

As platelet ADP P2Y12 receptor antagonists the compounds of the formula I and/or their physiologically tolerable salts and/or their prodrugs are generally suitable for the therapy and prophylaxis of conditions in which the activity of platelet ADP P2Y12 receptor plays a role or has an undesired extent, or which can favorably be influenced by inhibiting P2Y12 receptor or decreasing the activity, or for the prevention, alleviation or cure of which an inhibition of platelet ADP P2Y12 receptor or a decrease in the activity is desired by the physician. As inhibition of the platelet ADP P2Y12 receptor influences platelet activation, platelet aggregation and platelet degranulation and promote platelet disaggregation, the compounds of the formula I and/or their physiologically tolerable salts and/or their prodrugs are generally suitable for reducing blood thrombus formation, or for the therapy and prophylaxis of conditions in which the activity of the platelet aggregation and thus blood coagulation system plays a role or has an undesired extent, or which can favorably be influenced by reducing thrombus formation, or for the prevention, alleviation or cure of which a decreased activity of the platelet aggregation system is desired by the physician. A specific subject of the present invention thus are the reduction or inhibition of unwanted thrombus formation, in particular in an individual, by administering an effective amount of a compound of the formula I and/or a physiologically tolerable salt and/or a prodrug thereof, as well as pharmaceutical preparations thereof.

The present invention also relates to the compounds of the formula I and/or their physiologically tolerable salts and/or their prodrugs for use as pharmaceuticals (or medicaments), to the use of the compounds of the formula I and/or their physiologically tolerable salts and/or their prodrugs for the production of pharmaceuticals for inhibition of the P2Y12 receptor or for influencing platelet activation, platelet aggregation and platelet degranulation and promote platelet disaggregation, inflammatory response or for the therapy or prophylaxis of the diseases mentioned above or below, for example for the production of pharmaceuticals for the therapy and prophylaxis of cardiovascular disorders, thromboembolic diseases or restenosis. The invention also relates to the use of the compounds of the formula I and/or their physiologically tolerable salts and/or their prodrugs for the inhibition of P2Y12 receptor or for influencing platelet activation, platelet aggregation and platelet degranulation and promote platelet disaggregation or for the therapy or prophylaxis of the diseases mentioned above or below, for example for use in the therapy and prophylaxis of cardiovascular disorders, thromboembolic diseases or restenoses, and to methods of treatment aiming at such purposes including methods for said therapies and prophylaxis. The present invention also relates to pharmaceutical preparations (or pharmaceutical compositions) which contain an effective amount of at least one compound of the formula I and/or its physiologically tolerable salts and/or its prodrugs in addition to a customary pharmaceutically acceptable carrier, i.e. one or more pharmaceutically acceptable carrier substances or excipients and/or auxiliary substances or additives.

The invention also relates to the treatment of disease states such as abnormal thrombus formation, acute myocardial infarction, unstable angina, thromboembolism, acute vessel closure associated with thrombolytic therapy or percutaneous transluminal coronary angioplasty (PTCA), transient ischemic attacks, stroke, intermittent claudication or bypass grafting of the coronary or peripheral arteries, vessel luminal narrowing, restenosis post coronary or venous angioplasty, maintenance of vascular access patency in long-term hemodialysis patients, pathologic thrombus formation occurring in the veins of the lower extremities following abdominal, knee or hip surgery, pathologic thrombus formation occurring in the veins of the lower extremities following abdominal, knee and hip surgery, a risk of pulmonary thromboembolism, or disseminated systemic intravascular coagulatopathy occurring in vascular systems during septic shock, certain viral infections or cancer.

The compounds of the present invention can also be used to reduce an inflammatory response. Examples of specific disorders for the treatment or prophylaxis of which the compounds of the formula I can be used are coronary heart disease, myocardial infarction, angina pectoris, vascular restenosis, for example restenosis following angioplasty like PTCA, adult respiratory distress syndrome, multi-organ failure and disseminated intravascular clotting disorder. Examples of related complications associated with surgery are thromboses like deep vein and proximal vein thrombosis, which can occur following surgery.

The compounds of the formula I and their physiologically tolerable salts and their prodrugs can be administered to animals, preferably to mammals, and in particular to humans as pharmaceuticals for therapy or prophylaxis. They can be administered on their own, or in mixtures with one another or in the form of pharmaceutical preparations, which permit enteral or parenteral administration.

The pharmaceuticals can be administered orally, for example in the form of pills, tablets, lacquered tablets, coated tablets, granules, hard and soft gelatine capsules, solutions, syrups, emulsions, suspensions or aerosol mixtures. Administration, however, can also be carried out rectally, for example in the form of suppositories, or parenterally, for example intravenously, intramuscularly or subcutaneously, in the form of injection solutions or infusion solutions, microcapsules, implants or rods, or percutaneously or topically, for example in the form of ointments, solutions or tinctures, or in other ways, for example in the form of aerosols or nasal sprays.

The pharmaceutical preparations according to the invention are prepared in a manner known per se and familiar to one skilled in the art, pharmaceutically acceptable inert inorganic and/or organic carriers being used in addition to the compound(s) of the formula I and/or its (their) physiologically tolerable salts and/or its (their) prodrugs. For the production of pills, tablets, coated tablets and hard gelatine capsules it is possible to use, for example, lactose, cornstarch or derivatives thereof, talc, stearic acid or its salts, etc. Carriers for soft gelatine capsules and suppositories are, for example, fats, waxes, semisolid and liquid polyols, natural or hardened oils, etc. Suitable carriers for the production of solutions, for example injection solutions, or of emulsions or syrups are, for example, water, saline, alcohols, glycerol, polyols, sucrose, invert sugar, glucose, vegetable oils, etc. Suitable carriers for microcapsules, implants or rods are, for example, copolymers of glycolic acid and lactic acid. The pharmaceutical preparations normally contain about 0.5% to 90% by weight of the compounds of the formula I and/or their physiologically tolerable salts and/or their prodrugs. The amount of the active ingredient of the formula I and/or its physiologically tolerable salts and/or its prodrugs in the pharmaceutical preparations normally is from about 0.5 mg to about 1000 mg, preferably from about 1 mg to about 500 mg.

In addition to the active ingredients of the formula I and/or their physiologically acceptable salts and/or prodrugs and to carrier substances, the pharmaceutical preparations can contain additives such as, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents or antioxidants. They can also contain two or more compounds of the formula I, and/or their physiologically tolerable salts and/or their prodrugs. In case a pharmaceutical preparation contains two or more compounds of the formula I, the selection of the individual compounds can aim at a specific overall pharmacological profile of the pharmaceutical preparation. For example, a highly potent compound with a shorter duration of action may be combined with a long-acting compound of lower potency. The flexibility permitted with respect to the choice of substituents in the compounds of the formula I allows a great deal of control over the biological and physico-chemical properties of the compounds and thus allows the selection of such desired compounds. Furthermore, in addition to at least one compound of the formula I and/or a physiologically tolerable salt and/or its prodrug, the pharmaceutical preparations can also contain one or more other therapeutically or prophylactically active ingredients.

When using the compounds of the formula I the dose can vary within wide limits and, as is customary and is known to the physician, is to be suited to the individual conditions in each individual case. It depends, for example, on the specific compound employed, on the nature and severity of the disease to be treated, on the mode and the schedule of administration, or on whether an acute or chronic condition is treated or whether prophylaxis is carried out. An appropriate dosage can be established using clinical approaches well known in the medical art. In general, the daily dose for achieving the desired results in an adult weighing about 75 kg is from 0.01 mg/kg to 100 mp/kg, preferably from 0.1 mp/kg to 50 mp/kg, in particular from 0.1 mp/kg to 10 mp/kg, (in each case in mg per kg of body weight). The daily dose can be divided, in particular in the case of the administration of relatively large amounts, into several, for example 2, 3 or 4, part administrations. As usual, depending on individual behaviour it may be necessary to deviate upwards or downwards from the daily dose indicated.

The compounds of the present invention can be administered alone or in combination with one or more additional therapeutic agents. These other agents include, but are not limited to, anticoagulant or coagulation inhibitory agents, other antiplatelet or platelet inhibitory agents, or thrombolytic or fibrinolytic agents.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

Examples of suitable anti-arrhythmic agents for use in combination with the present compounds include: Class I agents (such as propafenone); Class II agents (such as carvadiol and propranolol); Class HI agents (such as sotalol, dofetilide, amiodarone, azimilide, and ibutilide); Class IV agents (such as ditiazem and verapamil); K+ channel openers such as IAch inhibitors, and IKur inhibitors (e.g., compounds such as those disclosed in WO01/40231).

Examples of suitable antihypertensive agents for use in combination with the compounds of the present invention include: alpha adrenergic blockers; beta adrenergic blockers; calcium channel blockers (e.g. diltiazem, verapamil, nifedipine, amlodipine, and mybefradil); diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, muzolimine, bumetanide, triamterene, amiloride, spironolactone); renin inhibitors; angiotensin-converting enzyme (ACE) inhibitors (e.g., captopril, zofenopril, fosinopril, enalapril, ceranopril, cilazopril, delapril, pentopril, quinapril, ramipril, lisinopril); angiotensin AT-I receptor antagonists (e.g., losartan, irbesartan, valsartan); ET-A receptor antagonists (e.g., sitaxsentan, atrsentan, and compounds disclosed in U.S. Pat. Nos. 5,612,359 and 6,043,265); Dual ET-A/AT-I antagonist (e.g., compounds disclosed in WO 00/01389); neutral endopeptidase (NEP) inhibitors; vasopepsidase inhibitors (dual NEP-ACE inhibitors) (e.g., omapatrilat, gemopatrilat, and nitrates); and 8-blockers (e.g., propanolol, nadolol, or carvedilol).

Examples of other suitable anti-platelet agents for use in combination with the compounds of the present invention, include, but are not limited to, the various known non-steroidal anti-inflammatory drugs (NSAIDS) such as acetaminophen, aspirin, codeine, diclofenac, droxicam, fentanyl, ibuprofen, indomethacin, ketorolac-, mefenamate, morphine, naproxen, phenacetin, piroxicam, sufentanyl, sulfinpyrazone, sulindac, and pharmaceutically acceptable salts or prodrugs thereof. Of the NSAIDS, aspirin (acetylsalicyclic acid or ASA) and piroxicam are preferred. Other suitable platelet inhibitory agents include glycoprotein IIb/IIIa blockers (e.g., abciximab, eptifibatide, tirofiban, integrelin), thromboxane-A2-receptor antagonists (e.g., ifetroban), thromboxane-A2-synthetase inhibitors, phosphodiesterase-III (PDE-III) inhibitors (e.g., dipyridamole, cilostazol), and PDE V inhibitors (such as sildenafil), protease-activated receptor 1 (PAR-I) antagonists (e.g., SCH-530348, SCH-203099, SCH-529153, and SCH-205831), and pharmaceutically acceptable salts or prodrugs thereof.

Examples of suitable anticoagulants for use in combination with the compounds of the present invention include warfarin and heparin (either unfractionated heparin such as enoxaparin and dalteparin or any commercially available low molecular weight heparin, for example LOVENOX™), synthetic pentasaccharide, direct acting thrombin inhibitors including hirudin and argatroban, factor Vila inhibitors, factor IXa inhibitors, factor Xa inhibitors (e.g., Arixtra™, apixaban, rivaroxaban, LY-517717, DU-176b, DX-9065a, and those disclosed in WO 98/57951, WO 03/026652, WO 01/047919, and WO 00/076970), factor XIa inhibitors, and inhibitors of activated TAFI and PAI-I known in the art. The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the secretion of platelet granule contents including serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, argatroban, dabigatran, AZD-0837, and those disclosed in WO 98/37075 and WO 02/044145, and pharmaceutically acceptable salts and prodrugs thereof. Boroarginine derivatives and boropeptides include N-acetyl and peptide derivatives of boronic acid, such as C-terminal a-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term thrombolytic (or fibrinolytic) agents (or thrombolytics or fibrinolytics), as used herein, denotes agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), factor Vila inhibitors, thrombin inhibitors, inhibitors of factors EKa, Xa, and XIa, PAI-I inhibitors (i.e., inactivators of tissue plasminogen activator inhibitors), inhibitors of activated TAFI, alpha-2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Examples of suitable calcium channel blockers (L-type or T-type) for use in combination with the compounds of the present invention include diltiazem, verapamil, nifedipine, amlodipine and mybefradil.

Examples of suitable cardiac glycosides for use in combination with the compounds of the present invention include digitalis and ouabain. Examples of suitable diruetics for use in combination with the compounds of the present invention include: chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, muzolimine, bumetanide, triamterene, amiloride, and spironolactone. Examples of suitable mineralocorticoid receptor antagonists for use in combination with the compounds of the present invention include sprionolactone and eplirinone.

Examples of suitable cholesterol/lipid lowering agents and lipid profile therapies for use in combination with the compounds of the present invention include: HMG-CoA reductase inhibitors (e.g., pravastatin lovastatin, atorvastatin, simvastatin, NK-104 (a.k.a. itavastatin, or nisvastatin or nisbastatin) and ZD-4522 (a.k.a. rosuvastatin, or atavastatin or visastatin)); squalene synthetase inhibitors; fibrates; bile acid sequestrants (such as questran); ACAT inhibitors; MTP inhibitors; lipooxygenase inhibitors; nicotonic acid; fenofibric acid derivatives (e.g., gemfibrozil, clofibrat, fenofibrate and benzafibrate); probucol; choesterol absorption inhibitors; and cholesterol ester transfer protein inhibitors (e.g., CP-529414). Examples of suitable anti-diabetic agents for use in combination with the compounds of the present invention include: biguanides (e.g. metformin); glucosidase inhibitors (e.g. acarbose); insulins (including insulin secretagogues or insulin sensitizers); meglitinides (e.g. repaglinide); sulfonylureas (e.g., glimepiride, glyburide and glipizide); biguanide/glyburide combinations (e.g., glucovance), thiozolidinediones (e.g. troglitazone, rosiglitazone, and pioglitazone), PPAR-alpha agonists, PPAR-gamma agonists, PPAR alpha/gamma dual agonists, SGLT2 inhibitors, inhibitors of fatty acid binding protein (aP2) such as those disclosed in WO00/59506, glucagon-like peptide-1 (GLP-I), and dipeptidyl peptidase IV (DPP4) inhibitors.

Examples of suitable anti-depressant agents for use in combination with the compounds of the present invention include nefazodone and sertraline. Examples of suitable anti-inflammatory agents for use in combination with the compounds of the present invention include: prednisone; dexamethasone; enbrel; protein tyrosine kinase (PTK) inhibitors; cyclooxygenase inhibitors (including NSAIDs, and COX-I and/or COX-2 inhibitors); aspirin; indomethacin; ibuprofen; prioxicam; naproxen; celecoxib; and/or rofecoxib.

Examples of suitable anti-osteoporosis agents for use in combination with the compounds of the present invention include alendronate and raloxifene. Examples of suitable hormone replacement therapies for use in combination with the compounds of the present invention include estrogen (e.g., congugated estrogens) and estradiol.

Examples of suitable anti-obesity agents for use in combination with the compounds of the present invention include orlistat, aP2 inhibitors (such as those disclosed in WO00/59506), and cannabinoid receptor CBI antagonists (e.g., rimonabant, AVE-1625, SR-147778, and CP-945598).

Examples of suitable anti-anxiety agents for use in combination with the compounds of the present invention include diazepam, lorazepam, buspirone, and hydroxyzine pamoate.

Examples of suitable anti-proliferative agents for use in combination with the compounds of the present invention include cyclosporin A, paclitaxel, adriamycin; epithilones, cisplatin, and carboplatin.

Examples of suitable anti-ulcer and gastroesophageal reflux disease agents for use in combination with the compounds of the present invention include famotidine, ranitidine, and omeprazole.

Administration of the compounds of the present invention (i.e., a first therapeutic agent) in combination with at least one additional therapeutic agent (i.e., a second therapeutic agent), preferably affords an efficacy advantage over the compounds and agents alone, preferably while permitting the use of lower doses of each. A lower dosage minimizes the potential of side effects, thereby providing an increased margin of safety. It is preferred that at least one of the therapeutic agents is administered in a sub-therapeutic dose. It is even more preferred that all of the therapeutic agents be administered in sub-therapeutic doses. Sub-therapeutic is intended to mean an amount of a therapeutic agent that by itself does not give the desired therapeutic effect for the condition or disease being treated. Synergistic combination is intended to mean that the observed effect of the combination is greater than the sum of the individual agents administered alone.

The compounds of the present invention are also useful as standard or reference compounds, for example as a quality standard or control, in tests or assays involving the inhibition of platelet ADP receptor. Such compounds may be provided in a commercial kit, for example, for use in pharmaceutical research involving platelet ADP receptor. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

A compound of the formula I can also advantageously be used as an antiaggregant outside an individual. For example, an effective amount of a compound of the invention can be contacted with a freshly drawn blood sample to prevent aggregation of the blood sample. Further, a compound of the formula I or its salts can be used for diagnostic purposes, for example in in vitro diagnoses, and as an auxiliary in biochemical investigations. For example, a compound of the formula I can be used in an assay to identify the presence of the P2Y12 receptor or to isolate the P2Y12 receptor containing tissue in a substantially purified form. A compound of the invention can be labelled with, for example, a radioisotope, and the labelled compound bound to the P2Y12 receptor is then detected using a routine method useful for detecting the particular label. Thus, a compound of the formula I or a salt thereof can be used as a probe to detect the location or amount of P2Y12 receptors activity in vivo, in vitro or ex vivo.

Furthermore, the compounds of the formula I can be used as synthesis intermediates for the preparation of other compounds, in particular of other pharmaceutical active ingredients, which are obtainable from the compounds of the formula I, for example by introduction of substituents or modification of functional groups.

The general synthetic sequences for preparing the compounds useful in the present invention are outlined in the examples given below. Both an explanation of, and the actual procedure for, the various aspects of the present invention are described where appropriate. The following examples are intended to be merely illustrative of the present invention, and not limiting thereof in either scope or spirit. Those with skill in the art will readily understand that known variations of the conditions and processes described in the examples can be used to synthesize the compounds of the present invention.

It is understood that changes that do not substantially affect the activity of the various embodiments of this invention are included within the invention disclosed herein. Thus, the following examples are intended to illustrate but not limit the present invention.

EXAMPLES

When in the final step of the synthesis of a compound an acid such as trifluoroacetic acid or acetic acid was used, for example when trifluoroacetic acid was employed to an acid-labile protecting group (eg. a tBu group) or when a compound was purified by chromatography using an eluent which contained such an acid, in some cases, depending on the work-up procedure, for example the details of a freeze-drying process, the compound was obtained partially or completely in the form of a salt of the acid used, for example in the form of the acetic acid salt, formic acid salt or trifluoroacetic acid salt or hydrochloric acid salt. Likewise starting materials or intermediates bearing a basic center like for example a basic nitrogen were either obtained and used as free base or in salt form like, for example, a trifluoroacetic acid salt, a hydrobromic acid salt, sulfuric acid salt, or a hydrochloric acid salt.

Abbreviations Used:

| | |
|---|---|
| tert-Butyl | tBu |
| 2,2'-bis(diphenylphoshino-1,1'-binaphthyl | Binap |
| Bis-(oxo-3-oxazolidinyl)-phosphoryl chloride | BOP-Cl |
| dibenzylidenacetone | dba |
| Dichloromethane | DCM |
| Dicyclohexyl-carbodiimide | DCC |
| Diethylphosphoryl cyanide | DEPC |
| Diisopropylethyl amine | DIPEA |
| 4-Dimethyaminopyridine | DMAP |
| N,N-Dimethylformamide | DMF |
| Dimethylsulfoxide | DMSO |
| 1,1'-Bis(diphenylphosphino)ferrocene | DPPF |
| O-(7-Azabenzotriazol-1-yl)-N,N,N',N'- 1-(3-Dimethylaminopropyl)-3-ethylcarbodiimide hydrochloride | EDC |
| O-(7-Azabenzotriazol-1-yl)-N,N,N',N'-tetramethyluronium-hexafluorophosphate | HATU |
| 1-Hydroxybenzotriazole | HOBT |
| N-Bromosuccinimide | NBS |
| N-Chlorosuccinimide | NCS |
| N-Iodosuccinimide | NIS |
| N-Ethylmorpholine | NEM |
| Methanol | MeOH |
| Room temperature 20° C. to 25° C. | RT |
| Saturated | sat. |
| Tetrahydrofuran | THF |
| Trifluoroacetic acid | TFA |
| O-((Ethoxycarbonyl)cyanomethyleneamino)-N,N,N',N'-tetramethyluronium tetrafluoroborate | TOTU |

Example 1

4-[(S)-4-Carboxy-2-({5-[2-((S)-2-cyclopropylcarbamoyl-pyrrolidin-1-yl)-2-oxo-ethoxy]-1-phenyl-1H-pyrazole-3-carbonyl}-amino)-butyryl]-piperazine-1-carboxylic acid ethyl ester (i) 4-((S)-2-Benzyloxycaronylamino-4-tert-butoxycarbonyl-butyryl)-piperazine-1-carboxylic acid ethyl ester To a solution of 15.0 g (S)-2-Benzyloxycarbonylaminopentanedioic acid 5-tert-butyl ester in 75 ml DMF were added 6.9 ml 1-ethoxycarbonylpiperazine, 22.6 ml N-ethylmorpholine and 14.6 g TOTU. After stirring for 12 h the solution was diluted with ethyl acetate and subsequently washed with aqueous LiCl (4%) and saturated aqueous NaHCO₃. The crude product obtained after evaporation of the solvent was used without further purification.

Yield: 20.9 g.

(ii) 4-((S)-2-Amino-4-tert-butoxycarbonyl-butyryl)-piperazine-1-carboxylic acid ethyl ester To a solution of 20.9 g 4-((S)-2-Benzyloxycarbonylamino-4-tert-butoxycarbonyl-butyryl)-piperazine-1-carboxylic acid ethyl ester in 120 ml ethanol were added 2.0 g Pd/C (10%) and the suspension stirred under an atmosphere of hydrogen (3 bar) for 12 h. The reaction mixture was filtrated over a plug of Celite, washed with ethanol and concentrated to give the crude product which was not further purified. Yield: 13.6 g colorless oil.

(iii) 4-{(S)-4-tert-Butoxycarbonyl-2-[(5-hydroxy-1-phenyl-1H-pyrazole-3-carbonyl)-amino]butyryl}-piperazine-1-carboxylic acid ethyl ester To a solution of 7.2 g 1-phenyl-3-carboxy-5-pyrazolone and 12.1 g 4-((S)-2-amino-4-tert-butoxycarbonyl-butyryl)-piperazine-1-carboxylic acid ethyl ester in 100 ml DMF 5.4 g HOBT and 6.7 g EDC were added and the reaction mixture was stirred for 12 h at RT. Then the reaction mixture was diluted with ethyl acetate and subsequently extracted with aqueous LiCl (4% w/w), 0.1 M HCl and aqueous NaHCO₃. The organic layer was dried over MgSO₄ and the solvent was removed under reduced pressure. The crude product thus obtained was used in the subsequent reaction.

Yield: 14.8 g.

(iv) 4-{(S)-2-[(5-Benzyloxycarbonylmethoxy-1-phenyl-1H-pyrazole-3-carbonyl)-amino]-4-tert-butoxycarbonyl-butyryl}-piperazine-1-carboxylic acid ethyl ester To a solution of 14.5 g 4-{(S)-4-tert-butoxycarbonyl-2-[(5-hydroxy-1-phenyl-1H-pyrazole-3-carbonyl)-amino]-butyryl}-piperazine-1-carboxylic acid ethyl ester in 110 ml DMF were added 4.5 ml benzyl bromoacetate and 17.8 g cesium carbonate. After stirring at RT for 12 h the solution was reduced to a volume of 50 ml, diluted with 400 ml ethyl acetate and extracted with aqueous LiCl (4% w/w). The crude product obtained after evaporation of the solvent was purified by flash chromatography on silica eluting with a gradient of n-heptane/ethyl acetate.

Yield: 13.2 g yellowish amorphous solid.

(iii) 4-{(S)-4-tert-Butoxycarbonyl-2-[(5-carboxymethoxy-1-phenyl-1H-pyrazole-3-carbonyl)-amino]-butyryl}-piperazine-1-carboxylic acid ethyl ester To a solution of 13.2 g 4-{(S)-2-[(5-Benzyloxycarbonylmethoxy-1-phenyl-1H-pyrazole-3-carbonyl)-amino]-4-tert-butoxycarbonyl-butyryl}-piperazine-1-carboxylic acid ethyl ester in 75 ml ethyl acetate were added under argon 1.1 g Pd/C (10%) and the suspension was stirred under an atmosphere of hydrogen (3 bar) for 16 h. The suspension was filtered over a plug of Celite® and washed with ethyl acetate. The crude product obtained after evaporation of the solvent was dried under vacuo at 40° C. for 24 h.

Yield: 12.1 g colorless solid.

(iv) 4-[(S)-2-({5-[2-((S)-2-Benzyloxycarbonyl-pyrrolidin-1-yl)-2-oxo-ethoxy]-1-phenyl-1H-pyrazole-3-carbonyl}-amino)-4-tert-butoxycarbonyl-butyryl]-piperazine-1-carboxylic acid ethyl ester To a solution of 9.5 g 4-{(S)-4-tert-Butoxycarbonyl-2-[(5-carboxymethoxy-1-phenyl-1H-pyrazole-3-carbonyl)-amino]-butyryl}-piperazine-1-carboxylic acid ethyl ester in 80 ml DMF were added 2.5 g HOBt, 5.7 ml DIPEA and 3.9 g L-proline benzyl ester hydrochloride at 0° C. At this temperature were added 3.1 g EDC portionwise and the suspension allowed to warm to RT over a period of 12 h. The solvent was evaporated, the residue dissolved in ethyl acetate and subsequently extracted with aqueous LiCl (4 w/w), 0.1 M HCl and aqueous NaHCO₃. The organic layer was dried over MgSO₄ and the solvent was removed under reduced pressure. The crude product thus obtained was used in the subsequent reaction.

Yield: 11.6 g amorphous solid.

(v) 4-[(S)-4-tert-Butoxycarbonyl-2-({5-[2-((S)-2-carboxy-pyrrolidin-1-yl)-2-oxo-ethoxy]-1-phenyl-1H-pyrazole-3-carbonyl}-amino)-butyryl]-piperazine-1-carboxylic acid ethyl ester To a solution of 11.6 g 4-[(S)-2-({5-[2-((S)-2-Benzyloxy-carbonyl-pyrrolidin-1-yl)-2-oxo-ethoxy]-1-phenyl-1H-pyrazole-3-carbonyl}-amino)-4-tert-butoxycarbonyl-butyryl]-piperazine-1-carboxylic acid ethyl ester in 75 ml ethyl acetate was added under argon 1 g Pd/C (10%) and the suspension was stirred under an atmosphere of hydrogen (3 bar) for 24 h. The suspension was filtered over a plug of Celite® and washed with ethyl acetate. The crude product obtained after evaporation of the solvent was used in the subsequent reaction. Yield: 9.9 g.

(vi) 4-[(S)-4-Carboxy-2-({5-[2-((S)-2-cyclopropyl-carbamoyl-pyrrolidin-1-yl)-2-oxo-ethoxy]-1-phenyl-1H-pyrazole-3-carbonyl}-amino)-butyryl]-piperazine-1-carboxylic acid ethyl ester To a solution of 133 mg 4-[(S)-4-tert-Butoxycarbonyl-2-({5-[2-((S)-2-carboxy-pyrrolidin-1-yl)-2-oxo-ethoxy]-1-phenyl-1H-pyrazole-3-carbonyl}-amino)-butyryl]-piperazine-1-carboxylic acid ethyl ester in 5 ml DMF were added 32 µl DIPEA and 74 mg HATU. After 20 minutes 14 µl cyclopropylamine were added and the reaction mixture was stirred for 12 h. After dilution with ethyl acetate the reaction mixture was extracted with aqueous LiCl (4% w/w) and aqueous NaHCO₃. The organic layer was dried over MgSO₄ and the solvent was removed under reduced pressure. The crude product was dissolved in 4 ml DCM and treated with 133 µl TFA. After stirring for 12 h the solvents were removed under reduced pressure and the residue purified by preparative HPLC (C18 reverse phase column, elution with a water/MeCN gradient with 0.1% TFA). The product was obtained as its trifluoroacetate salt. Yield: 48 mg MS (ES+): m/e=668.

Example 2

4-{(S)-4-Carboxy-2-[(5-{2-oxo-2-[(S)-2-(2,2,2-trifluoroethyl-carbamoyl)pyrrolidin-1-yl]-ethoxy}-1-phenyl-1H-pyrazole-3-carbonyl)-amino]-butyryl}-piperazine-1-carboxylic acid ethyl ester The title compound was prepared by adapting the procedures described in example 1 with the difference that 2,2,2-trifluoroethylamine was used instead of cyclopropylamine.

Yield: 99 mg MS (ES+): m/e=710.

Example 3

4-{(S)-4-Carboxy-2-[(5-{2-[(S)-2-(2-methylsulfanyl-ethylcarbamoyl)-pyrrolidin-1-yl]-2-oxo-ethoxy}-1-phenyl-1H-pyrazole-3-carbonyl)-amino]-butyryl}-piperazine-1-carboxylic acid ethyl ester The title compound was prepared by adapting the procedures described in example 1 with the difference that 2-methylsulfanyl-ethylamine was used instead of cyclopropylamine.

Yield: 122 mg MS (ES+): m/e=702.

Example 4

4-{(S)-4-Carboxy-2-[(5-{2-[(S)-2-dimethylcarbamoyl)-pyrrolidin-1-yl]-2-oxo-ethoxy}-1-phenyl-1H-pyrazole-3-carbonyl)-amino]-butyryl}-piperazine-1-carboxylic acid ethyl ester The title compound was prepared by adapting the procedures described in example 1 with the difference that dimethylamine hydrochloride was used instead of cyclopropylamine.

Yield: 101 mg MS (ES+): m/e=656.

Example 5

4-{(S)-4-Carboxy-2-[(5-{2-[(S)-2-cyclobutylcarbamoyl)-pyrrolidin-1-yl]-2-oxo-ethoxy}-1-phenyl-1H-pyrazole-3-carbonyl)-amino]-butyryl}-piperazine-1-carboxylic acid ethyl ester The title compound was prepared by adapting the procedures described in example 1 with the difference that cyclobutylamine was used instead of cyclopropylamine.

Yield: 91 mg MS (ES+): m/e=682.

Example 6

4-{(S)-4-Carboxy-2-[(5-{2-[(S)-2-(2-fluoro-ethylcarbamoyl)-pyrrolidin-1-yl]-2-oxo-ethoxy}-1-phenyl-1H-pyrazole-3-carbonyl)-amino]-butyryl}-piperazine-1-carboxylic acid ethyl ester The title compound was prepared by adapting the procedures described in example 1 with the difference that 2-fluoroethylamine hydrochloride was used instead of cyclopropylamine. Yield: 100 mg MS (ES+): m/e=674.

Example 7

4-{(S)-4-Carboxy-2-[(5-{2-[(S)-2-(2-methylcarbamoyl)-pyrrolidin-1-yl]-2-oxo-ethoxy}-1-phenyl-1H-pyrazole-3-carbonyl)-amino]-butyryl}-piperazine-1-carboxylic acid ethyl ester The title compound was prepared by adapting the procedures described in example 1 with the difference that methylamine hydrochloride was used instead of cyclopropylamine.

Yield: 46 mg MS (ES+): m/e=642.

Example 8

4-{(S)-4-Carboxy-2-[(5-{2-[(S)-2-ethylcarbamoyl-pyrrolidin-1-yl]-2-oxo-ethoxy}-1-phenyl-1H-pyrazole-3-carbonyl)-amino]-butyryl}-piperazine-1-carboxylic acid ethyl ester The title compound was prepared by adapting the procedures described in example 1 with the difference that ethylamine was used instead of cyclopropylamine.

Yield: 60 mg MS (ES+): m/e=656.

Example 9

4-{(S)-4-Carboxy-2-[(5-{2-[(S)-2-propylcarbamoyl-pyrrolidin-1-yl]-2-oxo-ethoxy}-1-phenyl-1H-pyrazole-3-carbonyl)-amino]-butyryl}-piperazine-1-carboxylic acid ethyl ester The title compound was prepared by adapting the procedures described in example 1 with the difference that propylamine was used instead of cyclopropylamine.
Yield: 110 mg MS (ES+): m/e=670.

Example 10

4-{(S)-4-Carboxy-2-[(5-{2-[(S)-2-isopropylcarbamoyl-pyrrolidin-1-yl]-2-oxo-ethoxy}-1-phenyl-1H-pyrazole-3-carbonyl)-amino]-butyryl}-piperazine-1-carboxylic acid ethyl ester The title compound was prepared by adapting the procedures described in example 1 with the difference that isopropylamine was used instead of cyclopropylamine.
Yield: 110 mg MS (ES+): m/e=670.

Example 11

4-{(S)-4-Carboxy-2-[(5-{2-[(S)-2-butylcarbamoyl-pyrrolidin-1-yl]-2-oxo-ethoxy}-1-phenyl-1H-pyrazole-3-carbonyl)-amino]-butyryl}-piperazine-1-carboxylic acid ethyl ester The title compound was prepared by adapting the procedures described in example 1 with the difference that butylamine was used instead of cyclopropylamine.
Yield: 130 mg MS (ES+): m/e=684.

Example 12

4-{(S)-4-Carboxy-2-[(5-{2-[(S)-2-tert-butylcarbamoyl-pyrrolidin-1-yl]-2-oxo-ethoxy}-1-phenyl-1H-pyrazole-3-carbonyl)-amino]-butyryl}-piperazine-1-carboxylic acid ethyl ester The title compound was prepared by adapting the procedures described in example 1 with the difference that tert-butylamine was used instead of cyclopropylamine.
Yield: 85 mg MS (ES+): m/e=684.

Example 13

4-{(S)-4-Carboxy-2-[(5-{2-[(S)-2-cyclopentylcarbamoyl-pyrrolidin-1-yl]-2-oxo-ethoxy}-1-phenyl-1H-pyrazole-3-carbonyl)-amino]-butyryl}-piperazine-1-carboxylic acid ethyl ester The title compound was prepared by adapting the procedures described in example 1 with the difference that cyclopentylamine was used instead of cyclopropylamine.
Yield: 95 mg MS (ES+): m/e=696.

Example 14

4-{(S)-2-[(5-{2-[(S)-2-(Azetidine-1-carbonyl)-pyrrolidin-1-yl]-2-oxo-ethoxy}-1-phenyl-1H-pyrazole-3-carbonyl)-amino]-4-carboxy-butyryl}-piperazine-1-carboxylic acid ethyl ester The title compound was prepared by adapting the procedures described in example 1 with the difference that azetidine was used instead of cyclopropylamine.
Yield: 95 mg MS (ES+): m/e=668.

Example 15

4-{(S)-4-Carboxy-2-[(5-{2-[(S)-2-(2,2-difluoro-ethylcarbamoyl)-pyrrolidin-1-yl]-2-oxo-ethoxy}-1-phenyl-1H-pyrazole-3-carbonyl)-amino]-butyryl}-piperazine-1-carboxylic acid ethyl ester The title compound was prepared by adapting the procedures described in example 1 with the difference that 2,2-difluoroethylamine was used instead of cyclopropylamine.
Yield: 90 mg MS (ES+): m/e=692.

Example 16

4-{(S)-4-Carboxy-2-[(5-{2-[(S)-2-(cyclopropylmethyl-carbamoyl)-pyrrolidin-1-yl]-2-oxo-ethoxy}-1-phenyl-1H-pyrazole-3-carbonyl)-amino]-butyryl}-piperazine-1-carboxylic acid ethyl ester The title compound was prepared by adapting the procedures described in example 1 with the difference that aminomethylcyclopropane was used instead of cyclopropylamine.
Yield: 150 mg MS (ES+): m/e=682.

Example 17

4-{(S)-4-Carboxy-2-[(5-{2-oxo-2-[(S)-2-(pyrrolidine-1-carbonyl)-pyrrolidin-1-yl]-ethoxy}-1-phenyl-1H-pyrazole-3-carbonyl)-amino]-butyryl}-piperazine-1-carboxylic acid ethyl ester The title compound was prepared by adapting the procedures described in example 1 with the difference that pyrrolidine was used instead of cyclopropylamine.
Yield: 74 mg MS (ES+): m/e=682.

Example 18

4-{(S)-4-Carboxy-2-[(5-{2-oxo-2-[(S)-2-(piperidine-1-carbonyl)-pyrrolidin-1-yl]-ethoxy}-1-phenyl-1H-pyrazole-3-carbonyl)-amino]-butyryl}-piperazine-1-carboxylic acid ethyl ester The title compound was prepared by adapting the procedures described in example 1 with the difference that piperidine was used instead of cyclopropylamine.
Yield: 243 mg MS (ES+): m/e=696.

Example 19

4-{(S)-4-Carboxy-2-[(5-{2-[(S)-2-(4,4-difluoro-piperidine-1-carbonyl)-pyrrolidin-1-yl]-2-oxo-ethoxy}-1-phenyl-1H-pyrazole-3-carbonyl)-amino]-butyryl}-piperazine-1-carboxylic acid ethyl ester The title compound was prepared by adapting the procedures described in example 1 with the difference that 4,4- difluoropiperidine hydrochloride was used instead of cyclopropylamine. Yield: 230 mg MS (ES+): m/e=732.

Example 20

4-{(S)-4-Carboxy-2-[(5-{2-[(S)-2-(cyclobutylmethyl-carbamoyl)-pyrrolidin-1-yl]-2-oxo-ethoxy}-1-phenyl-1H-pyrazole-3-carbonyl)-amino]-butyryl}-piperazine-1-carboxylic acid ethyl ester The title compound was prepared by adapting the procedures described in example 1 with the difference that cyclobutylmethylamine was used instead of cyclopropylamine. Yield: 204 mg MS (ES+): m/e=696.

Example 21

4-{(S)-4-Carboxy-2-[(5-{2-[(S)-2-(2,2-difluoro-cyclopropylcarbamoyl)-pyrrolidin-1-yl]-2-oxo-ethoxy}-1-phenyl-1H-pyrazole-3-carbonyl)-amino]-butyryl}-piperazine-1-carboxylic acid ethyl ester i) 2,2-Difluorocyclopropylamine hydrotrifluoroacetate To a solution of 100 mg 2,2-difluorocyclopropanecarboxylic acid in 2.35 ml t-BuOH were added 212 μl diphenyl phosphoryl azide and 137 μl triethylamine. The mixture was stirred at 90° C. for 8 h before being concentrated in vacuo. The crude product thus obtained was purified by flash chromatography on silica eluting with heptane/ethyl acetate 2/1 yielding 150 mg (2,2-difluoro-cyclopropyl)-carbamic acid tert-butyl ester as colorless needles. Subsequent treatment with 576 μl trifluoroacetic acid in 4 ml dichloromethane for 4 h delivered the title compound after evaporation of the solvents.

ii) 4-{(S)-4-Carboxy-2-[(5-{2-[(S)-2-(2,2-difluoro-cyclopropylcarbamoyl)-pyrrolidin-1-yl]-2-oxo-ethoxy}-1-phenyl-1H-pyrazole-3-carbonyl)-amino]-butyryl}-piperazine-1-carboxylic acid ethyl ester The title compound was prepared by adapting the procedures described in example 1 with the difference that 2,2-difluorocyclopropylamine hydrotrifluoroacetate was used instead of cyclopropylamine. Yield: 180 mg MS (ES+): m/e=704.

Example 22

4-{(S)-4-Carboxy-2-[(5-{2-[(S)-2-(cyclobutyl-methyl-carbamoyl)-pyrrolidin-1-yl]-2-oxo-ethoxy}-1-phenyl-1H-pyrazole-3-carbonyl)-amino]-butyryl}-piperazine-1-carboxylic acid ethyl ester The title compound was prepared by adapting the procedures described in example 1 with the difference that N-cyclobutyl-N-methylamine hydrochloride was used instead of cyclopropylamine. Yield: 50 mg MS (ES+): m/e=696.

Example 23

4-[(S)-4-Carboxy-2-({5-[2-((R)-3-hydroxy-pyrrolidin-1-yl)-2-oxo-ethoxy]-1-phenyl-1H-pyrazole-3-carbonyl}-amino)-butyryl]-piperazine-1-carboxylic acid ethyl ester To a solution of 90 mg 4-{(S)-4-tert-Butoxycarbonyl-2-[(5-carboxymethoxy-1-phenyl-1H-pyrazole-3-carbonyl)-amino]-butyryl}-piperazine-1-carboxylic acid ethyl ester in 5 ml DMF were added 23 mg HOBt, 29 mg EDC and 53 μl DIPEA at RT. After 20 minutes 19 mg (R)-3-pyrrolidinol hydrochloride were added and the reaction mixture stirred for 24 h. After dilution with ethyl acetate the reaction mixture was extracted with aqueous LiCl (4% w/w) and water. The organic layer was dried over MgSO$_4$ and the solvent was removed under reduced pressure. The crude product was dissolved in 1.5 ml DCM and treated with 127 μl TFA. After stirring for 12 h the solvents were removed under reduced pressure and the residue purified by preparative HPLC (C18 reverse phase column, elution with a water/MeCN gradient with 0.1% TFA). The product was obtained as its trifluoroacetate salt. Yield: 45 mg MS (ES+): m/e=601.

Example 24

4-[(S)-4-Carboxy-2-({5-[2-((2S,4R)-2-ethoxycarbonyl-4-hydroxy-pyrrolidin-1-yl)-2-oxo-ethoxy]-1-phenyl-1H-pyrazole-3-carbonyl}-amino)-butyryl]-piperazine-1-carboxylic acid ethyl ester The title compound was prepared by adapting the procedures described in example 23 with the difference that L-hydroxyproline ethyl ester hydrochloride was used instead of (R)-3-pyrrolidinol hydrochloride. Yield: 55 mg MS (ES+): m/e=673.

Example 25

4-[(S)-4-Carboxy-2-({5-[2-((S)-2-carboxy-azetidin-1-yl)-2-oxo-ethoxy]-1-phenyl-1H-pyrazole-3-carbonyl}-amino)-butyryl]-piperazine-1-carboxylic acid ethyl ester The title compound was prepared by adapting the procedures described in example 23 with the difference that L-azetidine carboxylic acid was used instead of (R)-3-pyrrolidinol hydrochloride. Yield: 8 mg MS (ES+): m/e=615.

Example 26

4-[(S)-4-Carboxy-2-({5-[2-((2R,4R)-2-carboxy-4-hydroxy-pyrrolidin-1-yl)-2-oxo-ethoxy]-1-phenyl-1H-pyrazole-3-carbonyl}-amino)-butyryl]-piperazine-1-carboxylic acid ethyl ester The title compound was prepared by adapting the procedures described in example 23 with the difference that cis-4-hydroxy-D-proline was used instead of (R)-3-pyrrolidinol hydrochloride. Yield: 28 mg MS (ES+): m/e=645.

Example 27

4-[(S)-2-({5-[2-(4-Acetyl-piperazin-1-yl)-2-oxo-ethoxy]-1-phenyl-1H-pyrazole-3-carbonyl}-amino)-4-carboxy-butyryl]-piperazine-1-carboxylic acid ethyl ester The title compound was prepared by adapting the procedures described in example 23 with the difference that 1-acetyl piperazine was used instead of (R)-3-pyrrolidinol hydrochloride. Yield: 57 mg MS (ES+): m/e=642.

Example 28

4-[(S)-4-Carboxy-2-({5-[2-(4-ethyl-piperazin-1-yl)-2-oxo-ethoxy]-1-phenyl-1H-pyrazole-3-carbonyl}-amino)-butyryl]-piperazine-1-carboxylic acid ethyl ester The title compound was prepared by adapting the procedures described in example 23 with the difference that N-ethyl piperazine was used instead of (R)-3-pyrrolidinol hydrochloride. Yield: 56 mg MS (ES+): m/e=628.

Example 29

4-[(S)-2-({5-[2-(3-Acetylamino-pyrrolidin-1-yl)-2-oxo-ethoxy]-1-phenyl-1H-pyrazole-3-carbonyl}-amino)-4-carboxy-butyryl]-piperazine-1-carboxylic acid ethyl ester The title compound was prepared by adapting the procedures described in example 23 with the difference that 3-acetamidopyrrolidine was used instead of (R)-3-pyrrolidinol hydrochloride. Yield: 37 mg MS (ES+): m/e=642.

Example 30

4-[(S)-4-Carboxy-2-({5-[2-oxo-2-(3-oxo-piperazin-1-yl)-ethoxy]-1-phenyl-1H-pyrazole-3-carbonyl}-amino)-butyryl]-piperazine-1-carboxylic acid ethyl ester The title compound was prepared by adapting the procedures described in example 23 with the difference that piperazin-2-one was used instead of (R)-3-pyrrolidinol hydrochloride and HATU instead of EDC/HOBt as coupling reagent.
Yield: 30 mg MS (ES+): m/e=614.

Example 31

4-((S)-4-Carboxy-2-{[5-(2-oxo-2-pyrrolidin-1-yl-ethoxy)-1-phenyl-1H-pyrazole-3-carbonyl]-amino}-butyryl)-piperazine-1-carboxylic acid ethyl ester The title compound was prepared by adapting the procedures described in example 23 with the difference that pyrrolidine was used instead of (R)-3-pyrrolidinol hydrochloride.
Yield: 74 mg MS (ES+): m/e=682.

Example 32

4-[(S)-4-Carboxy-2-({5-[2-((S)-2-carboxy-pyrrolidin-1-yl)-2-oxo-ethoxy]-1-phenyl-1H-pyrazole-3-carbonyl}-amino)-butyryl]-piperazine-1-carboxylic acid ethyl ester The title compound was prepared by adapting the procedures described in example 23 with the difference that L-proline tert-butyl ester was used instead of (R)-3-pyrrolidinol hydrochloride. Yield: 55 mg MS (ES+): m/e=629.

Example 33

4-[(S)-4-Carboxy-2-({5-[2-((2S,4R)-2-carboxy-4-hydroxy-pyrrolidin-1-yl)-2-oxo-ethoxy]-1-phenyl-1H-pyrazole-3-carbonyl}-amino)-butyryl]-piperazine-1-carboxylic acid ethyl ester The title compound was prepared by adapting the procedures described in example 23 with the difference that trans-4-hydroxy-L-proline methyl ester hydrochloride was used instead of (R)-3-pyrrolidinol hydrochloride. Yield: 30 mg MS (ES+): m/e=659.

Example 34

4-[(S)-4-Carboxy-2-({5-[2-(3-methanesulfonyl-pyrrolidin-1-yl)-2-oxo-ethoxy]-1-phenyl-1H-pyrazole-3-carbonyl}-amino)-butyryl]-piperazine-1-carboxylic acid ethyl ester The title compound was prepared by adapting the procedures described in example 23 with the difference that 3-(methylsulfonyl)pyrrolidine was used instead of (R)-3-pyrrolidinol hydrochloride. Yield: 52 mg MS (ES+): m/e=663.

Example 35

4-[(S)-4-Carboxy-2-({5-[2-((2S,4S)-4-hydroxy-2-methoxycarbonyl-pyrrolidin-1-yl)-2-oxo-ethoxy]-1-phenyl-1H-pyrazole-3-carbonyl}-amino)-butyryl]-piperazine-1-carboxylic acid ethyl ester The title compound was prepared by adapting the procedures described in example 23 with the difference that cis-4-hydroxy-L-proline methyl ester hydrochloride was used instead of (R)-3-pyrrolidinol hydrochloride. Yield: 5 mg MS (ES+): m/e=659.

Example 36

4-{(S)-4-Carboxy-2-[(5-{2-[4-(2-hydroxy-ethyl)-piperazin-1-yl]-2-oxo-ethoxy}-1-phenyl-1H-pyrazole-3-carbonyl)-amino]-butyryl}-piperazine-1-carboxylic acid ethyl ester The title compound was prepared by adapting the procedures described in example 23 with the difference that 2-piperazin-1-yl-ethanol was used instead of (R)-3-pyrrolidinol hydrochloride. Yield: 25 mg MS (ES+): m/e=644.

Example 37

4-[(S)-4-Carboxy-2-({5-[2-(4-hydroxy-piperidin-1-yl)-2-oxo-ethoxy]-1-phenyl-1H-pyrazole-3-carbonyl}-amino)-butyryl]-piperazine-1-carboxylic acid ethyl ester The title compound was prepared by adapting the procedures described in example 23 with the difference that 4-hydroxy piperidine hydrochloride was used instead of (R)-3-pyrrolidinol hydrochloride. Yield: 27 mg MS (ES+): m/e=615.

Example 38

4-[(S)-4-Carboxy-2-({5-[2-oxo-2-((S)-2-trifluoromethyl-pyrrolidin-1-yl)-ethoxy]-1-phenyl-1H-pyrazole-3-carbonyl}-amino)-butyryl]-piperazine-1-carboxylic acid ethyl ester The title compound was prepared by adapting the procedures described in example 23 with the difference that (S)-2-(trifluoromethyl)pyrrolidine was used instead of (R)-3-pyrrolidinol hydrochloride. Yield: 45 mg MS (ES+): m/e=653.

Example 39

4-[(S)-2-({5-[2-((S)-2-Carbamoyl-pyrrolidin-1-yl)-2-oxo-ethoxy]-1-phenyl-1H-pyrazole-3-carbonyl}-amino)-4-carboxy-butyryl]-piperazine-1-carboxylic acid ethyl ester The title compound was prepared by adapting the procedures described in example 23 with the difference that L-proline amide hydrochloride was used instead of (R)-3-pyrrolidinol hydrochloride. Yield: 50 mg MS (ES+): m/e=628.

Example 40

4-[(S)-4-Carboxy-2-({5-[2-((S)-2-cyclopropylcarbamoyl-azetidin-1-yl)-2-oxo-ethoxy]-1-phenyl-1H-pyrazole-3-carbonyl}-amino)-butyryl]-piperazine-1-carboxylic acid ethyl ester The title compound was prepared by adapting the procedures described in example 23 with the difference that (S)-azetidine-2-carboxylic acid cyclopropylamide hydrochloride was used instead of (R)-3-pyrrolidinol hydrochloride.
Yield: 26 mg MS (ES+): m/e=654.

Example 41

4-[(S)-4-Carboxy-2-({5-[2-((S)-2-cyclobutylcarbamoyl-azetidin-1-yl)-2-oxo-ethoxy]-1-phenyl-1H-pyrazole-3-carbonyl}-amino)-butyryl]-piperazine-1-carboxylic acid ethyl ester The title compound was prepared by adapting the procedures described in example 23 with the difference that (S)-azetidine-2-carboxylic acid cycbutylamide hydrochloride was used instead of (R)-3-pyrrolidinol hydrochloride.
Yield: 98 mg MS (ES+): m/e=668.

Example 42

4-[(S)-4-Carboxy-2-({5-[2-(3-cyclopropylcarbamoyl-azetidin-1-yl)-2-oxo-ethoxy]-1-phenyl-1H-pyrazole-3-carbonyl}-amino)-butyryl]-piperazine-1-carboxylic acid ethyl ester The title compound was prepared by adapting the procedures described in example 23 with the difference that azetidine-3-carboxylic acid cyclopropylamide hydrochloride was used instead of (R)-3-pyrrolidinol hydrochloride.
Yield: 66 mg MS (ES+): m/e=654.

Example 43

4-[(S)-4-Carboxy-2-({5-[2-(3-cyclobutylcarbamoyl-azetidin-1-yl)-2-oxo-ethoxy]-1-phenyl-1H-pyrazole-3-carbonyl}-amino)-butyryl]-piperazine-1-carboxylic acid ethyl ester The title compound was prepared by adapting the procedures described in example 23 with the difference that azetidine-3-carboxylic acid cyclobutylamide hydrochloride was used instead of (R)-3-pyrrolidinol hydrochloride.
Yield: 63 mg MS (ES+): m/e=668.

Example 44

4-[(S)-4-Carboxy-2-({5-[2-((S)-2-cyclopropylcarbamoyl-pyrrolidin-1-yl)-1,1-dimethyl-2-oxo-ethoxy]-1-phenyl-1H-pyrazole-3-carbonyl}-amino)-butyryl]-piperazine-1-carboxylic acid ethyl ester (i) 4-((S)-4-tert-Butoxycarbonyl-2-{[5-(1-carboxy-1-methyl-ethoxy)-1-phenyl-1H-pyrazole-3-carbonyl]-amino}-butyryl)-piperazine-1-carboxylic acid ethyl ester To a solution of 1 g 4-{(S)-4-tert-butoxycarbonyl-2-[(5-hydroxy-1-phenyl-1H-pyrazole-3-carbonyl)-amino]-butyryl}-piperazine-1-carboxylic acid ethyl ester in 100 ml DMF were subsequently added 646 μl methyl 2-bromoisobutyrate and 1.8 g cesium carbonate over a period of 4 h. After stirring at RT for 2 h the solution was acidified with 1 M HCl, diluted with 100 ml ethyl acetate and extracted with aqueous LiCl (4% w/w). The crude product obtained after evaporation of the solvent was purified by flash chromatography on silica eluting with a gradient of n-heptane/ethyl acetate to yield the corresponding methyl ester as yellowish oil (710 mg). The ester was taken up in THF/MeOH/H₂O 4/1/1 (6 ml) and treated with 45 mg LiOH at 0° C. After complete conversion the reaction mixture was acidified to pH 5 and evaporated under reduced pressure. The crude product thus obtained (610 mg) was not further purified.

(ii) 4-[(S)-4-Carboxy-2-({5-[2-((S)-2-cyclopropyl-carbamoyl-pyrrolidin-1-yl)-1,1-dimethyl-2-oxo-ethoxy]-1-phenyl-1H-pyrazole-3-carbonyl}-amino)-butyryl]-piperazine-1-carboxylic acid ethyl ester To a solution of 100 mg 4-((S)-4-tert-butoxycarbonyl-2-{[5-(1-carboxy-1-methyl-ethoxy)-1-phenyl-1H-pyrazole-3-carbonyl]-amino}-butyryl)-piperazine-1-carboxylic acid ethyl ester in 5 ml DMF were added 37 mg HOBt, 47 mg EDC and 65 μl DIPEA. After 20 minutes 47 mg (S)-pyrrolidine-2-carboxylic acid cyclopropylamide hydrochloride were added and the mixture stirred at RT for 6 h. The solvent was evaporated, the residue dissolved in ethyl acetate and subsequently extracted with aqueous LiCl (4% w/w), 0.1 M HCl and aqueous NaHCO₃. The organic layer was dried over MgSO₄ and the solvent was removed under reduced pressure. The crude product was dissolved in 2.5 ml DCM and treated with 500 μl TFA. After stirring for 12 h the solvents were removed under reduced pressure and the residue purified by preparative HPLC (C18 reverse phase column, elution with a water/MeCN gradient with 0.1% TFA). The product was obtained as its trifluoroacetate salt. Yield: 80 mg MS (ES+): m/e=696.

Example 45

4-[(S)-4-Carboxy-2-({5-[2-((2S,4R)-4-hydroxy-2-methoxycarbonyl-pyrrolidin-1-yl)-1,1-dimethyl-2-oxo-ethoxy]-1-phenyl-1H-pyrazole-3-carbonyl}-amino)-butyryl]-piperazine-1-carboxylic acid ethyl ester The title compound was prepared by adapting the procedures described in example 44 with the difference that trans-4-hydroxy-L-proline methyl ester hydrochloride was used instead of (S)-pyrrolidine-2-carboxylic acid cyclopropylamide hydrochloride.
Yield: 54 mg MS (ES+): m/e=687.

Example 46

4-[(S)-4-Carboxy-2-({5-[2-((3S,4S)-3,4-dihydroxy-pyrrolidin-1-yl)-1,1-dimethyl-2-oxo-ethoxy]-1-phenyl-1H-pyrazole-3-carbonyl}-amino)-butyryl]-piperazine-1-carboxylic acid ethyl ester The title compound was prepared by adapting the procedures described in example 44 with the difference that (3S,4S)-3,4-Bis-(tert-butyl-dimethyl-silanyloxy)-pyrrolidine was used instead of (S)-pyrrolidine-2-carboxylic acid cyclopropylamide hydrochloride and that the crude product after TFA treatment was desilylated using tetra-n-butyl ammonium fluoride in THF prior to preparative chromatography.
Yield: 20 mg MS (ES+): m/e=645.

Example 47

4-[(S)-4-Carboxy-2-({5-[2-((R)-2-cyclopropylcarbamoyl-pyrrolidin-1-yl)-1,1-dimethyl-2-oxo-ethoxy]-1-phenyl-1H-pyrazole-3-carbonyl}-amino)-butyryl]-piperazine-1-carboxylic acid ethyl ester The title compound was prepared by adapting the procedures described in example 44 with the difference that (R)-pyrrolidine-2-carboxylic acid cyclopropylamide hydrochloride was used instead of (S)-pyrrolidine-2-carboxylic acid cyclopropylamide hydrochloride.
Yield: 140 mg MS (ES+): m/e=696.

Example 48

4-[(S)-4-Carboxy-2-({5-[2-((2S,4R)-4-hydroxy-2-methoxycarbonyl-pyrrolidin-1-yl)-1-methyl-2-oxo-ethoxy]-1-phenyl-1H-pyrazole-3-carbonyl}-amino)-butyryl]piperazine-1-carboxylicacid ethyl ester (i) 4-((S)-4-Carboxy-2-{[5-(1-carboxy-ethoxy)-1-phenyl-1H-pyrazole-3-carbonyl]-amino}-butyryl)-piperazine-1-carboxylic acid ethyl ester To a solution of 1.50 g 4-{(S)-4-tert-butoxycarbonyl-2-[(5-hydroxy-1-phenyl-1H-pyrazole-3-carbonyl)-amino]-butyryl}-piperazine-1-carboxylic acid ethyl ester in 12 ml DMF were added 670 µl ethyl 2-bromopropionate and 3.2 g cesium carbonate. After stirring at RT for 24 h the solution was diluted with ethyl acetate and extracted with aqueous LiCl (4 w/w). The crude product obtained after evaporation of the solvent was dissolved in THF and treated with 1 N NaOH. When conversion was complete (4 h) Amberlite IR-120® was added, the suspension filtrated and the filtrate evaporated to give the crude product (1.56 g)

(ii) 4-[(S)-4-Carboxy-2-({5-[2-((2S,4R)-4-hydroxy-2-methoxycarbonyl-pyrrolidin-1-yl)-1-methyl-2-oxo-ethoxy]-1-phenyl-1H-pyrazole-3-carbonyl}-amino)-butyryl]piperazine-1-carboxylicacid ethyl ester To a solution of 100 mg 4-((S)-4-tert-butoxycarbonyl-2-{[5-(1-carboxy-ethoxy)-1-phenyl-1H-pyrazole-3-carbonyl]-amino}-butyryl)-piperazine-1-carboxylic acid ethyl ester in 2 ml DMF were added 38 mg HOBt, 48 mg EDC and 63 µl DIPEA. After 20 minutes 45 mg trans-4-hydroxy-L-proline methyl ester hydrochloride were added and the mixture stirred at RT for 16 h. Saturated NaHCO₃ solution (1.5 ml) was added and the mixture passed through a Chem Elute® cartridge eluting with DCM. The crude product obtained after evaporation of the solvent was dissolved in 1 ml DCM and treated with 100 µl TFA. After stirring for 12 h the solvents were removed under reduced pressure and the residue purified by preparative HPLC (C18 reverse phase column, elution with a water/MeCN gradient with 0.1% TFA). The product was obtained as its trifluoroacetate salt.
Yield: 8 mg MS (ES+): m/e=673.

Example 49

4-[(S)-4-Carboxy-2-({5-[2-((3S,4S)-3,4-dihydroxy-pyrrolidin-1-yl)-1-methyl-2-oxo-ethoxy]-1-phenyl-1H-pyrazole-3-carbonyl}-amino)-butyryl]-piperazine-1-carboxylicacid ethyl ester The title compound was prepared by adapting the procedures described in example 48 with the difference that (3S,4S)-3,4-Bis-(tert-butyl-dimethyl-silanyloxy)-pyrrolidine was used instead of trans-4-hydroxy-L-proline methyl ester hydrochloride and that desilylation was performed prior to TFA treatment using tris(dimethylamino)-sulfur-trimethylsilyl-difluoride in DMF. Yield: 10 mg MS (ES+): m/e=631.

Example 50

4-[(S)-4-Carboxy-2-({5-[2-((S)-2-cyclopropylcarbamoyl-pyrrolidin-1-yl)-1-methyl-2-oxo-ethoxy]-1-phenyl-1H-pyrazole-3-carbonyl}-amino)-butyryl]-piperazine-1-carboxylic acid ethyl ester The title compound was prepared by adapting the procedures described in example 48 with the difference that (S)-pyrrolidine-2-carboxylic acid cyclopropylamide hydrochloride was used instead of trans-4-hydroxy-L-proline methyl ester hydrochloride.
Yield: 25 mg MS (ES+): m/e=682.

Example 51

4-[(S)-4-Carboxy-2-({5-[2-((S)-2-cyclopropylcarbamoyl-azetidin-1-yl)-1-methyl-2-oxo-ethoxy]-1-phenyl-1H-pyrazole-3-carbonyl}-amino)-butyryl]-piperazine-1-carboxylic acid ethyl ester The title compound was prepared by adapting the procedures described in example 48 with the difference that (S)-Azetidine-2-carboxylic acid cyclopropylamide hydrochloride was used instead of trans-4-hydroxy-L-proline methyl ester hydrochloride.
Yield: 11 mg MS (ES+): m/e=668.

Example 52

4-[(S)-4-Carboxy-2-({5-[2-((S)-2-carboxy-pyrrolidin-1-yl)-1-methyl-2-oxo-ethoxy]-1-phenyl-1H-pyrazole-3-carbonyl}-amino)-butyryl]-piperazine-1-carboxylic acid ethyl ester The title compound was prepared by adapting the procedures described in example 48 with the difference that L-proline benzyl ester hydrochloride was used instead of trans-4-hydroxy-L-proline methyl ester hydrochloride and that purification of the crude product was performed by flash chromatography on silica eluting with a DCM/methanol gradient. The pure product thus obtained (477 mg) was debenzylated using Pd/C (10%) and hydrogen using ethyl acetate as solvent. The reaction mixture was filtrated via a plug of Celite® and washed with ethyl acetate. Final deprotection with TFA in DCM yielded the product.

Yield: 183 mg MS (ES+): m/e=643.

Example 53

4-{(S)-4-Carboxy-2-[(5-{1-methyl-2-oxo-2-[(S)-2-(2,2,2-trifluoro-ethylcarbamoyl)-pyrrolidin-1-yl]-ethoxy}-1-phenyl-1H-pyrazole-3-carbonyl)-amino]-butyryl}-piperazine-1-carboxylic acid ethyl ester The title compound was prepared by adapting the procedures described in example 48 with the difference that debenzylation was followed by reaction with 2,2,2-trifluoroethylamine using EDC/HOBt and DIPEA as coupling reagents.

Yield: 15 mg MS (ES+): m/e=724.

Example 54

4-[(S)-4-Carboxy-2-({5-[2-((S)-2-dimethylcarbamoyl-pyrrolidin-1-yl)-1-methyl-2-oxo-ethoxy]-1-phenyl-1H-pyrazole-3-carbonyl}-amino)-butyryl]-piperazine-1-carboxylic acid ethyl ester The title compound was prepared by adapting the procedures described in example 53 with the difference that dimethylamine hydrochloride was used instead of 2,2,2-trifluoroethylamine. Yield: 49 mg MS (ES+): m/e=670.

Example 55

4-{(S)-3-Carboxy-2-[(5-{2-[(S)-2-(cyclopropylmethyl-carbamoyl)-pyrrolidin-1-yl]-2-oxo-ethoxy}-1-phenyl-1H-pyrazole-3-carbonyl)-amino]-propionyl}-piperazine-1-carboxylic acid ethyl ester (i) 4-{(S)-3-tert-Butoxycarbonyl-2-[(5-hydroxy-1-phenyl-1H-pyrazole-3-carbonyl)-amino]-propionyl}-piperazine-1-carboxylic acid ethyl ester To a solution of 6.6 g 1-phenyl-3-carboxy-5-pyrazolone and 10.6 g 4-((S)-2-Amino-3-tert-butoxycarbonyl-propionyl)-piperazine-1-carboxylic acid ethyl ester in 30 ml DMF 4.9 g HOBT, 10.6 ml DIPEA and 6.2 g EDC were added and the reaction mixture was stirred for 16 h at RT. Then the reaction mixture was evaporated, diluted with ethyl acetate and subsequently extracted with aqueous LiCl (4% w/w) and aqueous NaHCO₃. The organic layer was dried over MgSO₄ and the solvent was removed under reduced pressure. The crude product thus obtained was used in the subsequent reaction.

Yield: 14.0 g.

(ii) 4-{(S)-2-[(5-Benzyloxycarbonylmethoxy-1-phenyl-1H-pyrazole-3-carbonyl)-amino]-3-tert-butoxycarbonyl-propionyl}-piperazine-1-carboxylic acid ethyl ester To a solution of 8.0 g 4-{(S)-3-tert-Butoxycarbonyl-2-[(5-hydroxy-1-phenyl-1H-pyrazole-3-carbonyl)-amino]propionyl}-piperazine-1-carboxylic acid ethyl ester in 50 ml DMF were added 2.5 ml benzyl bromoacetate and 10.1 g cesium carbonate. After stirring at RT for 12 h the solution was reduced to a volume of 50 ml, diluted with 400 ml ethyl acetate and extracted with aqueous LiCl (4% w/w) and aqueous NaHCO₃. The crude product obtained after evaporation of the solvent was used in the subsequent reaction.

Yield: 11.6 g.

(iii) 4-{(S)-3-tert-Butoxycarbonyl-2-[(5-carboxymethoxy-1-phenyl-1H-pyrazole-3-carbonyl)-amino]-propionyl}-piperazine-1-carboxylic acid ethyl ester To a solution of 11.6 g 4-{(S)-2-[(5-Benzyloxycarbonylmethoxy-1-phenyl-1H-pyrazole-3-carbonyl)-amino]-3-tert-butoxycarbonyl-propionyl}-piperazine-1-carboxylic acid ethyl ester in 60 ml ethyl acetate were added under argon 1.5 g Pd/C (10%) and the suspension was stirred under an atmosphere of hydrogen (3 bar) for 16 h. The suspension was filtered over a plug of Celite® and washed with ethyl acetate. The crude product obtained after evaporation of the solvent was dried under vacuo.

Yield: 8.3 g.

(iv) 4-[(S)-2-({5-[2-((S)-2-Benzyloxycarbonyl-pyrrolidin-1-yl)-2-oxo-ethoxy]-1-phenyl-1H-pyrazole-3-carbonyl}-amino)-3-tert-butoxycarbonyl-propionyl]-piperazine-1-carboxylic acid ethyl ester To a solution of 3.0 g 4-[(S)-2-({5-[2-((S)-2-Benzyloxycarbonyl-pyrrolidin-1-yl)-2-oxo-ethoxy]-1-phenyl-1H-pyrazole-3-carbonyl}-amino)-3-tert-butoxycarbonyl-propionyl]-piperazine-1-carboxylic acid ethyl ester in 10 ml DMF were added 0.8 g HOBt, 1.8 ml DIPEA and 1.3 g L-proline benzyl ester hydrochloride at RT. Then 1.0 g EDC was added portionwise and the suspension stirred at RT for 12 h. The reaction mixture was diluted with ethyl acetate and subsequently extracted with aqueous LiCl (4% w/w), 0.1 M HCl and aqueous NaHCO₃. The organic layer was dried over MgSO₄ and the solvent was removed under reduced pressure. The crude product thus obtained was used in the subsequent reaction. Yield: 4.0 g.

(v) 4-[(S)-3-tert-Butoxycarbonyl-2-({5-[2-((S)-2-carboxy-pyrrolidin-1-yl)-2-oxo-ethoxy]-1-phenyl-1H-pyrazole-3-carbonyl}-amino)-propionyl]-piperazine-1-carboxylic acid ethyl ester To a solution of 4.0 g 4-[(S)-2-({5-[2-((S)-2-Benzyloxycarbonyl-pyrrolidin-1-yl)-2-oxo-ethoxy]-1-phenyl-1H-pyrazole-3-carbonyl}-amino)-3-tert-butoxycarbonyl-propionyl]-piperazine-1-carboxylic acid ethyl ester in 50 ml ethyl acetate were added under argon 0.5 g Pd/C (10%) and the suspension was stirred under an atmosphere of hydrogen (3 bar) for 24 h. The suspension was filtered over a plug of Celite® and washed with ethyl acetate. The crude product obtained after evaporation of the solvent was used in the subsequent reaction. Yield: 3.0 g colorless foam.

(vi) 4-{(S)-3-Carboxy-2-[(5-{2-[(S)-2-(cyclopropyl methyl-carbamoyl)-pyrrolidin-1-yl]-2-oxo-ethoxy}-1-phenyl-1H-pyrazole-3-carbonyl)-amino]-propionyl}-piperazine-1-carboxylic acid ethyl ester To a solution of 300 mg 4-[(S)-3-tert-Butoxycarbonyl-2-({5-[2-((S)-2-carboxy-pyrrolidin-1-yl)-2-oxo-ethoxy]-1-phenyl-1H-pyrazole-3-carbonyl}-amino)-propionyl]-piperazine-1-carboxylic acid ethyl ester in 5 ml DMF were added 76 μl DIPEA and 170 mg HATU. After 20 minutes 39 μl aminomethylcyclopropane were added and the reaction mixture stirred for 12 h. After evaporation of the solvent the crude product was dissolved in 5 ml DCM and treated with 695 μl TFA. After stirring for 4 h the solvents were removed under reduced pressure and the residue immediately purified by preparative HPLC (C18 reverse phase column, elution with a water/MeCN gradient with 0.1% TFA). The fractions containing the product were immediately lyophilized to yield the pure product as its trifluoroacetate salt.

Yield: 150 mg MS (ES+): m/e=668.

Example 56

4-[(S)-3-Carboxy-2-({5-[2-((S)-2-cyclopropylcarbamoyl-pyrrolidin-1-yl)-2-oxo-ethoxy]-1-phenyl-1H-pyrazole-3-carbonyl}-amino)-propionyl]-piperazine-1-carboxylic acid ethyl ester The title compound was prepared by adapting the procedures described in example 55 with the difference that cyclopropylamine was used instead of aminomethylcyclopropane.
Yield: 156 mg MS (ES+): m/e=654.

Example 57

4-{(S)-3-Carboxy-2-[(5-{2-[(S)-2-(2,2-difluoro-ethylcarbamoyl)-pyrrolidin-1-yl]-2-oxo-ethoxy}-1-phenyl-1H-pyrazole-3-carbonyl)-amino]-propionyl}-piperazine-1-carboxylic acid ethyl ester The title compound was prepared by adapting the procedures described in example 55 with the difference that 2,2-difluoroethylamine was used instead of aminomethylcyclopropane. Yield: 157 mg MS (ES+): m/e=678.

Example 58

4-{(S)-3-Carboxy-2-[(5-{2-[(S)-2-(2,2,2-trifluoro-ethylcarbamoyl)-pyrrolidin-1-yl]-2-oxo-ethoxy}-1-phenyl-1H-pyrazole-3-carbonyl)-amino]-propionyl}-piperazine-1-carboxylic acid ethyl ester The title compound was prepared by adapting the procedures described in example 55 with the difference that 2,2,2-trifluoroethylamine was used instead of aminomethylcyclopropane. Yield: 157 mg MS (ES+): m/e=696.

Example 59

4-{(S)-3-Carboxy-2-[(5-{2-[(S)-2-(2-fluoro-ethylcarbamoyl)-pyrrolidin-1-yl]-2-oxo-ethoxy}-1-phenyl-1H-pyrazole-3-carbonyl)-amino]-propionyl}-piperazine-1-carboxylic acid ethyl ester The title compound was prepared by adapting the procedures described in example 55 with the difference that 2-fluoroethylamine hydrochloride was used instead of aminomethylcyclopropane. Yield: 146 mg MS (ES+): m/e=660.

Example 60

4-[(S)-3-Carboxy-2-({5-[2-oxo-2-(2-oxo-pyrrolidin-1-yl)-ethoxy]-1-phenyl-1H-pyrazole-3-carbonyl}-amino)-butyryl]-piperazine-1-carboxylic acid ethyl ester To a solution of 100 mg 4-{(S)-4-tert-butoxycarbonyl-2-[(5-hydroxy-1-phenyl-1H-pyrazole-3-carbonyl)-amino]-butyryl}-piperazine-1-carboxylic acid ethyl ester in 5 ml DMF were added 31 mg 1-(2-chloro-acetyl)-pyrrolidin-2-on and 62 mg cesium carbonate. After stirring at RT for 12 h the reaction mixture was diluted with ethyl acetate and extracted with water. The product obtained after evaporation of the solvent was treated with 0.4 ml TFA in 1.5 ml DCM. After stirring for 24 h the solvents were evaporated and the residue was purified by preparative HPLC (C18 reverse phase column, elution with a water/MeCN gradient with 0.1% TFA). The product was obtained as its trifluoroacetate salt.

Yield: 8 mg MS (ES+): m/e=599.

Example 61

4-[(S)-4-Carboxy-2-({5-[(R)-2-((S)-2-cyclopropylcarbamoyl-pyrrolidin-1-yl)-1-methyl-2-oxo-ethoxy]-1-phenyl-1H-pyrazole-3-carbonyl}-amino)-butyryl]-piperazine-1-carboxylic acid ethyl ester (i) 4-((S)-2-{[5-((R)-1-Benzyloxycarbonyl-ethoxy)-1-phenyl-1H-pyrazole-3-carbonyl]-amino}-4-tert-butoxycarbonyl-butyryl)-piperazine-1-carboxylic acid ethyl ester To a solution of 4.00 g 4-{(S)-4-tert-Butoxycarbonyl-2-[(4-hydroxy-6-phenyl-pyridine-2-carbonyl)-amino]-butyryl}-piperazine-1-carboxylic acid ethyl ester in 30 ml DMF were added 1.84 g (S)-2-bromo-propionic acid benzyl ester (prepared by standard benzylation procedure using (S)-2-bromopropionic acid and benzyl alcohol/p-TsOH) and 4.92 g cesium carbonate. After stirring at RT for 12 h the solution was diluted with 100 ml ethyl acetate and extracted with aqueous LiCl (4% w/w). The crude product obtained after evaporation of the solvent was used in the subsequent reaction.

Yield: 5.90 g.

(ii) 4-((S)-4-tert-Butoxycarbonyl-2-{[5-((R)-1-carboxy-ethoxy)-1-phenyl-1H-pyrazole-3-carbonyl]-amino}-butyryl)-piperazine-1-carboxylic acid ethyl ester To a solution of 5.90 g 4-((S)-2-{[5-((R)-1-Benzyloxycarbonyl-ethoxy)-1-phenyl-1H-pyrazole-3-carbonyl]-amino}-4-tert-butoxycarbonyl-butyryl)-piperazine-1-carboxylic acid ethyl ester in 30 ml ethyl acetate were added under argon 1.0 g Pd/C (10%) and the suspension was stirred under an atmosphere of hydrogen (1 bar) for 16 h. The suspension was filtered over a plug of Celite® and washed with ethyl acetate. The crude product obtained after evaporation of the solvent was dried under vacuo. Yield: 4.69 g.

(iii) 4-[(S)-2-({5-[(R)-2-((S)-2-Benzyloxycarbonyl-pyrrolidin-1-yl)-1-methyl-2-oxo-ethoxy]-1-phenyl-1H-pyrazole-3-carbonyl}-amino)-4-tert-butoxycarbonyl-butyryl]-piperazine-1-carboxylic acid ethyl ester To a solution of 2.000 g 4-((S)-4-tert-Butoxycarbonyl-2-{[5-((R)-1-carboxy-ethoxy)-1-phenyl-1H-pyrazole-3-carbonyl]-amino}-butyryl)-piperazine-1-carboxylic acid ethyl ester in 15 ml DMF were added 0.509 g HOBt, 1.4 ml DIPEA and 0.804 g L-proline benzyl ester hydrochloride at RT. Then 0.637 g EDC were added portionwise and the suspension stirred at RT for 12 h. The reaction mixture was diluted with ethyl acetate and subsequently extracted with aqueous LiCl (4% w/w), aqueous NaHCO₃ and brine. The organic layer

73 was dried over MgSO₄ and the solvent was removed under reduced pressure. The crude product thus obtained was used in the subsequent reaction.

Yield: 2.640 g.

(iv) 4-[(S)-4-tert-Butoxycarbonyl-2-({5-[(R)-2-((S)-2-carboxy-pyrrolidin-1-yl)-1-methyl-2-oxo-ethoxy]-1-phenyl-1H-pyrazole-3-carbonyl}-amino)-butyryl]-piperazine-1-carboxylic acid ethyl ester To a solution of 2.640 g 4-[(S)-2-({5-[(R)-2-((S)-2-Benzyloxycarbonyl-pyrrolidin-1-yl)-1-methyl-2-oxo-ethoxy]-1-phenyl-1H-pyrazole-3-carbonyl}-amino)-4-tert-butoxycarbonyl-butyryl]-piperazine-1-carboxylic acid ethyl ester in 50 ml ethyl acetate were added under argon 0.5 g Pd/C (10%) and the suspension was stirred under an atmosphere of hydrogen (1 bar) for 24 h. The suspension was filtered over a plug of Celite® and washed with ethyl acetate. The crude product obtained after evaporation of the solvent was used in the subsequent reaction.

Yield: 1.895 g colorless foam.

(v) 4-[(S)-4-Carboxy-2-({5-[(R)-2-((S)-2-cyclopropylcarbamoyl-pyrrolidin-1-yl)-1-methyl-2-oxo-ethoxy]-1-phenyl-1H-pyrazole-3-carbonyl}-amino)-butyryl]-piperazine-1-carboxylic acid ethyl ester To a solution of 200 mg 4-[(S)-4-tert-Butoxycarbonyl-2-({5-[(R)-2-((S)-2-carboxy-pyrrolidin-1-yl)-1-methyl-2-oxo-ethoxy]-1-phenyl-1H-pyrazole-3-carbonyl}-amino)-butyryl]-piperazine-1-carboxylic acid ethyl ester in 2 ml DMF were added 20 µl DIPEA and 108 mg HATU. After 20 minutes 22 µl cyclopropylamine were added and the reaction mixture stirred for 12 h. After evaporation of the solvent the crude product was dissolved in 2 ml DCM and treated with 200 µl TFA. After stirring for 4 h the solvents were removed under reduced pressure and the residue purified by preparative HPLC (C18 reverse phase column, elution with a water/MeCN gradient with 0.1% TFA). The fractions containing the product were lyophilized to yield the pure product as its trifluoroacetate salt.

Yield: 111 mg MS (ES+): m/e=682.

Example 62

4-[(S)-4-Carboxy-2-({5-[(R)-2-((S)-2-cyclobutylcarbamoyl-pyrrolidin-1-yl)-1-methyl-2-oxo-ethoxy]-1-phenyl-1H-pyrazole-3-carbonyl}-amino)-butyryl]-piperazine-1-carboxylic acid ethyl ester The title compound was prepared by adapting the procedures described in example 61 with the difference that cyclobutylamine was used instead of cyclopropylamine.

Yield: 104 mg MS (ES+): m/e=696.

Example 63

4-[(S)-4-Carboxy-2-({5-[(R)-2-((S)-2-cyclopropylmethylcarbamoyl-pyrrolidin-1-yl)-1-methyl-2-oxo-ethoxy]-1-phenyl-1H-pyrazole-3-carbonyl}-amino)-butyryl]-piperazine-1-carboxylic acid ethyl ester The title compound was prepared by adapting the procedures described in example 61 with the difference that aminomethylcyclopropane was used instead of cyclopropylamine.

Yield: 104 mg MS (ES+): m/e=696.

74

Example 64

4-{(S)-4-Carboxy-2-[(5-{(R)-1-methyl-2-oxo-2-[(S)-2-(pyrrolidine-1-carbonyl)-pyrrolidin-1-yl]-ethoxy}-1-phenyl-1H-pyrazole-3-carbonyl)-amino]-butyryl}-piperazine-1-carboxylic acid ethyl ester The title compound was prepared by adapting the procedures described in example 61 with the difference that pyrrolidine was used instead of cyclopropylamine.

Yield: 90 mg MS (ES+): m/e=696.

Example 65

4-[(S)-4-Carboxy-2-({5-[(R)-2-((S)-2-(2,2,2-trifluoroethylcarbamoyl)-pyrrolidin-1-yl)-1-methyl-2-oxoethoxy]-1-phenyl-1H-pyrazole-3-carbonyl}-amino)-butyryl]-piperazine-1-carboxylic acid ethyl ester The title compound was prepared by adapting the procedures described in example 61 with the difference that 2,2,2-trifluoroethylamine was used instead of cyclopropylamine.

Yield: 104 mg MS (ES+): m/e=724.

Example 66

4-[(S)-4-Carboxy-2-({5-[(S)-2-((S)-2-cyclopropylcarbamoyl-pyrrolidin-1-yl)-1-methyl-2-oxo-ethoxy]-1-phenyl-1H-pyrazole-3-carbonyl}-amino)-butyryl]-piperazine-1-carboxylic acid ethyl ester (i) 4-((S)-2-{[5-((S)-1-Benzyloxycarbonyl-ethoxy)-1-phenyl-1H-pyrazole-3-carbonyl]-amino}-4-tert-butoxycarbonyl-butyryl)-piperazine-1-carboxylic acid ethyl ester To a solution of 4.00 g 4-{(S)-4-tert-Butoxycarbonyl-2-[(4-hydroxy-6-phenyl-pyridine-2-carbonyl)-amino]-butyryl}-piperazine-1-carboxylic acid ethyl ester in 30 ml DMF were added 1.84 g (R)-2-bromo-propionic acid benzyl ester (prepared by standard benzylation procedure using (R)-2-bromopropionic acid and benzyl alcohol p-TsOH) and 4.92 g cesium carbonate. After stirring at RT for 12 h the solution was diluted with 100 ml ethyl acetate and extracted with aqueous LiCl (4% w/w). The crude product obtained after evaporation of the solvent was used in the subsequent reaction. Yield: 5.84 g.

(ii) 4-((S)-4-tert-Butoxycarbonyl-2-{[5-((S)-1-carboxy-ethoxy)-1-phenyl-1H-pyrazole-3-carbonyl]-amino}-butyryl)-piperazine-1-carboxylic acid ethyl ester To a solution of 5.84 g 4-((S)-2-{[5-((S)-1-Benzyloxycarbonyl-ethoxy)-1-phenyl-1H-pyrazole-3-carbonyl]-amino}-4-tert-butoxycarbonyl-butyryl)-piperazine-1-carboxylic acid ethyl ester in 30 ml ethyl acetate was added under argon 1.0 g Pd/C (10%) and the suspension was stirred under an atmosphere of hydrogen (1 bar) for 16 h. The suspension was filtered over a plug of Celite® and washed with ethyl acetate.

The crude product obtained after evaporation of the solvent was dried under vacuo. Yield: 4.59 g.

(iii) 4-[(S)-2-({5-[(S)-2-((S)-2-Benzyloxycarbonyl-pyrrolidin-1-yl)-1-methyl-2-oxo-ethoxy]-1-phenyl-1H-pyrazole-3-carbonyl}-amino)-4-tert-butoxycarbonyl-butyryl]-piperazine-1-carboxylic acid ethyl ester To a solution of 2.000 g 4-((S)-4-tert-Butoxycarbonyl-2-{[5-((S)-1-carboxy-ethoxy)-1-phenyl-1H-pyrazole-3-carbonyl]-amino}-butyryl)-piperazine-1-carboxylic acid ethyl ester in 15 ml DMF were added 0.509 g HOBt, 1.37 ml DIPEA and 0.804 g L-proline benzyl ester hydrochloride at RT. Then 0.637 g EDC was added portionwise and the suspension stirred at RT for 12 h. The reaction mixture was diluted with ethyl acetate and subsequently extracted with aqueous LiCl (4% w/w), aqueous NaHCO$_3$ and brine. The organic layer was dried over MgSO$_4$ and the solvent was removed under reduced pressure. The crude product thus obtained was used in the subsequent reaction. Yield: 2.177 g.

(iv) 4-[(S)-4-tert-Butoxycarbonyl-2-({5-[(S)-2-((S)-2-carboxy-pyrrolidin-1-yl)-1-methyl-2-oxo-ethoxy]-1-phenyl-1H-pyrazole-3-carbonyl}-amino)-butyryl]-piperazine-1-carboxylic acid ethyl ester To a solution of 2.177 g 4-[(S)-2-({5-[(S)-2-((S)-2-Benzyloxycarbonyl-pyrrolidin-1-yl)-1-methyl-2-oxo-ethoxy]-1-phenyl-1H-pyrazole-3-carbonyl}-amino)-4-tert-butoxycarbonyl-butyryl]-piperazine-1-carboxylic acid ethyl ester in 50 ml ethyl acetate were added under argon 0.5 g Pd/C (10%) and the suspension was stirred under an atmosphere of hydrogen (1 bar) for 24 h. The suspension was filtered over a plug of Celite® and washed with ethyl acetate. The crude product obtained after evaporation of the solvent was used in the subsequent reaction. Yield: 1.784 g colorless foam.

(v) 4-[(S)-4-Carboxy-2-({5-[(S)-2-((S)-2-cyclopropylcarbamoyl-pyrrolidin-1-yl)-1-methyl-2-oxo-ethoxy]-1-phenyl-1H-pyrazole-3-carbonyl}-amino)-butyryl]-piperazine-1-carboxylic acid ethyl ester To a solution of 200 mg 4-[(S)-4-tert-Butoxycarbonyl-2-({5-[(S)-2-((S)-2-carboxy-pyrrolidin-1-yl)-1-methyl-2-oxo-ethoxy]-1-phenyl-1H-pyrazole-3-carbonyl}-amino)-butyryl]-piperazine-1-carboxylic acid ethyl ester in 2 ml DMF were added 20 μl DIPEA and 108 mg HATU. After 20 minutes 22 μl cyclopropylamine were added and the reaction mixture stirred for 12 h. After evaporation of the solvent the crude product was dissolved in 2 ml DCM and treated with 200 μl TFA. After stirring for 4 h the solvents were removed under reduced pressure and the residue purified by preparative HPLC (C18 reverse phase column, elution with a water/MeCN gradient with 0.1% TFA). The fractions containing the product were immediately lyophilized to yield the pure product as its trifluoroacetate salt.
Yield: 115 mg MS (ES+): m/e=682.

Example 67

4-[(S)-4-Carboxy-2-({5-[(S)-2-((S)-2-cyclobutylcarbamoyl-pyrrolidin-1-yl)-1-methyl-2-oxo-ethoxy]-1-phenyl-1H-pyrazole-3-carbonyl}-amino)-butyryl]-piperazine-1-carboxylic acid ethyl ester The title compound was prepared by adapting the procedures described in example 66 with the difference that cyclobutylamine was used instead of cyclopropylamine.
Yield: 110 mg MS (ES+): m/e=696.

Example 68

4-[(S)-4-Carboxy-2-({5-[(S)-2-((S)-2-cyclopropylmethylcarbamoyl-pyrrolidin-1-yl)-1-methyl-2-oxo-ethoxy]-1-phenyl-1H-pyrazole-3-carbonyl}-amino)-butyryl]-piperazine-1-carboxylic acid ethyl ester The title compound was prepared by adapting the procedures described in example 66 with the difference that aminomethylcyclopropane was used instead of cyclopropylamine.
Yield: 108 mg MS (ES+): m/e=696.

Example 69

4-{(S)-4-Carboxy-2-[(5-{(S)-1-methyl-2-oxo-2-[(S)-2-(pyrrolidine-1-carbonyl)-pyrrolidin-1-yl]-ethoxy}-1-phenyl-1H-pyrazole-3-carbonyl)-amino]-butyryl}-piperazine-1-carboxylic acid ethyl ester The title compound was prepared by adapting the procedures described in example 66 with the difference that pyrrolidine was used instead of cyclopropylamine.
Yield: 96 mg MS (ES+): m/e=696.

Example 70

4-[(S)-4-Carboxy-2-({5-[(S)-2-((S)-2-(2,2,2-trifluoroethylcarbamoyl)-pyrrolidin-1-yl)-1-methyl-2-oxo-ethoxy]-1-phenyl-1H-pyrazole-3-carbonyl}-amino)-butyryl]-piperazine-1-carboxylic acid ethyl ester The title compound was prepared by adapting the procedures described in example 66 with the difference that 2,2,2-trifluoroethylamine was used instead of cyclopropylamine.
Yield: 114 mg MS (ES+): m/e=724.

Example 71

4-((S)-4-Carboxy-2-{[5-[2-((S)-2-cyclopropylcarbamoyl-pyrrolidin-1-yl)-2-oxo-ethoxy]-1-(3-fluoro-phenyl)-1H-pyrazole-3-carbonyl]-amino}-butyryl)-piperazine-1-carboxylic acid ethyl ester (i) 4-((S)-4-tert-Butoxycarbonyl-2-{[1-(3-fluoro-phenyl)-5-hydroxy-1H-pyrazole-3-carbonyl]-amino}-butyryl)-piperazine-1-carboxylic acid ethyl ester To a solution of 2.500 g 1-(3-fluoro-phenyl)-5-hydroxy-1H-pyrazole-3-carboxylic acid (prepared by standard procedure using 3-fluorophenylhydrazine hydrochloride and sodium diethyl-2-oxosuccinate followed by ester hydrolysis) and 3.864 g 4-((S)-2-amino-4-tert-butoxycarbonyl-butyryl)-piperazine-1-carboxylic acid ethyl ester in 20 ml DMF 1.723 g HOBt, 1.9 ml DIPEA and 2.157 g EDC were added and the reaction mixture was stirred for 16 h at RT. Then the reaction mixture was evaporated, diluted with ethyl acetate and subsequently extracted with aqueous LiCl (4% w/w) and aqueous NaHCO$_3$. The organic layer was dried over MgSO$_4$ and the solvent was removed under reduced pressure. The crude product thus obtained was used in the subsequent reaction.
Yield: 7.2 g.

(ii) 4-((S)-2-{[5-Benzyloxycarbonylmethoxy-1-(3-fluoro-phenyl)-1H-pyrazole-3-carbonyl]-amino}-4-tert-butoxycarbonyl-butyryl)-piperazine-1-carboxylic acid ethyl ester To a solution of 3.000 g 4-((S)-4-tert-Butoxycarbonyl-2-{[1-(3-fluoro-phenyl)-5-hydroxy-1H-pyrazole-3-carbonyl]-amino}-butyryl)-piperazine-1-carboxylic acid ethyl ester in 20 ml DMF were added 0.908 ml benzyl bromoacetate and 3.571 g cesium carbonate. After stirring at RT for 12 h the solution was reduced to a volume of 50 ml, diluted with 200 ml ethyl acetate and extracted with aqueous LiCl (4% w/w) and aqueous NaHCO$_3$. The crude product obtained after evaporation of the solvent was used in the subsequent reaction.
Yield: 3.11 g.

(iii) 4-((S)-4-tert-Butoxycarbonyl-2-{[5-carboxymethoxy-1-(3-fluoro-phenyl)-1H-pyrazole-3-carbonyl]-amino}-butyryl)-piperazine-1-carboxylic acid ethyl ester To a solution of 3.100 g 4-((S)-2-{[5-Benzyloxycarbonylmethoxy-1-(3-fluoro-phenyl)-1H-pyrazole-3-carbonyl]-amino}-4-tert-butoxycarbonyl-butyryl)-piperazine-1-carboxylic acid ethyl ester in 20 ml ethyl acetate were added under argon 0.5 g Pd/C (10%) and the suspension was stirred under an atmosphere of hydrogen (3 bar) for 16 h. The suspension was filtered over a plug of Celite® and washed with ethyl acetate. The crude product obtained after evaporation of the solvent was dried under vacuo. Yield: 2.77 g.

(iv) 4-((S)-2-{[5-[2-((S)-2-Benzyloxycarbonyl-pyrrolidin-1-yl)-2-oxo-ethoxy]-1-(3-fluoro-phenyl)-1H-pyrazole-3-carbonyl]-amino}-4-tert-butoxycarbonyl-butyryl)-piperazine-1-carboxylic acid ethyl ester To a solution of 2.000 g 4-((S)-4-tert-Butoxycarbonyl-2-{[5-carboxymethoxy-1-(3-fluoro-phenyl)-1H-pyrazole-3-carbonyl]-amino}-butyryl)-piperazine-1-carboxylic acid ethyl ester in 20 ml DMF were added 0.506 g HOBt, 1.2 ml DIPEA and 0.798 g L-proline benzyl ester hydrochloride at RT. Then 0.633 g EDC was added portionwise and the suspension stirred at RT for 12 h. The reaction mixture was diluted with ethyl acetate and subsequently extracted with aqueous LiCl (4% w/w), 0.1 M HCl and aqueous NaHCO$_3$. The organic layer was dried over MgSO$_4$ and the solvent was removed under reduced pressure. The crude product thus obtained was used in the subsequent reaction.
Yield: 2.24 g.

(v) 4-((S)-4-tert-Butoxycarbonyl-2-{[5-[2-((S)-2-carboxy-pyrrolidin-1-yl)-2-oxo-ethoxy]-1-(3-fluoro-phenyl)-1H-pyrazole-3-carbonyl]-amino}-butyryl)-piperazine-1-carboxylic acid ethyl ester To a solution of 2.24 g 4-((S)-2-{[5-[2-((S)-2-Benzyloxycarbonyl-pyrrolidin-1-yl)-2-oxo-ethoxy]-1-(3-fluoro-phenyl)-1H-pyrazole-3-carbonyl]-amino}-4-tert-butoxycarbonyl-butyryl)-piperazine-1-carboxylic acid ethyl ester in 25 ml ethyl acetate were added under argon 0.5 g Pd/C (10%) and the suspension was stirred under an atmosphere of hydrogen (3 bar) for 24 h. The suspension was filtered over a plug of Celite® and washed with ethyl acetate. The crude product obtained after evaporation of the solvent was used in the subsequent reaction. Yield: 1.80 g colorless foam.

(vi) 4-((S)-4-Carboxy-2-{[5-[2-((S)-2-cyclopropyl-carbamoyl-pyrrolidin-1-yl)-2-oxo-ethoxy]-1-(3-fluoro-phenyl)-1H-pyrazole-3-carbonyl]-amino}-butyryl)-piperazine-1-carboxylic acid ethyl ester To a solution of 200 mg 4-((S)-4-tert-Butoxycarbonyl-2-{[5-[2-((S)-2-carboxy-pyrrolidin-1-yl)-2-oxo-ethoxy]-1-(3-fluoro-phenyl)-1H-pyrazole-3-carbonyl]-amino}-butyryl)-piperazine-1-carboxylic acid ethyl ester in 5 ml DMF were added 261 µl DIPEA and 108 mg HATU. After 20 minutes 20 µl cyclopropylamine were added and the reaction mixture stirred for 12 h. After evaporation of the solvent the crude product was dissolved in 5 ml DCM and treated with 309 µl TFA. After stirring for 4 h the solvents were removed under reduced pressure and the residue purified by preparative HPLC (C18 reverse phase column, elution with a water/MeCN gradient with 0.1% TFA). The fractions containing the product were lyophilized to yield the pure product as its trifluoroacetate salt.
Yield: 16 mg MS (ES+): m/e=686.

Example 72

4-((S)-4-Carboxy-2-{[5-[2-((S)-2-(2-fluoroethylcarbamoyl)-pyrrolidin-1-yl)-2-oxo-ethoxy]-1-(3-fluoro-phenyl)-1H-pyrazole-3-carbonyl]-amino}-butyryl)-piperazine-1-carboxylic acid ethyl ester The title compound was prepared by adapting the procedures described in example 71 with the difference that 2-fluoroethylamine hydrochloride was used instead of cyclopropylamine. Yield: 67 mg MS (ES+): m/e=692.

Example 73

4-((S)-4-Carboxy-2-{[5-[2-((S)-2-cyclobutylcarbamoyl-pyrrolidin-1-yl)-2-oxo-ethoxy]-1-(3-fluoro-phenyl)-1H-pyrazole-3-carbonyl]-amino}-butyryl)-piperazine-1-carboxylic acid ethyl ester The title compound was prepared by adapting the procedures described in example 71 with the difference that cyclobutylamine was used instead of cyclopropylamine.
Yield: 70 mg MS (ES+): m/e=700.

Example 74

4-((S)-4-Carboxy-2-{[5-[2-((S)-2-cyclopropylmethylcarbamoyl-pyrrolidin-1-yl)-2-oxo-ethoxy]-1-(3-fluoro-phenyl)-1H-pyrazole-3-carbonyl]-amino}-butyryl)-piperazine-1-carboxylic acid ethyl ester The title compound was prepared by adapting the procedures described in example 71 with the difference that aminomethylcyclopropane was used instead of cyclopropylamine.
Yield: 63 mg MS (ES+): m/e=700.

Example 75

4-((S)-4-Carboxy-2-{[5-[2-((S)-2-(2,2,2-trifluoroethylcarbamoyl)-pyrrolidin-1-yl)-2-oxo-ethoxy]-1-(3-fluoro-phenyl)-1H-pyrazole-3-carbonyl]-amino}-butyryl)-piperazine-1-carboxylic acid ethyl ester The title compound was prepared by adapting the procedures described in example 71 with the difference that 2,2,2-trifluoroethylamine was used instead of cyclopropylamine.
Yield: 65 mg MS (ES+): m/e=728.

Example 76

4-((S)-4-Carboxy-2-{[5-[2-((S)-2-(2,2-difluoroethyl-carbamoyl)-pyrrolidin-1-yl)-2-oxo-ethoxy]-1-(3-fluoro-phenyl)-1H-pyrazole-3-carbonyl]-amino}-butyryl)-piperazine-1-carboxylic acid ethyl ester The title compound was prepared by adapting the procedures described in example 71 with the difference that 2,2-difluoroethylamine was used instead of cyclopropylamine. Yield: 50 mg MS (ES+): m/e=710.

Example 77

4-((S)-3-Carboxy-2-{[5-[2-((S)-2-cyclopropylmethyl-carbamoyl-pyrrolidin-1-yl)-2-oxo-ethoxy]-1-(3-fluoro-phenyl)-1H-pyrazole-3-carbonyl]-amino}-propionyl)-piperazine-1-carboxylic acid ethyl ester (i) 4-((S)-3-tert-Butoxycarbonyl-2-{[1-(3-fluoro-phenyl)-5-hydroxy-1H-pyrazole-3-carbonyl]-amino}-butyryl)-piperazine-1-carboxylic acid ethyl ester To a solution of 3.199 g 1-(3-fluoro-phenyl)-5-hydroxy-1H-pyrazole-3-carboxylic acid (prepared by standard procedure using 3-fluorophenylhydrazine hydrochloride and sodium diethyl-2-oxosuccinate followed by ester hydrolysis) and 4.743 g 4-((S)-2-amino-3-tert-butoxycarbonyl-propionyl)-piperazine-1-carboxylic acid ethyl ester in 26 ml DMF 2.205 g HOBt, 2.5 ml DIPEA and 2.760 g EDC were added and the reaction mixture was stirred for 16 h at RT. Then the reaction mixture was evaporated, diluted with ethyl acetate and subsequently extracted with aqueous LiCl (4% w/w) and aqueous NaHCO₃. The organic layer was dried over MgSO₄ and the solvent was removed under reduced pressure. The crude product thus obtained was used in the subsequent reaction.
Yield: 7.2 g.

(ii) 4-((S)-2-{[5-Benzyloxycarbonylmethoxy-1-(3-fluoro-phenyl)-1H-pyrazole-3-carbonyl]-amino}-3-tert-butoxycarbonyl-propionyl)-piperazine-1-carboxylic acid ethyl ester To a solution of 4.0 g 4-((S)-3-tert-Butoxycarbonyl-2-{[1-(3-fluoro-phenyl)-5-hydroxy-1H-pyrazole-3-carbonyl]-amino}-propionyl)-piperazine-1-carboxylic acid ethyl ester in 20 ml DMF were added 1.242 ml benzyl bromoacetate and 4.884 g cesium carbonate. After stirring at RT for 12 h the solution was reduced to a volume of 50 ml, diluted with 200 ml ethyl acetate and extracted with aqueous LiCl (4% w/w) and aqueous NaHCO₃. The crude product obtained after evaporation of the solvent was used in the subsequent reaction.
Yield: 4.15 g.

(iii) 4-((S)-3-tert-Butoxycarbonyl-2-{[5-carboxymethoxy-1-(3-fluoro-phenyl)-1H-pyrazole-3-carbonyl]-amino}-propionyl)-piperazine-1-carboxylic acid ethyl ester To a solution of 4.100 g 4-((S)-2-{[5-Benzyloxycarbonyl-methoxy-1-(3-fluoro-phenyl)-1H-pyrazole-3-carbonyl]-amino}-3-tert-butoxycarbonyl-propionyl)-piperazine-1-carboxylic acid ethyl ester in 30 ml ethyl acetate were added under argon 0.5 g Pd/C (10%) and the suspension was stirred under an atmosphere of hydrogen (3 bar) for 16 h. The suspension was filtered over a plug of Celite® and washed with ethyl acetate. The crude product obtained after evaporation of the solvent was dried under vacuo. Yield: 3.17 g.

(iv) 4-((S)-2-{[5-[2-((S)-2-Benzyloxycarbonyl-pyrrolidin-1-yl)-2-oxo-ethoxy]-1-(3-fluoro-phenyl)-1H-pyrazole-3-carbonyl]-amino}-3-tert-butoxycarbonyl-propionyl)-piperazine-1-carboxylic acid ethyl ester To a solution of 2.000 g 4-((S)-3-tert-Butoxycarbonyl-2-{[5-carboxymethoxy-1-(3-fluoro-phenyl)-1H-pyrazole-3-carbonyl]-amino}-propionyl)-piperazine-1-carboxylic acid ethyl ester in 20 ml DMF were added 0.518 g HOBt, 1.2 ml DIPEA and 0.817 g L-proline benzyl ester hydrochloride at RT. Then 0.648 g EDC was added portionwise and the suspension stirred at RT for 12 h. The reaction mixture was diluted with ethyl acetate and subsequently extracted with aqueous LiCl (4% w/w), 0.1 M HCl and aqueous NaHCO₃. The organic layer was dried over MgSO₄ and the solvent was removed under reduced pressure. The crude product thus obtained was used in the subsequent reaction. Yield: 2.5 g.

(v) 4-((S)-3-tert-Butoxycarbonyl-2-{[5-[2-((S)-2-carboxy-pyrrolidin-1-yl)-2-oxo-ethoxy]-1-(3-fluoro-phenyl)-1H-pyrazole-3-carbonyl]-amino}-propionyl)-piperazine-1-carboxylic acid ethyl ester To a solution of 2.50 g 4-((S)-2-{[5-[2-((S)-2-Benzyloxycarbonyl-pyrrolidin-1-yl)-2-oxo-ethoxy]-1-(3-fluoro-phenyl)-1H-pyrazole-3-carbonyl]-amino}-3-tert-butoxycarbonyl-propionyl)-piperazine-1-carboxylic acid ethyl ester in 25 ml ethyl acetate were added under argon 0.5 g Pd/C (10%) and the suspension was stirred under an atmosphere of hydrogen (3 bar) for 24 h. The suspension was filtered over a plug of Celite® and washed with ethyl acetate. The crude product obtained after evaporation of the solvent was used in the subsequent reaction. Yield: 2.06 g colorless foam.

(vi) 4-((S)-3-Carboxy-2-{[5-[2-((S)-2-cyclopropylmethyl-carbamoyl-pyrrolidin-1-yl)-2-oxo-ethoxy]-1-(3-fluoro-phenyl)-1H-pyrazole-3-carbonyl]-amino}-propionyl)-piperazine-1-carboxylic acid ethyl ester To a solution of 300 mg 4-((S)-3-tert-Butoxycarbonyl-2-{[5-[2-((S)-2-carboxy-pyrrolidin-1-yl)-2-oxo-ethoxy]-1-(3-fluoro-phenyl)-1H-pyrazole-3-carbonyl]-amino}-propionyl)-piperazine-1-carboxylic acid ethyl ester in 5 ml DMF were added 72 µl DIPEA and 166 mg HATU. After 20 minutes 38 µl aminomethylcyclopropane were added and the reaction mixture stirred for 12 h. After evaporation of the solvent the crude product was dissolved in 5 ml DCM and treated with 400 µl TFA. After stirring for 4 h the solvents were removed under reduced pressure and the residue immediately purified by preparative HPLC (C18 reverse phase column, elution with a water/MeCN gradient with 0.1% TFA). The fractions containing the product were lyophilized to yield the pure product as its trifluoroacetate salt.
Yield: 72 mg MS (ES+): m/e=686.

Example 78

4-((S)-3-Carboxy-2-{[5-[2-((S)-2-(2-fluoroethylcarbamoyl)-pyrrolidin-1-yl)-2-oxo-ethoxy]-1-(3-fluoro-phenyl)-1H-pyrazole-3-carbonyl]-amino}-propionyl)-piperazine-1-carboxylic acid ethyl ester The title compound was prepared by adapting the procedures described in example 77 with the difference that 2-fluo-

Example 79

4-((S)-3-Carboxy-2-{[5-[2-((S)-2-(2,2-difluoroethyl-carbamoyl)-pyrrolidin-1-yl)-2-oxo-ethoxy]-1-(3-fluoro-phenyl)-1H-pyrazole-3-carbonyl]-amino}-propionyl)-piperazine-1-carboxylic acid ethyl ester The title compound was prepared by adapting the procedures described in example 77 with the difference that 2,2-difluoroethylamine was used instead of aminomethylcyclopropane. Yield: 60 mg MS (ES+): m/e=696.

Example 80

4-((S)-3-Carboxy-2-{[5-[2-((S)-2-cyclopropyl-carbamoyl-pyrrolidin-1-yl)-2-oxo-ethoxy]-1-(3-fluoro-phenyl)-1H-pyrazole-3-carbonyl]-amino}-propionyl)-piperazine-1-carboxylic acid ethyl ester The title compound was prepared by adapting the procedures described in example 77 with the difference that cyclopropylamine was used instead of aminomethylcyclopropane. Yield: 64 mg MS (ES+): m/e=672.

Example 81

4-((S)-4-Carboxy-2-{[5-[2-((S)-2-cyclopropylcarbamoyl-pyrrolidin-1-yl)-2-oxo-ethoxy]-1-(3,4-difluoro-phenyl)-1H-pyrazole-3-carbonyl]-amino}-butyryl)-piperazine-1-carboxylic acid ethyl ester (i) 4-((S)-4-tert-Butoxycarbonyl-2-{[1-(3,4-difluoro-phenyl)-5-hydroxy-1H-pyrazole-3-carbonyl]-amino}-butyryl)-piperazine-1-carboxylic acid ethyl ester To a solution of 4.400 g 1-(3,4-difluoro-phenyl)-5-hydroxy-1H-pyrazole-3-carboxylic acid (prepared by standard procedure using 3,4-difluorophenylhydrazine hydrochloride and sodium diethyl-2-oxosuccinate, followed by ester hydrolysis) and 6.292 g 4-((S)-2-amino-3-tert-butoxycarbonyl-butyryl)-piperazine-1-carboxylic acid ethyl ester in 40 ml DMF 2.806 g HOBt, 3.2 ml DIPEA and 3.512 g EDC were added and the reaction mixture was stirred for 16 h at RT. Then the reaction mixture was diluted with ethyl acetate and subsequently extracted with aqueous LiCl (4% w/w), 0.1 M HCl and aqueous NaHCO$_3$. The organic layer was dried over MgSO$_4$ and the solvent was removed under reduced pressure. The crude product thus obtained was used in the subsequent reaction. Yield: 11.0 g.

(ii) 4-((S)-2-{[5-Benzyloxycarbonylmethoxy-1-(3,4-difluoro-phenyl)-1H-pyrazole-3-carbonyl]-amino}-4-tert-butoxycarbonyl-butyryl)-piperazine-1-carboxylic acid ethyl ester To a solution of 4.000 g 4-((S)-4-tert-Butoxycarbonyl-2-{[1-(3,4-difluoro-phenyl)-5-hydroxy-1H-pyrazole-3-carbonyl]-amino}-butyryl)-piperazine-1-carboxylic acid ethyl ester in 26 ml DMF were added 1.172 ml benzyl bromoacetate and 4.607 g cesium carbonate. After stirring at RT for 12 h the solution was diluted with 100 ml ethyl acetate and extracted with aqueous LiCl (4% w/w) and aqueous NaHCO$_3$. The crude product obtained after evaporation of the solvent was used in the subsequent reaction.
Yield: 4.8 g.

(iii) 4-((S)-4-tert-Butoxycarbonyl-2-{[5-carboxymethoxy-1-(3,4-di-fluoro-phenyl)-1H-pyrazole-3-carbonyl]amino}-butyryl)-piperazine-1-carboxylic acid ethyl ester To a solution of 4.800 g 4-((S)-2-{[5-Benzyloxycarbonyl-methoxy-1-(3,4-difluoro-phenyl)-1H-pyrazole-3-carbonyl]-amino}-4-tert-butoxycarbonyl-butyryl)-piperazine-1-carboxylic acid ethyl ester in 60 ml ethyl acetate were added under argon 0.7 g Pd/C (10%) and the suspension was stirred under an atmosphere of hydrogen (3 bar) for 16 h. The suspension was filtered over a plug of Celite® and washed with ethyl acetate. The crude product obtained after evaporation of the solvent was dried under vacuo. Yield: 4.0 g.

(iv) 4-((S)-2-{[5-[2-((S)-2-Benzyloxycarbonyl-pyrrolidin-1-yl)-2-oxo-ethoxy]-1-(3,4-difluoro-phenyl)-1H-pyrazole-3-carbonyl]-amino}-4-tert-butoxycarbonyl-butyryl)-piperazine-1-carboxylic acid ethyl ester To a solution of 2.5 g 4-((S)-4-tert-Butoxycarbonyl-2-{[5-carboxymethoxy-1-(3,4-difluoro-phenyl)-1H-pyrazole-3-carbonyl]-amino}-butyryl)-piperazine-1-carboxylic acid ethyl ester in 30 ml DMF were added 0.614 g HOBt, 1.32 ml DIPEA and 0.969 g L-proline benzyl ester hydrochloride at RT. Then 0.769 g EDC were added portionwise and the suspension stirred at RT for 12 h. The reaction mixture was diluted with ethyl acetate and subsequently extracted with aqueous LiCl (4% w/w), 0.1 M HCl and aqueous NaHCO$_3$. The organic layer was dried over MgSO$_4$ and the solvent was removed under reduced pressure. The crude product thus obtained was used in the subsequent reaction.
Yield: 3.5 g.

(v) 4-((S)-4-tert-Butoxycarbonyl-2-{[5-[2-((S)-2-carboxy-pyrrolidin-1-yl)-2-oxo-ethoxy]-1-(3,4-difluoro-phenyl)-1H-pyrazole-3-carbonyl]-amino}-butyryl)-piperazine-1-carboxylic acid ethyl ester To a solution of 3.5 g 4-((S)-2-{[5-[2-((S)-2-Benzyloxy-carbonyl-pyrrolidin-1-yl)-2-oxo-ethoxy]-1-(3,4-difluoro-phenyl)-1H-pyrazole-3-carbonyl]-amino}-4-tert-butoxycarbonyl-butyryl)-piperazine-1-carboxylic acid ethyl ester in 80 ml ethyl acetate were added under argon 1.5 g Pd/C (10%) and the suspension was stirred under an atmosphere of hydrogen (3 bar) for 24 h. The suspension was filtered over a plug of Celite® and washed with ethyl acetate. The crude product obtained after evaporation of the solvent was used in the subsequent reaction. Yield: 2.5 g colorless foam.

vi) 4-((S)-4-Carboxy-2-{[5-[2-((S)-2-cyclopropyl-carbamoyl-pyrrolidin-1-yl)-2-oxo-ethoxy]-1-(3,4-difluoro-phenyl)-1H-pyrazole-3-carbonyl]-amino}-butyryl)-piperazine-1-carboxylic acid ethyl ester To a solution of 150 mg 4-((S)-4-tert-Butoxycarbonyl-2-{[5-[2-((S)-2-carboxy-pyrrolidin-1-yl)-2-oxo-ethoxy]-1-(3,4-difluoro-phenyl)-1H-pyrazole-3-carbonyl]-amino}-butyryl)-piperazine-1-carboxylic acid ethyl ester in 3 ml DMF were added 34 µl DIPEA and 79 mg HATU. After 20 minutes 14 µl cyclopropylamine were added and the reaction mixture stirred for 12 h. After evaporation of the solvent the crude product was dissolved in 5 ml DCM and treated with 695 µl TFA. After stirring for 4 h the solvents were removed under reduced pressure and the residue immediately purified by preparative HPLC (C18 reverse phase column, elution with a water/MeCN gradient with 0.1% TFA). The fractions containing the product were immediately lyophilized to yield the pure product as its trifluoroacetate salt. Yield: 36 mg MS (ES+): m/e=704.

Example 82

4-((S)-4-Carboxy-2-{[5-[2-((S)-2-(2-fluoroethylcarbamoyl)-pyrrolidin-1-yl)-2-oxo-ethoxy]-1-(3,4-difluoro-phenyl)-1H-pyrazole-3-carbonyl]-amino}-butyryl)-piperazine-1-carboxylic acid ethyl ester The title compound was prepared by adapting the procedures described in example 81 with the difference that 2-fluoroethylamine hydrochloride was used instead of cyclopropylamine. Yield: 68 mg MS (ES+): m/e=710.

Example 83

4-((S)-4-Carboxy-2-{[5-[2-((S)-2-cyclobutylcarbamoyl-pyrrolidin-1-yl)-2-oxo-ethoxy]-1-(3,4-difluoro-phenyl)-1H-pyrazole-3-carbonyl]-amino}-butyryl)-piperazine-1-carboxylic acid ethyl ester The title compound was prepared by adapting the procedures described in example 81 with the difference that cyclobutylamine was used instead of cyclopropylamine. Yield: 43 mg MS (ES+): m/e=718.

Example 84

4-((S)-4-Carboxy-2-{[5-[2-((S)-2-cyclopropylmethylcarbamoyl-pyrrolidin-1-yl)-2-oxo-ethoxy]-1-(3,4-difluoro-phenyl)-1H-pyrazole-3-carbonyl]-amino}-butyryl)-piperazine-1-carboxylic acid ethyl ester The title compound was prepared by adapting the procedures described in example 81 with the difference that aminomethylcyclopropane was used instead of cyclopropylamine.
Yield: 42 mg MS (ES+): m/e=718.

Example 85

4-((S)-4-Carboxy-2-{[5-[2-((S)-2-(2,2,2-trifluoroethylcarbamoyl)-pyrrolidin-1-yl)-2-oxo-ethoxy]-1-(3,4-difluoro-phenyl)-1H-pyrazole-3-carbonyl]-amino}-butyryl)-piperazine-1-carboxylic acid ethyl ester The title compound was prepared by adapting the procedures described in example 81 with the difference that 2,2,2-trifluoroethylamine was used instead of cyclopropylamine.
Yield: 56 mg MS (ES+): m/e=746.

Example 86

4-((S)-4-Carboxy-2-{[5-[2-((S)-2-(2,2-difluoroethylcarbamoyl)-pyrrolidin-1-yl)-2-oxo-ethoxy]-1-(3,4-difluoro-phenyl)-1H-pyrazole-3-carbonyl]-amino}-butyryl)-piperazine-1-carboxylic acid ethyl ester The title compound was prepared by adapting the procedures described in example 81 with the difference that 2,2-difluoroethylamine was used instead of cyclopropylamine.
Yield: 48 mg MS (ES+): m/e=728.

Example 87

4-[(S)-3-Acetylamino-2-({5-[2-((S)-2-cyclobutylcarbamoyl-pyrrolidin-1-yl)-2-oxo-ethoxy]-1-phenyl-1H-pyrazole-3-carbonyl}-amino)-propionyl]-piperazine-1-carboxylic acid ethyl ester i) 4-[(S)-3-tert-Butoxycarbonylamino-2-(9H-fluoren-9-ylmethoxycarbonylamino)-propionyl]-piperazine-1-carboxylic acid ethyl ester To a solution of 0.86 ml 1-ethoxycarbonylpiperazine, 0.83 ml N-ethylmorpholine and 2.50 g N-α-Fmoc-N-β-Boc-L-diaminopropionic acid in 50 ml DMF were added 1.92 g TOTU at 0° C. After 1 h the reaction mixture was diluted with 100 ml ethyl acetate and subsequently extracted with aqueous LiCl (4%), half-saturated aqueous NaHCO$_3$ and water. The crude product obtained after evaporation of the solvent was used in the subsequent reaction.
Yield: 3.3 g colorless foam.

ii) 4-((S)-2-Amino-3-tert-butoxycarbonylamino-propionyl)-piperazine-1-carboxylic acid ethyl ester A solution of 1.71 g 4-[(S)-3-tert-butoxycarbonylamino-2-(9H-fluoren-9-ylmethoxycarbonylamino)-propionyl]-piperazine-1-carboxylic acid ethyl ester in 50 ml THF was stirred in the presence of 4 ml 1-octanethiol and 90 µl DBU. After 12 h the mixture was concentrated, the residue dissolved in dichloromethane and extracted with 0.1 M HCl. The aqueous phase was brought to pH9 by adding aqueous NaHCO$_3$ before being extracted with dichloromethane. The product was obtained after evaporation of the solvent and was used in the subsequent reaction.
Yield: 0.83 g colorless foam.

iii) 5-Benzyloxycarbonylmethoxy-1-phenyl-1H-pyrazole-3-carboxylic acid ethyl ester To a solution of 10.0 g 5-hydroxy-1-phenyl-1H-pyrazole-3-carboxylic acid ethyl ester in 100 ml DMF were added 7.1 ml benzyl bromoacetate and 24.0 g cesium carbonate. After stirring for 16 h at RT the suspension was filtered, washed with DMF and concentrated. The residue was taken up with ethyl acetate and extracted with aqueous LiCl (4%). Evaporation of the solvent yielded the crude product which was used in the subsequent debenzylation. Yield: 15.5 g yellow oil.

iv) 5-Carboxymethoxy-1-phenyl-1H-pyrazole-3-carboxylic acid ethyl ester

To a solution of 15.5 g 5-benzyloxycarbonylmethoxy-1-phenyl-1H-pyrazole-3-carboxylic acid ethyl ester in 100 ml ethyl acetate was added 1 g Pd/C (10%) and the resulting suspension stirred under an atmosphere of hydrogen (1 bar) for 24 h. The reaction mixture was filtered over a plug of Celite, washed with ethyl acetate and methanol giving the crude product after evaporation of the solvents. Yield: 9.5 g colorless platelets.

v) 5-[2-((S)-2-Benzyloxycarbonyl-pyrrolidin-1-yl)-2-oxo-ethoxy]-1-phenyl-1H-pyrazole-3-carboxylic acid ethyl ester To a solution of 9.5 g 5-carboxymethoxy-1-phenyl-1H-pyrazole-3-carboxylic acid ethyl ester in 100 ml DMF were added 5.0 g HOBt, 6.3 g EDC and 10.9 ml DIPEA. After 5 minutes 7.9 g L-proline benzyl ester hydrochloride were added and the resulting solution stirred for 16 h. The reaction mixture was concentrated, dissolved in dichloromethane and extracted with aqueous LiCl (4%) and saturated NaHCO$_3$. The crude product obtained after evaporation of the solvent was purified by flash chromatography on silica using ethyl acetate/heptane 1:1 as eluent. Yield: 13.2 g colorless foam.

vi) 5-[2-((S)-2-Carboxy-pyrrolidin-1-yl)-2-oxo-ethoxy]-1-phenyl-1H-pyrazole-3-carboxylic acid ethyl ester To a solution of 13.2 g 5-[2-((S)-2-benzyloxycarbonyl-pyrrolidin-1-yl)-2-oxo-ethoxy]-1-phenyl-1H-pyrazole-3-carboxylic acid ethyl ester in 100 ml ethyl acetate was added 1 g Pd/C (10%) and the resulting suspension stirred under an atmosphere of hydrogen (3 bar) for 6 h. The reaction mixture was filtered over a plug of Celite and washed with ethanol giving the crude product after evaporation of the solvents which was used without further purification.

Yield: 8.9 g colorless foam.

vii) 5-[2-((S)-2-Cyclobutylcarbamoyl-pyrrolidin-1-yl)-2-oxo-ethoxy]-1-phenyl-1H-pyrazole-3-carboxylic acid ethyl ester To a solution of 4.5 g 5-[2-((S)-2-carboxy-pyrrolidin-1-yl)-2-oxo-ethoxy]-1-phenyl-1H-pyrazole-3-carboxylic acid ethyl ester in 105 ml DMF were added 4.4 g HATU and 1.9 ml DIPEA. After 10 minutes 1.0 ml cyclobutylamine was added and after 30 minutes the reaction mixture was concentrated. The residue was taken up in dichloromethane and extracted with aqueous LiCl (4%), 0.1 M HCl and saturated NaHCO$_3$. The crude product obtained after evaporation of the solvent was purified by flash chromatography on silica using ethyl acetate/heptane 4:1 as eluent. Yield: 3.2 g colorless oil.

viii) 5-[2-((S)-2-Cyclobutylcarbamoyl-pyrrolidin-1-yl)-2-oxo-ethoxy]-1-phenyl-1H-pyrazole-3-carboxylic acid To a solution of 3.2 g 5-[2-((S)-2-cyclobutylcarbamoyl-pyrrolidin-1-yl)-2-oxo-ethoxy]-1-phenyl-1H-pyrazole-3-carboxylic acid ethyl ester in 40 ml THF and 5 ml water were added 340 mg NaOH portionwise at 0° C. After 4 h the solution was neutralized with Amberlite IR-120 ion exchange resin, filtered and washed with methanol. The crude product obtained after evaporation of the solvents was used in the subsequent reaction.

Yield: 3.0 g.

ix) 4-[(S)-3-tert-Butoxycarbonylamino-2-({5-[2-((S)-2-cyclobutylcarbamoyl-pyrrolidin-1-yl)-2-oxo-ethoxy]-1-phenyl-1H-pyrazole-3-carbonyl}-amino)-propionyl]-piperazine-1-carboxylic acid ethyl ester To a solution of 390 mg 5-[2-((S)-2-cyclobutylcarbamoyl-pyrrolidin-1-yl)-2-oxo-ethoxy]-1-phenyl-1H-pyrazole-3-carboxylic acid in 5 ml DMF were added 359 mg HATU and 156 µl DIPEA. After 10 minutes a solution of 326 mg 4-((S)-2-amino-3-tert-butoxycarbonyl-amino-propionyl)-piperazine-1-carboxylic acid ethyl ester in 2 ml DMF was added and after 30 minutes the reaction mixture was diluted with ethyl acetate and extracted with aqueous LiCl (4%), 0.1 M HCl and saturated NaHCO$_3$. The crude product (600 mg) thus obtained after evaporation of the solvent was deprotected in the following step.

x) 4-[(S)-3-Amino-2-({5-[2-((S)-2-cyclobutylcarbamoyl-pyrrolidin-1-yl)-2-oxo-ethoxy]-1-phenyl-1H-pyrazole-3-carbonyl}-amino)-propionyl]-piperazine-1-carboxylic acid ethyl ester trifluoroacetate A solution of 600 mg 4-[(S)-3-tert-butoxycarbonylamino-2-({5-[2-((S)-2-cyclobutylcarbamoyl-pyrrolidin-1-yl)-2-oxo-ethoxy]-1-phenyl-1H-pyrazole-3-carbonyl}-amino)-propionyl]-piperazine-1-carboxylic acid ethyl ester in 20 ml dichloromethane was treated with 600 µl TFA. After stirring for 12 h the solvents were removed under reduced pressure giving the crude trifluoroacetate salt of which for analytical reasons an aliquot (50 mg) was purified by preparative HPLC (C18 reverse phase column, elution with a water/MeCN gradient with 0.1% TFA). Yield: 29 mg MS (ES+): m/e=639.

xi) 4-[(S)-3-Acetylamino-2-({5-[2-((S)-2-cyclobutylcarbamoyl-pyrrolidin-1-yl)-2-oxo-ethoxy]-1-phenyl-1H-pyrazole-3-carbonyl}-amino)-propionyl]-piperazine-1-carboxylic acid ethyl ester To a solution of 100 mg 4-[(S)-3-amino-2-({5-[2-((S)-2-cyclobutylcarbamoyl-pyrrolidin-1-yl)-2-oxo-ethoxy]-1-phenyl-1H-pyrazole-3-carbonyl}-amino)-propionyl]-piperazine-1-carboxylic acid ethyl ester trifluoroacetate in 2 ml dichloromethane were added 32 µl pyridine, 1.6 mg DMAP and 16 µl Ac$_2$O at 0° C. After 1 h stirring at this temperature the reaction mixture was diluted with dichloromethane and washed with 0.1 M HCl and half-saturated aqueous NaHCO$_3$. The crude product obtained after evaporation of the solvent was purified by preparative HPLC (C18 reverse phase column, elution with a water/MeCN gradient with 0.1% TFA). Yield: 35 mg MS (ES+): m/e=681.

Example 88

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-3-methanesulfonylamino-propionyl]-piperazine-1-carboxylic acid ethyl ester The title compound was prepared by adapting the procedures described in example 87 with the difference that methanesulfonyl chloride was used instead of Ac$_2$O and triethylamine instead of pyridine. Yield: 35 mg MS (ES+): m/e=717.

Example 89

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-3-methoxycarbonylamino-propionyl]-piperazine-1-carboxylic acid ethyl ester The title compound was prepared by adapting the procedures described in example 87 with the difference that methoxycarbonyl chloride was used instead of Ac$_2$O and triethylamine instead of pyridine. Yield: 50 mg MS (ES+): m/e=697.

Example 90

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-3-(ethoxyoxalyl-amino)-propionyl]-piperazine-1-carboxylic acid ethyl ester The title compound was prepared by adapting the procedures described in example 87 with the difference that ethyl oxalyl chloride was used instead of Ac$_2$O.

Yield: 23 mg MS (ES+): m/e=739.

Example 91

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-3-(cyclopropanecarbonyl-amino)-propionyl]-piperazine-1-carboxylic acid ethyl ester The title compound was prepared by adapting the procedures described in example 87 with the difference that cyclopropanecarbonyl chloride was used instead of Ac$_2$O.
Yield: 44 mg MS (ES+): m/e=707.

Example 92

4-[(S)-4-Acetylamino-2-({5-[2-((S)-2-cyclobutylcarbamoyl-pyrrolidin-1-yl)-2-oxo-ethoxy]-1-phenyl-1H-pyrazole-3-carbonyl}-amino)-butyryl]-piperazine-1-carboxylic acid ethyl ester i) 4-[(S)-4-tert-Butoxycarbonylamino-2-(9H-fluoren-9-ylmethoxycarbonylamino)-butyryl]-piperazine-1-carboxylic acid ethyl ester To a solution of 1.33 ml 1-ethoxycarbonylpiperazine, 1.27 ml N-ethylmorpholine and 4.0 g N-α-Fmoc-N-β-Boc-L-diaminobutyric acid in 40 ml DMF were added 2.98 g TOTU at 0° C. After 1 h the reaction mixture was diluted with 100 ml ethyl acetate and subsequently extracted with aqueous LiCl (4%), half-saturated aqueous NaHCO$_3$ and water. The crude product obtained after evaporation of the solvent was used in the subsequent reaction.
Yield: 4.96 g colorless foam.

ii) 4-((S)-2-Amino-4-tert-butoxycarbonylamino-butyryl)-piperazine-1-carboxylic acid ethyl ester A solution of 1.71 g 4-[(S)-4-tert-butoxycarbonylamino-2-(9H-fluoren-9-ylmethoxycarbonylamino)-butyryl]-piperazine-1-carboxylic acid ethyl ester in 30 ml THF was stirred in the presence of 8.9 ml 1-octanethiol and 101 µl DBU. After 12 h the mixture was concentrated, the residue dissolved in dichloromethane and extracted with 0.1 M HCl. The aqueous phase was brought to pH 9 by adding aqueous NaHCO$_3$ before being extracted with dichloromethane. The product was obtained after evaporation of the solvent and was used in the subsequent reaction. Yield: 2.27 g colorless foam.

iii) 4-[(S)-4-tert-Butoxycarbonylamino-2-({5-[2-((S)-2-cyclobutylcarbamoyl-pyrrolidin-1-yl)-2-oxo-ethoxy]-1-phenyl-1H-pyrazole-3-carbonyl}-amino)-butyryl]-piperazine-1-carboxylic acid ethyl ester To a solution of 705 mg 5-[2-((S)-2-cyclobutylcarbamoyl-pyrrolidin-1-yl)-2-oxo-ethoxy]-1-phenyl-1H-pyrazole-3-carboxylic acid in 5 ml DMF were added 648 mg HATU and 875 µl DIPEA. After 10 minutes a solution of 612 mg 4-((S)-2-amino-4-tert-butoxycarbonyl-amino-butyryl)-piperazine-1-carboxylic acid ethyl ester in 3 ml DMF was added and after 30 minutes the reaction mixture was diluted with ethyl acetate and extracted with aqueous LiCl (4%), 0.1 M HCl and saturated NaHCO$_3$. The crude product (1.22 g) thus obtained after evaporation of the solvent was deprotected in the following step.

iv) 4-[(S)-4-Amino-2-({5-[2-((S)-2-cyclobutylcarbamoyl-pyrrolidin-1-yl)-2-oxo-ethoxy]-1-phenyl-1H-pyrazole-3-carbonyl}-amino)-butyryl]-piperazine-1-carboxylic acid ethyl ester trifluoroacetate A solution of 1.22 g 4-[(S)-4-tert-butoxycarbonylamino-2-({5-[2-((S)-2-cyclobutyl-carbamoyl-pyrrolidin-1-yl)-2-oxo-ethoxy]-1-phenyl-1H-pyrazole-3-carbonyl}-amino)-butyryl]-piperazine-1-carboxylic acid ethyl ester in 10 ml DCM was treated with 1.2 ml TFA. After stirring for 12 h the solvents were removed under reduced pressure giving the crude trifluoroacetate salt of which for analytical reasons an aliquot (270 mg) was purified by preparative HPLC (C18 reverse phase column, elution with a water/MeCN gradient with 0.1% TFA). Yield: 79 mg MS (ES+): m/e=653.

v) 4-[(S)-4-Acetylamino-2-({5-[2-((S)-2-cyclobutyl-carbamoyl-pyrrolidin-1-yl)-2-oxo-ethoxy]-1-phenyl-1H-pyrazole-3-carbonyl}-amino)-butyryl]-piperazine-1-carboxylic acid ethyl ester To a solution of 302 mg 4-[(S)-4-amino-2-({5-[2-((S)-2-cyclobutylcarbamoyl-pyrrolidin-1-yl)-2-oxo-ethoxy]-1-phenyl-1H-pyrazole-3-carbonyl}-amino)-butyryl]-piperazine-1-carboxylic acid ethyl ester trifluoroacetate in 5 ml dichloromethane were added 96 µl pyridine, 5 mg DMAP and 48 µl Ac$_2$O at 0° C. After 1 h stirring at this temperature the reaction mixture was diluted with dichloromethane and washed with 0.1 M HCl and half-saturated aqueous NaHCO$_3$. The crude product obtained after evaporation of the solvent was purified by preparative HPLC (C18 reverse phase column, elution with a water/MeCN gradient with 0.1% TFA). Yield: 27 mg MS (ES+): m/e=695.

Example 93

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-methoxycarbonylamino-butyryl]-piperazine-1-carboxylic acid ethyl ester The title compound was prepared by adapting the procedures described in example 92 with the difference that methoxycarbonyl chloride was used instead of Ac$_2$O and triethylamine instead of pyridine. Yield: 66 mg MS (ES+): m/e=711.

Example 94

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-methanesulfonylamino-butyryl]-piperazine-1-carboxylic acid ethyl ester The title compound was prepared by adapting the procedures described in example 92 with the difference that methanesulfonyl chloride was used instead of Ac$_2$O and triethylamine instead of pyridine. Yield: 64 mg MS (ES+): m/e=731.

Example 95

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-(cyclopropanecarbonyl-amino)-butyryl]-piperazine-1-carboxylic acid ethyl ester The title compound was prepared by adapting the procedures described in example 92 with the difference that cyclopropanecarbonyl chloride was used instead of Ac$_2$O.
Yield: 36 mg MS (ES+): m/e=721.

Example 96

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-(ethoxyoxalyl-amino)-butyryl]-piperazine-1-carboxylic acid ethyl ester The title compound was prepared by adapting the procedures described in example 92 with the difference that ethyl oxalyl chloride was used instead of $Ac_2O$.
Yield: 65 mg MS (ES+): m/e=753.

Example 97

4-[(S)-4-(Cyclobutanecarbonyl-amino)-2-({5-[2-((S)-2-cyclobutylcarbamoyl-pyrrolidin-1-yl)-2-oxo-ethoxy]-1-phenyl-1H-pyrazole-3-carbonyl}-amino)-butyryl]-piperazine-1-carboxylic acid ethyl ester The title compound was prepared by adapting the procedures described in example 92 with the difference that cyclobutanecarbonyl chloride was used instead of $Ac_2O$.
Yield: 1 mg MS (ES+): m/e=735.

Example 98

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-(2,2,2-trifluoro-acetylamino)-butyryl]-piperazine-1-carboxylic acid ethyl ester The title compound was prepared by adapting the procedures described in example 92 with the difference that pivaloyl chloride was used instead of $Ac_2O$. In this case, the amino functionality was trifluoroacetylated instead of being pivaloylated.
Yield: 56 mg MS (ES+): m/e=749.

Example 99

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-(2,2-dimethyl-propionylamino)-butyryl]-piperazine-1-carboxylic acid ethyl ester The title compound was prepared by adapting the procedures described in example 92 with the difference that pivaloyl chloride was used instead of $Ac_2O$ and that the amine hydrotrifluoroacetate was transformed to the amine prior to the reaction by treating with basic ion exchange resin. Yield: 43 mg MS (ES+): m/e=737.

Example 100

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-isobutyrylamino-butyryl]-piperazine-1-carboxylic acid ethyl ester The title compound was prepared by adapting the procedures described in example 92 with the difference that isobutyryl chloride was used instead of $Ac_2O$ and that the amine hydrotrifluoroacetate was transformed to the amine prior to the reaction by treating with basic ion exchange resin. Yield: 119 mg MS (ES+): m/e=723.

Example 101

(S)-4-({5-[2-((S)-2-Cyclobutylcarbamoyl-pyrrolidin-1-yl)-2-oxo-ethoxy]-1-phenyl-1H-pyrazole-3-carbonyl}-amino)-5-[4-(3-methoxy-phenyl)-piperazin-1-yl]-5-oxo-pentanoic acid i) (S)-4-Benzyloxycarbonylamino-5-[4-(3-methoxy-phenyl)-piperazin-1-yl]-5-oxo-pentanoic acid tert-butyl ester To a solution of 2.0 g Z-L-glutamic acid-γ-tert-butyl ester in 10 ml DMF were added 1.14 g 1-(3-methoxyphenyl)piperazine, 3.0 ml N-ethylmorpholine and 1.95 g TOTU. After stirring for 12 h at RT the solution was diluted with ethyl acetate and washed with aqueous LiCl (4%) and saturated $NaHCO_3$. The crude product obtained after evaporation of the solvent was directly used in the next reaction step without further purification.
Yield: 4.0 g.

ii) (S)-4-Amino-5-[4-(3-methoxy-phenyl)-piperazin-1-yl]-5-oxo-pentanoic acid tert-butyl ester To a solution of 4.00 g (S)-4-benzyloxycarbonylamino-5-[4-(3-methoxy-phenyl)-piperazin-1-yl]-5-oxo-pentanoic acid tert-butyl ester in 60 ml EtOH were added 0.7 g Pd/C (10%) and the suspension stirred under an atmosphere of hydrogen (3 bar) for 12 h. The reaction mixture was filtrated over Celite and washed with EtOH. The title compound was used without further purification after evaporation of the solvent. Yield: 2.90 g.

iii) (S)-4-({5-[2-((S)-2-Cyclobutylcarbamoyl-pyrrolidin-1-yl)-2-oxo-ethoxy]-1-phenyl-1H-pyrazole-3-carbonyl}-amino)-5-[4-(3-methoxy-phenyl)-piperazin-1-yl]-5-oxo-pentanoic acid To a solution of 80 mg 5-[2-((S)-2-cyclobutylcarbamoyl-pyrrolidin-1-yl)-2-oxo-ethoxy]-1-phenyl-1H-pyrazole-3-carboxylic acid in 3 ml DMF were added 48 µl DIPEA, 74 mg HATU and 73 mg (S)-4-amino-5-[4-(3-methoxy-phenyl)-piperazin-1-yl]-5-oxo-pentanoic acid tert-butyl ester. After stirring for 2 h saturated $NaHCO_3$ solution was added and the mixture loaded on a Chem Elut® cartridge, the crude product being eluted with dichloromethane. The solution was concentrated to a volume of 5 ml and stirred in the presence of 144 µl TFA. After stirring for 4 h the solvents were removed under reduced pressure and the residue purified by preparative HPLC (C18 reverse phase column, elution with a water/MeCN gradient with 0.1% TFA). The fractions containing the product were lyophilized to yield the pure product as its trifluoroacetate salt.
Yield: 28 mg MS (ES+): m/e=716.

Example 102

(S)-5-(4-Butoxycarbonylamino-piperidin-1-yl)-4-({5-[2-((S)-2-cyclobutylcarbamoyl-pyrrolidin-1-yl)-2-oxo-ethoxy]-1-phenyl-1H-pyrazole-3-carbonyl}-amino)-5-oxo-pentanoic acid i) 4-tert-Butoxycarbonylamino-piperidine-1-carboxylic acid benzyl ester To a solution of 4.94 g piperidin-4-yl-carbamic acid tert-butyl ester, 300 mg DMAP and 5.2 ml triethylamine in 50 ml dichloromethane were added 6.3 ml benzyl chloroformate dropwise at 0° C. After 8 h the suspension was diluted with dichloromethane and washed with half-saturated NaHCO₃ and 0.1 M HCl. The crude product obtained after evaporation of the solvent was suspended in heptane, the supernatant solution being decanted yielding the product as colorless solid. Yield: 7.9 g.

ii) 4-Amino-piperidine-1-carboxylic acid benzyl ester hydrotrifluoroacetate

A solution of 4.4 g 4-tert-butoxycarbonylamino-piperidine-1-carboxylic acid benzyl ester in 90 ml dichloromethane was stirred in the presence of 10 ml TFA for 3 h. The product was obtained after evaporation of the solvent and used without further purification.
Yield: 7.6 g.

iii) 4-Butoxycarbonylamino-piperidine-1-carboxylic acid benzyl ester

To a solution of 4.4 g 4-amino-piperidine-1-carboxylic acid benzyl ester hydrotrifluoroacetate and 5.3 ml triethylamine in 100 ml dichloromethane were added 1.8 ml butylchloroformate dropwise at 0° C. The suspension was stirred for 12 h, diluted with dichloromethane and washed with 0.1 M HCl and aqueous NaHCO₃. The crude product was purified by flash chromatography on silica using ethyl acetate/heptan 1:2 as eluent.
Yield: 1.8 g colorless foam.

iv) Piperidin-4-yl-carbamic acid butyl ester

To a solution of 1.8 g 4-butoxycarbonylamino-piperidine-1-carboxylic acid benzyl ester in 60 ml EtOH were added 200 mg Pd/C (10%) and the suspension stirred under an atmosphere of hydrogen (1 bar) for 2 h. The reaction mixture was filtered over a plug of Celite and washed with EtOH to give the product as colorless oil after evaporation of the solvent.
Yield: 1.0 g.

v) (S)-4-Benzyloxycarbonylamino-5-(4-butoxycarbonylamino-piperidin-1-yl)-5-oxo-pentanoic acid tert-butyl ester To a solution of 0.79 g Z-L-glutamic acid-γ-tert-butyl ester in 25 ml DMF were added 0.47 g piperidin-4-yl-carbamic acid butyl ester, 1.1 ml N-ethylmorpholine and 0.8 g TOTU. After stirring for 1 h at RT the solution was diluted with ethyl acetate and washed with aqueous LiCl (4%) and saturated NaHCO₃. The crude product obtained after evaporation of the solvent was purified by flash chromatography on silica using ethyl acetate/heptan 70:30 as eluent. Yield: 0.91 g.

vi) (S)-4-Amino-5-(4-butoxycarbonylamino-piperidin-1-yl)-5-oxo-pentanoic acid tert-butyl ester To a solution of 0.91 g (S)-4-Benzyloxycarbonylamino-5-(4-butoxycarbonylamino-piperidin-1-yl)-5-oxo-pentanoic acid tert-butyl ester in 10 ml EtOH were added 0.2 g Pd/C (10%) and the suspension stirred under an atmosphere of hydrogen (3 bar) for 12 h. The reaction mixture was filtrated over Celite and washed with EtOH. The title compound was used without further purification after evaporation of the solvent. Yield: 0.67 g.

vii) (S)-5-(4-Butoxycarbonylamino-piperidin-1-yl)-4-({5-[2-((S)-2-cyclobutylcarbamoyl-pyrrolidin-1-yl)-2-oxo-ethoxy]-1-phenyl-1H-pyrazole-3-carbonyl}-amino)-5-oxo-pentanoic acid To a solution of 80 mg 5-[2-((S)-2-cyclobutylcarbamoyl-pyrrolidin-1-yl)-2-oxo-ethoxy]-1-phenyl-1H-pyrazole-3-carboxylic acid in 3 ml DMF were added 48 µl DIPEA, 74 mg HATU and 74 mg (S)-4-Amino-5-(4-butoxycarbonylamino-piperidin-1-yl)-5-oxo-pentanoic acid tert-butyl ester. After stirring for 2 h saturated NaHCO₃ solution was added and the mixture loaded on a Chem Elut® cartridge, the crude product being eluted with dichloromethane. The solution was concentrated to a volume of 5 ml and stirred in the presence of 144 µl TFA. After stirring for 4 h the solvents were removed under reduced pressure and the residue purified by preparative HPLC (C18 reverse phase column, elution with a water/MeCN gradient with 0.1% TFA). The fractions containing the product were lyophilized to yield the pure product as its trifluoroacetate salt.
Yield: 24 mg MS (ES+): m/e=724.

Example 103

(S)-5-[4-(3-Chloro-benzoyl)-piperidin-1-yl]-4-({5-[2-((S)-2-cyclobutylcarbamoyl-pyrrolidin-1-yl)-2-oxo-ethoxy]-1-phenyl-1H-pyrazole-3-carbonyl}-amino)-5-oxo-pentanoic acid i) (S)-2-({5-[2-((S)-2-Cyclobutylcarbamoyl-pyrrolidin-1-yl)-2-oxo-ethoxy]-1-phenyl-1H-pyrazole-3-carbonyl}-amino)-pentanedioic acid 5-tert-butyl ester 1-methyl ester To a solution of 1.1 g 5-[2-((S)-2-cyclobutylcarbamoyl-pyrrolidin-1-yl)-2-oxo-ethoxy]-1-phenyl-1H-pyrazole-3-carboxylic acid in 20 ml DMF were added 1 ml DIPEA, 0.41 g HOBt, 0.51 g EDC and 0.68 g H-Glu(OtBu)-OMe hydrochloride. After stirring for 24 h the solution was concentrated, taken up with dichloromethane and subsequently extracted with aqueous LiCl (4%), 0.1 M HCl and saturated NaHCO₃. The crude product was purified by flash chromatography on silica using an ethyl acetate/heptane 50:50 to 100:0 gradient.
Yield: 1.88 g colorless foam.

ii) (S)-2-({5-[2-((S)-2-Cyclobutylcarbamoyl-pyrrolidin-1-yl)-2-oxo-ethoxy]-1-phenyl-1H-pyrazole-3-carbonyl}-amino)-pentanedioic acid 5-tert-butyl ester To a solution of 1.88 g (S)-2-({5-[2-((S)-2-cyclobutylcarbamoyl-pyrrolidin-1-yl)-2-oxo-ethoxy]-1-phenyl-1H-pyrazole-3-carbonyl}-amino)-pentanedioic acid 5-tert-butyl ester 1-methyl ester in 12 ml THF were added 73 mg LiOH (as solution in 4 ml water). After 2 h the reaction mixture was neutralized with Amberlite IR-120, filtrated and washed with methanol.
Yield: 1.80 g colorless oil.

iii) (S)-5-[4-(3-Chloro-benzoyl)-piperidin-1-yl]-4-({5-[2-((S)-2-cyclobutylcarbamoyl-pyrrolidin-1-yl)-2-oxo-ethoxy]-1-phenyl-1H-pyrazole-3-carbonyl}-amino)-5-oxo-pentanoic acid To a solution of 150 mg (S)-2-({5-[2-((S)-2-cyclobutylcarbamoyl-pyrrolidin-1-yl)-2-oxo-ethoxy]-1-phenyl-1H-pyrazole-3-carbonyl}-amino)-pentanedioic acid 5-tert-butyl ester in 7 ml DMF were added 62 µl DIPEA, 95 mg HATU and 56 mg 4-(3-chlorobenzoyl)-piperidine. After stirring for 12 h saturated NaHCO$_3$ solution was added and the mixture loaded on a Chem Elut® cartridge, the crude product being eluted with dichloromethane. The solution was concentrated to a volume of 1 ml and stirred in the presence of 100 µl TFA. After stirring for 4 h the solvents were removed under reduced pressure and the residue purified by preparative HPLC (C18 reverse phase column, elution with a water/MeCN gradient with 0.1% TFA). The fractions containing the product were lyophilized to yield the pure product. Yield: 135 mg MS (ES+): m/e=747.

Example 104

(S)-5-(4-Benzoyl-piperazin-1-yl)-4-({5-[2-((S)-2-cyclobutylcarbamoyl-pyrrolidin-1-yl)-2-oxo-ethoxy]-1-phenyl-1H-pyrazole-3-carbonyl}-amino)-5-oxo-pentanoic acid The title compound was prepared by adapting the procedures described in example 103 with the difference that 1-benzoylpiperazine was used instead of 4-(3-chlorobenzoyl)-piperidine. Yield: 134 mg MS (ES−): m/e=714.

Example 105

4-[(S)-4-Carboxy-2-({5-[2-((S)-2-cyclobutylcarbamoyl-pyrrolidin-1-yl)-2-oxo-ethoxy]-1-phenyl-1H-pyrazole-3-carbonyl}-amino)-butyrylamino]-piperidine-1-carboxylic acid ethyl ester The title compound was prepared by adapting the procedures described in example 103 with the difference that ethyl 4-amino-1-piperidinecarboxylate was used instead of 4-(3-chlorobenzoyl)-piperidine. Yield: 35 mg MS (ES+): m/e=696.

Example 106

(S)-5-(4-Benzoyl-piperidin-1-yl)-4-({5-[2-((S)-2-cyclobutylcarbamoyl-pyrrolidin-1-yl)-2-oxo-ethoxy]-1-phenyl-1H-pyrazole-3-carbonyl}-amino)-5-oxo-pentanoic acid The title compound was prepared by adapting the procedures described in example 103 with the difference that 4-benzoylpiperidine hydrochloride was used instead of 4-(3-chlorobenzoyl)-piperidine. Yield: 100 mg MS (ES+): m/e=713.

Example 107

3-[(S)-4-Carboxy-2-({5-[2-((S)-2-cyclobutylcarbamoyl-pyrrolidin-1-yl)-2-oxo-ethoxy]-1-phenyl-1H-pyrazole-3-carbonyl}-amino)-butyrylamino]-pyrrolidine-1-carboxylic acid butyl ester i) 3-Benzyloxycarbonylamino-pyrrolidine-1-carboxylic acid tert-butyl ester A mixture of 2.05 g 3-amino-1-N-Boc-pyrrolidine, 1.85 g NaHCO$_3$ and 3.17 g N-(Benzyloxycarbonyloxy)succinimide in 10 ml dioxane/water 1:1 was stirred for 12 h at RT. The reaction mixture was diluted with ethyl acetate, the phases separated and the organic phase washed with saturated NaHCO$_3$ and brine. The crude product obtained after evaporation of the solvent was used in the next reaction step without further purification.
Yield: 3.21 g.

ii) Pyrrolidin-3-yl-carbamic acid benzyl ester hydrotrifluoracetate

To a solution of 3.21 g 3-Benzyloxycarbonylamino-pyrrolidine-1-carboxylic acid tert-butyl ester in 40 ml dichloromethane were added 11 ml TFA. After 16 h the solution was evaporated to give the crude hydrotrifluoroacetate. Yield: 3.20 g.

iii) 3-Benzyloxycarbonylamino-pyrrolidine-1-carboxylic acid butyl ester

To a solution of 3.20 g pyrrolidin-3-yl-carbamic acid benzyl ester hydrotrifluoracetate in 50 ml dichloromethane were added dropwise 3.7 ml triethylamine and 1.3 ml butylchloroformate at 0° C. After stirring for 12 h the reaction mixture was diluted with dichloromethane, washed with 0.1 M HCl, saturated NaHCO$_3$ and brine. The crude product thus obtained was purified by flash chromatography on silica using ethyl acetate/heptane 1:2 as eluent.
Yield: 467 mg.

iv) 3-Amino-pyrrolidine-1-carboxylic acid butyl ester

A solution of 467 mg 3-benzyloxycarbonylamino-pyrrolidine-1-carboxylic acid butyl ester in 10 ml ethyl acetate was stirred in the presence of 50 mg Pd/C (10%) under an atmosphere of hydrogen (1 bar) for 12 h. The reaction mixture was filtrated, washed with ethyl acetate and concentrated to give the title compound as colorless oil.
Yield: 255 mg.

v) 3-[(S)-4-Carboxy-2-({5-[2-((S)-2-cyclobutylcarbamoyl-pyrrolidin-1-yl)-2-oxo-ethoxy]-1-phenyl-1H-pyrazole-3-carbonyl}-amino)-butyrylamino]-pyrrolidine-1-carboxylic acid butyl ester To a solution of 303 mg (S)-2-({5-[2-((S)-2-cyclobutylcarbamoyl-pyrrolidin-1-yl)-2-oxo-ethoxy]-1-phenyl-1H-pyrazole-3-carbonyl}-amino)-pentanedioic acid 5-tert-butyl ester in 5 ml DMF were added 34 µl DIPEA, 193 mg HATU and 103 mg 3-amino-pyrrolidine-1-carboxylic acid butyl ester. After stirring for 12 h the reaction mixture was diluted with ethyl acetate, washed with aqueous LiCl (4%) and saturated NaHCO$_3$ solution. The solution was concentrated, dissolved in dichloromethane and stirred in the presence of 384 µl TFA. After stirring for 4 h the solvents were removed under reduced pressure and the residue purified by preparative HPLC (C18 reverse phase column, elution with a water/MeCN gradient with 0.1% TFA). The fractions containing the product were lyophilized to yield the pure product. Yield: 290 mg MS (ES+): m/e=710.

Example 108

(S)-5-(3-Butoxycarbonylamino-pyrrolidin-1-yl)-4-({5-[2-((S)-2-cyclobutylcarbamoyl-pyrrolidin-1-yl)-2-oxo-ethoxy]-1-phenyl-1H-pyrazole-3-carbonyl}-amino)-5-oxo-pentanoic acid i) 3-tert-Butoxycarbonylamino-pyrrolidine-1-carboxylic acid benzyl ester A mixture of 2.05 g 3-(tert-butoxycarbonylamino)pyrrolidine, 1.85 g NaHCO$_3$ and 3.17 g N-(Benzyloxycarbonyloxy)

succinimide in 10 ml dioxane/water 1:1 was stirred for 12 h at RT. The reaction mixture was diluted with ethyl acetate, the phases separated and the organic phase washed with saturated NaHCO₃ and brine. The crude product obtained after evaporation of the solvent was used in the next reaction step without further purification.
Yield: 3.81 g.

ii) 3-Amino-pyrrolidine-1-carboxylic acid benzyl ester hydrotrifluoroacetate To a solution of 3.21 g 3-tert-butoxycarbonylamino-pyrrolidine-1-carboxylic acid benzyl ester in 40 ml dichloromethane were added 13 ml TFA. After 16 h the solution was evaporated to give the crude hydrotrifluoroacetate. Yield: 3.20 g.

iii) 3-Butoxycarbonylamino-pyrrolidine-1-carboxylic acid benzyl ester

To a solution of 3.00 g 3-amino-pyrrolidine-1-carboxylic acid benzyl ester hydrotrifluoroacetate in 50 ml dichloromethane were added dropwise 3.7 ml triethylamine and 1.3 ml butylchloroformate at 0° C. After stirring for 12 h the reaction mixture was diluted with dichloromethane, washed with 0.1 M HCl, saturated aqueous NaHCO₃ and brine. The crude product thus obtained was purified by flash chromatography on silica using ethyl acetate/heptane 2:3 as eluent. Yield: 648 mg.

iv) Pyrrolidin-3-yl-carbamic acid butyl ester

A solution of 467 mg 3-butoxycarbonylamino-pyrrolidine-1-carboxylic acid benzyl ester in 10 ml ethyl acetate was stirred in the presence of 100 mg Pd/C (10%) under an atmosphere of hydrogen (1 bar) for 12 h. The reaction mixture was filtrated, washed with ethyl acetate and concentrated to give the title compound as colorless oil.
Yield: 337 mg.

v) (S)-5-(3-Butoxycarbonylamino-pyrrolidin-1-yl)-4-({5-[2-((S)-2-cyclobutylcarbamoyl-pyrrolidin-1-yl)-2-oxo-ethoxy]-1-phenyl-1H-pyrazole-3-carbonyl}-amino)-5-oxo-pentanoic acid To a solution of 303 mg (S)-2-({5-[2-((S)-2-cyclobutylcarbamoyl-pyrrolidin-1-yl)-2-oxo-ethoxy]-1-phenyl-1H-pyrazole-3-carbonyl}-amino)-pentanedioic acid 5-tert-butyl ester in 5 ml DMF were added 34 µl DIPEA, 193 mg HATU and 103 mg pyrrolidin-3-yl-carbamic acid butyl ester. After stirring for 12 h the reaction mixture was diluted with ethyl acetate, washed with aqueous LiCl (4%) and saturated aqueous NaHCO₃ solution. The solution was concentrated, dissolved in 2 ml dichloromethane and stirred in the presence of 384 µl TFA. After stirring for 4 h the solvents were removed under reduced pressure and the residue purified by preparative HPLC (C18 reverse phase column, elution with a water/MeCN gradient with 0.1% TFA). The fractions containing the product were lyophilized to yield the pure product. Yield: 229 mg MS (ES+): m/e=710.

Example 109

4-[(S)-4-Carboxy-2-({5-[2-(3-cyclopropylcarbamoyl-pyrrolidin-1-yl)-2-oxo-ethoxy]-1-phenyl-1H-pyrazole-3-carbonyl}-amino)-butyryl]-piperazine-1-carboxylic acid ethyl ester i) Pyrrolidine-1,3-dicarboxylic acid 3-benzyl ester 1-tert-butyl ester

To a solution of 1.00 g Boc-1-pyrrolidine-3-carboxylic acid in 10 ml toluene were added 0.61 ml benzyl bromide and 0.76 ml DBU. After stirring for 12 h the reaction mixture was washed with water and the crude product obtained after evaporation of the solvent was purified by flash chromatography on silica using ethyl acetate/heptane 1:3 as eluent.
Yield: 1.20 g.

ii) Pyrrolidine-3-carboxylic acid benzyl ester hydrotrifluoroacetate

To a solution of 1.20 g pyrrolidine-1,3-dicarboxylic acid 3-benzyl ester 1-tert-butyl ester in 10 ml dichloromethane were added 2.9 ml TFA. After stirring for 12 h the reaction mixture was concentrated and the residue codistilled with toluene (3×) to give the crude trifluoroacetate salt as colorless oil. Yield: 1.20 g.

iii) 4-[(S)-2-({5-[2-(3-Benzyloxycarbonyl-pyrrolidin-1-yl)-2-oxo-ethoxy]-1-phenyl-1H-pyrazole-3-carbonyl}-amino)-4-tert-butoxycarbonyl-butyryl]-piperazine-1-carboxylic acid ethyl ester To a solution of 1.14 g 4-{(S)-4-tert-butoxycarbonyl-2-[(5-carboxymethoxy-1-phenyl-1H-pyrazole-3-carbonyl)-amino]-butyryl}-piperazine-1-carboxylic acid ethyl ester in 10 ml DMF were added 719 mg HOBt, 900 mg EDC, 1.6 ml DIPEA and 1.50 g pyrrolidine-3-carboxylic acid benzyl ester hydrotrifluoroacetate. After stirring for 12 h the reaction mixture was diluted with ethyl acetate, washed with aqueous LiCl (4%) and saturated aqueous NaHCO₃. The crude product obtained after evaporation of the solvent was used without further purification. Yield: 2.32 g.

iv) 4-[(S)-4-tert-Butoxycarbonyl-2-({5-[2-(3-carboxy-pyrrolidin-1-yl)-2-oxo-ethoxy]-1-phenyl-1H-pyrazole-3-carbonyl}-amino)-butyryl]-piperazine-1-carboxylic acid ethyl ester To a solution of 2.32 g 4-[(S)-2-({5-[2-(3-benzyloxycarbonyl-pyrrolidin-1-yl)-2-oxo-ethoxy]-1-phenyl-1H-pyrazole-3-carbonyl}-amino)-4-tert-butoxycarbonyl-butyryl]-piperazine-1-carboxylic acid ethyl ester in 50 ml ethyl acetate was added 1.0 g Pd/C (10%) and the suspension stirred under an atmosphere of hydrogen (3 bar) for 24 h. The reaction mixture was filtrated over a plug of Celite, washed with ethyl acetate and concentrated.
Yield: 2.0 g.

v) 4-[(S)-4-Carboxy-2-({5-[2-(3-cyclopropylcarbamoyl-pyrrolidin-1-yl)-2-oxo-ethoxy]-1-phenyl-1H-pyrazole-3-carbonyl}-amino)-butyryl]-piperazine-1-carboxylic acid ethyl ester To a solution of 200 mg 4-[(S)-4-tert-butoxycarbonyl-2-({5-[2-(3-carboxy-pyrrolidin-1-yl)-2-oxo-ethoxy]-1-phenyl-1H-pyrazole-3-carbonyl}-amino)-butyryl]-piperazine-1-carboxylic acid ethyl ester in 5 ml DMF were added 48 µl DIPEA, 11 mg HATU and 20 µl cyclopropylamine. After stirring for 12 h saturated aqueous NaHCO₃ solution was added and the mixture loaded on a Chem Elut® cartridge, the crude product being eluted with dichloromethane. The solution was concentrated to a volume of 5 ml and stirred in the presence of 324 µl TFA. After stirring for 14 h the solvents were removed under reduced pressure and the residue purified by preparative HPLC (C18 reverse phase column, elution with a water/MeCN gradient with 0.1% TFA). The fractions containing the product were lyophilized to yield the pure product. Yield: 30 mg MS (ES+): m/e=668.

Example 110

4-{(S)-4-Carboxy-2-[(5-{2-[3-(cyclopropylmethyl-carbamoyl)-pyrrolidin-1-yl]-2-oxo-ethoxy}-1-phenyl-1H-pyrazole-3-carbonyl)-amino]-butyryl}-piperazine-1-carboxylic acid ethyl ester The title compound was prepared by adapting the procedures described in example 109 with the difference that aminomethylcyclopropane was used instead of cyclopropylamine.
Yield: 60 mg MS (ES+): m/e=682.

Example 111

4-[(S)-4-Carboxy-2-({5-[2-(3-cyclobutylcarbamoyl-pyrrolidin-1-yl]-2-oxo-ethoxy]-1-phenyl-1H-pyrazole-3-carbonyl}-amino)-butyryl]-piperazine-1-carboxylic acid ethyl ester The title compound was prepared by adapting the procedures described in example 109 with the difference that cyclobutylamine was used instead of cyclopropylamine.
Yield: 65 mg MS (ES+): m/e=682.

Example 112

4-{(S)-4-Carboxy-2-[(5-{2-[3-(2,2-difluoro-ethylcarbamoyl)-pyrrolidin-1-yl]-2-oxo-ethoxy}-1-phenyl-1H-pyrazole-3-carbonyl)-amino]-butyryl}-piperazine-1-carboxylic acid ethyl ester The title compound was prepared by adapting the procedures described in example 109 with the difference that 2,2-difluoroethylamine was used instead of cyclopropylamine.
Yield: 60 mg MS (ES+): m/e=692.

Example 113

4-{(S)-4-Carboxy-2-[(5-{2-[3-(2,2,2-trifluoro-ethylcarbamoyl)-pyrrolidin-1-yl]-2-oxo-ethoxy}-1-phenyl-1H-pyrazole-3-carbonyl)-amino]-butyryl}-piperazine-1-carboxylic acid ethyl ester The title compound was prepared by adapting the procedures described in example 109 with the difference that 2,2,2-trifluoroethylamine was used instead of cyclopropylamine.
Yield: 35 mg MS (ES+): m/e=710.

Example 114

4-{(S)-4-Carboxy-2-[(5-{2-[3-(2-fluoro-ethylcarbamoyl)-pyrrolidin-1-yl]-2-oxo-ethoxy}-1-phenyl-1H-pyrazole-3-carbonyl)-amino]-butyryl}-piperazine-1-carboxylic acid ethyl ester The title compound was prepared by adapting the procedures described in example 109 with the difference that 2-fluoroethylamine hydrochloride was used instead of cyclopropylamine. Yield: 67 mg MS (ES+): m/e=674.

Example 115

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-hydroxy-butyryl]-piperazine-1-carboxylic acid ethyl ester i) 4-((S)-4-Benzyloxy-2-tert-butoxycarbonylamino-butyryl)-piperazine-1-carboxylic acid ethyl ester To a solution of 900 mg (S)-4-benzyloxy-2-tert-butoxycarbonylamino-butyric acid in 10 ml DMF were added 1.5 ml N-ethylmorpholine, 0.43 ml 1-ethoxycarbonylpiperazine and 955 mg TOTU. The solution was stirred for 12 h before being diluted with ethyl acetate and extracted subsequently with aqueous LiCl (4%), 0.1 M HCl and saturated NaHCO$_3$. The crude product obtained after evaporation of the solvent was used without further purification. Yield: 1.23 g.

ii) 4-((S)-2-Amino-4-benzyloxy-butyryl)-piperazine-1-carboxylic acid ethyl ester hydrotrifluoroacetate To a solution of 1.23 g 4-((S)-4-benzyloxy-2-tert-butoxycarbonylamino-butyryl)-piperazine-1-carboxylic acid ethyl ester in 7 ml dichloromethane were added 2 ml TFA. After stirring for 12 h and evaporation of the solvents the crude trifluoroacetate salt was obtained as colorless oil. Yield: 1.30 g.

iii) 4-[(S)-4-Benzyloxy-2-({5-[2-((S)-2-cyclobutyl-carbamoyl-pyrrolidin-1-yl)-2-oxo-ethoxy]-1-phenyl-1H-pyrazole-3-carbonyl}-amino)-butyryl]-piperazine-1-carboxylic acid ethyl ester To a solution of 355 mg 5-[2-((S)-2-cyclobutylcarbamoyl-pyrrolidin-1-yl)-2-oxo-ethoxy]-1-phenyl-1H-pyrazole-3-carboxylic acid in 3 ml DMF were added 356 µl DIPEA, 328 mg HATU and 400 mg 4-((S)-2-amino-4-benzyloxy-butyryl)-piperazine-1-carboxylic acid ethyl ester hydrotrifluoroacetate. After stirring for 12 h the reaction mixture was diluted with ethyl acetate and subsequently washed with aqueous LiCl (4%), 0.1 M HCl and saturated NaHCO$_3$. The crude product obtained after evaporation of the solvent was used without further purification. Yield: 543 mg.

iv) 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-hydroxy-butyryl]-piperazine-1-carboxylic acid ethyl ester To a solution of 543 mg 4-[(S)-4-benzyloxy-2-({5-[2-((S)-2-cyclobutylcarbamoyl-pyrrolidin-1-yl)-2-oxo-ethoxy]-1-phenyl-1H-pyrazole-3-carbonyl}-amino)-butyryl]-piperazine-1-carboxylic acid ethyl ester in 15 ml ethyl acetate were added 200 mg Pd/C (10%) and the suspension stirred under an atmosphere of hydrogen (1 bar) for 12 h. The reaction mixture was filtrated, washed with ethyl acetate and concentrated. The crude product was purified by preparative HPLC (C18 reverse phase column, elution with a water/MeCN gradient with 0.1% TFA). The fractions containing the product were lyophilized to yield the pure product. Yield: 178 mg MS (ES+): m/e=654.

Example 116

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-5-hydroxy-pentanoyl]-piperazine-1-carboxylic acid butyl ester i) (S)-2-tert-Butoxycarbonylamino-5-(tert-butyl-diphenyl-silanyloxy)-pentanoic acid benzyl ester To a solution of 2.5 g (S)-2-tert-Butoxycarbonylamino-5-hydroxy-pentanoic acid benzyl ester (prepared by adapting the procedure described by Diederichsen et al., Org. Biomol. Chem., 2005, 3, 1058) in 50 ml DMF were added 2.0 ml TBDPSCl, 1.2 ml triethylamine and 95 mg DMAP and the resulting suspension was stirred for 4 days. The solvent was evaporated, the residue dissolved in ethyl acetate and washed with aqueous LiCl (4 w/w), 0.1 M HCl and saturated NaHCO$_3$. The crude product obtained after evaporation of the solvent was purified by chromatography on silica using heptane/ethyl acetate 12/1 as eluent. Yield: 2.0 g colorless oil.

ii) (S)-2-tert-Butoxycarbonylamino-5-(tert-butyl-diphenyl-silanyloxy)-pentanoic acid To a solution of 1.9 g (S)-2-tert-Butoxycarbonylamino-5-(tert-butyl-diphenyl-silanyloxy)-pentanoic acid benzyl ester in 40 ml ethyl acetate were added 200 mg Pd/C (10%) and the suspension was stirred under an atmosphere of hydrogen (3 bar) for 16 h.

The reaction mixture was filtered over a plug of Celite, washed with ethyl acetate and concentrated.

The product thus obtained was used in the subsequent reaction. Yield: 1.6 g.

iii) 4-[(S)-2-tert-Butoxycarbonylamino-5-(tert-butyl-diphenyl-silanyloxy)-pentanoyl]-piperazine-1-carboxylic acid butyl ester To a solution of 1.6 g (S)-2-tert-Butoxycarbonylamino-5-(tert-butyl-diphenyl-silanyloxy)-pentanoic acid in 8 ml DMF were added 1.7 ml N-ethylmorpholine, 1.0 g 1-butoxy-carbonylpiperazine hydrotrifluoroacetate and 1.1 g TOTU. The solution was stirred for 12 h before being diluted with ethyl acetate and extracted subsequently with aqueous LiCl (4%), 0.1 M HCl and saturated aqueous NaHCO$_3$. The crude product obtained after evaporation of the solvent was used without further purification. Yield: 1.8 g.

iv) 4-[(S)-2-Amino-5-(tert-butyl-diphenyl-silanyloxy)-pentanoyl]-piperazine-1-carboxylic acid butyl ester hydrochloride A solution of 900 mg 4-[(S)-2-tert-Butoxycarbonylamino-5-(tert-butyl-diphenyl-silanyloxy)-pentanoyl]-piperazine-1-carboxylic acid butyl ester in 5 ml dioxane and 5 ml HCl (4 M in dioxane) was stirred for 3 h at RT. After this time the reaction mixture was neutralized with (Polystyryl-methyl) trimethylammonium bicarbonate, the suspension filtered, washed with ethyl acetate and the wash solutions evaporated to give the crude product. Yield: 760 mg.

v) 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-5-(tert-butyl-diphenyl-silanyloxy)-pentanoyl]-piperazine-1-carboxylic acid butyl ester To a solution of 194 mg 5-[2-((S)-2-cyclobutylcarbamoyl-pyrrolidin-1-yl)-2-oxo-ethoxy]-1-phenyl-1H-pyrazole-3-carboxylic acid in 10 ml DMF were added 195 µl DIPEA, 135 mg EDC, 108 mg HOBt and 255 mg 4-[(S)-2-Amino-5-(tert-butyl-diphenyl-silanyloxy)-pentanoyl]-piperazine-1-carboxylic acid butyl ester hydrochloride. After stirring for 12 h the reaction mixture was diluted with ethyl acetate and subsequently washed with aqueous LiCl (4%), 0.1 M HCl and saturated NaHCO$_3$. The crude product obtained after evaporation of the solvent was used in the subsequent deprotection reaction. Yield: 400 mg.

vi) 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-5-hydroxy-pentanoyl]-piperazine-1-carboxylic acid butyl ester To solution of 400 mg 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-5-(tert-butyl-diphenyl-silanyloxy)-pentanoyl]-piperazine-1-carboxylic acid butyl ester in 40 ml THF were added 0.6 ml TBAF (1 M in THF) and the solution was stirred for 12 h. The reaction mixture was concentrated, the residue dissolved in dichloromethane and extracted with water (3×). The organic layer was evaporated and the residue purified by preparative HPLC (C18 reverse phase column, elution with a water/MeCN gradient with 0.1% TFA). The fractions containing the product were lyophilized to yield the pure product.

Yield: 45 mg MS (ES+): m/e=696.

Example 117

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4,5-dihydroxy-pentanoyl]-piperazine-1-carboxylic acid ethyl ester i) 4-((S)-2-tert-Butoxycarbonylamino-pent-4-enoyl)-piperazine-1-carboxylic acid ethyl ester To a solution of 540 mg Boc-L-Allylglycine in 5 ml DMF were added 0.32 ml N-ethylmorpholine, 0.37 ml ethoxycarbonylpiperazine and 0.83 g TOTU at 0° C. The solution was stirred for 1 h before being diluted with ethyl acetate and extracted subsequently with aqueous LiCl (4%), 0.1 M HCl and half-saturated aqueous NaHCO$_3$. The crude product obtained after evaporation of the solvent was used without further purification.

Yield: 859 mg.

ii) 4-((S)-2-Benzyloxycarbonylamino-pent-4-enoyl)-piperazine-1-carboxylic acid ethyl ester A solution of 767 mg 4-((S)-2-tert-Butoxycarbonylamino-pent-4-enoyl)-piperazine-1-carboxylic acid ethyl ester in 5 ml dichloromethane and 1.6 ml TFA was stirred for 2 h. The reaction mixture was concentrated, the residue dissolved in 4 ml dioxane/water (1:1) and 661 mg NaHCO$_3$ and 688 mg N-(Benzyloxycarbonyloxy)succinimide were added. After 12 h the reaction mixture was diluted with ethyl acetate and washed with water, 0.1 M HCl and half-saturated aqueous NaHCO$_3$ solution. The crude product obtained after evaporation of the solvent was purified by chromatography on silica using ethyl acetate/heptane 1:2 to 2:1 as eluent. Yield: 640 mg.

iii) 4-((S)-2-Benzyloxycarbonylamino-4,5-dihydroxy-pentanoyl)-piperazine-1-carboxylic acid ethyl ester To a solution of 640 mg 4-((S)-2-Benzyloxycarbonylamino-pent-4-enoyl)-piperazine-1-carboxylic acid ethyl ester in 10 ml acetone/water (4/1) were added 2.1 ml OsO$_4$ (2.5 w/w in t-BuOH) and 567 mg 4-Methylmorpholine-N-oxide monohydrate at 0° C. After 1 h solid NaHSO$_3$ was added, the suspension stirred for 5 minutes, filtered and the filtrate concentrated. The residue was redissolved in dichloromethane and washed with aqueous NaHSO$_3$ (5%) and brine. The crude product obtained after evaporation of the solvent was directly used in the next reaction step. Yield: 755 mg.

iv) 4-[(S)-2-Benzyloxycarbonylamino-3-(2,2-dimethyl-[1,3]dioxolan-4-yl)-propionyl]-piperazine-1-carboxylic acid ethyl ester To a solution of 755 mg 4-((S)-2-Benzyloxycarbonylamino-4,5-dihydroxy-pentanoyl)-piperazine-1-carboxylic acid ethyl ester in 10 ml dichloromethane were added 10 mg p-toluenesulfonic acid and 10 ml 2,2-dimethoxypropane and the solution stirred for 1 h. The reaction mixture was concentrated, the residue dissolved in dichloromethane and washed with saturated aqueous NaHCO$_3$ and brine. The crude product obtained after evaporation of the solvent was directly used in the next reaction step. Yield: 612 mg.

v) 4-[(S)-2-Amino-3-(2,2-dimethyl-[1,3]dioxolan-4-yl)-propionyl]-piperazine-1-carboxylic acid ethyl ester To a solution of 612 mg 4-[(S)-2-Benzyloxycarbonylamino-3-(2,2-dimethyl-[1,3]dioxolan-4-yl)-propionyl]-piperazine-1-carboxylic acid ethyl ester in 15 ml ethyl acetate were added 200 mg Pd/C (10%) and the suspension stirred under an atmosphere of hydrogen (1 bar) for 12 h. The reaction mixture was filtered over a plug of Celite, washed with ethyl acetate, concentrated and the crude product used without further purification. Yield: 344 mg.

vi) 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-3-(2,2-dimethyl-[1,3]dioxolan-4-yl)-propionyl]piperazine-1-carboxylic acid ethyl ester To a solution of 120 mg 5-[2-((S)-2-cyclobutylcarbamoyl-pyrrolidin-1-yl)-2-oxo-ethoxy]-1-phenyl-1H-pyrazole-3-carboxylic acid in 3 ml DMF were added 50 µl DIPEA, 111 mg HATU and 96 mg 4-[(S)-2-Amino-3-(2,2-dimethyl-[1,3]dioxolan-4-yl)-propionyl]-piperazine-1-carboxylic acid ethyl ester. After stirring for 12 h the reaction mixture was diluted with ethyl acetate and subsequently washed with aqueous LiCl (4%), 0.1 M HCl and saturated aqueous NaHCO$_3$. The crude product obtained after evaporation of the solvent was used in the subsequent deprotection reaction. Yield: 238 mg.

vii) 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4,5-dihydroxy-pentanoyl]-piperazine-1-carboxylic acid ethyl ester To a solution of 15 mg 4-[(S)-2-({5-[2-((S)-2-Cyclobutyl-carbamoyl-pyrrolidin-1-yl)-2-oxo-ethoxy]-1-phenyl-1H-pyrazole-3-carbonyl}-amino)-3-(2,2-dimethyl-[1,3]dioxolan-4-yl)-propionyl]-piperazine-1-carboxylic acid ethyl ester in 5 ml MeOH were added 5 mg pyridinium p-toluenesulfonate and the solution was stirred for 2 h before being concentrated in vacuo. The residue thus obtained was purified by preparative HPLC (C18 reverse phase column, elution with a water/MeCN gradient with 0.1% TFA). The fractions containing the product were lyophilized to yield the pure product.

Yield: 6 mg MS (ES+): m/e=684.

Example 118

4-[(S)-4-Carboxy-2-({5-[2-((S)-2-cyclopropylcarbamoyl-pyrrolidin-1-yl)-2-oxo-ethoxy]-1-phenyl-1H-pyrazole-3-carbonyl}-amino)-butyryl]-piperazine-1-carboxylic acid butyl ester i) piperazine-1,4-dicarboxylic acid butyl ester tert-butyl ester To a solution of 10.9 g tert-butyl 1-piperazinecarboxylate in 145 ml dichloromethane were added 17.8 ml triethylamine. The solution was cooled to 0° C. and 8.3 ml butylchloroformate added dropwise at this temperature. After stirring for 1 h the reaction mixture was diluted with dichloromethane and washed with 0.1 M HCl and saturated NaHCO$_3$. The crude product obtained after evaporation of the solvent was directly used in the next reaction step. Yield: 18.0 g.

ii) piperazine-1-carboxylic acid butyl ester hydrotrifluoroacetate

To a solution of 18.0 g piperazine-1,4-dicarboxylic acid butyl ester tert-butyl ester in 70 ml dichloromethane were added 23 ml TFA. After stirring for 12 h the solution was concentrated and the residue codistilled with toluene twice. Yield: 18.5 g.

iii) 4-((S)-2-Benzyloxycarbonylamino-4-tert-butoxycarbonyl-butyryl)-piperazine-1-carboxylic acid butyl ester To a solution of 9.06 g (S)-2-Benzyloxycarbonylamino-pentanedioic acid 5-tert-butyl ester in 100 ml DMF were added 5.00 g piperazine-1-carboxylic acid butyl ester hydrotrifluoroacetate, 13.7 ml N-ethylmorpholine and 8.8 g TOTU. After stirring for 12 h the solution was diluted with ethyl acetate and subsequently washed with aqueous LiCl (4%) and saturated NaHCO$_3$. The crude product obtained after evaporation of the solvent was used without further purification. Yield: 15.8 g.

iv) 4-((S)-2-Amino-4-tert-butoxycarbonyl-butyryl)-piperazine-1-carboxylic acid butyl ester To a solution of 15.8 g 4-((S)-2-Benzyloxycarbonylamino-4-tert-butoxycarbonyl-butyryl)-piperazine-1-carboxylic acid butyl ester in 60 ml ethanol were added 1.8 g Pd/C (10%) and the suspension stirred under an atmosphere of hydrogen (3 bar) for 12 h. The reaction mixture was filtrated over a plug of Celite, washed with ethanol and concentrated to give the crude product which was purified by flash chromatography on silica using dichloro-methane/methanol 90:10 as eluent. Yield: 9.6 g colorless oil.

v) 4-{(S)-4-tert-Butoxycarbonyl-2-[(5-hydroxy-1-phenyl-1H-pyrazole-3-carbonyl)-amino]-butyryl}-piperazine-1-carboxylic acid butyl ester To a solution of 2.75 g 1-phenyl-3-carboxy-5-pyrazolone and 5.00 g 4-((S)-2-amino-4-tert-butoxycarbonyl-butyryl)-piperazine-1-carboxylic acid butyl ester in 15 ml DMF 2.06 g HOBt, 4.5 ml DIPEA and 2.58 g EDC were added and the reaction mixture was stirred for 12 h at RT. Then the reaction mixture was diluted with ethyl acetate and subsequently extracted with aqueous LiCl (4% w/w), 0.1 M HCl and aqueous NaHCO₃. The organic layer was dried over MgSO₄ and the solvent was removed under reduced pressure. The crude product thus obtained was used in the subsequent reaction.
Yield: 10.70 g.

vi) 4-{(S)-2-[(5-Benzyloxycarbonylmethoxy-1-phenyl-1H-pyrazole-3-carbonyl)-amino]-4-tert-butoxycarbonyl-butyryl}-piperazine-1-carboxylic acid butyl ester To a solution of 7.00 g 4-{(S)-4-tert-butoxycarbonyl-2-[(5-hydroxy-1-phenyl-1H-pyrazole-3-carbonyl)-amino]-butyryl}-piperazine-1-carboxylic acid butyl ester in 45 ml DMF were added 2.1 ml benzyl bromoacetate and 8.2 g cesium carbonate. After stirring at RT for 12 h the reaction mixture was diluted with ethyl acetate and extracted with aqueous LiCl (4% w/w) and saturated aqueous NaHCO₃. The crude product obtained after evaporation of the solvent was not further purified. Yield: 7.02 g yellowish oil.

vii) 4-{(S)-4-tert-Butoxycarbonyl-2-[(5-carboxymethoxy-1-phenyl-1H-pyrazole-3-carbonyl)-amino]-butyryl}-piperazine-1-carboxylic acid butyl ester To a solution of 7.02 g 4-{(S)-2-[(5-Benzyloxycarbonylmethoxy-1-phenyl-1H-pyrazole-3-carbonyl)-amino]-4-carboxy-butyryl}-piperazine-1-carboxylic acid butyl ester in 70 ml ethyl acetate were added under argon 0.7 g Pd/C (10%) and the suspension was stirred under an atmosphere of hydrogen (3 bar) for 16 h. The suspension was filtered over a plug of Celite® and washed with ethyl acetate. The crude product was obtained after evaporation of the solvent. Yield: 5.4 g yellowish oil.

viii) 4-[(S)-2-({5-[2-((S)-2-Benzyloxycarbonyl-pyrrolidin-1-yl)-2-oxo-ethoxy]-1-phenyl-1H-pyrazole-3-carbonyl}-amino)-4-tert-butoxycarbonyl-butyryl]-piperazine-1-carboxylic acid butyl ester To a solution of 2.50 g 4-{(S)-4-tert-butoxycarbonyl-2-[(5-carboxymethoxy-1-phenyl-1H-pyrazole-3-carbonyl)-amino]-butyryl}-piperazine-1-carboxylic acid butyl ester in 30 ml DMF were added 621 mg HOBt, 1.3 ml DIPEA, 778 mg EDC and 981 mg L-proline benzyl ester hydrochloride. After stirring for 12 h the solvent was evaporated, the residue dissolved in ethyl acetate and subsequently extracted with aqueous LiCl (4% w/w) and aqueous NaHCO₃. The organic layer was dried over MgSO₄ and the solvent was removed under reduced pressure. The crude product thus obtained was used in the subsequent reaction.
Yield: 3.9 g.

ix) 4-[(S)-4-tert-Butoxycarbonyl-2-({5-[2-((S)-2-carboxy-pyrrolidin-1-yl)-2-oxo-ethoxy]-1-phenyl-1H-pyrazole-3-carbonyl}-amino)-butyryl]-piperazine-1-carboxylic acid butyl ester To a solution of 3.9 g 4-[(S)-2-({5-[2-((S)-2-Benzyloxycarbonyl-pyrrolidin-1-yl)-2-oxo-ethoxy]-1-phenyl-1H-pyrazole-3-carbonyl}-amino)-4-tert-butoxycarbonyl-butyryl]-piperazine-1-carboxylic acid butyl ester in 80 ml ethyl acetate were added under argon 2 g Pd/C (10%) and the suspension was stirred under an atmosphere of hydrogen (3 bar) for 24 h. The suspension was filtered over a plug of Celite® and washed with ethyl acetate. The crude product obtained after evaporation of the solvent was used in the subsequent reaction. Yield: 2.6 g.

x) 4-[(S)-4-Carboxy-2-({5-[2-((S)-2-cyclopropylcarbamoyl-pyrrolidin-1-yl)-2-oxo-ethoxy]-1-phenyl-1H-pyrazole-3-carbonyl}-amino)-butyryl]-piperazine-1-carboxylic acid butyl ester To a solution of 300 mg 4-[(S)-4-tert-butoxycarbonyl-2-({5-[2-((S)-2-carboxy-pyrrolidin-1-yl)-2-oxo-ethoxy]-1-phenyl-1H-pyrazole-3-carbonyl}-amino)-butyryl]-piperazine-1-carboxylic acid butyl ester in 5 ml DMF were added 66 µl DIPEA and 160 mg HATU. After 20 minutes 29 µl cyclopropylamine were added. After stirring for 12 h saturated NaHCO₃ solution was added and the mixture loaded on a Chem Elut® cartridge, the crude product being eluted with dichloromethane. The solution was concentrated to a volume of 5 ml and stirred in the presence of 476 µl TFA. After stirring for 4 h the solvents were removed under reduced pressure and the residue purified by preparative HPLC (C18 reverse phase column, elution with a water/MeCN gradient with 0.1% TFA). The fractions containing the product were lyophilized to yield the pure product.
Yield: 142 mg MS (ES+): m/e=696.

Example 119

4-[(S)-4-Carboxy-2-({5-[2-((S)-2-cyclobutylcarbamoyl-pyrrolidin-1-yl)-2-oxo-ethoxy]-1-phenyl-1H-pyrazole-3-carbonyl}-amino)-butyryl]-piperazine-1-carboxylic acid butyl ester The title compound was prepared by adapting the procedures described in example 118 with the difference that cyclobutylamine was used instead of cyclopropylamine.
Yield: 168 mg MS (ES+): m/e=710.

Example 120

4-[(S)-4-Carboxy-2-({5-[2-((S)-2-cyclopropylmethylcarbamoyl-pyrrolidin-1-yl)-2-oxo-ethoxy]-1-phenyl-1H-pyrazole-3-carbonyl}-amino)-butyryl]-piperazine-1-carboxylic acid butyl ester The title compound was prepared by adapting the procedures described in example 118 with the difference that aminomethylcyclopropane was used instead of cyclopropylamine.
Yield: 174 mg MS (ES+): m/e=710.

Example 121

4-{(S)-4-Carboxy-2-[(5-{2-[(S)-2-(2,2-difluoro-ethylcarbamoyl)-pyrrolidin-1-yl]-2-oxo-ethoxy}-1-phenyl-1H-pyrazole-3-carbonyl)-amino]-butyryl}-piperazine-1-carboxylic acid butyl ester The title compound was prepared by adapting the procedures described in example 118 with the difference that 2,2-difluoroethylamine was used instead of cyclopropylamine. Yield: 135 mg MS (ES+): m/e=720.

Example 122

4-{(S)-4-Carboxy-2-[(5-{2-[(S)-2-(2-fluoro-ethylcarbamoyl)-pyrrolidin-1-yl]-2-oxo-ethoxy}-1-phenyl-1H-pyrazole-3-carbonyl)-amino]-butyryl}-piperazine-1-carboxylic acid butyl ester The title compound was prepared by adapting the procedures described in example 118 with the difference that 2-fluoroethylamine hydrochloride was used instead of cyclopropylamine. Yield: 172 mg MS (ES+): m/e=702.

Example 123

4-{(S)-4-Carboxy-2-[(5-{2-[(S)-2-(2,2,2-trifluoro-ethylcarbamoyl)-pyrrolidin-1-yl]-2-oxo-ethoxy}-1-phenyl-1H-pyrazole-3-carbonyl)-amino]-butyryl}-piperazine-1-carboxylic acid butyl ester The title compound was prepared by adapting the procedures described in example 118 with the difference that 2,2,2-trifluoroethylamine was used instead of cyclopropylamine. Yield: 182 mg MS (ES+): m/e=738.

Example 124

4-{(S)-4-Carboxy-2-[(5-{2-[(S)-2-(cyclobutyl-methyl-carbamoyl)-pyrrolidin-1-yl]-2-oxo-ethoxy}-1-phenyl-1H-pyrazole-3-carbonyl)-amino]-butyryl}-piperazine-1-carboxylic acid butyl ester The title compound was prepared by adapting the procedures described in example 118 with the difference that N-methyl-N-cyclobutylamine was used instead of cyclopropylamine. Yield: 64 mg MS (ES+): m/e=723.

Example 125

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-(2H-tetrazol-5-yl)-butyryl]-piperazine-1-carboxylic acid ethyl ester i) (S)-4-Benzylcarbamoyl-2-tert-butoxycarbonylamino-butyric acid benzyl ester To a solution of 1.00 g (S)-2-tert-butoxycarbonylaminopentanedioic acid 1-benzyl ester in 15 ml DMF were added 1.24 g HATU, 1.1 ml DIPEA and 0.32 ml benzylamine at 0° C.

After stirring for 12 h the reaction mixture was concentrated, the residue dissolved in dichloromethane and subsequently extracted with aqueous LiCl (4%), 0.1 M HCl and saturated NaHCO₃. The crude product obtained after evaporation of the solvent was purified by flash chromatography on silica using ethyl acetate/heptane 1:1 as eluent.

Yield: 1.18 g colorless amorphous solid ii) (S)-4-(4-Benzyl-2H-tetrazol-5-yl)-2-tert-butoxycarbonylamino-butyric acid benzyl ester To a suspension of 0.83 g (S)-4-benzylcarbamoyl-2-tert-butoxycarbonylamino-butyric acid benzyl ester and 1.28 g triphenylphosphine in 16 ml acetonitrile were added dropwise at 0° C. 1.00 ml diisopropylazodicarboxylate and after 2 minutes 0.67 ml trimethylsilylazide over a period of 10 minutes. After 30 minutes the mixture was allowed to warm to RT and stirred for 12 h. The mixture was cooled to 0° C. and 0.67 ml aqueous sodium nitrite (2.9 M) were added, after 30 minutes a solution of 1.07 g ceric ammonium nitrate in 10 ml water was added and stirred for another 20 minutes. After this time the mixture was poured into ice and extracted twice with dichloromethane.

The crude product thus obtained after evaporation of the solvent was purified by flash chromatography on silica eluting with ethyl acetate/heptane 1:3 to 1:2.

Yield: 786 mg colorless needles iii) (S)-2-tert-Butoxycarbonylamino-4-(2H-tetrazol-5-yl)-butyric acid To a solution of 786 mg (S)-4-(4-benzyl-2H-tetrazol-5-yl)-2-tert-butoxycarbonylamino-butyric acid benzyl ester in 20 ml ethyl acetate was added 1.0 g Pd/C (10%) and the suspension stirred under an atmosphere of hydrogen (1 bar) for 48 h. The reaction mixture was filtrated over a plug of Celite® and washed with ethyl acetate. Yield: 516 mg colorless solid iv) 4-[(S)-2-tert-Butoxycarbonylamino-4-(2H-tetrazol-5-yl)-butyryl]-piperazine-1-carboxylic acid ethyl ester To a solution of 82 mg (S)-2-tert-butoxycarbonylamino-4-(2H-tetrazol-5-yl)-butyric acid in 2 ml DMF were added 115 mg HATU, 100 µl DIPEA and 44 µl 1-ethoxycarbonyl-piperazine. After 1 h the solution was concentrated and the residue directly used in the next reaction step. Yield: 120 mg.

v) 4-[(S)-2-Amino-4-(2H-tetrazol-5-yl)-butyryl]-piperazine-1-carboxylic acid ethyl ester hydrotrifluoroacetate To a solution of 120 mg 4-[(S)-2-tert-butoxycarbonylamino-4-(2H-tetrazol-5-yl)-butyryl]-piperazine-1-carboxylic acid ethyl ester in 1.5 ml dichloromethane were added 0.4 ml TFA. After 2 h stirring at RT the solvents were removed and the residue was used without further purification. Yield: 130 mg.

vi) 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-(2H-tetrazol-5-yl)-butyryl]-piperazine-1-carboxylic acid ethyl ester To a solution of 126 mg 5-[2-((S)-2-cyclobutylcarbamoyl-pyrrolidin-1-yl)-2-oxo-ethoxy]-1-phenyl-1H-pyrazole-3-carboxylic acid in 2 ml DMF were added 160 µl DIPEA, 116 mg HATU and 130 mg 4-[(S)-2-amino-4-(2H-tetrazol-5-yl)-butyryl]-piperazine-1-carboxylic acid ethyl ester hydrotrifluoroacetate. After 30 minutes the reaction mixture was concentrated and the crude product obtained purified by preparative HPLC (C18 reverse phase column, elution with a water/MeCN gradient with 0.1% TFA). The fractions containing the product were lyophilized to yield the pure product. Yield: 29 mg MS (ES+): m/e=706.

Example 126

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-(2H-tetrazol-5-yl)-butyryl]-piperazine-1-carboxylic acid butyl ester i) 4-[(S)-2-tert-Butoxycarbonylamino-4-(2H-tetrazol-5-yl)-butyryl]-piperazine-1-carboxylic acid butyl ester To a solution of 222 mg (S)-2-tert-butoxycarbonylamino-4-(2H-tetrazol-5-yl)-butyric acid in 5 ml DMF were added 300 mg HATU, 541 µl DIPEA and 245 mg piperazine-1-carboxylic acid butyl ester hydrotrifluoroacetate. After 1 h the solution was concentrated, taken up with dichloromethane and washed with aqueous LiCl (4%) and 0.1 M HCl. The crude product thus obtained was used in the next reaction step without further purification.

Yield: 360 mg.

ii) 4-[(S)-2-Amino-4-(2H-tetrazol-5-yl)-butyryl]-piperazine-1-carboxylic acid butyl ester hydrotrifluoroacetate To a solution of 360 mg 4-[(S)-2-tert-butoxycarbonylamino-4-(2H-tetrazol-5-yl)-butyryl]-piperazine-1-carboxylic acid butyl ester in 5 ml dichloromethane were added 0.5 ml TFA. After 2 h stirring at RT the solvents were removed and the residue was used without further purification. Yield: 360 mg.

iii) 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-(2H-tetrazol-5-yl)-butyryl]-piperazine-1-carboxylic acid butyl ester To a solution of 327 mg 5-[2-((S)-2-cyclobutylcarbamoyl-pyrrolidin-1-yl)-2-oxo-ethoxy]-1-phenyl-1H-pyrazole-3-carboxylic acid in 5 ml DMF were added 415 µl DIPEA, 302 mg HATU and 360 mg 4-[(S)-2-amino-4-(2H-tetrazol-5-yl)-butyryl]-piperazine-1-carboxylic acid butyl ester hydrotrifluoroacetate. After 30 minutes the reaction mixture was concentrated and the crude product obtained purified by preparative HPLC (C18 reverse phase column, elution with a water/MeCN gradient with 0.1% TFA). The fractions containing the product were lyophilized to yield the pure product. Yield: 180 mg MS (ES+): m/e=734.

Example 127

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-ethoxycarbonyl-butyryl]-piperazine-1-carboxylic acid ethyl ester To a solution of 60 mg 4-[(S)-4-Carboxy-2-({5-[2-((S)-2-cyclobutylcarbamoyl-pyrrolidin-1-yl)-2-oxo-ethoxy]-1-phenyl-1H-pyrazole-3-carbonyl}-amino)-butyryl]-piperazine-1-carboxylic acid ethyl ester in 2 ml dichloromethane were added 20 mg EDC, 13 mg DMAP and 26 µl ethanol. After 3 h the reaction mixture was concentrated and the residue purified by preparative HPLC (C18 reverse phase column, elution with a water/MeCN gradient with 0.1% TFA). The fractions containing the product were lyophilized to yield the pure product. Yield: 37 mg MS (ES+): m/e=710.

Example 128

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-cyclopropylmethoxycarbonyl-butyryl]-piperazine-1-carboxylic acid ethyl ester The title compound was prepared by adapting the procedures described in example 127 with the difference that cyclopropylcarbinol was used instead of ethanol.

Yield: 40 mg MS (ES+): m/e=736.

Example 129

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-cyclohexyloxycarbonyl-butyryl]-piperazine-1-carboxylic acid ethyl ester The title compound was prepared by adapting the procedures described in example 127 with the difference that cyclohexanol was used instead of ethanol.

Yield: 36 mg MS (ES+): m/e=764.

Example 130

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-cyclopentyloxycarbonyl-butyryl]-piperazine-1-carboxylic acid ethyl ester The title compound was prepared by adapting the procedures described in example 127 with the difference that cyclopentanol was used instead of ethanol.

Yield: 35 mg MS (ES+): m/e=750.

Example 131

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-cyclobutoxycarbonyl-butyryl]-piperazine-1-carboxylic acid ethyl ester The title compound was prepared by adapting the procedures described in example 127 with the difference that cyclobutanol was used instead of ethanol.

Yield: 30 mg MS (ES+): m/e=736.

Example 132

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-benzyloxycarbonyl-butyryl]-piperazine-1-carboxylic acid ethyl ester The title compound was prepared by adapting the procedures described in example 127 with the difference that benzylalcohol was used instead of ethanol.

Yield: 38 mg MS (ES+): m/e=772.

Example 133

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-propoxycarbonyl-butyryl]-piperazine-1-carboxylic acid ethyl ester The title compound was prepared by adapting the procedures described in example 127 with the difference that propanol was used instead of ethanol.
Yield: 34 mg MS (ES+): m/e=724.

Example 134

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-butoxycarbonyl-butyryl]-piperazine-1-carboxylic acid ethyl ester The title compound was prepared by adapting the procedures described in example 127 with the difference that butanol was used instead of ethanol.
Yield: 34 mg MS (ES+): m/e=738.

Example 135

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-isobutoxycarbonyl-butyryl]-piperazine-1-carboxylic acid ethyl ester The title compound was prepared by adapting the procedures described in example 127 with the difference that isobutanol was used instead of ethanol.
Yield: 34 mg MS (ES+): m/e=738.

Example 136

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-methoxycarbonyl-butyryl]-piperazine-1-carboxylic acid ethyl ester The title compound was prepared by adapting the procedures described in example 127 with the difference that methanol was used instead of ethanol.
Yield: 31 mg MS (ES+): m/e=696.

Example 137

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-isopropoxycarbonyl-butyryl]-piperazine-1-carboxylic acid ethyl ester The title compound was prepared by adapting the procedures described in example 127 with the difference that cyclopropylcarbinol was used instead of ethanol.
Yield: 288 mg MS (ES+): m/e=724.

Example 138

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-cyclopentylmethoxycarbonyl-butyryl]-piperazine-1-carboxylic acid ethyl ester The title compound was prepared by adapting the procedures described in example 127 with the difference that cyclopentylmethanol was used instead of ethanol.
Yield: 655 mg MS (ES+): m/e=764.

Example 139

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-(2,2-dimethyl-propionyloxymethoxycarbonyl)-butyryl]-piperazine-1-carboxylic acid ethyl ester To a solution of 150 mg 4-[(S)-4-Carboxy-2-({5-[2-((S)-2-cyclobutylcarbamoyl-pyrrolidin-1-yl)-2-oxo-ethoxy]-1-phenyl-1H-pyrazole-3-carbonyl}-amino)-butyryl]-piperazine-1-carboxylic acid ethyl ester in 7 ml acetone were added 40 mg chloromethylpivalate, 8 mg tetrabutylammonium iodide, 72 mg cesium carbonate and 61 µl triethylamine. The reaction mixture was refluxed for 4 h under argon. Additional 40 mg chloromethylpivalate, 8 mg tetrabutylammonium iodide, 72 mg cesium carbonate and 61 µl triethylamine were added and the suspension refluxed for another 7 h. The reaction mixture was concentrated and the residue was purified by preparative HPLC (C18 reverse phase column, elution with a water/MeCN gradient with 0.1% TFA). The fractions containing the product were lyophilized to yield the pure product.
Yield: 75 mg MS (ES+): m/e=796.

Example 140

4-((S)-2-{[5-[2-((S)-2-Cyclobutylcarbamoyl-pyrrolidin-1-yl)-2-oxo-ethoxy]-1-(3-fluoro-phenyl)-1H-pyrazole-3-carbonyl]-amino}-4-ethoxyoxycarbonyl-butyryl)-piperazine-1-carboxylic acid ethyl ester To a solution of 1.60 g 4-((S)-4-Carboxy-2-{[5-[2-((S)-2-cyclobutylcarbamoyl-pyrrolidin-1-yl)-2-oxo-ethoxy]-1-(3-fluoro-phenyl)-1H-pyrazole-3-carbonyl]-amino}-butyryl)-piperazine-1-carboxylic acid ethyl ester in 30 ml dichloromethane were added 526 mg EDC, 335 mg DMAP and 676 µl ethanol. After 3 h the reaction mixture was concentrated and the residue purified by preparative HPLC (C18 reverse phase column, elution with a water/MeCN gradient with 0.1% TFA). The fractions containing the product were lyophilized to yield the pure product. Yield: 295 mg MS (ES+): m/e=728.

Example 141

4-((S)-2-{[5-[2-((S)-2-Cyclobutylcarbamoyl-pyrrolidin-1-yl)-2-oxo-ethoxy]-1-(3-fluoro-phenyl)-1H-pyrazole-3-carbonyl]-amino}-4-isopropoxycarbonyl-butyryl)-piperazine-1-carboxylic acid ethyl ester The title compound was prepared by adapting the procedures described in example 140 with the difference that isopropanol was used instead of ethanol.
Yield: 530 mg MS (ES+): m/e=742.

Example 142

4-((S)-2-{[5-[2-((S)-2-Cyclobutylcarbamoyl-pyrrolidin-1-yl)-2-oxo-ethoxy]-1-(3,4-difluoro-phenyl)-1H-pyrazole-3-carbonyl]-amino}-4-ethoxycarbonyl-butyryl)-piperazine-1-carboxylic acid ethyl ester To a solution of 1.50 g 4-((S)-4-Carboxy-2-{[5-[2-((S)-2-cyclobutylcarbamoyl-pyrrolidin-1-yl)-2-oxo-ethoxy]-1-(3,4-difluoro-phenyl)-1H-pyrazole-3-carbonyl]-amino}-butyryl)-piperazine-1-carboxylic acid ethyl ester in 25 ml dichloromethane were added 481 mg EDC, 306 mg DMAP and 617 µl ethanol. After 3 h the reaction mixture was concentrated and the residue purified by preparative HPLC (C18 reverse phase column, elution with a water/MeCN gradient with 0.1% TFA). The fractions containing the product were lyophilized to yield the pure product. Yield: 520 mg MS (ES+): m/e=746.

Example 143

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-ethoxycarbonyl-butyryl]-piperazine-1-carboxylic acid butyl ester To a solution of 1.30 g 4-[(S)-4-Carboxy-2-({5-[2-((S)-2-cyclobutylcarbamoyl-pyrrolidin-1-yl)-2-oxo-ethoxy]-1-phenyl-1H-pyrazole-3-carbonyl}-amino)-butyryl]-piperazine-1-carboxylic acid butyl ester in 22 ml dichloromethane were added 421 mg EDC, 268 mg DMAP and 541 µl ethanol. After 3 h the reaction mixture was concentrated and the residue purified by preparative HPLC (C18 reverse phase column, elution with a water/MeCN gradient with 0.1% TFA). The fractions containing the product were lyophilized to yield the pure product. Yield: 550 mg MS (ES+): m/e=738.

Example 144

(R)-4-[(S)-4-Carboxy-2-({5-[2-((S)-2-cyclobutylcarbamoyl-pyrrolidin-1-yl)-2-oxo-ethoxy]-1-phenyl-1H-pyrazole-3-carbonyl}-amino)-butyryl]-2-methyl-piperazine-1-carboxylic acid ethyl ester i) (R)-2-Methyl-piperazine-1,4-dicarboxylic acid 4-tert-butyl ester 1-ethyl ester To a solution of 1.50 g (R)-4-N-Boc-2-methyl-piperazine in 10 ml dichloromethane were added at 0° C. 2.29 ml triethylamine and 0.72 ml ethyl chloroformate. After 12 h the reaction mixture was diluted with dichloromethane and extracted with 0.1 M HCl and saturated aqueous NaHCO₃. The organic layer was dried over MgSO₄ and the crude product obtained after evaporation of the solvent was used in the subsequent reaction.
Yield: 2.05 g.

ii) (R)-2-Methyl-piperazine-1-carboxylic acid ethyl ester

A solution of 2.05 g (R)-2-Methyl-piperazine-1,4-dicarboxylic acid 4-tert-butyl ester 1-ethyl ester in 15 ml dichloromethane was treated with 11.2 ml TFA and the resulting solution stirred for 12 h. The solvents were removed in vacuum and the crude hydrotrifluoroacetate transformed to the free amine by treatment with (Polystyrylmethyl)trimethylammonium bicarbonate in MeCN. Yield: 1.45 g.

iii) (R)-4-[(S)-4-Carboxy-2-({5-[2-((S)-2-cyclobutyl-carbamoyl-pyrrolidin-1-yl)-2-oxo-ethoxy]-1-phenyl-1H-pyrazole-3-carbonyl}-amino)-butyryl]-2-methyl-piperazine-1-carboxylic acid ethyl ester To a solution of 100 mg (S)-2-({5-[2-((S)-2-cyclobutylcarbamoyl-pyrrolidin-1-yl)-2-oxo-ethoxy]-1-phenyl-1H-pyrazole-3-carbonyl}-amino)-pentanedioic acid 5-tert-butyl ester in 5 ml DMF were added 28 µl DIPEA, 64 mg HATU and 29 mg (R)-2-Methyl-piperazine-1-carboxylic acid ethyl ester. After stirring for 36 h the solution was concentrated, the residue dissolved in 1.5 ml dichloromethane and treated with 186 µl TFA. After stirring for 4 h the solvents were removed under reduced pressure and the residue purified by preparative HPLC (C18 reverse phase column, elution with a water/MeCN gradient with 0.1% TFA). The fractions containing the product were lyophilized to yield the pure product.
Yield: 70 mg MS (ES+): m/e=696.

Example 145

(R)-4-{(S)-4-Carboxy-2-[(5-{2-[(S)-2-(2-fluoro-ethylcarbamoyl)-pyrrolidin-1-yl]-2-oxo-ethoxy}-1-phenyl-1H-pyrazole-3-carbonyl)-amino]-butyryl}-2-methyl-piperazine-1-carboxylic acid ethyl ester i) 5-{2-[(S)-2-(2-Fluoro-ethylcarbamoyl)-pyrrolidin-1-yl]-2-oxo-ethoxy}-1-phenyl-1H-pyrazole-3-carboxylic acid ethyl ester To a solution of 1.3 g 5-[2-((S)-2-carboxy-pyrrolidin-1-yl)-2-oxo-ethoxy]-1-phenyl-1H-pyrazole-3-carboxylic acid ethyl ester in 20 ml DMF were added 1.28 g HATU and 0.56 ml DIPEA. After 10 minutes 334 mg 2-fluoroethylamine hydrochloride were added. Additional 100 mg 2-fluoroethylamine hydrochloride and 400 mg HATU were added after 2 h. The reaction mixture was allowed to stir for further 12 h before being diluted with dichloromethane and extracted with aqueous LiCl (4%), 0.1 M HCl and saturated NaHCO₃. The crude product obtained after evaporation of the solvent was purified by flash chromatography on silica using ethyl acetate/heptane 80:20 to ethyl acetate/heptane 100:0 as eluent. Yield: 1.5 g colorless oil.

ii) 5-[2-((S)-2-(2-Fluoro-ethylcarbamoyl)-pyrrolidin-1-yl)-2-oxo-ethoxy]-1-phenyl-1H-pyrazole-3-carboxylic acid To a solution of 1.50 g 5-[2-((S)-2-(2-Fluoro-ethylcarbamoyl)-pyrrolidin-1-yl)-2-oxo-ethoxy]-1-phenyl-1H-pyrazole-3-carboxylic acid ethyl ester in 28 ml THF and 7 ml water were added 1.7 ml aqueous NaOH (2 M) portionwise at 0° C. After 2 h the solution was neutralized with Amberlite IR-120 ion exchange resin, filtered and washed with methanol. The crude product obtained after evaporation of the solvents was used in the subsequent reaction. Yield: 1.38 g.

iii) (S)-2-({5-[2-((S)-2-(2-Fluoro-ethylcarbamoyl)-pyrrolidin-1-yl)-2-oxo-ethoxy]-1-phenyl-1H-pyrazole-3-carbonyl}-amino)-pentanedioic acid 5-tert-butyl ester 1-methyl ester To a solution of 950 mg 5-[2-((S)-2-(2-Fluoro-ethylcarbamoyl)-pyrrolidin-1-yl)-2-oxo-ethoxy]-1-phenyl-1H-pyrazole-3-carboxylic acid in 15 ml DMF were added 0.39 ml DIPEA, 893 mg HATU and 596 mg H-Glu(OtBu)-OMe hydrochloride. After stirring for 24 h the solution was concentrated, taken up with dichloromethane and subsequently extracted with aqueous LiCl (4%), 0.1 M HCl and saturated NaHCO₃. The crude product obtained after evaporation of the solvent was used in the subsequent reaction. Yield: 1.3 g.

iv) (S)-2-({5-[2-((S)-2-(2-Fluoro-ethylcarbamoyl)-pyrrolidin-1-yl)-2-oxo-ethoxy]-1-phenyl-1H-pyrazole-3-carbonyl}-amino)-pentanedioic acid 5-tert-butyl ester To a solution of 1.30 g (S)-2-({5-[2-((S)-2-(2-Fluoro-ethylcarbamoyl)-pyrrolidin-1-yl)-2-oxo-ethoxy]-1-phenyl-1H- pyrazole-3-carbonyl}-amino)-pentanedioic acid 5-tert-butyl ester 1-methyl ester in 9 ml THF were added 52 mg LiOH (as solution in 3 ml water). After 2 h the reaction mixture was neutralized with Amberlite IR-120, filtrated and washed with methanol.

Yield: 0.82 g colorless oil.

v) (R)-4-{(S)-4-Carboxy-2-[(5-{2-[(S)-2-(2-fluoro-ethylcarbamoyl)-pyrrolidin-1-yl]-2-oxo-ethoxy}-1-phenyl-1H-pyrazole-3-carbonyl)-amino]-butyryl}-2-methyl-piperazine-1-carboxylic acid ethyl ester To a solution of 81 mg (S)-2-({5-[2-((S)-2-(2-Fluoroethyl-carbamoyl)-pyrrolidin-1-yl)-2-oxo-ethoxy]-1-phenyl-1H-pyrazole-3-carbonyl}-amino)-pentanedioic acid 5-tert-butyl ester in 5 ml DMF were added 22 µl DIPEA, 52 mg HATU and 24 mg (R)-2-Methyl-piperazine-1-carboxylic acid ethyl ester. After stirring for 24 h the solution was concentrated, the residue dissolved in 1.5 ml dichloromethane and treated with 300 µl TFA. After stirring for 16 h the solvents were removed under reduced pressure and the residue purified by preparative HPLC (C18 reverse phase column, elution with a water/MeCN gradient with 0.1% TFA). The fractions containing the product were lyophilized to yield the pure product.

Yield: 60 mg MS (ES+): m/e=688.

Example 146

(R)-4-{(S)-4-Carboxy-2-[(5-{2-[(S)-2-(cyclopropyl-methyl-carbamoyl)-pyrrolidin-1-yl]-2-oxo-ethoxy}-1-phenyl-1H-pyrazole-3-carbonyl)-amino]-butyryl}-2-methyl-piperazine-1-carboxylic acid ethyl ester i) 5-{2-[(S)-2-(Cyclopropyl methyl-carbamoyl)-pyrrolidin-1-yl]-2-oxo-ethoxy}-1-phenyl-1H-pyrazole-3-carboxylic acid ethyl ester To a solution of 1.3 g 5-[2-((S)-2-carboxy-pyrrolidin-1-yl)-2-oxo-ethoxy]-1-phenyl-1H-pyrazole-3-carboxylic acid ethyl ester in 20 ml DMF were added 1.28 g HATU and 0.56 ml DIPEA. After 10 minutes 0.29 ml aminomethylcyclopropane were added. After 12 h the reaction mixture was diluted with dichloromethane and extracted with aqueous LiCl (4%), 0.1 M HCl and saturated aqueous NaHCO$_3$. The crude product obtained after evaporation of the solvent was used in the subsequent reaction. Yield: 1.45 g.

ii) 5-[2-((S)-2-(Cyclopropylmethyl-carbamoyl)-pyrrolidin-1-yl)-2-oxo-ethoxy]-1-phenyl-1H-pyrazole-3-carboxylic acid To a solution of 1.45 g 5-[2-((S)-2-(Cyclopropylmethyl-carbamoyl)-pyrrolidin-1-yl)-2-oxo-ethoxy]-1-phenyl-1H-pyrazole-3-carboxylic acid ethyl ester in 18 ml THF and 5 ml water were added 2.3 ml aqueous NaOH (2 M) portionwise at 0° C. After 12 h the solution was neutralized with Amberlite IR-120 ion exchange resin, filtered and washed with methanol. The crude product obtained after evaporation of the solvents was used in the subsequent reaction. Yield: 1.50 g.

iii) (S)-2-({5-[2-((S)-2-(Cyclopropylmethyl-carbamoyl)-pyrrolidin-1-yl)-2-oxo-ethoxy]-1-phenyl-1H-pyrazole-3-carbonyl}-amino)-pentanedioic acid 5-tert-butyl ester 1-methyl ester To a solution of 1.50 g 5-[2-((S)-2-(Cyclopropylmethyl-carbamoyl)-pyrrolidin-1-yl)-2-oxo-ethoxy]-1-phenyl-1H-pyrazole-3-carboxylic acid in 22 ml DMF were added 0.60 ml DIPEA, 1.38 g HATU and 923 mg H-Glu(OtBu)-OMe hydrochloride. After stirring for 24 h the solution was concentrated, taken up with dichloromethane and subsequently extracted with aqueous LiCl (4%), 0.1 M HCl and saturated NaHCO$_3$. The crude product obtained after evaporation of the solvent was purified by chromatography on silica using DCM/MeOH 97:3 as eluent. Yield: 2.0 g.

iv) (S)-2-({5-[2-((S)-2-(Cyclopropylmethyl-carbamoyl)-pyrrolidin-1-yl)-2-oxo-ethoxy]-1-phenyl-1H-pyrazole-3-carbonyl}-amino)-pentanedioic acid 5-tert-butyl ester To a solution of 2.0 g (S)-2-({5-[2-((S)-2-(Cyclopropylmethyl-carbamoyl)-pyrrolidin-1-yl)-2-oxo-ethoxy]-1-phenyl-1H-pyrazole-3-carbonyl}-amino)-pentanedioic acid 5-tert-butyl ester 1-methyl ester in 13 ml THF were added 78 mg LiOH (as solution in 4 ml water). After 2 h the reaction mixture was neutralized with Amberlite IR-120, filtrated and washed with methanol.

Yield: 1.6 g.

v) (R)-4-{(S)-4-Carboxy-2-[(5-{2-[(S)-2-(Cyclopropylmethyl carbamoyl)-pyrrolidin-1-yl]-2-oxo-ethoxy}-1-phenyl-1H-pyrazole-3-carbonyl)-amino]-butyryl}-2-methyl-piperazine-1-carboxylic acid ethyl ester To a solution of 100 mg (S)-2-({5-[2-((S)-2-(Cyclopropylmethyl-carbamoyl)-pyrrolidin-1-yl)-2-oxo-ethoxy]-1-phenyl-1H-pyrazole-3-carbonyl}-amino)-pentanedioic acid 5-tert-butyl ester in 6 ml DMF were added 28 µl DIPEA, 64 mg HATU and 29 mg (R)-2-Methyl-piperazine-1-carboxylic acid ethyl ester. After stirring for 16 h the solution was concentrated, the residue dissolved in 1.5 ml dichloromethane and treated with 560 µl TFA. After stirring for 16 h the solvents were removed under reduced pressure and the residue purified by preparative HPLC (C18 reverse phase column, elution with a water/MeCN gradient with 0.1% TFA). The fractions containing the product were lyophilized to yield the pure product. Yield: 65 mg MS (ES+): m/e=696.

Example 147

(S)-4-[(S)-4-Carboxy-2-({5-[2-((S)-2-cyclobutylcarbamoyl-pyrrolidin-1-yl)-2-oxo-ethoxy]-1-phenyl-1H-pyrazole-3-carbonyl}-amino)-butyryl]-2-methyl-piperazine-1-carboxylic acid ethyl ester i) (S)-2-Methyl-piperazine-1,4-dicarboxylic acid 4-tert-butyl ester 1-ethyl ester To a solution of 1.50 g (S)-4-N-Boc-2-methyl-piperazine in 10 ml dichloromethane were added at 0° C. 2.29 ml triethylamine and 0.72 ml ethyl chloroformate. After 12 h the reaction mixture was diluted with dichloromethane and extracted with 0.1 M HCl and saturated aqueous NaHCO$_3$. The organic layer was dried over MgSO$_4$ and the crude product obtained after evaporation of the solvent was used in the subsequent reaction.

Yield: 2.05 g.

ii) (S)-2-Methyl-piperazine-1-carboxylic acid ethyl ester

A solution of 2.05 g (S)-2-Methyl-piperazine-1,4-dicarboxylic acid 4-tert-butyl ester 1-ethyl ester in 15 ml dichloromethane was treated with 11.2 ml TFA and the resulting solution stirred for 12 h. The solvents were removed in vacuum and the crude hydrotrifluoroacetate transformed to the free amine by treatment with (Polystyrylmethyl)trimethylammonium bicarbonate in MeCN. Yield: 1.70 g.

iii) (S)-4-[(S)-4-Carboxy-2-({5-[2-((S)-2-cyclobutylcarbamoyl-pyrrolidin-1-yl)-2-oxo-ethoxy]-1-phenyl-1H-pyrazole-3-carbonyl}-amino)-butyryl]-2-methyl-piperazine-1-carboxylic acid ethyl ester To a solution of 100 mg (S)-2-({5-[2-((S)-2-cyclobutylcarbamoyl-pyrrolidin-1-yl)-2-oxo-ethoxy]-1-phenyl-1H-pyrazole-3-carbonyl}-amino)-pentanedioic acid 5-tert-butyl ester in 5 ml DMF were added 28 µl DIPEA, 64 mg HATU and 29 mg (S)-2-Methyl-piperazine-1-carboxylic acid ethyl ester. After stirring for 36 h the solution was concentrated, the residue dissolved in 1.5 ml dichloromethane and treated with 186 µl TFA. After stirring for 4 h the solvents were removed under reduced pressure and the residue purified by preparative HPLC (C18 reverse phase column, elution with a water/MeCN gradient with 0.1% TFA). The fractions containing the product were lyophilized to yield the pure product.
Yield: 65 mg MS (ES+): m/e=696.

Example 148

(S)-4-{(S)-4-Carboxy-2-[(5-{2-[(S)-2-(2-fluoro-ethylcarbamoyl)-pyrrolidin-1-yl]-2-oxo-ethoxy}-1-phenyl-1H-pyrazole-3-carbonyl)-amino]-butyryl}-2-methyl-piperazine-1-carboxylic acid ethyl ester The title compound was prepared by adapting the procedures described in example 147 with the difference that (S)-2-({5-[2-((S)-2-(2-Fluoro-ethylcarbamoyl-pyrrolidin-1-yl)-2-oxo-ethoxy]-1-phenyl-1H-pyrazole-3-carbonyl}-amino)-pentanedioic acid 5-tert-butyl ester was used instead of (S)-2-({5-[2-((S)-2-cyclobutylcarbamoyl-pyrrolidin-1-yl)-2-oxo-ethoxy]-1-phenyl-1H-pyrazole-3-carbonyl}-amino)-pentanedioic acid 5-tert-butyl ester.
Yield: 100 mg MS (ES+): m/e=688.

Example 149

(S)-4-{(S)-4-Carboxy-2-[(5-{2-[(S)-2-(cyclopropyl-methyl-carbamoyl)-pyrrolidin-1-yl]-2-oxo-ethoxy}-1-phenyl-1H-pyrazole-3-carbonyl)-amino]-butyryl}-2-methyl-piperazine-1-carboxylic acid ethyl ester The title compound was prepared by adapting the procedures described in example 147 with the difference that (S)-2-({5-[2-((S)-2-(cyclopropylmethyl-carbamoyl)-pyrrolidin-1-yl)-2-oxo-ethoxy]-1-phenyl-1H-pyrazole-3-carbonyl}-amino)-pentanedioic acid 5-tert-butyl ester was used instead of (S)-2-({5-[2-((S)-2-cyclobutylcarbamoyl-pyrrolidin-1-yl)-2-oxo-ethoxy]-1-phenyl-1H-pyrazole-3-carbonyl}-amino)-pentanedioic acid 5-tert-butyl ester.
Yield: 70 mg MS (ES+): m/e=696.

Example 150

(R)-4-[(S)-4-Carboxy-2-({5-[2-((S)-2-cyclobutylcarbamoyl-pyrrolidin-1-yl)-2-oxo-ethoxy]-1-phenyl-1H-pyrazole-3-carbonyl}-amino)-butyryl]-3-methyl-piperazine-1-carboxylic acid ethyl ester i) (R)-2-Methyl-piperazine-1,4-dicarboxylic acid 1-benzyl ester 4-tert-butyl ester A mixture of 2.4 g (R)-4-N-Boc-2-methyl-piperazine, 3.5 g N-(Benzyloxycarbonyl-oxy)succinimide and 2.0 g NaHCO₃ in 10 ml dioxane/water 1/1 was stirred for 12 h. The mixture was diluted with ethyl acetate, the phases separated and the organic phase washed with water, saturated aqueous NaHCO₃, 0.1 M HCl and brine. The crude product obtained after drying over MgSO₄ and evaporation of the solvents was used in the subsequent reaction. Yield: 4.3 g.

ii) (R)-2-Methyl-piperazine-1-carboxylic acid benzyl ester hydrotrifluoroacetate A solution of 4.3 g (R)-2-Methyl-piperazine-1,4-dicarboxylic acid 1-benzyl ester 4-tert-butyl ester in 20 ml dichloromethane was stirred in the presence of 10 ml TFA for 16 h. The solution was concentrated and the residue codistilled twice with toluene to give the crude hydrotrifluoroacetate. Yield: 6.1 g.

iii) (R)-2-Methyl-piperazine-1,4-dicarboxylic acid 1-benzyl ester 4-ethyl ester

To a solution of 3.0 g (R)-2-Methyl-piperazine-1-carboxylic acid benzyl ester hydrotrifluoroacetate in 17 ml dichloromethane were added at 0° C. 3.5 ml triethylamine and 1.2 ml ethyl chloroformate. After 12 h the reaction mixture was diluted with dichloromethane and extracted with 0.1 M HCl and saturated aqueous NaHCO₃. The organic layer was dried over MgSO₄ and the crude product obtained after evaporation purified by chromatography on silica using heptane/ethyl acetate 2/1 as eluent. Yield: 3.0 g.

iv) (R)-3-Methyl-piperazine-1-carboxylic acid ethyl ester

A suspension of 3.0 g (R)-2-Methyl-piperazine-1,4-dicarboxylic acid 1-benzyl ester 4-ethyl ester and 0.4 g Pd/C (10%) in 48 ml ethyl acetate was stirred under an atmosphere of hydrogen (3 bar) for 12 h. The mixture was filtrated over a plug of Celite, washed with ethyl acetate and the combined wash solutions concentrated to give the title compound as colourless oil. Yield: 1.5 g.

v) (R)-4-[(S)-4-Carboxy-2-({5-[2-((S)-2-cyclobutyl-carbamoyl-pyrrolidin-1-yl)-2-oxo-ethoxy]-1-phenyl-1H-pyrazole-3-carbonyl}-amino)-butyryl]-3-methyl-piperazine-1-carboxylic acid ethyl ester To a solution of 100 mg (S)-2-({5-[2-((S)-2-cyclobutylcarbamoyl-pyrrolidin-1-yl)-2-oxo-ethoxy]-1-phenyl-1H-pyrazole-3-carbonyl}-amino)-pentanedioic acid 5-tert-butyl ester in 5 ml DMF were added 28 µl DIPEA, 64 mg HATU and 28 mg (R)-3-Methyl-piperazine-1-carboxylic acid ethyl ester. After stirring for 36 h the solution was concentrated, the residue dissolved in 1.5 ml dichloromethane and treated with 360 µl TFA. After stirring for 4 h the solvents were removed under reduced pressure and the residue purified by preparative HPLC (C18 reverse phase column, elution with a water/MeCN gradient with 0.1% TFA). The fractions containing the product were lyophilized to yield the pure product.
Yield: 75 mg MS (ES+): m/e=696.

Example 151

(R)-4-[(S)-4-Carboxy-2-({5-[2-((S)-2-(2-fluoroethyl-carbamoyl)-pyrrolidin-1-yl)-2-oxo-ethoxy]-1-phenyl-1H-pyrazole-3-carbonyl}-amino)-butyryl]-3-methyl-piperazine-1-carboxylic acid ethyl ester The title compound was prepared by adapting the procedures described in example 150 with the difference that (S)-

2-({5-[2-((S)-2-(2-Fluoro-ethylcarbamoyl-pyrrolidin-1-yl)-2-oxo-ethoxy]-1-phenyl-1H-pyrazole-3-carbonyl}-amino)-pentanedioic acid 5-tert-butyl ester was used instead of (S)-2-({5-[2-((S)-2-cyclobutylcarbamoyl-pyrrolidin-1-yl)-2-oxo-ethoxy]-1-phenyl-1H-pyrazole-3-carbonyl}-amino)-pentanedioic acid 5-tert-butyl ester.

Yield: 55 mg MS (ES+): m/e=688.

Example 152

(R)-4-[(S)-4-Carboxy-2-({5-[2-((S)-2-(cyclopropyl-methyl-carbamoyl)-pyrrolidin-1-yl)-2-oxo-ethoxy]-1-phenyl-1H-pyrazole-3-carbonyl}-amino)-butyryl]-3-methyl-piperazine-1-carboxylic acid ethyl ester The title compound was prepared by adapting the procedures described in example 150 with the difference that (S)-2-({5-[2-((S)-2-(cyclopropylmethyl-carbamoyl)-pyrrolidin-1-yl)-2-oxo-ethoxy]-1-phenyl-1H-pyrazole-3-carbonyl}-amino)-pentanedioic acid 5-tert-butyl ester was used instead of (S)-2-({5-[2-((S)-2-cyclobutylcarbamoyl-pyrrolidin-1-yl)-2-oxo-ethoxy]-1-phenyl-1H-pyrazole-3-carbonyl}-amino)-pentanedioic acid 5-tert-butyl ester.

Yield: 65 mg MS (ES+): m/e=696.

Example 153

(S)-4-[(S)-4-Carboxy-2-({5-[2-((S)-2-cyclobutylcar-bamoyl-pyrrolidin-1-yl)-2-oxo-ethoxy]-1-phenyl-1H-pyrazole-3-carbonyl}-amino)-butyryl]-3-methyl-piperazine-1-carboxylic acid ethyl ester i) (S)-2-Methyl-piperazine-1,4-dicarboxylic acid 1-benzyl ester 4-tert-butyl ester A mixture of 2.5 g (S)-4-N-Boc-2-methyl-piperazine, 3.5 g N-(Benzyloxycarbonyl-oxy)succinimide and 2.0 g NaHCO$_3$ in 10 ml dioxane/water 1/1 was stirred for 12 h. The mixture was diluted with ethyl acetate, the phases separated and the organic phase washed with water, saturated aqueous NaHCO$_3$, 0.1 M HCl and brine. The crude product obtained after drying over MgSO$_4$ and evaporation of the solvents was used in the subsequent reaction. Yield: 4.3 g.

ii) (S)-2-Methyl-piperazine-1-carboxylic acid benzyl ester hydrotrifluoroacetate A solution of 4.3 g (S)-2-Methyl-piperazine-1,4-dicarboxylic acid 1-benzyl ester 4-tert-butyl ester in 20 ml dichloromethane was stirred in the presence of 10 ml TFA for 16 h. The solution was concentrated and the residue codistilled twice with toluene to give the crude hydrotrifluoroacetate. Yield: 6.4 g.

iii) (S)-2-Methyl-piperazine-1,4-dicarboxylic acid 1-benzyl ester 4-ethyl ester

To a solution of 3.0 g (S)-2-Methyl-piperazine-1-carboxylic acid benzyl ester hydrotrifluoroacetate in 17 ml dichloromethane were added at 0° C. 7.1 ml triethylamine and 1.2 ml ethyl chloroformate. After 12 h the reaction mixture was diluted with dichloromethane and extracted with 0.1 M HCl and saturated aqueous NaHCO$_3$. The organic layer was dried over MgSO$_4$ and the crude product obtained after evaporation purified by chromatography on silica using heptane/ethyl acetate 2/1 as eluent. Yield: 3.5 g.

iv) (S)-3-Methyl-piperazine-1-carboxylic acid ethyl ester

A suspension of 3.5 g (S)-2-Methyl-piperazine-1,4-dicarboxylic acid 1-benzyl ester 4-ethyl ester and 0.4 g Pd/C (10%) in 56 ml ethyl acetate was stirred under an atmosphere of hydrogen (3 bar) for 12 h. The mixture was filtrated over a plug of Celite, washed with ethyl acetate and the combined wash solutions concentrated to give the title compound as colourless oil. Yield: 1.6 g.

v) (S)-4-[(S)-4-Carboxy-2-({5-[2-((S)-2-cyclobutyl-carbamoyl-pyrrolidin-1-yl)-2-oxo-ethoxy]-1-phenyl-1H-pyrazole-3-carbonyl}-amino)-butyryl]-3-methyl-piperazine-1-carboxylic acid ethyl ester To a solution of 100 mg (S)-2-({5-[2-((S)-2-cyclobutylcar-bamoyl-pyrrolidin-1-yl)-2-oxo-ethoxy]-1-phenyl-1H-pyrazole-3-carbonyl}-amino)-pentanedioic acid 5-tert-butyl ester in 5 ml DMF were added 28 µl DIPEA, 63 mg HATU and 28 mg (S)-3-Methyl-piperazine-1-carboxylic acid ethyl ester. After stirring for 36 h the solution was concentrated, the residue dissolved in 1.5 ml dichloromethane and treated with 360 µl TFA. After stirring for 4 h the solvents were removed under reduced pressure and the residue purified by preparative HPLC (C18 reverse phase column, elution with a water/MeCN gradient with 0.1% TFA). The fractions containing the product were lyophilized to yield the pure product.

Yield: 75 mg MS (ES+): m/e=696.

Example 154

(S)-4-[(S)-4-Carboxy-2-({5-[2-((S)-2-(2-fluoro-ethyl-carbamoyl)-pyrrolidin-1-yl)-2-oxo-ethoxy]-1-phenyl-1H-pyrazole-3-carbonyl}-amino)-butyryl]-3-methyl-piperazine-1-carboxylic acid ethyl ester The title compound was prepared by adapting the procedures described in example 153 with the difference that (S)-2-({5-[2-((S)-2-(2-Fluoro-ethylcarbamoyl-pyrrolidin-1-yl)-2-oxo-ethoxy]-1-phenyl-1H-pyrazole-3-carbonyl}-amino)-pentanedioic acid 5-tert-butyl ester was used instead of (S)-2-({5-[2-((S)-2-cyclobutylcarbamoyl-pyrrolidin-1-yl)-2-oxo-ethoxy]-1-phenyl-1H-pyrazole-3-carbonyl}-amino)-pentanedioic acid 5-tert-butyl ester.

Yield: 50 mg MS (ES+): m/e=688.

Example 155

(S)-4-[(S)-4-Carboxy-2-({5-[2-((S)-2-(cyclopropyl-methyl-carbamoyl)-pyrrolidin-1-yl)-2-oxo-ethoxy]-1-phenyl-1H-pyrazole-3-carbonyl}-amino)-butyryl]-3-methyl-piperazine-1-carboxylic acid ethyl ester The title compound was prepared by adapting the procedures described in example 153 with the difference that (S)-2-({5-[2-((S)-2-(cyclopropylmethyl-carbamoyl)-pyrrolidin-1-yl)-2-oxo-ethoxy]-1-phenyl-1H-pyrazole-3-carbonyl}-amino)-pentanedioic acid 5-tert-butyl ester was used instead of (S)-2-({5-[2-((S)-2-cyclobutylcarbamoyl-pyrrolidin-1-yl)-2-oxo-ethoxy]-1-phenyl-1H-pyrazole-3-carbonyl}-amino)-pentanedioic acid 5-tert-butyl ester.

Yield: 70 mg MS (ES+): m/e=696.

Example 156

4-[(S)-4-Carboxy-2-({5-[2-((S)-2-cyclobutylcarbamoyl-pyrrolidin-1-yl)-2-oxo-ethoxy]-1-phenyl-1H-pyrazole-3-carbonyl}-amino)-butyryl]-piperazine-1-carboxylic acid phenyl ester i) piperazine-1,4-dicarboxylic acid tert-butyl ester phenyl ester

To a solution of 1.0 g tert-butyl 1-piperazinecarboxylate and 1.5 ml triethylamine in 5 ml dichloromethane were added at 0° C. 0.8 ml phenylchloroformate. After stirring for 12 h, 2 ml of water were added and the mixture loaded on a chem Elute® cartridge. Elution with dichloromethane yielded the crude product which was used in the subsequent reaction.

ii) piperazine-1-carboxylic acid phenyl ester hydrotrifluoroacetate

Crude piperazine-1,4-dicarboxylic acid tert-butyl ester phenyl ester was dissolved in 10 ml dichloromethane and treated with 4 ml TFA. After stirring for 12 h the solution was concentrated and the residue codistilled twice with toluene. Yield: 3.0 g.

iii) 4-[(S)-4-Carboxy-2-({5-[2-((S)-2-cyclobutylcarbamoyl-pyrrolidin-1-yl)-2-oxo-ethoxy]-1-phenyl-1H-pyrazole-3-carbonyl}-amino)-butyryl]-piperazine-1-carboxylic acid phenyl ester To a solution of 100 mg (S)-2-({5-[2-((S)-2-cyclobutylcarbamoyl-pyrrolidin-1-yl)-2-oxo-ethoxy]-1-phenyl-1H-pyrazole-3-carbonyl}-amino)-pentanedioic acid 5-tert-butyl ester in 5 ml DMF were added 55 µl DIPEA, 64 mg HATU and 54 mg piperazine-1-carboxylic acid phenyl ester hydrotrifluoroacetate. After stirring for 36 h the solution was concentrated, the residue dissolved in 1.5 ml dichloromethane and treated with 190 µl TFA. After stirring for 4 h the solvents were removed under reduced pressure and the residue purified by preparative HPLC (C18 reverse phase column, elution with a water/MeCN gradient with 0.1% TFA). The fractions containing the product were lyophilized to yield the pure product. Yield: 40 mg MS (ES+): m/e=730.

Example 157

4-[(S)-4-Carboxy-2-({5-[2-((S)-2-(2-fluoroethyl-carbamoyl)-pyrrolidin-1-yl)-2-oxo-ethoxy]-1-phenyl-1H-pyrazole-3-carbonyl}-amino)-butyryl]-piperazine-1-carboxylic acid phenyl ester The title compound was prepared by adapting the procedures described in example 156 with the difference that (S)-2-({5-[2-((S)-2-(2-Fluoro-ethylcarbamoyl-pyrrolidin-1-yl)-2-oxo-ethoxy]-1-phenyl-1H-pyrazole-3-carbonyl}-amino)-pentanedioic acid 5-tert-butyl ester was used instead of (S)-2-({5-[2-((S)-2-cyclobutylcarbamoyl-pyrrolidin-1-yl)-2-oxo-ethoxy]-1-phenyl-1H-pyrazole-3-carbonyl}-amino)-pentanedioic acid 5-tert-butyl ester.
Yield: 55 mg MS (ES+): m/e=722.

Example 158

4-[(S)-4-Carboxy-2-({5-[2-((S)-2-(cyclopropylmethyl-carbamoyl)-pyrrolidin-1-yl)-2-oxo-ethoxy]-1-phenyl-1H-pyrazole-3-carbonyl}-amino)-butyryl]-piperazine-1-carboxylic acid phenyl ester The title compound was prepared by adapting the procedures described in example 156 with the difference that (S)-2-({5-[2-((S)-2-(cyclopropylmethyl-carbamoyl)-pyrrolidin-1-yl)-2-oxo-ethoxy]-1-phenyl-1H-pyrazole-3-carbonyl}-amino)-pentanedioic acid 5-tert-butyl ester was used instead of (S)-2-({5-[2-((S)-2-cyclobutylcarbamoyl-pyrrolidin-1-yl)-2-oxo-ethoxy]-1-phenyl-1H-pyrazole-3-carbonyl}-amino)-pentanedioic acid 5-tert-butyl ester.
Yield: 60 mg MS (ES+): m/e=730.

Example 159

4-[(S)-4-Carboxy-2-({5-[2-((S)-2-cyclobutylcarbamoyl-pyrrolidin-1-yl)-2-oxo-ethoxy]-1-phenyl-1H-pyrazole-3-carbonyl}-amino)-butyryl]-piperazine-1-carboxylic acid benzyl ester To a solution of 100 mg (S)-2-({5-[2-((S)-2-cyclobutylcarbamoyl-pyrrolidin-1-yl)-2-oxo-ethoxy]-1-phenyl-1H-pyrazole-3-carbonyl}-amino)-pentanedioic acid 5-tert-butyl ester in 5 ml DMF were added 55 µl DIPEA, 64 mg HATU and 56 mg piperazine-1-carboxylic acid benzyl ester. After stirring for 24 h the solution was concentrated, the residue dissolved in 1.5 ml dichloromethane and treated with 360 µl TFA. After stirring for 4 h the solvents were removed under reduced pressure and the residue purified by preparative HPLC (C18 reverse phase column, elution with a water/MeCN gradient with 0.1% TFA). The fractions containing the product were lyophilized to yield the pure product.
Yield: 44 mg MS (ES+): m/e=744.

Example 160

4-[(S)-4-Carboxy-2-({5-[2-((S)-2-(2-fluoroethyl-carbamoyl)-pyrrolidin-1-yl)-2-oxo-ethoxy]-1-phenyl-1H-pyrazole-3-carbonyl}-amino)-butyryl]-piperazine-1-carboxylic acid benzyl ester The title compound was prepared by adapting the procedures described in example 159 with the difference that (S)-2-({5-[2-((S)-2-(2-Fluoro-ethylcarbamoyl-pyrrolidin-1-yl)-2-oxo-ethoxy]-1-phenyl-1H-pyrazole-3-carbonyl}-amino)-pentanedioic acid 5-tert-butyl ester was used instead of (S)-2-({5-[2-((S)-2-cyclobutylcarbamoyl-pyrrolidin-1-yl)-2-oxo-ethoxy]-1-phenyl-1H-pyrazole-3-carbonyl}-amino)-pentanedioic acid 5-tert-butyl ester.
Yield: 35 mg MS (ES+): m/e=736.

Example 161

4-[(S)-4-Carboxy-2-({5-[2-((S)-2-(cyclopropylmethyl-carbamoyl)-pyrrolidin-1-yl)-2-oxo-ethoxy]-1-phenyl-1H-pyrazole-3-carbonyl}-amino)-butyryl]-piperazine-1-carboxylic acid benzyl ester The title compound was prepared by adapting the procedures described in example 159 with the difference that (S)-2-({5-[2-((S)-2-(cyclopropylmethyl-carbamoyl)-pyrrolidin- 1-yl)-2-oxo-ethoxy]-1-phenyl-1H-pyrazole-3-carbonyl}-amino)-pentanedioic acid 5-tert-butyl ester was used instead of (S)-2-({5-[2-((S)-2-cyclobutylcarbamoyl-pyrrolidin-1-yl)-2-oxo-ethoxy]-1-phenyl-1H-pyrazole-3-carbonyl}-amino)-pentanedioic acid 5-tert-butyl ester.

Yield: 39 mg MS (ES+): m/e=744.

Example 162

4-[(S)-4-Carboxy-2-({5-[2-((S)-2-cyclobutylcarbamoyl-pyrrolidin-1-yl)-2-oxo-ethoxy]-1-phenyl-1H-pyrazole-3-carbonyl}-amino)-butyryl]-piperazine-1-carboxylic acid propyl ester i) piperazine-1,4-dicarboxylic acid propyl ester tert-butyl ester

To a solution of 5.0 g tert-butyl 1-piperazinecarboxylate in 64 ml dichloromethane were added 8.2 ml triethylamine. The solution was cooled to 0° C. and 3.3 ml propylchloroformate were added dropwise at this temperature. After stirring for 12 h the reaction mixture was diluted with dichloromethane and washed with 0.1 M HCl and saturated NaHCO₃. The crude product obtained after evaporation of the solvent was directly used in the next reaction step.

Yield: 7.5 g.

ii) piperazine-1-carboxylic acid propyl ester hydrotrifluoroacetate

To a solution of 7.5 g piperazine-1,4-dicarboxylic acid propyl ester tert-butyl ester in 70 ml dichloromethane were added 10 ml TFA. After stirring for 36 h the solution was concentrated and the residue codistilled with toluene twice.

Yield: 9.2 g.

iii) 4-((S)-2-Benzyloxycarbonylamino-4-tert-butoxycarbonyl-butyryl)-piperazine-1-carboxylic acid propyl ester To a solution of 8.8 g N(S)-2-Benzyloxycarbonylamino-pentanedioic acid 5-tert-butyl ester in 70 ml DMF were added 4.5 g piperazine-1-carboxylic acid propyl ester hydrotrifluoroacetate, 13.3 ml N-ethylmorpholine and 8.6 g TOTU. After stirring for 12 h the solution was diluted with ethyl acetate and subsequently washed with aqueous LiCl (4%) and saturated aqueous NaHCO₃. The crude product obtained after evaporation of the solvent was used without further purification. Yield: 15.1 g.

iv) 4-((S)-2-Amino-4-tert-butoxycarbonyl-butyryl)-piperazine-1-carboxylic acid propyl ester To a solution of 15.8 g 4-((S)-2-Benzyloxycarbonylamino-4-tert-butoxycarbonyl-butyryl)-piperazine-1-carboxylic acid propyl ester in 100 ml ethyl acetate were added 0.4 g Pd/C (10%) and the suspension stirred under an atmosphere of hydrogen (3 bar) for 12 h. The reaction mixture was filtrated over a plug of Celite, washed with ethanol and concentrated to give the crude product which was used in the subsequent reaction. Yield: 10.2 g.

v) 4-[(S)-4-Carboxy-2-({5-[2-((S)-2-cyclobutylcarbamoyl-pyrrolidin-1-yl)-2-oxo-ethoxy]-1-phenyl-1H-pyrazole-3-carbonyl}-amino)-butyryl]-piperazine-1-carboxylic acid propyl ester To a solution of 808 mg 5-[2-((S)-2-cyclobutylcarbamoyl-pyrrolidin-1-yl)-2-oxo-ethoxy]-1-phenyl-1H-pyrazole-3-carboxylic acid in 10 ml DMF were added 800 µl DIPEA, 450 mg HOBT, 563 mg EDC and 700 mg 4-((S)-2-Amino-4-tert-butoxycarbonyl-butyryl)-piperazine-1-carboxylic acid propyl ester. After stirring for 16 h the mixture was concentrated, the residue dissolved in ethyl acetate and washed with aqueous LiCl (4 w/w), 0.1 M HCl and saturated aqueous NaHCO₃. The organic phase was concentrated, the residue obtained redissolved in 20 ml dichloromethane and stirred in the presence of 3 ml TFA. After stirring for 16 h the solvents were removed under reduced pressure and an aliquot (200 mg) of the residue purified by preparative HPLC (C18 reverse phase column, elution with a water/MeCN gradient with 0.1% TFA). The fractions containing the product were lyophilized to yield the pure product as its trifluoroacetate salt.

Yield: 70 mg MS (ES+): m/e=696.

Example 163

4-[(S)-4-Carboxy-2-({5-[2-((S)-2-cyclobutylcarbamoyl-pyrrolidin-1-yl)-2-oxo-ethoxy]-1-phenyl-1H-pyrazole-3-carbonyl}-amino)-butyryl]-piperazine-1-carboxylic acid cyclobutyl ester i) piperazine-1,4-dicarboxylic acid benzyl ester cyclobutyl ester

To a solution of 2.6 g triphosgene and 1.7 ml cyclobutanol in 40 ml dichloromethane were added 6.2 ml triethylamine dropwise at 0° C. After 30 minutes 4.4 ml benzyl 1-piperazinecarboxylate and 3.2 ml triethylamine were added at 0° C. The reaction mixture was allowed to warm to RT for 16 h. Excess triphosgene was destroyed by adding a solution of 2 g NaOH in 200 ml water and stirring for 2 h. The layers were separated, the organic layer dried over MgSO₄ and concentrated. The crude product thus obtained was purified by chromatography on silica using heptane/ethyl acetate 4/1 to 2/1 as eluent.

Yield: 5.9 g.

ii) piperazine-1-carboxylic acid cyclobutyl ester

A suspension of 5.90 g piperazine-1,4-dicarboxylic acid benzyl ester cyclobutyl ester and 0.25 g Pd/C (10%) in 50 ml ethyl acetate was stirred under an atmosphere of hydrogen (3 bar) for 12 h. The mixture was filtrated over a plug of Celite, washed with ethyl acetate and the combined wash solutions concentrated to give the title compound as colourless oil.

Yield: 3.3 g.

iii) 4-((S)-2-Benzyloxycarbonylamino-4-tert-butoxycarbonyl-butyryl)-piperazine-1-carboxylic acid cyclobutyl ester To a solution of 6.0 g (S)-2-Benzyloxycarbonylamino-pentanedioic acid 5-tert-butyl ester in 50 ml DMF were added 3.3 g piperazine-1-carboxylic acid cyclobutyl ester, 9.1 ml N-ethylmorpholine and 5.9 g TOTU. After stirring for 12 h the solution was diluted with ethyl acetate and subsequently washed with aqueous LiCl (4%) and saturated aqueous NaHCO₃. The crude product obtained after evaporation of the solvent was used without further purification. Yield: 11.1 g.

iv) 4-((S)-2-Amino-4-tert-butoxycarbonyl-butyryl)-piperazine-1-carboxylic acid cyclobutyl ester To a solution of 11.1 g 4-((S)-2-Benzyloxycarbonylamino-4-tert-butoxycarbonyl-butyryl)-piperazine-1-carboxylic acid cyclobutyl ester in 80 ml ethyl acetate were added 0.6 g Pd/C (10%) and the suspension stirred under an atmosphere of hydrogen (3 bar) for 12 h. The reaction mixture was filtrated over a plug of Celite, washed with ethanol and concentrated to give the crude product which was used in the subsequent reaction. Yield: 7.2 g.

v) 4-[(S)-4-Carboxy-2-({5-[2-((S)-2-cyclobutylcarbamoyl-pyrrolidin-1-yl)-2-oxo-ethoxy]-1-phenyl-1H-pyrazole-3-carbonyl}-amino)-butyryl]-piperazine-1-carboxylic acid cyclobutyl ester To a solution of 782 mg 5-[2-((S)-2-cyclobutylcarbamoyl-pyrrolidin-1-yl)-2-oxo-ethoxy]-1-phenyl-1H-pyrazole-3-carboxylic acid in 10 ml DMF were added 783 µl DIPEA, 435 mg HOBT, 545 mg EDC and 700 mg 4-((S)-2-Amino-4-tert-butoxycarbonyl-butyryl)-piperazine-1-carboxylic acid cyclobutyl ester. After stirring for 16 h the mixture was concentrated, the residue dissolved in ethyl acetate and washed with aqueous LiCl (4 w/w), 0.1 M HCl and saturated aqueous $NaHCO_3$. The organic phase was concentrated, the residue obtained redissolved in 20 ml dichloromethane and stirred in the presence of 2 ml TFA. After stirring for 16 h the solvents were removed under reduced pressure and an aliquot (200 mg) of the residue purified by preparative HPLC (C18 reverse phase column, elution with a water/MeCN gradient with 0.1% TFA). The fractions containing the product were lyophilized to yield the pure product as its trifluoroacetate salt.
Yield: 90 mg MS (ES+): m/e=708.

Example 164

4-[(S)-4-Carboxy-2-({5-[2-((S)-2-cyclobutylcarbamoyl-4,4-difluoro-pyrrolidin-1-yl)-2-oxo-ethoxy]-1-phenyl-1H-pyrazole-3-carbonyl}-amino)-butyryl]-piperazine-1-carboxylic acid ethyl ester i) (S)-4,4-Difluoro-pyrrolidine-2-carboxylic acid methyl ester hydrotrifluoroacetate To a solution of 650 mg (S)-4,4-Difluoro-pyrrolidine-1,2-dicarboxylic acid 1-tert-butyl ester 2-methyl ester in 10 ml dichloromethane were added 1.5 ml TFA. After stirring for 12 h the solution was concentrated to give the crude hydrotrifluoroacetate.

ii) 4-[(S)-4-tert-Butoxycarbonyl-2-({5-[2-((S)-4,4-difluoro-2-methoxycarbonyl-pyrrolidin-1-yl)-2-oxo-ethoxy]-1-phenyl-1H-pyrazole-3-carbonyl}-amino)-butyryl]-piperazine-1-carboxylic acid ethyl ester To a solution of 1.2 g 4-{(S)-4-tert-Butoxycarbonyl-2-[(5-carboxymethoxy-1-phenyl-1H-pyrazole-3-carbonyl)-amino]-butyryl}-piperazine-1-carboxylic acid ethyl ester in 35 ml DMF were added 278 mg HOAt, 1.6 g EDC, 1.1 ml DIPEA and 684 mg (S)-4,4-Difluoro-pyrrolidine-2-carboxylic acid methyl ester hydrotrifluoroacetate. After 36 h the mixture was diluted with ethyl acetate and subsequently extracted with aqueous LiCl (4% w/w), 0.1 M HCl and saturated aqueous $NaHCO_3$. The organic layer was dried over $MgSO_4$ and the solvent was removed under reduced pressure. The crude product thus obtained was purified by chromatography on silica using heptan/ethyl acetate 40/60 to 33/67 as eluent.
Yield: 881 mg.

iii) 4-[(S)-4-tert-Butoxycarbonyl-2-({5-[2-((S)-2-carboxy-4,4-difluoro-pyrrolidin-1-yl)-2-oxo-ethoxy]-1-phenyl-1H-pyrazole-3-carbonyl}-amino)-butyryl]-piperazine-1-carboxylic acid ethyl ester To a solution of 881 mg 4-[(S)-4-tert-butoxycarbonyl-2-({5-[2-((S)-4,4-difluoro-2-methoxy-carbonyl-pyrrolidin-1-yl)-2-oxo-ethoxy]-1-phenyl-1H-pyrazole-3-carbonyl}-amino)-butyryl]-piperazine-1-carboxylic acid ethyl ester in 24 ml THF and 6 ml $H_2O$ were added 30 mg LiOH at 0° C. The reaction mixture was allowed to warm to RT and was then stirred for 3 h before being acidified by using Amberlite IR-120. The reaction mixture was filtered, washed with MeOH and the combined wash solutions concentrated to give the crude product which was used in the subsequent reaction. Yield: 711 mg.

iv) 4-[(S)-4-Carboxy-2-({5-[2-((S)-2-cyclobutylcarbamoyl-4,4-difluoro-pyrrolidin-1-yl)-2-oxo-ethoxy]-1-phenyl-1H-pyrazole-3-carbonyl}-amino)-butyryl]-piperazine-1-carboxylic acid ethyl ester To a solution of 100 mg 4-[(S)-4-tert-Butoxycarbonyl-2-({5-[2-((S)-2-carboxy-4,4-difluoro-pyrrolidin-1-yl)-2-oxo-ethoxy]-1-phenyl-1H-pyrazole-3-carbonyl}-amino)-butyryl]-piperazine-1-carboxylic acid ethyl ester in 5 ml DMF were added 24 µl DIPEA, 53 mg HATU and 12 µl cyclobutylamine. After stirring for 4 h the mixture was dissolved in ethyl acetate and washed with aqueous LiCl (4% w/w) and saturated aqueous $NaHCO_3$. The solvent was evaporated, the residue dissolved in 1.5 ml dichloromethane and treated with 300 µl TFA. After stirring for 34 h the solvents were removed under reduced pressure and the residue purified by preparative HPLC (C18 reverse phase column, elution with a water/MeCN gradient with 0.1% TFA). The fractions containing the product were lyophilized to yield the pure product. Yield: 43 mg MS (ES+): m/e=718.

Example 165

4-[(S)-4-Carboxy-2-({5-[2-((S)-2-cyploroylcarbamoyl-4,4-difluoro-pyrrolidin-1-yl)-2-oxo-ethoxy]-1-phenyl-1H-pyrazole-3-carbonyl}-amino)-butyryl]-piperazine-1-carboxylic acid ethyl ester The title compound was prepared by adapting the procedures described in example 164 with the difference that cyclopropylamine was used instead of cyclobutylamine.
Yield: 28 mg MS (ES+): m/e=704.

Example 166

4-[(S)-4-Carboxy-2-({5-[2-((S)-2-(cyploroylmethyl-carbamoyl)-4,4-difluoro-pyrrolidin-1-yl)-2-oxo-ethoxy]-1-phenyl-1H-pyrazole-3-carbonyl}-amino)-butyryl]-piperazine-1-carboxylic acid ethyl ester The title compound was prepared by adapting the procedures described in example 164 with the difference that aminomethylcyclopropane was used instead of cyclobutylamine.
Yield: 36 mg MS (ES+): m/e=718.

Example 167

4-[(S)-4-Carboxy-2-({5-[2-oxo-2-(2-thiophen-2-yl-pyrrolidin-1-yl)-ethoxy]-1-phenyl-1H-pyrazole-3-carbonyl}-amino)-butyryl]-piperazine-1-carboxylic acid ethyl ester To a solution of 250 mg 4-{(S)-4-tert-Butoxycarbonyl-2-[(5-carboxymethoxy-1-phenyl-1H-pyrazole-3-carbonyl)-amino]-butyryl}-piperazine-1-carboxylic acid ethyl ester in 8 ml DMF were added 58 mg HOAt, 162 mg HATU, 0.22 ml DIPEA and 65 mg 2-thiophen-2-yl-pyrrolidine. After 16 h the mixture was diluted with ethyl acetate and subsequently extracted with aqueous LiCl (4% w/w) and saturated aqueous NaHCO$_3$. The organic layer was dried over MgSO$_4$, the solvent removed under reduced pressure and the residue obtained redissolved in 8 ml dichloromethane and stirred in the presence of 1.2 ml TFA. After stirring for 16 h the solvents were removed under reduced pressure and the crude product thus obtained was purified by preparative HPLC (C18 reverse phase column, elution with a water/MeCN gradient with 0.1% TFA). The fractions containing the product were lyophilized to yield the pure product as its trifluoroacetate salt.

Yield: 137 mg MS (ES+): m/e=667.

Example 168

4-[(S)-4-Carboxy-2-({5-[2-(2-furan-2-yl-pyrrolidin-1-yl)-2-oxo-ethoxy]-1-phenyl-1H-pyrazole-3-carbonyl}-amino)-butyryl]-piperazine-1-carboxylic acid ethyl ester The title compound was prepared by adapting the procedures described in example 167 with the difference that 2-furan-2-yl-pyrrolidine hydrochloride was used instead of 2-thiophen-2-yl-pyrrolidine. Yield: 57 mg MS (ES+): m/e=651.

Example 169

4-{(S)-4-Carboxy-2-[(5-{2-[2-(5-methyl-furan-2-yl)-pyrrolidin-1-yl]-2-oxo-ethoxy}-1-phenyl-1H-pyrazole-3-carbonyl)-amino]-butyryl}-piperazine-1-carboxylic acid ethyl ester The title compound was prepared by adapting the procedures described in example 167 with the difference that 2-(5-Methyl-furan-2-yl)-pyrrolidine oxalate was used instead of 2-thiophen-2-yl-pyrrolidine. Yield: 15 mg MS (ES+): m/e=665.

Example 170

4-[(S)-4-Carboxy-2-({5-[2-oxo-2-((S)-2-phenyl-pyrrolidin-1-yl)-ethoxy]-1-phenyl-1H-pyrazole-3-carbonyl}-amino)-butyryl]-piperazine-1-carboxylic acid ethyl ester The title compound was prepared by adapting the procedures described in example 167 with the difference that (S)-2-phenyl-pyrrolidine was used instead of 2-thiophen-2-yl-pyrrolidine. Yield: 41 mg MS (ES+): m/e=661.

Example 171

4-{(S)-4-Carboxy-2-[(5-{2-[(S)-2-(4-methyl-oxazol-2-yl)-pyrrolidin-1-yl]-2-oxo-ethoxy}-1-phenyl-1H-pyrazole-3-carbonyl)-amino]-butyryl}-piperazine-1-carboxylic acid ethyl ester i) (S)-Pyrrolidine-1,2-dicarboxylic acid 1-benzyl ester 2-(2-oxo-propyl) ester To a solution of 2.0 g Z-Pro-OH n 20 ml dichloromethane were added 0.58 ml hydroxyl-acetone and 10 mg DMAP. The solution was cooled to 0° C. and a solution of 1.7 g DCC in 20 ml dichloromethane was added dropwise. The suspension was allowed to warm to RT for 16 h before being filtered over a short plug of Celite. The reaction mixture was washed with dichloro-methane and the combined wash solutions evaporated. The residue thus obtained was purified by chromatography on silica using heptane/ethyl acetate 1:1 as eluent.

Yield: 1.95 g.

ii) (S)-2-(4-Methyl-oxazol-2-yl)-pyrrolidine-1-carboxylic acid benzyl ester To a solution of 412 mg (S)-pyrrolidine-1,2-dicarboxylic acid 1-benzyl ester 2-(2-oxo-propyl) ester in 10 ml AcOH were added 978 mg ammonium acetate and the solution stirred in the microwave at 160° C. for 1 h. The reaction mixture was concentrated and the residue purified by preparative HPLC (C18 reverse phase column, elution with a water/MeCN gradient with 0.1% TFA) giving 100 mg of the title compound and 100 mg of (S)-2-(4-Methyl-1H-imidazol-2-yl)-pyrrolidine-1-carboxylic acid benzyl ester after lyophilisation of the corresponding product fractions.

iii) 4-Methyl-2-(S)-pyrrolidin-2-yl-oxazole

A solution of 100 mg (S)-2-(4-methyl-oxazol-2-yl)-pyrrolidine-1-carboxylic acid benzyl ester in 5 ml EtOH was stirred in the presence of 15 mg Pd/C (10%) under an atmosphere of hydrogen (1 bar) for 2 h. The reaction mixture was filtered over a plug of Celite and washed with EtOH. Evaporation of the solvent gave the product as colorless oil.

Yield: 36 mg.

iv) 4-{(S)-4-Carboxy-2-[(5-{2-[(S)-2-(4-methyl-oxazol-2-yl)-pyrrolidin-1-yl]-2-oxo-ethoxy}-1-phenyl-1H-pyrazole-3-carbonyl)-amino]-butyryl}-piperazine-1-carboxylic acid ethyl ester The title compound was prepared by adapting the procedures described in example 167 with the difference that 4-Methyl-2-(S)-pyrrolidin-2-yl-oxazole was used instead of 2-thiophen-2-yl-pyrrolidine. Yield: 30 mg MS (ES+): m/e=666.

Example 172

4-{(S)-4-Carboxy-2-[(5-{2-[(S)-2-(4-methyl-1H-imidazol-2-yl)-pyrrolidin-1-yl]-2-oxo-ethoxy}-1-phenyl-1H-pyrazole-3-carbonyl)-amino]-butyryl}-piperazine-1-carboxylic acid ethyl ester i) 4-Methyl-2-(S)-pyrrolidin-2-yl-1H-imidazole

A solution of 100 mg (S)-2-(4-Methyl-1H-imidazol-2-yl)-pyrrolidine-1-carboxylic acid benzyl ester in 5 ml EtOH was stirred in the presence of 15 mg Pd/C (10%) under an atmosphere of hydrogen (1 bar) for 2 h. The reaction mixture was filtered over a plug of Celite and washed with EtOH. Evaporation of the solvent gave the product as colorless oil.
Yield: 54 mg.

ii) 4-{(S)-4-Carboxy-2-[(5-{2-[(S)-2-(4-methyl-1H-imidazol-2-yl)-pyrrolidin-1-yl]-2-oxo-ethoxy}-1-phenyl-1H-pyrazole-3-carbonyl)-amino]-butyryl}-piperazine-1-carboxylic acid ethyl ester The title compound was prepared by adapting the procedures described in example 167 with the difference that 4-Methyl-2-(S)-pyrrolidin-2-yl-1H-imidazole was used instead of 2-thiophen-2-yl-pyrrolidine. Yield: 19 mg MS (ES+): m/e=665.

Example 173

4-{(S)-4-Carboxy-2-[(5-{2-[(S)-2-(3-methyl-isoxazol-5-yl)-pyrrolidin-1-yl]-2-oxo-ethoxy}-1-phenyl-1H-pyrazole-3-carbonyl)-amino]-butyryl}-piperazine-1-carboxylic acid ethyl ester i) (S)-1-Benzyl-pyrrolidine-2-carboxylic acid methyl ester To a suspension of 3.6 g H-Pro-OMe hydrochloride in 40 ml dichloromethane were added 6.7 ml triethylamine. After 5 minutes the reaction mixture was filtered over a plug of Celite, washed with dichloromethane and the filtrate treated with 3.1 ml benzyl bromide. After stirring for 12 h the reaction mixture was washed with saturated aqueous NaHCO$_3$ and the residue obtained after evaporation of the solvent purified by chromatography on silica using ethyl acetate/heptane 1/7 as eluent. Yield: 2.9 g colorless oil.

ii) 1-((S)-1-Benzyl-pyrrolidin-2-yl)-butane-1,3-dione 3-oxime

To 12.5 ml BuLi (1.6 M in hexane) was added a solution of 0.73 g acetone oxime in 8 ml THF at 0° C. After 30 minutes a solution of 1.0 g (S)-1-Benzyl-pyrrolidine-2-carboxylic acid methyl ester in 5 ml THF was added dropwise over a period of 20 minutes at this temperature. The resulting suspension was stirred for another 3 h at 0° C. before being cannulated into 21 ml 3 M HCl. The phases were separated; the aqueous phase was brought to pH8 using solid NaHCO$_3$ and extracted with dichloromethane (3×) to give the crude product. Yield: 1.3 g mixture of E/Z isomers.

iii) 5-((S)-1-Benzyl-pyrrolidin-2-yl)-3-methyl-isoxazole

To a solution of 878 mg 1-((S)-1-Benzyl-pyrrolidin-2-yl)-butane-1,3-dione 3-oxime in 50 ml dichloromethane were added 0.52 ml methanesulfonyl chloride and 0.94 ml triethylamine at 0° C. The solution was allowed to warm to RT within 5 h. The reaction mixture was extracted with 1 M HCl (3×), the aqueous extracts were neutralized with solid NaHCO$_3$ and extracted with dichloromethane (3×) to give the crude product which was purified by chromatography on silica using ethyl acetate/heptane 1/2 as eluent.
Yield: 285 mg.

iv) 3-Methyl-5-(S)-pyrrolidin-2-yl-isoxazole hydrotrifluoroacetate

To a solution of 260 mg 5-((S)-1-Benzyl-pyrrolidin-2-yl)-3-methyl-isoxazole in 39 ml 1,2-dichloroethane were added 0.12 ml 1-chloroethylchloroformate at 0° C. After 10 minutes the reaction mixture was warmed to 85° C. and the solution refluxed for 4 h. The reaction mixture was concentrated and the residue obtained dissolved in 26 ml MeOH and stirred at 50° C. for 45 minutes. After evaporation of the solvent under reduced pressure the residue obtained purified by preparative HPLC (C18 reverse phase column, elution with a water/MeCN gradient with 0.1% TFA). The fractions containing the product were lyophilized to yield the pure product as its trifluoroacetate salt.
Yield: 10 mg.

v) 4-{(S)-4-Carboxy-2-[(5-{2-[(S)-2-(3-methyl-isoxazol-5-yl)-pyrrolidin-1-yl]-2-oxo-ethoxy}-1-phenyl-1H-pyrazole-3-carbonyl)-amino]-butyryl}-piperazine-1-carboxylic acid ethyl ester The title compound was prepared by adapting the procedures described in example 167 with the difference that 3-Methyl-5-(S)-pyrrolidin-2-yl-isoxazole hydrotrifluoroacetate was used instead of 2-thiophen-2-yl-pyrrolidine. Yield: 8 mg MS (ES+): m/e=666.

Example 174

4-{(S)-4-Carboxy-2-[(5-{2-[(S)-2-(3-methyl-[1,2,4]oxadiazol-5-yl)-pyrrolidin-1-yl]-2-oxo-ethoxy}-1-phenyl-1H-pyrazole-3-carbonyl)-amino]-butyryl}-piperazine-1-carboxylic acid ethyl ester i) (S)-2-(3-Methyl-[1,2,4]oxadiazol-5-yl)-pyrrolidine-1-carboxylic acid benzyl ester To a solution of 122 mg Z-Pro-OH in 4 ml DMF was added a solution of 325 mg 1,1'-carbonyldiimidazole in 5 ml DMF and the solution was stirred for 30 minutes at RT before a solution of 148 mg acetamide oxime in 3 ml DMF was added. The reaction mixture was stirred for 12 h before 325 mg 1,1'-carbonyldiimidazole were added and the mixture stirred at 115° C. for 5 h. Then, the reaction mixture was diluted with ethyl acetate and washed with aqueous LiCl (4% w/w), saturated aqueous NaHCO$_3$ and 0.1 M HCl. The crude product obtained after evaporation of the solvent was used in the next reaction step without further purification. Yield: 337 mg.

ii) 3-Methyl-5-(S)-pyrrolidin-2-yl-[1,2,4]oxadiazole

To a solution of 150 mg (S)-2-(3-methyl-[1,2,4]oxadiazol-5-yl)-pyrrolidine-1-carboxylic acid benzyl ester in 10 ml TFA were added 3 ml thioanisole and the solution stirred for 5 h at RT. The reaction mixture was concentrated and the residue codistilled with toluene (2×) to give the crude product.

iii) 4-{(S)-4-Carboxy-2-[(5-{2-[(S)-2-(3-methyl-[1,2,4]oxadiazol-5-yl)-pyrrolidin-1-yl]-2-oxo-ethoxy}-1-phenyl-1H-pyrazole-3-carbonyl)-amino]-butyryl}-piperazine-1-carboxylic acid ethyl ester The title compound was prepared by adapting the procedures described in example 167 with the difference that 3-Methyl-5-(S)-pyrrolidin-2-yl-[1,2,4]oxadiazole hydrotrifluoroacetate was used instead of 2-thiophen-2-yl-pyrrolidine.
Yield: 104 mg MS (ES+): m/e=667.

Example 175

4-[2-({5-[2-((S)-2-Cyclobutylcarbamoyl-pyrrolidin-1-yl)-2-oxo-ethoxy]-1-phenyl-1H-pyrazole-3-carbonyl}-amino)-3-fluoro-butyryl]-piperazine-1-carboxylic acid propyl ester i) 2-Benzyloxycarbonylamino-3-fluoro-butyric acid

To a solution of 500 mg 2-amino-3-fluorobutyric acid in 4 ml dioxane and 4 ml water were added 694 mg NaHCO$_3$. After stirring for 12 h it was acidified to pH2 with 2 N HCl and diluted with dichloromethane. The organic layer was separated, washed with brine and dried over MgSO$_4$. Evaporation of the solvent gave the crude product which was used without further purification. Yield: 1.51 g.

ii) piperazine-1,4-dicarboxylic acid propyl ester benzyl ester

To a solution of 15.0 g benzyl 1-piperazinecarboxylate in 100 ml dichloromethane were added 20.7 ml triethylamine. The solution was cooled to 0° C. and 8.4 ml propylchloroformate added dropwise at this temperature. After stirring for 1 h the reaction mixture was diluted with dichloromethane and washed with 0.1 M HCl and saturated NaHCO$_3$. The crude product obtained after evaporation of the solvent was purified by flash chromatography on silica using an ethyl acetate/heptane gradient. Yield: 19.3 g.

iii) piperazine-1-carboxylic acid propyl ester

To a solution of 19.3 g piperazine-1,4-dicarboxylic acid propyl ester benzyl ester in 200 ml ethanol were added 2.0 g Pd/C (10%) and the suspension stirred under an atmosphere of hydrogen (3 bar) for 3 h. The reaction mixture was filtrated over a plug of Celite, washed with ethanol and concentrated to give the crude product which was used in the subsequent reaction. Yield: 10.5 g.

iv) 4-(2-Benzyloxycarbonylamino-3-fluoro-butyryl)-piperazine-1-carboxylic acid propyl ester To a solution of 500 mg 2-Benzyloxycarbonylamino-3-fluoro-butyric acid in 3 ml DMF were added 310 mg 1-propoxycarbonylpiperazine, 0.50 ml N-ethylmorpholine and 643 mg TOTU. After stirring for 12 h it was diluted with ethyl acetate and extracted with aqueous LiCl (4% w/w), aqueous NaHCO$_3$, 0.1 M HCl and brine. The organic layer was dried over MgSO$_4$ and concentrated to furnish the crude coupling product which was used without further purification in the next step. Yield: 591 mg v) 4-(2-Amino-3-fluoro-butyryl)-piperazine-1-carboxylic acid propyl ester

To a solution of 591 mg 4-(2-Benzyloxycarbonylamino-3-fluoro-butyryl)-piperazine-1-carboxylic acid propyl ester in 20 ml ethanol were added 0.1 g Pd/C (10%) and the suspension stirred under an atmosphere of hydrogen (1 bar) for 1 h. The reaction mixture was filtrated over a plug of Celite, washed with ethanol and concentrated to give the crude product which was used in the subsequent reaction. Yield: 347 mg.

vi) 4-[2-({5-[2-((S)-2-Cyclobutylcarbamoyl-pyrrolidin-1-yl)-2-oxo-ethoxy]-1-phenyl-1H-pyrazole-3-carbonyl}-amino)-3-fluoro-butyryl]-piperazine-1-carboxylic acid propyl ester To a solution of 150 mg 5-[2-((S)-2-Cyclobutylcarbamoyl-pyrrolidin-1-yl)-2-oxo-ethoxy]-1-phenyl-1H-pyrazole-3-carboxylic acid in 4 ml DMF were added 138 mg HATU, 124 l DIPEA and 100 mg 4-(2-Amino-3-fluoro-butyryl)-piperazine-1-carboxylic acid propyl ester. After stirring for 12 h saturated NaHCO$_3$ solution (1.5 ml) was added and the mixture passed through a Chem Elute® cartridge eluting with DCM. The crude product obtained after evaporation of the solvent was purified by preparative HPLC (C18 reverse phase column, elution with a water/MeCN gradient with 0.1% TFA) to give the title compound.
Yield: 115 mg MS (ES+): m/e=670.

Example 176

4-[2-({5-[2-((S)-2-Cyclobutylcarbamoyl-pyrrolidin-1-yl)-2-oxo-ethoxy]-1-phenyl-1H-pyrazole-3-carbonyl}-amino)-3-fluoro-butyryl]-piperazine-1-carboxylic acid butyl ester The title compound was prepared by adapting the procedures described in example 275 with the difference that piperazine-1-carboxylic acid butyl ester was used instead of piperazine-1-carboxylic acid propyl ester. Yield: 113 mg MS (ES+): m/e=684.

Example 177

4-[(S)-4-Carboxy-2-({5-[2-((S)-2-carboxy-4,4-difluoro-pyrrolidin-1-yl)-2-oxo-ethoxy]-1-phenyl-1H-pyrazole-3-carbonyl}-amino)-butyryl]-piperazine-1-carboxylic acid ethyl ester To a solution of 100 mg 4-[(S)-4-tert-Butoxycarbonyl-2-({5-[2-((S)-2-carboxy-4,4-difluoro-pyrrolidin-1-yl)-2-oxo-ethoxy]-1-phenyl-1H-pyrazole-3-carbonyl}-amino)-butyryl]-piperazine-1-carboxylic acid ethyl ester in 2 ml dichloromethane were added 300 μl TFA. After stirring for 12 h the solvents were removed under reduced pressure and the residue purified by preparative HPLC (C18 reverse phase column, elution with a water/MeCN gradient with 0.1% TFA). The fractions containing the product were lyophilized to yield the pure product. Yield: 63 mg MS (ES+): m/e=665.

Example 178

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-5-hydroxy-pentanoyl]-piperazine-1-carboxylic acid butyl ester i) (S)-2-tert-Butoxycarbonylamino-5-hydroxy-pentanoic acid benzyl ester

To a solution of 7.0 g Boc-Glu-OBn in 100 ml THF were added dropwise under Argon at −10° C. 2.9 ml N-ethylmorpholine and 3.0 ml isobutyl chloroformate. The reaction mixture was stirred for 10 minutes before 2.4 g sodium borohydride were added. Methanol (400 ml) was added slowly over a period of 70 minutes at this temperature. It was stirred for additional 30 minutes at RT before being neutralized with 1 N HCl. The mixture was concentrated, dissolved in ethyl acetate and washed with 1 N HCl and brine. The crude product obtained after evaporation of the solvent was purified by flash chromatography on silica using an ethyl acetate/heptane gradient. Yield: 5.3 g.

(ii) (S)-2-tert-Butoxycarbonylamino-5-(tert-butyl-diphenyl-silanyloxy)-pentanoic acid benzyl ester (S)-2-tert-Butoxycarbonylamino-5-hydroxy-pentanoic acid benzyl ester (2.5 g) was dissolved in 50 ml DMF and treated with 2.0 ml tert-butyldiphenylchlorosilane, 1.2 ml triethylamine and 95 mg DMAP. After stirring for 12 h equivalent portions of the reagents were added and the mixture stirred for additional 12 h. The mixture was concentrated, the residue was dissolved in ethyl acetate and washed with aqueous LiCl (4%), 0.1 M HCl and saturated aqueous NaHCO$_3$. The crude product obtained after evaporation of the solvent was purified by flash chromatography on silica using an ethyl acetate/heptane gradient. Yield: 2.0 g.

(iii) (S)-2-tert-Butoxycarbonylamino-5-(tert-butyl-diphenyl-silanyloxy)-pentanoic acid To a solution of 1.92 g (S)-2-tert-Butoxycarbonylamino-5-(tert-butyl-diphenyl-silanyloxy)-pentanoic acid benzyl ester in 40 ml ethyl acetate were added under argon 0.2 g Pd/C (10%) and the suspension was stirred under an atmosphere of hydrogen (3 bar) for 16 h. The suspension was filtered over a plug of Celite® and washed with ethyl acetate. The crude product was obtained after evaporation of the solvent. Yield: 1.61 g colorless oil.

(iv) 4-[(S)-2-tert-Butoxycarbonylamino-5-(tert-butyl-diphenyl-silanyloxy)-pentanoyl]-piperazine-1-carboxylic acid butyl ester To a solution of 1.61 g (S)-2-tert-Butoxycarbonylamino-5-(tert-butyl-diphenyl-silanyloxy)-pentanoic acid in 8 ml DMF were added 1.02 g piperazine-1-carboxylic acid butyl ester hydrotrifluoroacetate, 1.7 ml N-ethylmorpholine and 1.1 g TOTU. After stirring for 12 h the solution was diluted with ethyl acetate and subsequently washed with aqueous LiCl (4%), 0.1 M HCl and saturated aqueous NaHCO$_3$. The crude product obtained after evaporation of the solvent was used without further purification. Yield: 1.80 g.

(v) 4-[(S)-2-Amino-5-(tert-butyl-diphenyl-silanyloxy)-pentanoyl]-piperazine-1-carboxylic acid butyl ester hydrochloride To a solution of 900 mg 4-[(S)-2-tert-Butoxycarbonylamino-5-(tert-butyl-diphenyl-silanyloxy)-pentanoyl]-piperazine-1-carboxylic acid butyl ester in 5 ml dioxane were added 5 ml HCl in dioxane (4 M). After 2.5 h conversion was complete and the reaction mixture was neutralized with basic ion exchange resin III (Merck), filtered and concentrated.
Yield: 760 mg.

vi) 4-[(S)-5-(tert-Butyl-diphenyl-silanyloxy)-2-({5-[2-((S)-2-cyclobutylcarbamoyl-pyrrolidin-1-yl)-2-oxo-ethoxy]-1-phenyl-1H-pyrazole-3-carbonyl}-amino)-pentanoyl]-piperazine-1-carboxylic acid butyl ester To a solution of 195 mg 5-[2-((S)-2-Cyclobutylcarbamoyl-pyrrolidin-1-yl)-2-oxo-ethoxy]-1-phenyl-1H-pyrazole-3-carboxylic acid in 10 ml DMF were added 108 mg HOBt, 135 mg EDC and 0.2 ml DIPEA. After 20 minutes 255 mg 4-[(S)-2-Amino-5-(tert-butyl-diphenyl-silanyloxy)-pentanoyl]-piperazine-1-carboxylic acid butyl ester hydrochloride were added and the mixture stirred for 12 h. The reaction mixture was concentrated, diluted with ethyl acetate and washed with aqueous LiCl (4%), 0.1 M HCl and saturated aqueous NaHCO$_3$. The crude product thus obtained was pure enough for the following transformation. Yield: 400 mg.

(vii) 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-5-hydroxy-pentanoyl]-piperazine-1-carboxylic acid butyl ester To a solution of 400 mg 4-[(S)-5-(tert-Butyl-diphenyl-silanyloxy)-2-({5-[2-((S)-2-cyclobutylcarbamoyl-pyrrolidin-1-yl)-2-oxo-ethoxy]-1-phenyl-1H-pyrazole-3-carbonyl}-amino)-pentanoyl]-piperazine-1-carboxylic acid butyl ester in 40 ml THF were added 0.6 ml of TBAF (1 M in THF) and the mixture stirred at RT for 12 h. It was concentrated, the residue was dissolved in DCM and washed with water (3×). The solvent was removed under reduced pressure and the residue purified by preparative HPLC (C18 reverse phase column, elution with a water/MeCN gradient with 0.1% TFA). The fractions containing the product were lyophilized to yield the pure product.

Yield: 45 mg MS (ES+): m/e=696.

Example 179

4-((S)-4-Carboxy-2-{[5-[2-((S)-2-cyclobutylcarbamoyl-pyrrolidin-1-yl)-2-oxo-ethoxy]-1-(4-trifluoromethyl-phenyl)-1H-pyrazole-3-carbonyl]-amino}-butyryl)-piperazine-1-carboxylic acid ethyl ester i) 5-Hydroxy-1-(4-trifluoromethyl-phenyl)-1H-pyrazole-3-carboxylic acid ethyl ester A solution of 6.83 g 4-(trifluoromethyl)phenylhydrazine and 9.05 g diethyl oxalacetate sodium salt in 120 ml acetic acid was stirred at 100° C. for 2 h. The product precipitated was filtered, codistilled twice with toluene and suspended with heptane/ethyl acetate 3:1. The suspension was filtered again and the cude product obtained dried in vacuo.
Yield: 7.43 g ii) 5-Hydroxy-1-(4-trifluoromethyl-phenyl)-1H-pyrazole-3-carboxylic acid

To a solution of 4.00 g 5-Hydroxy-1-(4-trifluoromethyl-phenyl)-1H-pyrazole-3-carboxylic acid ethyl ester in 20 ml THF and 6 ml water were added 480 mg LiOH. After 12 h additional 2 ml 2 N NaOH were added to complete ester hydrolysis. The organic solvent was removed in vacuo, the aqueous phase extracted once with ethyl acetate and the aqueous phase acidified with 6 M HCl. The suspension obtained was filtered and the filtrate saturated with NaCl before being extracted with ethyl acetate. The residue obtained after evaporation of the solvent was combined with the crude product after filtration and was found to be pure enough for the subsequent transformation.
Yield: 3.11 g iii) 4-{(S)-4-tert-Butoxycarbonyl-2-[(5-hydroxy-1-(4-trifluormethyl)phenyl-1H-pyrazole-3-carbonyl)-amino]-butyryl}-piperazine-1-carboxylic acid ethyl ester To a solution of 3.01 g 5-Hydroxy-1-(4-trifluoromethyl-phenyl)-1H-pyrazole-3-carboxylic acid and 3.80 g 4-((S)-2-amino-4-tert-butoxycarbonyl-butyryl)-piperazine-1-carboxylic acid ethyl ester in 25 ml DMF 1.51 g HOAT, 2.12 g EDC and 4.2 ml DIPEA were added and the reaction mixture was stirred for 12 h at RT. Then the reaction mixture was diluted with ethyl acetate and subsequently extracted with aqueous LiCl (4% w/w), 0.1 M HCl and aqueous NaHCO$_3$. The organic layer was dried over MgSO$_4$ and the solvent was removed under reduced pressure. The crude product thus obtained was purified by flash chromatography on silica using a dichloromethane/methanol gradient.
Yield: 4.41 g.

iv) 4-{(S)-2-[(5-Benzyloxycarbonylmethoxy-1-(4-trifluoromethyl)phenyl-1H-pyrazole-3-carbonyl)-amino]-4-tert-butoxycarbonyl-butyryl}-piperazine-1-carboxylic acid ethyl ester To a solution of 4.41 g 4-{(S)-4-tert-butoxycarbonyl-2-[(5-hydroxy-1-(4-trifluoromethyl)phenyl-1H-pyrazole-3-carbonyl)-amino]-butyryl}-piperazine-1-carboxylic acid ethyl ester in 20 ml DMF were added 1.17 ml benzyl bromoacetate and 4.81 g cesium carbonate. After stirring at RT for 48 h the suspension was filtered over a plug of Celite, the filtrate diluted with ethyl acetate and extracted with aqueous LiCl (4% w/w), 0.1 M HCl and aqueous NaHCO$_3$. The crude product obtained after evaporation of the solvent was purified by flash chromatography on silica eluting with a gradient of n-heptane/ethyl acetate. Yield: 2.41 g yellowish amorphous solid.

v) 4-{(S)-4-tert-Butoxycarbonyl-2-[(5-carboxymethoxy-1-(4-trifluoromethyl)phenyl-1H-pyrazole-3-carbonyl)-amino]butyryl}-piperazine-1-carboxylic acid ethyl ester To a solution of 2.41 g 4-{(S)-2-[(5-Benzyloxycarbonyl-methoxy-1-(4-trifluoromethyl)phenyl-1H-pyrazole-3-carbonyl)-amino]-4-tert-butoxycarbonyl-butyryl}-piperazine-1-carboxylic acid ethyl ester in 25 ml EtOH were added under argon 0.3 g Pd/C (10%) and the suspension was stirred under an atmosphere of hydrogen (3 bar) for 16 h. The suspension was filtered over a plug of Celite® and washed with EtOH. The crude product obtained after evaporation of the solvent was dried under vacuo at 40° C. for 24 h.
Yield: 2.02 g colorless solid.

vi) 4-[(S)-2-({5-[2-((S)-2-Benzyloxycarbonyl-pyrrolidin-1-yl)-2-oxo-ethoxy]-1-(4-trifluoromethyl)phenyl-1H-pyrazole-3-carbonyl}-amino)-4-tert-butoxycarbonyl-butyryl]-piperazine-1-carboxylic acid ethyl ester To a solution of 2.02 g 4-{(S)-4-tert-Butoxycarbonyl-2-[(5-carboxymethoxy-1-(4-trifluoromethyl)phenyl-1H-pyrazole-3-carbonyl)-amino]-butyryl}-piperazine-1-carboxylic acid ethyl ester in 14 ml DMF were added 471 mg HOBt, 1.3 ml DIPEA and 744 mg L-proline benzyl ester hydrochloride at room temperature. Then 590 mg EDC were added portionwise and the solution stirred over a period of 12 h. The solvent was evaporated, the residue dissolved in ethyl acetate and subsequently extracted with aqueous LiCl (4 w/w), 0.1 M HCl, aqueous NaHCO$_3$ and brine. The organic layer was dried over MgSO$_4$ and the solvent was removed under reduced pressure. The crude product thus obtained was used in the subsequent reaction. Yield: 2.72 g amorphous solid.

(vii) 4-[(S)-4-tert-Butoxycarbonyl-2-({5-[2-((S)-2-carboxy-pyrrolidin-1-yl)-2-oxo-ethoxy]-1-(4-trifluoromethyl)phenyl-1H-pyrazole-3-carbonyl}-amino)-butyryl]-piperazine-1-carboxylic acid ethyl ester To a solution of 2.72 g 4-[(S)-2-({5-[2-((S)-2-Benzyloxy-carbonyl-pyrrolidin-1-yl)-2-oxo-ethoxy]-1-(4-trifluoromethyl)phenyl-1H-pyrazole-3-carbonyl}-amino)-4-tert-butoxycarbonyl-butyryl]-piperazine-1-carboxylic acid ethyl ester in 25 ml ethyl acetate was added under argon 0.3 g Pd/C (10%) and the suspension was stirred under an atmosphere of hydrogen (3 bar) for 24 h. The suspension was filtered over a plug of Celite® and washed with ethyl acetate. The crude product obtained after evaporation of the solvent was used in the subsequent reaction. Yield: 2.15 g.

viii) 4-[(S)-4-Carboxy-2-({5-[2-((S)-2-cyclobutylcarbamoyl-pyrrolidin-1-yl)-2-oxo-ethoxy]-1-(4-trifluoromethyl)phenyl-1H-pyrazole-3-carbonyl}-amino)-butyryl]-piperazine-1-carboxylic acid ethyl ester To a solution of 300 mg 4-[(S)-4-tert-Butoxycarbonyl-2-({5-[2-((S)-2-carboxy-pyrrolidin-1-yl)-2-oxo-ethoxy]-1-(4-trifluoromethyl)phenyl-1H-pyrazole-3-carbonyl}-amino)-butyryl]-piperazine-1-carboxylic acid ethyl ester in 4 ml DMF were added 102 µl DIPEA and 152 mg HATU. After 20 minutes 34 µl cyclobutylamine were added and the reaction mixture was stirred for 12 h. After dilution with dichloromethane the reaction mixture was extracted with aqueous LiCl (4% w/w), 0.1 M HCl and aqueous NaHCO$_3$. The organic layer was dried over MgSO$_4$ and the solvent was removed under reduced pressure. The crude product was dissolved in 3 ml DCM and treated with 365 µl TFA. After stirring for 12 h the solvents were removed under reduced pressure and the residue purified by preparative HPLC (C18 reverse phase column, elution with a water/MeCN gradient with 0.1% TFA) to give the title compound. Yield: 42 mg MS (ES+): m/e=750.

Example 180

4-{(S)-4-Carboxy-2-[(5-{2-[(S)-2-(3-cyclopropyl-[1,2,4]oxadiazol-5-yl)-pyrrolidin-1-yl]-2-oxo-ethoxy}-1-phenyl-1H-pyrazole-3-carbonyl)-amino]-butyryl}-piperazine-1-carboxylic acid ethyl ester i) (S)-2-(3-Cyclopropyl-1,2,4-oxadiazol-5-yl)-pyrrolidine-1-carboxylic acid benzyl ester To a solution of 500 mg Z-Pro-OH in 6 ml DMF was added a solution of 325 mg 1,1'-carbonyldiimidazole in 2 ml DMF. After stirring for 30 minutes a solution of 201 mg N-Hydroxy-cyclopropanecarboxamidine in 2 ml DMF was added and the solution stirred for 12 h at room temperature until LCMS showed complete conversion to the intermediate O-acyl amide oxime. Further 325 mg CDI were added and the mixture stirred at 115° C. for 5 h. It was diluted with ethyl acetate and extracted with aqueous LiCl (4% w/w), aqueous NaHCO$_3$ and 0.1 M HCl. The organic layer was dried over MgSO$_4$ and concentrated to furnish the crude product as colorless oil. Yield: 228 mg.

ii) 3-Cyclopropyl-5-(S)-pyrrolidin-2-yl-[1,2,4]oxadiazole

A mixture of 228 mg (S)-2-(3-Cyclopropyl-1,2,4-oxadiazol-5-yl)-pyrrolidine-1-carboxylic acid benzyl ester, 15 ml TFA and 4 ml thioanisole was stirred at room temperature for 12 h. It was concentrated and thoroughly codistilled with toluene to give the crude amine as colorless oil. Yield: 130 mg iii) 4-{(S)-4-Carboxy-2-[(5-{2-[(S)-2-(3-cyclopropyl-[1,2,4]oxadiazol-5-yl)-pyrrolidin-1-yl]-2-oxo-ethoxy}-1-phenyl-1H-pyrazole-3-carbonyl)-amino]-butyryl}-piperazine-1-carboxylic acid ethyl ester To a solution of 213 mg 4-{(S)-4-tert-Butoxycarbonyl-2-[(5-carboxymethoxy-1-phenyl-1H-pyrazole-3-carbonyl)-amino]-butyryl}-piperazine-1-carboxylic acid ethyl ester in 7 ml DMF were added 138 mg HATU, 50 mg HOAT, 0.19 ml DIPEA and 65 mg 3-Cyclopropyl-5-(S)-pyrrolidin-2-yl-[1,2,4]oxadiazole. It was concentrated, the residue dissolved in dichloromethane and extracted with aqueous LiCl (4% w/w), aqueous NaHCO$_3$ and 0.1 M HCl. The organic layer was dried over MgSO$_4$ and concentrated to furnish the crude coupling product as colorless oil. The latter one was dissolved in 10 ml DCM and treated with 403 µl TFA. After stirring for 12 h the solvents were removed under reduced pressure and the residue purified by preparative HPLC (C18 reverse phase column, elution with a water/MeCN gradient with 0.1% TFA) to give the title compound.

Yield: 30 mg MS (ES+): m/e=692.

Example 181

4-[2-({5-[2-((S)-2-Cyclobutylcarbamoyl-pyrrolidin-1-yl)-2-oxo-ethoxy]-1-phenyl-1H-pyrazole-3-carbonyl}-amino)-acetyl]-piperazine-1-carboxylic acid ethyl ester i) ({5-[2-((S)-2-Cyclobutylcarbamoyl-pyrrolidin-1-yl)-2-oxo-ethoxy]-1-phenyl-1H-pyrazole-3-carbonyl}-amino)-acetic acid tert-butyl ester To a solution of 920 mg 5-[2-((S)-2-Cyclobutylcarbamoyl-pyrrolidin-1-yl)-2-oxo-ethoxy]-1-phenyl-1H-pyrazole-3-carboxylic acid in 46 ml DMF were added 342 mg HOBt, 428 mg EDC, 0.78 ml DIPEA and 374 mg glycine tert-butyl ester hydrochloride. After stirring for 12 h it was concentrated and the residue dissolved in dichloromethane. It was extracted with aqueous LiCl (4% w/w), aqueous NaHCO$_3$ and 0.1 M HCl. The organic layer was dried over MgSO$_4$ and concentrated to furnish the crude coupling product as colorless oil.

Yield: 1.12 g.

ii) ({5-[2-((S)-2-Cyclobutylcarbamoyl-pyrrolidin-1-yl)-2-oxo-ethoxy]-1-phenyl-1H-pyrazole-3-carbonyl}-amino)-acetic acid To a solution of 1.33 g ({5-[2-((S)-2-Cyclobutylcarbamoyl-pyrrolidin-1-yl)-2-oxo-ethoxy]-1-phenyl-1H-pyrazole-3-carbonyl}-amino)-acetic acid tert-butyl ester in 20 ml dichloromethane were added 3.8 ml TFA. After stirring for 5 h it was concentrated and codistilled twice with toluene to give the crude product. Yield: 1.58 g iii) 4-[2-({5-[2-((S)-2-Cyclobutylcarbamoyl-pyrrolidin-1-yl)-2-oxo-ethoxy]-1-phenyl-1H-pyrazole-3-carbonyl}-amino)-acetyl]-piperazine-1-carboxylic acid ethyl ester To a solution of 100 mg ({5-[2-((S)-2-Cyclobutylcarbamoyl-pyrrolidin-1-yl)-2-oxo-ethoxy]-1-phenyl-1H-pyrazole-3-carbonyl}-amino)-acetic acid in 2 ml DMF were added 0.15 ml DIPEA, 81 mg HATU and 0.03 ml 1-ethoxycarbonylpiperazine. After stirring for 1 h it was diluted with dichlormethane and extracted with aqueous LiCl (4% w/w), aqueous NaHCO$_3$ and 0.1 M HCl. The crude product obtained after evaporation of the solvent was purified by preparative HPLC (C18 reverse phase column, elution with a water/MeCN gradient with 0.1% TFA) to give the title compound.

Yield: 25 mg MS (ES+): m/e=607.

Example 182

4-[2-({5-[2-((S)-2-Cyclobutylcarbamoyl-pyrrolidin-1-yl)-2-oxo-ethoxy]-1-phenyl-1H-pyrazole-3-carbonyl}-amino)-acetyl]-piperazine-1-carboxylic acid butyl ester The title compound was prepared by adapting the procedures described in example 181 with the difference that 1-butoxycarbonylpiperazine hydrotrifluoroacetate was used instead of 1-ethoxycarbonylpiperazine. Yield: 8 mg MS (ES+): m/e=638.

Example 183

4-[(R)-2-({5-[2-((S)-2-Cyclobutylcarbamoyl-pyrrolidin-1-yl)-2-oxo-ethoxy]-1-phenyl-1H-pyrazole-3-carbonyl}-amino)-propionyl]-piperazine-1-carboxylic acid ethyl ester i) (R)-2-({5-[2-((S)-2-Cyclobutylcarbamoyl-pyrrolidin-1-yl)-2-oxo-ethoxy]-1-phenyl-1H-pyrazole-3-carbonyl}-amino)-propionic acid tert-butyl ester To a solution of 500 mg 5-[2-((S)-2-Cyclobutylcarbamoyl-pyrrolidin-1-yl)-2-oxo-ethoxy]-1-phenyl-1H-pyrazole-3-carboxylic acid in 5 ml DMF were added 186 mg HOBt, 232 mg EDC, 0.50 ml DIPEA and 220 mg D-Ala-OtBu×HCl. After stirring for 12 h it was concentrated and the residue dissolved in ethyl acetate. It was extracted with aqueous LiCl (4% w/w), aqueous NaHCO$_3$ and 0.1 M HCl. The organic layer was dried over MgSO$_4$ and concentrated to furnish the crude coupling product as colorless oil.

Yield: 745 mg.

ii) (R)-2-({5-[2-((S)-2-Cyclobutylcarbamoyl-pyrrolidin-1-yl)-2-oxo-ethoxy]-1-phenyl-1H-pyrazole-3-carbonyl}-amino)-propionic acid To a solution of 745 mg (R)-2-({5-[2-((S)-2-Cyclobutylcarbamoyl-pyrrolidin-1-yl)-2-oxo-ethoxy]-1-phenyl-1H-pyrazole-3-carbonyl}-amino)-propionic acid tert-butyl ester in 5 ml dichloromethane were added 1.6 ml TFA. After stirring for 6 h it was concentrated and codistilled twice with toluene to give the crude product. Yield: 770 mg iii) 4-[(R)-2-({5-[2-((S)-2-Cyclobutylcarbamoyl-pyrrolidin-1-yl)-2-oxo-ethoxy]-1-phenyl-1H-pyrazole-3-carbonyl}-amino)-propionyl]-piperazine-1-carboxylic acid ethyl ester To a solution of 190 mg (R)-2-({5-[2-((S)-2-Cyclobutylcarbamoyl-pyrrolidin-1-yl)-2-oxo-ethoxy]-1-phenyl-1H- pyrazole-3-carbonyl}-amino)-propionic acid in 3 ml DMF were added 0.27 ml DIPEA, 150 mg HATU and 0.06 ml 1-ethoxycarbonylpiperazine. After stirring for 1 h it was diluted with dichlormethane and extracted with aqueous LiCl (4% w/w), aqueous NaHCO$_3$ and 0.1 M HCl. The crude product obtained after evaporation of the solvent was purified by preparative HPLC (C18 reverse phase column, elution with a water/MeCN gradient with 0.1% TFA) to give the title compound.
Yield: 60 mg MS (ES+): m/e=624.

Example 184

4-[(R)-2-({5-[2-((S)-2-Cyclobutylcarbamoyl-pyrrolidin-1-yl)-2-oxo-ethoxy]-1-phenyl-1H-pyrazole-3-carbonyl}-amino)-propionyl]-piperazine-1-carboxylic acid butyl ester The title compound was prepared by adapting the procedures described in example 183 with the difference that 1-butoxycarbonylpiperazine hydrotrifluoroacetate was used instead of 1-ethoxycarbonylpiperazine. Yield: 56 mg MS (ES+): m/e=652.

Example 185

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-propionyl]-piperazine-1-carboxylic acid ethyl ester i) (S)-2-({5-[2-((S)-2-Cyclobutylcarbamoyl-pyrrolidin-1-yl)-2-oxo-ethoxy]-1-phenyl-1H-pyrazole-3-carbonyl}-amino)-propionic acid tert-butyl ester To a solution of 500 mg 5-[2-((S)-2-Cyclobutylcarbamoyl-pyrrolidin-1-yl)-2-oxo-ethoxy]-1-phenyl-1H-pyrazole-3-carboxylic acid in 5 ml DMF were added 186 mg HOBt, 232 mg EDC, 0.50 ml DIPEA and 220 mg L-Ala-OtBuxHCl. After stirring for 12 h it was concentrated and the residue dissolved in ethyl acetate. It was extracted with aqueous LiCl (4% w/w), aqueous NaHCO$_3$ and 0.1 M HCl. The organic layer was dried over MgSO$_4$ and concentrated to furnish the crude coupling product as colorless oil.
Yield: 634 mg.

ii) (S)-2-({5-[2-((S)-2-Cyclobutylcarbamoyl-pyrrolidin-1-yl)-2-oxo-ethoxy]-1-phenyl-1H-pyrazole-3-carbonyl}-amino)-propionic acid To a solution of 634 mg (S)-2-({5-[2-((S)-2-Cyclobutylcarbamoyl-pyrrolidin-1-yl)-2-oxo-ethoxy]-1-phenyl-1H-pyrazole-3-carbonyl}-amino)-propionic acid tert-butyl ester in 5 ml dichloromethane were added 0.8 ml TFA. After stirring for 6 h it was concentrated and codistilled twice with toluene to give the crude product. Yield: 905 mg iii) 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-propionyl]-piperazine-1-carboxylic acid ethyl ester To a solution of 225 mg (S)-2-({5-[2-((S)-2-Cyclobutylcarbamoyl-pyrrolidin-1-yl)-2-oxo-ethoxy]-1-phenyl-1H-pyrazole-3-carbonyl}-amino)-propionic acid in 4 ml DMF were added 0.32 ml DIPEA, 177 mg HATU and 0.07 ml 1-ethoxycarbonyl-piperazine. After stirring for 1 h it was diluted with dichlormethane and extracted with aqueous LiCl (4% w/w), aqueous NaHCO$_3$ and 0.1 M HCl. The crude product obtained after evaporation of the solvent was purified by preparative HPLC (C18 reverse phase column, elution with a water/MeCN gradient with 0.1% TFA) to give the title compound.
Yield: 67 mg MS (ES+): m/e=624.

Example 186

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-propionyl]-piperazine-1-carboxylic acid butyl ester The title compound was prepared by adapting the procedures described in example 185 with the difference that 1-butoxycarbonylpiperazine hydrotrifluoroacetate was used instead of 1-ethoxycarbonylpiperazine. Yield: 45 mg MS (ES+): m/e=652.

Example 187

4-{(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-[(2,2-difluoro-cyclopropanecarbonyl)-amino]-butyryl}-piperazine-1-carboxylic acid ethyl ester i) 4-[(S)-4-Amino-2-({5-[2-((S)-2-cyclobutylcarbamoyl-pyrrolidin-1-yl)-2-oxo-ethoxy]-1-phenyl-1H-pyrazole-3-carbonyl}-amino)-butyryl]-piperazine-1-carboxylic acid ethyl ester A solution of 362 mg 4-[(S)-4-Amino-2-({5-[2-((S)-2-cyclobutylcarbamoyl-pyrrolidin-1-yl)-2-oxo-ethoxy]-1-phenyl-1H-pyrazole-3-carbonyl}-amino)-butyryl]-piperazine-1-carboxylic acid ethyl ester hydrotrifluoroacetate in 10 ml MeCN was shaken in the presence of (Polystyrylmethyl) trimethylammonium bicarbonate (3 equivalents) for 10 minutes. It was filtered to yield the pure amine after evaporation of the solvent. Yield: 295 mg ii) 4-{(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-[(2,2-difluoro-cyclopropanecarbonyl)-amino]-butyryl}-piperazine-1-carboxylic acid ethyl ester To a solution of 19 mg 2,2-Difluorocyclopropane carboxylic acid in 3 ml DMF were added 0.03 ml DIPEA, 58 mg HATU and 100 mg 4-[(S)-4-Amino-2-({5-[2-((S)-2-cyclobutylcarbamoyl-pyrrolidin-1-yl)-2-oxo-ethoxy]-1-phenyl-1H-pyrazole-3-carbonyl}-amino)-butyryl]-piperazine-1-carboxylic acid ethyl ester. After stirring for 12 h it was diluted with dichlormethane and extracted with aqueous LiCl (4% w/w), aqueous NaHCO$_3$ and 0.1 M HCl. The crude product obtained after evaporation of the solvent was purified by preparative HPLC (C18 reverse phase column, elution with a water/MeCN gradient with 0.1% TFA) to give the title compound. Yield: 55 mg MS (ES+): m/e=756.

Example 188

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-trifluoromethanesulfonylamino-butyryl]-piperazine-1-carboxylic acid ethyl ester To a solution of 100 mg 4-[(S)-4-Amino-2-({5-[2-((S)-2-cyclobutylcarbamoyl-pyrrolidin-1-yl)-2-oxo-ethoxy]-1-phenyl-1H-pyrazole-3-carbonyl}-amino)-butyryl]-piperazine-1-carboxylic acid ethyl ester in 5 ml dichloromethane were added at −78° C. 26 µl triethylamine and 27 µl trifluoromethanesulfonic acid anhydride. After 20 minutes stirring at this temperature 1 ml of aqueous NaHCO$_3$ was added, the solution quickly warmed to room temperature and the organic layer separated. The latter one was washed with brine and dried over MgSO$_4$ before being concentrated. The crude product was purified by preparative HPLC (C18 reverse phase column, elution with a water/MeCN gradient with 0.1% TFA) to give the title compound. Yield: 35 mg MS (ES+): m/e=784.

Example 189

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-methoxycarbonyl-butyryl]-piperazine-1-carboxylic acid cyclobutyl ester To a solution of 150 mg 4-[(S)-4-Carboxy-2-({5-[2-((S)-2-cyclobutylcarbamoyl-pyrrolidin-1-yl)-2-oxo-ethoxy]-1-phenyl-1H-pyrazole-3-carbonyl}-amino)-butyryl]-piperazine-1-carboxylic acid cyclobutyl ester in 3 ml DMF were added 42 mg EDC, 27 mg DMAP and 37 µl methanol. After 3 h the reaction mixture was concentrated and the residue purified by preparative HPLC (C18 reverse phase column, elution with a water/MeCN gradient with 0.1% TFA). The fractions containing the product were lyophilized to yield the pure product. Yield: 45 mg MS (ES+): m/e=722.

Example 190

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-methoxycarbonyl-butyryl]-piperazine-1-carboxylic acid propyl ester To a solution of 150 mg 4-[(S)-4-Carboxy-2-({5-[2-((S)-2-cyclobutylcarbamoyl-pyrrolidin-1-yl)-2-oxo-ethoxy]-1-phenyl-1H-pyrazole-3-carbonyl}-amino)-butyryl]-piperazine-1-carboxylic acid propyl ester in 3 ml DMF were added 42 mg EDC, 27 mg DMAP and 37 µl methanol. After 3 h the reaction mixture was concentrated and the residue purified by preparative HPLC (C18 reverse phase column, elution with a water/MeCN gradient with 0.1% TFA). The fractions containing the product were lyophilized to yield the pure product. Yield: 40 mg MS (ES+): m/e=710.

Example 191

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-methoxycarbonyl-butyryl]-piperazine-1-carboxylic acid butyl ester To a solution of 120 mg 4-[(S)-4-Carboxy-2-({5-[2-((S)-2-cyclobutylcarbamoyl-pyrrolidin-1-yl)-2-oxo-ethoxy]-1-phenyl-1H-pyrazole-3-carbonyl}-amino)-butyryl]-piperazine-1-carboxylic acid butyl ester in 3 ml DMF were added 39 mg EDC, 25 mg DMAP and 34 µl methanol. After 3 h the reaction mixture was concentrated and the residue purified by preparative HPLC (C18 reverse phase column, elution with a water/MeCN gradient with 0.1% TFA). The fractions containing the product were lyophilized to yield the pure product. Yield: 47 mg MS (ES+): m/e=724.

Example 192

4-[2-({5-[2-((S)-2-Cyclobutylcarbamoyl-pyrrolidin-1-yl)-2-oxo-ethoxy]-1-phenyl-1H-pyrazole-3-carbonyl}-amino)-acetyl]-piperazine-1-carboxylic acid cyclobutyl ester To a solution of 100 mg ({5-[2-((S)-2-Cyclobutylcarbamoyl-pyrrolidin-1-yl)-2-oxo-ethoxy]-1-phenyl-1H-pyrazole-3-carbonyl}-amino)-acetic acid in 2 ml DMF were added 0.15 ml DIPEA, 81 mg HATU and 0.03 mg 1-cyclobutoxycarbonylpiperazine. After stirring for 1 h it was diluted with dichloromethane and extracted with aqueous LiCl (4% w/w), aqueous NaHCO$_3$ and 0.1 M HCl. The crude product obtained after evaporation of the solvent was purified by preparative HPLC (C18 reverse phase column, elution with a water/MeCN gradient with 0.1% TFA) to give the title compound.

Yield: 12 mg MS (ES+): m/e=636.

Example 193

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-propionyl]-piperazine-1-carboxylic acid cyclobutyl ester To a solution of 100 mg (S)-2-({5-[2-((S)-2-Cyclobutylcarbamoyl-pyrrolidin-1-yl)-2-oxo-ethoxy]-1-phenyl-1H-pyrazole-3-carbonyl}-amino)-propionic acid in 2 ml DMF were added 0.14 ml DIPEA, 78 mg HATU and 0.38 mg 1-cyclobutoxycarbonyl-piperazine. After stirring for 1 h it was diluted with dichloromethane and extracted with aqueous LiCl (4 w/w), aqueous NaHCO$_3$ and 0.1 M HCl. The crude product obtained after evaporation of the solvent was purified by preparative HPLC (C18 reverse phase column, elution with a water/MeCN gradient with 0.1% TFA) to give the title compound.

Yield: 14 mg MS (ES+): m/e=650.

Example 194

4-[(R)-2-({5-[2-((S)-2-Cyclobutylcarbamoyl-pyrrolidin-1-yl)-2-oxo-ethoxy]-1-phenyl-1H-pyrazole-3-carbonyl}-amino)-propionyl]-piperazine-1-carboxylic acid cyclobutyl ester To a solution of 100 mg (R)-2-({5-[2-((S)-2-Cyclobutylcarbamoyl-pyrrolidin-1-yl)-2-oxo-ethoxy]-1-phenyl-1H-pyrazole-3-carbonyl}-amino)-propionic acid in 2 ml DMF were added 0.14 ml DIPEA, 78 mg HATU and 0.38 mg 1-cyclobutoxycarbonyl-piperazine. After stirring for 1 h it was diluted with dichloromethane and extracted with aqueous LiCl (4 w/w), aqueous NaHCO$_3$ and 0.1 M HCl. The crude product obtained after evaporation of the solvent was purified by preparative HPLC (C18 reverse phase column, elution with a water/MeCN gradient with 0.1% TFA) to give the title compound.

Yield: 11 mg MS (ES+): m/e=650.

Example 195

4-[(S)-6-Benzyloxy-2-({5-[2-((S)-2-cyclobutylcarbamoyl-pyrrolidin-1-yl)-2-oxo-ethoxy]-1-phenyl-1H-pyrazole-3-carbonyl}-amino)-hexanoyl]-piperazine-1-carboxylic acid ethyl ester i) (S)-4-[6-Benzyloxy-2-(9H-fluoren-9-ylmethoxycarbonylamino)-hexanoyl]-piperazine-1-carboxylic acid ethyl ester To a solution of 500 mg (S)-6-Benzyloxy-2-(9H-fluoren-9-ylmethoxycarbonylamino)-hexanoic acid in 7 ml DMF were added at 0° C. 172 mg piperazine-1-carboxylic acid ethyl ester, 0.14 ml N-ethylmorpholine and 357 mg TOTU. After stirring for 3 h the solution was diluted with ethyl acetate and subsequently washed with aqueous LiCl (4%) and half-saturated aqueous NaHCO$_3$. The crude product obtained after evaporation of the solvent was used without further purification. Yield: 663 mg.

ii) (S)-4-(2-Amino-6-benzyloxy-hexanoyl)-piperazine-1-carboxylic acid ethyl ester To a solution of 663 mg (S)-4-[6-Benzyloxy-2-(9H-fluoren-9-ylmethoxycarbonylamino)-hexanoyl]-piperazine-1-carboxylic acid ethyl ester in 4.9 ml DMF were added at room temperature 0.97 ml morpholine. After stirring for 2 h the reaction mixture was evaporated and the crude product thus obtained used in the next step without further purification.

iii) 4-[(S)-6-Benzyloxy-2-({5-[2-((S)-2-cyclobutylcarbamoyl-pyrrolidin-1-yl)-2-oxo-ethoxy]-1-phenyl-1H-pyrazole-3-carbonyl}-amino)-hexanoyl]-piperazine-1-carboxylic acid ethyl ester To a solution of 448 mg 5-[2-((S)-2-Cyclobutylcarbamoyl-pyrrolidin-1-yl)-2-oxo-ethoxy]-1-phenyl-1H-pyrazole-3-carboxylic acid in 10 ml DMF were added 216 mg HOBt, 271 mg EDC and 0.45 ml DIPEA. After 5 minutes 410 mg (S)-4-(2-Amino-6-benzyloxy-hexanoyl)-piperazine-1-carboxylic acid ethyl ester were added and the mixture stirred for 12 h. The reaction mixture was concentrated, diluted with ethyl acetate and washed with aqueous LiCl (4%), 0.1 M HCl and saturated aqueous NaHCO$_3$. The crude product was obtained by evaporation of the solvent. An aliquot (70 mg) was purified by preparative HPLC (C18 reverse phase column, elution with a water/MeCN gradient with 0.1% TFA) to give the title compound. Yield: 31 mg MS (ES+): m/e=772.

Example 196

4-[(S)-6-Benzyloxy-2-({5-[2-((S)-2-cyclobutylcarbamoyl-pyrrolidin-1-yl)-2-oxo-ethoxy]-1-phenyl-1H-pyrazole-3-carbonyl}-amino)-hexanoyl]-piperazine-1-carboxylic acid butyl ester i) (S)-4-[6-Benzyloxy-2-(9H-fluoren-9-ylmethoxycarbonylamino)-hexanoyl]-piperazine-1-carboxylic acid butyl ester To a solution of 500 mg (S)-6-Benzyloxy-2-(9H-fluoren-9-ylmethoxycarbonylamino)-hexanoic acid in 7 ml DMF were added at 0° C. 172 mg piperazine-1-carboxylic acid butyl ester hydrotrifluoroacetate, 0.14 ml N-ethylmorpholine and 357 mg TOTU. After stirring for 3 h the solution was diluted with ethyl acetate and subsequently washed with aqueous LiCl (4%) and half-saturated aqueous NaHCO$_3$. The crude product obtained after evaporation of the solvent was used without further purification. Yield: 650 mg.

ii) (S)-4-(2-Amino-6-benzyloxy-hexanoyl)-piperazine-1-carboxylic acid butyl ester To a solution of 650 mg (S)-4-[6-Benzyloxy-2-(9H-fluoren-9-ylmethoxycarbonylamino)-hexanoyl]-piperazine-1-carboxylic acid butyl ester in 3.6 ml DMF were added at room temperature 0.91 ml morpholine. After stirring for 2 h the reaction mixture was evaporated and the crude product thus obtained used in the next step without further purification.

iii) 4-[(S)-6-Benzyloxy-2-({5-[2-((S)-2-cyclobutylcarbamoyl-pyrrolidin-1-yl)-2-oxo-ethoxy]-1-phenyl-1H-pyrazole-3-carbonyl}-amino)-hexanoyl]-piperazine-1-carboxylic acid butyl ester To a solution of 427 mg 5-[2-((S)-2-Cyclobutylcarbamoyl-pyrrolidin-1-yl)-2-oxo-ethoxy]-1-phenyl-1H-pyrazole-3-carboxylic acid in 10 ml DMF were added 206 mg HOBt, 258 mg EDC and 0.43 ml DIPEA. After 5 minutes 420 mg (S)-4-(2-Amino-6-benzyloxy-hexanoyl)-piperazine-1-carboxylic acid butyl ester were added and the mixture stirred for 12 h. The reaction mixture was concentrated, diluted with ethyl acetate and washed with aqueous LiCl (4%), 0.1 M HCl and saturated aqueous NaHCO$_3$. The crude product was obtained by evaporation of the solvent. An aliquot (70 mg) was purified by preparative HPLC (C18 reverse phase column, elution with a water/MeCN gradient with 0.1% TFA) to give the title compound. Yield: 37 mg MS (ES+): m/e=800.

Example 197

4-[(S)-6-Benzyloxy-2-({5-[2-((S)-2-cyclobutylcarbamoyl-pyrrolidin-1-yl)-2-oxo-ethoxy]-1-phenyl-1H-pyrazole-3-carbonyl}-amino)-hexanoyl]-piperazine-1-carboxylic acid cyclobutyl ester i) (S)-4-[6-Benzyloxy-2-(9H-fluoren-9-ylmethoxycarbonylamino)-hexanoyl]-piperazine-1-carboxylic acid cyclobutyl ester To a solution of 500 mg (S)-6-Benzyloxy-2-(9H-fluoren-9-ylmethoxycarbonylamino)-hexanoic acid in 7 ml DMF were added at 0° C. 172 mg piperazine-1-carboxylic acid cyclobutyl ester, 0.14 ml N-ethylmorpholine and 357 mg TOTU. After stirring for 3 h the solution was diluted with ethyl acetate and subsequently washed with aqueous LiCl (4%) and half-saturated aqueous NaHCO$_3$. The crude product obtained after evaporation of the solvent was used without further purification. Yield: 726 mg.

ii) (S)-4-(2-Amino-6-benzyloxy-hexanoyl)-piperazine-1-carboxylic acid cyclobutyl ester To a solution of 726 mg (S)-4-[6-Benzyloxy-2-(9H-fluoren-9-ylmethoxycarbonylamino)-hexanoyl]-piperazine-1-carboxylic acid cyclobutyl ester in 4.0 ml DMF were added at room temperature 1.0 ml morpholine. After stirring for 2 h the reaction mixture was evaporated and the crude product thus obtained used in the next step without further purification.

iii) 4-[(S)-6-Benzyloxy-2-({5-[2-((S)-2-cyclobutyl-carbamoyl-pyrrolidin-1-yl)-2-oxo-ethoxy]-1-phenyl-1H-pyrazole-3-carbonyl}-amino)-hexanoyl]-piperazine-1-carboxylic acid cyclobutyl ester To a solution of 480 mg 5-[2-((S)-2-Cyclobutylcarbamoyl-pyrrolidin-1-yl)-2-oxo-ethoxy]-1-phenyl-1H-pyrazole-3-carboxylic acid in 10 ml DMF were added 232 mg HOBt, 290 mg EDC and 0.48 ml DIPEA. After 5 minutes 470 mg (S)-4-(2-Amino-6-benzyloxy-hexanoyl)-piperazine-1-carboxylic acid cyclobutyl ester were added and the mixture stirred for 12 h. The reaction mixture was concentrated, diluted with ethyl acetate and washed with aqueous LiCl (4%), 0.1 M HCl and saturated aqueous NaHCO$_3$. The crude product was obtained by evaporation of the solvent. An aliquot (80 mg) was purified by preparative HPLC (C18 reverse phase column, elution with a water/MeCN gradient with 0.1% TFA) to give the title compound. Yield: 40 mg MS (ES+): m/e=798.

Example 198

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-(2-ethoxy-ethoxycarbonyl)-butyryl]-piperazine-1-carboxylic acid ethyl ester The title compound was prepared by adapting the procedures described in example 127 with the difference that 2-ethoxyethanol was used instead of ethanol.
Yield: 55 mg MS (ES+): m/e=754.

Example 199

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-(tetrahydro-furan-2-ylmethoxy-carbonyl)-butyryl]-piperazine-1-carboxylic acid ethyl ester The title compound was prepared by adapting the procedures described in example 127 with the difference that tetrahydrofurfuryl alcohol was used instead of ethanol.
Yield: 60 mg MS (ES+): m/e=766.

Example 200

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-(3-methoxy-propoxycarbonyl)-butyryl]-piperazine-1-carboxylic acid ethyl ester The title compound was prepared by adapting the procedures described in example 127 with the difference that 3-methoxy1-propanol was used instead of ethanol.
Yield: 50 mg MS (ES+): m/e=754.

Example 201

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-(2-morpholin-4-yl-ethoxycarbonyl)-butyryl]-piperazine-1-carboxylic acid ethyl ester The title compound was prepared by adapting the procedures described in example 127 with the difference that N-(2-hydroxyethyl)morpholine was used instead of ethanol.
Yield: 67 mg MS (ES+): m/e=795.

Example 202

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-(tetrahydro-furan-3-ylmethoxy-carbonyl)-butyryl]piperazine-1-carboxylic acid ethyl ester The title compound was prepared by adapting the procedures described in example 127 with the difference that tetrahydro-3-furanmethanol was used instead of ethanol.
Yield: 70 mg MS (ES+): m/e=766.

Example 203

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-(3-methyl-oxetan-3-ylmethoxy-carbonyl)-butyryl]-piperazine-1-carboxylic acid ethyl ester The title compound was prepared by adapting the procedures described in example 127 with the difference that 3-methyl-3-oxetanemethanol was used instead of ethanol.
Yield: 60 mg MS (ES+): m/e=766.

Example 204

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-(3-ethyl-oxetan-3-ylmethoxy-carbonyl)-butyryl]-piperazine-1-carboxylic acid ethyl ester The title compound was prepared by adapting the procedures described in example 127 with the difference that 3-ethyl-3-oxetanemethanol was used instead of ethanol.
Yield: 65 mg MS (ES+): m/e=780.

Example 205

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-(3-methoxy-butoxycarbonyl)-butyryl]-piperazine-1-carboxylic acid ethyl ester The title compound was prepared by adapting the procedures described in example 127 with the difference that 3-methoxy-1-butanol was used instead of ethanol.
Yield: 61 mg MS (ES+): m/e=768.

Example 206

4-[(R)-2-({5-[2-((S)-2-Cyclobutylcarbamoyl-pyrrolidin-1-yl)-2-oxo-ethoxy]-1-phenyl-1H-pyrazole-3-carbonyl}-amino)-propionyl]-piperazine-1-carboxylic acid propyl ester The title compound was prepared by adapting the procedures described in example 194 with the difference that 1-propoxycarbonyl-piperazine was used instead of 1-cyclobutoxycarbonyl-piperazine. Yield: 35 mg MS (ES+): m/e=638.

Example 207

5-[2-((S)-2-Cyclobutylcarbamoyl-pyrrolidin-1-yl)-2-oxo-ethoxy]-1-phenyl-1H-pyrazole-3-carboxylic acid {(R)-2-[4-(3-methoxy-phenyl)-piperazin-1-yl]-1-methyl-2-oxo-ethyl}-amide The title compound was prepared by adapting the procedures described in example 194 with the difference that 1-(3-methoxyphenyl)piperazine was used instead of 1-cyclobutoxycarbonyl-piperazine. Yield: 35 mg MS (ES+): m/e=638.

Example 208

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-propionyl]-piperazine-1-carboxylic acid propyl ester The title compound was prepared by adapting the procedures described in example 193 with the difference that 1-propoxycarbonyl-piperazine was used instead of 1-cyclobutoxycarbonyl-piperazine. Yield: 18 mg MS (ES+): m/e=638.

Example 209

5-[2-((S)-2-Cyclobutylcarbamoyl-pyrrolidin-1-yl)-2-oxo-ethoxy]-1-phenyl-1H-pyrazole-3-carboxylic acid {(S)-2-[4-(3-methoxy-phenyl)-piperazin-1-yl]-1-methyl-2-oxo-ethyl}-amide The title compound was prepared by adapting the procedures described in example 193 with the difference that 1-(3-methoxyphenyl)piperazine was used instead of 1-cyclobutoxycarbonyl-piperazine. Yield: 35 mg MS (ES+): m/e=658.

Example 210

4-[2-({5-[2-((S)-2-Cyclobutylcarbamoyl-pyrrolidin-1-yl)-2-oxo-ethoxy]-1-phenyl-1H-pyrazole-3-carbonyl}-amino)-acetyl]-piperazine-1-carboxylic acid propyl ester The title compound was prepared by adapting the procedures described in example 192 with the difference that 1-propoxycarbonyl-piperazine was used instead of 1-cyclobutoxycarbonyl-piperazine. Yield: 39 mg MS (ES+): m/e=624.

Example 211

4-[(S)-5-Acetoxy-2-({5-[2-((S)-2-cyclobutylcarbamoyl-pyrrolidin-1-yl)-2-oxo-ethoxy]-1-phenyl-1H-pyrazole-3-carbonyl}-amino)-pentanoyl]-piperazine-1-carboxylic acid butyl ester To a solution of 65 mg 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-5-hydroxy-pentanoyl]-piperazine-1-carboxylic acid butyl ester in 4 ml dichloromethane were added 15 l pyridine, 10 l acetic anhydride and a catalytic amount of DMAP. After stirring for 24 h at room temperature the reaction mixture was concentrated and the crude product thus obtained was purified by preparative HPLC (C18 reverse phase column, elution with a water/MeCN gradient with 0.1% TFA) to give the title compound.
Yield: 74 mg MS (ES+): m/e=738.

Example 212

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-5-isobutyryloxy-pentanoyl]-piperazine-1-carboxylic acid butyl ester The title compound was prepared by adapting the procedures described in example 211 with the difference that isobutyryl chloride was used instead of acetic anhydride.
Yield: 73 mg MS (ES+): m/e=766.

Example 213

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-6-hydroxy-hexanoyl]-piperazine-1-carboxylic acid butyl ester To a solution of 819 mg 4-[(S)-6-Benzyloxy-2-({5-[2-((S)-2-cyclobutylcarbamoyl-pyrrolidin-1-yl)-2-oxo-ethoxy]-1-phenyl-1H-pyrazole-3-carbonyl}-amino)-hexanoyl]-piperazine-1-carboxylic acid butyl ester in 20 ml ethyl acetate were added under argon 100 mg Pd/C (10%) and the suspension was stirred under an atmosphere of hydrogen (3 bar) for 12 h. The suspension was filtered over a plug of Celite® and washed with ethyl acetate. The crude product obtained after evaporation of the solvent was purified by preparative HPLC (C18 reverse phase column, elution with a water/MeCN gradient with 0.1% TFA) to give a mixture of the title compound (8 mg) and unreacted benzyl ether which was subjected to the same hydrogenolysis conditions described above to give the title compound.
Yield: 308 mg MS (ES+): m/e=710.

Example 214

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-6-hydroxy-hexanoyl]-piperazine-1-carboxylic acid cyclobutyl ester The title compound was prepared by adapting the procedures described in example 213 with the difference that 4-[(S)-6-Benzyloxy-2-({5-[2-((S)-2-cyclobutylcarbamoyl-pyrrolidin-1-yl)-2-oxo-ethoxy]-1-phenyl-1H-pyrazole-3-carbonyl}-amino)-hexanoyl]-piperazine-1-carboxylic acid cyclobutyl ester was used instead of 4-[(S)-6-Benzyloxy-2-({5-[2-((S)-2-cyclobutylcarbamoyl-pyrrolidin-1-yl)-2-oxo-ethoxy]-1-phenyl-1H-pyrazole-3-carbonyl}-amino)-hexanoyl]-piperazine-1-carboxylic acid butyl ester.
Yield: 369 mg MS (ES+): m/e=708.

Example 215

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-methyl-pentanoyl]-piperazine-1-carboxylic acid ethyl ester i) (S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-methyl-pentanoic acid tert-butyl ester To a solution of 250 mg 5-[2-((S)-2-Cyclobutylcarbamoyl-pyrrolidin-1-yl)-2-oxo-ethoxy]-1-phenyl-1H-pyrazole-3- carboxylic acid in 4 ml DMF were added 124 mg HOAt, 174 mg EDC, 0.37 ml DIPEA and 136 mg leucine tert-butyl ester hydrochloride. After stirring for 12 h it was concentrated and the residue dissolved in dichloromethane. It was extracted with aqueous LiCl (4% w/w), aqueous NaHCO$_3$ and 0.1 M HCl. The organic layer was dried over MgSO$_4$ and concentrated to furnish the crude coupling product as colorless oil. Yield: 422 mg.

ii) (S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-methyl-pentanoic acid To a solution of 422 mg (S)-2-({5-[2-((S)-2-Cyclobutyl-carbamoyl-pyrrolidin-1-yl)-2-oxo-ethoxy]-1-phenyl-1H-pyrazole-3-carbonyl}-amino)-4-methyl-pentanoic acid tert-butyl ester in 5 ml dichloromethane were added 1.5 ml TFA. After stirring for 16 h it was concentrated and codistilled twice with toluene to give the crude product which was used directly in the subsequent coupling step.

iii) 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-methyl-pentanoyl]-piperazine-1-carboxylic acid ethyl ester To a mixture of 116 mg (S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-methyl-pentanoic acid in 2.5 ml DMF were added 84 mg HATU, 116 l DIPEA and 32 l 1-ethoxycarbonylpiperazine. After stirring for 12 h it was concentrated and the crude product thus obtained was purified by preparative HPLC (C18 reverse phase column, elution with a water/MeCN gradient with 0.1% TFA) to give the title compound. Yield: 70 mg MS (ES+): m/e=666.

Example 216

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-pentanoyl]-piperazine-1-carboxylic acid ethyl ester The title compound was prepared by adapting the procedures described in example 215 with the difference that norvaline tert-butyl ester hydrochloride was used instead of leucine tert-butyl ester hydrochloride. Yield: 74 mg MS (ES+): m/e=652.

Example 217

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-3-methyl-butyryl]-piperazine-1-carboxylic acid ethyl ester The title compound was prepared by adapting the procedures described in example 215 with the difference that valine tert-butyl ester hydrochloride was used instead of leucine tert-butyl ester hydrochloride. Yield: 90 mg MS (ES+): m/e=652.

Example 218

4-[(2S,3S)-2-({5-[2-((S)-2-Cyclobutylcarbamoyl-pyrrolidin-1-yl)-2-oxo-ethoxy]-1-phenyl-1H-pyrazole-3-carbonyl}-amino)-3-methyl-pentanoyl]-piperazine-1-carboxylic acid ethyl ester The title compound was prepared by adapting the procedures described in example 215 with the difference that iso-leucine tert-butyl ester hydrochloride was used instead of leucine tert-butyl ester hydrochloride. Yield: 72 mg MS (ES+): m/e=666.

Example 219

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-2-cyclohexyl-acetyl]-piperazine-1-carboxylic acid ethyl ester i) (S)-({5-[2-((S)-2-Cyclobutylcarbamoyl-pyrrolidin-1-yl)-2-oxo-ethoxy]-1-phenyl-1H-pyrazole-3-carbonyl}-amino)-cyclohexyl-acetic acid methyl ester To a solution of 250 mg 5-[2-((S)-2-Cyclobutylcarbamoyl-pyrrolidin-1-yl)-2-oxo-ethoxy]-1-phenyl-1H-pyrazole-3-carboxylic acid in 4 ml DMF were added 124 mg HOAt, 174 mg EDC, 0.37 ml DIPEA and 126 mg amino cyclohexylacetic acid methyl ester hydrochloride. After stirring for 12 h it was concentrated and the residue dissolved in dichloromethane. It was extracted with aqueous LiCl (4% w/w), aqueous NaHCO$_3$ and 0.1 M HCl. The organic layer was dried over MgSO$_4$ and concentrated to furnish the crude coupling product as colorless oil. Yield: 428 mg.

ii) (S)-({5-[2-((S)-2-Cyclobutylcarbamoyl-pyrrolidin-1-yl)-2-oxo-ethoxy]-1-phenyl-1H-pyrazole-3-carbonyl}-amino)-cyclohexyl-acetic acid To a solution of 428 mg (S)-({5-[2-((S)-2-Cyclobutylcarbamoyl-pyrrolidin-1-yl)-2-oxo-ethoxy]-1-phenyl-1H-pyrazole-3-carbonyl}-amino)-cyclohexyl-acetic acid methyl ester in 20 ml THF and 5 ml water were added 30 mg lithium hydroxide at 0° C. After stirring for 4 h it was acidified with 1 N HCl and concentrated in vacuo to give the crude product as colorless oil. Yield: 380 mg.

iii) 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-2-cyclohexyl-acetyl]-piperazine-1-carboxylic acid ethyl ester To a mixture of 122 mg (S)-({5-[2-((S)-2-Cyclobutylcarbamoyl-pyrrolidin-1-yl)-2-oxo-ethoxy]-1-phenyl-1H-pyrazole-3-carbonyl}-amino)-cyclohexyl-acetic acid in 2.5 ml DMF were added 84 mg HATU, 116 l DIPEA and 32 l 1-ethoxycarbonylpiperazine. After stirring for 12 h it was concentrated and the crude product thus obtained was purified by preparative HPLC (C18 reverse phase column, elution with a water/MeCN gradient with 0.1% TFA) to give the title compound. Yield: 60 mg MS (ES+): m/e=692.

Example 220

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-3-cyclohexyl-propionyl]-piperazine-1-carboxylic acid ethyl ester The title compound was prepared by adapting the procedures described in example 219 with the difference that cyclohexylalanine methyl ester hydrochloride was used instead of amino cyclohexylacetic acid methyl ester hydrochloride.
Yield: 52 mg MS (ES+): m/e=706.

Example 221

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-pentanoyl]-piperazine-1-carboxylic acid butyl ester The title compound was prepared by adapting the procedures described in example 216 with the difference that 1-butoxycarbonylpiperazine was used instead of 1-ethoycarbonylpiperazine. Yield: 80 mg MS (ES+): m/e=680.

Example 222

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-3-methyl-butyryl]-piperazine-1-carboxylic acid butyl ester The title compound was prepared by adapting the procedures described in example 217 with the difference that 1-butoxycarbonylpiperazine was used instead of 1-ethoycarbonylpiperazine. Yield: 85 mg MS (ES+): m/e=680.

Example 223

4-[(2S,3S)-2-({5-[2-((S)-2-Cyclobutylcarbamoyl-pyrrolidin-1-yl)-2-oxo-ethoxy]-1-phenyl-1H-pyrazole-3-carbonyl}-amino)-3-methyl-pentanoyl]-piperazine-1-carboxylic acid butyl ester The title compound was prepared by adapting the procedures described in example 218 with the difference that 1-butoxycarbonylpiperazine was used instead of 1-ethoycarbonylpiperazine. Yield: 72 mg MS (ES+): m/e=694.

Example 224

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-2-cyclohexyl-acetyl]-piperazine-1-carboxylic acid butyl ester The title compound was prepared by adapting the procedures described in example 219 with the difference that 1-butoxycarbonylpiperazine was used instead of 1-ethoycarbonylpiperazine. Yield: 60 mg MS (ES+): m/e=720.

Example 225

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-3-cyclohexyl-propionyl]-piperazine-1-carboxylic acid butyl ester The title compound was prepared by adapting the procedures described in example 220 with the difference that 1-butoxycarbonylpiperazine was used instead of 1-ethoycarbonylpiperazine. Yield: 25 mg MS (ES+): m/e=734.

Example 226

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-methyl-pentanoyl]-piperazine-1-carboxylic acid butyl ester The title compound was prepared by adapting the procedures described in example 215 with the difference that 1-butoxycarbonylpiperazine was used instead of 1-ethoycarbonylpiperazine. Yield: 73 mg MS (ES+): m/e=694.

Example 227

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-3-ethoxy-propionyl]-piperazine-1-carboxylic acid butyl ester i) 4-((S)-2-Amino-3-ethoxy-propionyl)-piperazine-1-carboxylic acid butyl ester To a solution of 146 mg (S)-N-Boc-2-amino-3-ethoxypropionic acid in 2 ml DMF were added 0.34 ml N-ethylmorpholine, 200 mg 1-butoxycarbonylpiperazine hydrotrifluoroacetate and 219 mg TOTU. After stirring for 12 h it was added saturated aqueous NaHCO$_3$ and the mixture was loaded on a Chem Elut® cartridge, the crude product being eluted with ethyl acetate. The solution was concentrated, the residue obtained dissolved in 5 ml dichloromethane and stirred in the presence of 1 ml TFA. After 12 h stirring it was concentrated and the residue codistilled twice with toluene.

ii) 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-3-ethoxy-propionyl]-piperazine-1-carboxylic acid butyl ester To a solution of 75 mg 5-[2-((S)-2-Cyclobutylcarbamoyl-pyrrolidin-1-yl)-2-oxo-ethoxy]-1-phenyl-1H-pyrazole-3-carboxylic acid in 5 ml DMF were added 37 mg HOAt, 53 mg EDC, 0.13 ml DIPEA and 55 mg 4-((S)-2-Amino-3-ethoxy-propionyl)-piperazine-1-carboxylic acid butyl ester. After stirring for 12 h it was concentrated and the residue purified by preparative HPLC (C18 reverse phase column, elution with a water/MeCN gradient with 0.1% TFA) to give the title compound. Yield: 86 mg MS (ES+): m/e=696.

Example 228

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-3-hydroxy-3-methyl-butyryl]-piperazine-1-carboxylic acid butyl ester The title compound was prepared by adapting the procedures described in example 227 with the difference that Boc-(S)-2-amino-3-hydroxy-3-methylbutanoic acid was used instead of (S)-N-Boc-2-amino-3-ethoxypropionic acid.
Yield: 52 mg MS (ES+): m/e=696.

Example 229

4-[(2S,3R)-2-({5-[2-((S)-2-Cyclobutylcarbamoyl-pyrrolidin-1-yl)-2-oxo-ethoxy]-1-phenyl-1H-pyrazole-3-carbonyl}-amino)-3-methyl-pentanoyl]-piperazine-1-carboxylic acid butyl ester The title compound was prepared by adapting the procedures described in example 227 with the difference that Bocallo-isoleucine was used instead of (S)-N-Boc-2-amino-3-ethoxypropionic acid. Yield: 15 mg MS (ES+): m/e=694.

Example 230

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-2-cyclopropyl-acetyl]-piperazine-1-carboxylic acid butyl ester The title compound was prepared by adapting the procedures described in example 227 with the difference that Boc-cyclopropylglycine was used instead of (S)-N-Boc-2-amino-3-ethoxypropionic acid. Yield: 81 mg MS (ES+): m/e=678.

Example 231

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-methoxy-butyryl]-piperazine-1-carboxylic acid butyl ester The title compound was prepared by adapting the procedures described in example 227 with the difference that (S)-2-tert-Butoxycarbonylamino-4-methoxy-butyric acid was used instead of (S)-N-Boc-2-amino-3-ethoxypropionic acid. Yield: 63 mg MS (ES+): m/e=696.

Example 232

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-3-methoxy-propionyl]-piperazine-1-carboxylic acid butyl ester The title compound was prepared by adapting the procedures described in example 227 with the difference that (S)-2-tert-Butoxycarbonylamino-4-methoxy-propionic acid was used instead of (S)-N-Boc-2-amino-3-ethoxypropionic acid. Yield: 50 mg MS (ES+): m/e=682.

Example 233

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-butyryl]-piperazine-1-carboxylic acid butyl ester The title compound was prepared by adapting the procedures described in example 227 with the difference that (S)-2-tert-Butoxycarbonylamino-butyric acid was used instead of (S)-N-Boc-2-amino-3-ethoxypropionic acid. Yield: 70 mg MS (ES+): m/e=666.

Example 234

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-3-cyclopropyl-propionyl]-piperazine-1-carboxylic acid butyl ester The title compound was prepared by adapting the procedures described in example 227 with the difference that (S)-2-tert-Butoxycarbonylamino-3-cyclopropyl-propionic acid was used instead of (S)-N-Boc-2-amino-3-ethoxypropionic acid. Yield: 62 mg MS (ES+): m/e=692.

Example 235

4-[(S)-3-Cyclobutyl-2-({5-[2-((S)-2-cyclobutylcarbamoyl-pyrrolidin-1-yl)-2-oxo-ethoxy]-1-phenyl-1H-pyrazole-3-carbonyl}-amino)-propionyl]-piperazine-1-carboxylic acid butyl ester The title compound was prepared by adapting the procedures described in example 227 with the difference that (S)-2-tert-Butoxycarbonylamino-3-cyclobutyl-propionic acid was used instead of (S)-N-Boc-2-amino-3-ethoxypropionic acid. Yield: 70 mg MS (ES+): m/e=706.

Example 236

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-6-hydroxy-hexanoyl]-piperazine-1-carboxylic acid ethyl ester The title compound was prepared by adapting the procedures described in example 213 with the difference that 4-[(S)-6-Benzyloxy-2-({5-[2-((S)-2-cyclobutylcarbamoyl-pyrrolidin-1-yl)-2-oxo-ethoxy]-1-phenyl-1H-pyrazole-3-carbonyl}-amino)-hexanoyl]-piperazine-1-carboxylic acid ethyl ester was used instead of 4-[(S)-6-Benzyloxy-2-({5-[2-((S)-2-cyclobutylcarbamoyl-pyrrolidin-1-yl)-2-oxo-ethoxy]-1-phenyl-1H-pyrazole-3-carbonyl}-amino)-hexanoyl]-piperazine-1-carboxylic acid butyl ester. Yield: 332 mg MS (ES+): m/e=682.

Example 237

4-[(S)-6-Acetoxy-2-({5-[2-((S)-2-cyclobutylcarbamoyl-pyrrolidin-1-yl)-2-oxo-ethoxy]-1-phenyl-1H-pyrazole-3-carbonyl}-amino)-hexanoyl]-piperazine-1-carboxylic acid ethyl ester The title compound was prepared by adapting the procedures described in example 211 with the difference that 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-6-hydroxy-hexanoyl]-piperazine-1-carboxylic acid ethyl ester was used instead of 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-5-hydroxy-pentanoyl]-piperazine-1-carboxylic acid butyl ester. Yield: 57 mg MS (ES+): m/e=724.

Example 238

4-[(S)-6-Acetoxy-2-({5-[2-((S)-2-cyclobutylcarbamoyl-pyrrolidin-1-yl)-2-oxo-ethoxy]-1-phenyl-1H-pyrazole-3-carbonyl}-amino)-hexanoyl]-piperazine-1-carboxylic acid butyl ester The title compound was prepared by adapting the procedures described in example 211 with the difference that 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-6-hydroxy-hexanoyl]-piperazine-1-carboxylic acid butyl ester was used instead of 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-5-hydroxy-pentanoyl]-piperazine-1-carboxylic acid butyl ester.
Yield: 52 mg MS (ES+): m/e=752.

Example 239

4-[(S)-6-Acetoxy-2-({5-[2-((S)-2-cyclobutylcarbamoyl-pyrrolidin-1-yl)-2-oxo-ethoxy]-1-phenyl-1H-pyrazole-3-carbonyl}-amino)-hexanoyl]-piperazine-1-carboxylic acid cyclobutyl ester The title compound was prepared by adapting the procedures described in example 211 with the difference that 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-6-hydroxy-hexanoyl]-piperazine-1-carboxylic acid cyclobutyl ester was used instead of 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-5-hydroxy-pentanoyl]-piperazine-1-carboxylic acid butyl ester.
Yield: 50 mg MS (ES+): m/e=750.

Example 240

4-{(S)-2-[(5-{2-[(S)-2-(Cyclobutyl-methyl-carbamoyl)-pyrrolidin-1-yl]-2-oxo-ethoxy}-1-phenyl-1H-pyrazole-3-carbonyl)-amino]-6-hydroxy-hexanoyl}-piperazine-1-carboxylic acid cyclobutyl ester To a solution of 65 mg 4-{(S)-2-[(5-{2-[(S)-2-(Cyclobutylcarbamoyl)-pyrrolidin-1-yl]-2-oxo-ethoxy}-1-phenyl-1H-pyrazole-3-carbonyl)-amino]-6-hydroxy-hexanoyl}-piperazine-1-carboxylic acid cyclobutyl ester in 5 ml THF were added at −20° C. 6 l iodomethane and 5 mg sodium hydride (95%). After 2 h and 12 h equivalent amounts of iodomethane and sodium hydride were added before the reaction mixture was quenched with 0.1 M HCl and extracted with dichloromethane. The crude product obtained after evaporation of the solvent was purified by preparative HPLC (C18 reverse phase column, elution with a water/MeCN gradient with 0.1% TFA) to give the title compound as a mixture with its trifluoroacetyl ester. Repeated lyophilization from MeCN/water yielded the pure title compound. Yield: 17 mg MS (ES+): m/e=722.

Example 241

5-[2-((S)-2-Cyclobutylcarbamoyl-pyrrolidin-1-yl)-2-oxo-ethoxy]-1-phenyl-1H-pyrazole-3-carboxylic acid [2-oxo-2-(4-pentanoyl-piperazin-1-yl)-ethyl]amide i) 4-[2-({5-[2-((S)-2-Cyclobutylcarbamoyl-pyrrolidin-1-yl)-2-oxo-ethoxy]-1-phenyl-1H-pyrazole-3-carbonyl}-amino)-acetyl]-piperazine-1-carboxylic acid benzyl ester To a solution of 3.34 g ({5-[2-((S)-2-Cyclobutylcarbamoyl-pyrrolidin-1-yl)-2-oxo-ethoxy]-1-phenyl-1H-pyrazole-3-carbonyl}-amino)-acetic acid in 100 ml DMF were added 1.9 ml DIPEA, 2.7 g HATU and 1.4 ml 1-benzyloxycarbonylpiperazine. After stirring for 1 h it was diluted with ethyl acetate and extracted with aqueous LiCl (4% w/w), aqueous NaHCO₃ and 0.1 M HCl. The crude product obtained after evaporation of the solvent was purified by flash chromatography on silica using an ethyl acetate/methanol gradient.
Yield: 2.5 g colorless oil ii) 5-[2-((S)-2-Cyclobutylcarbamoyl-pyrrolidin-1-yl)-2-oxo-ethoxy]-1-phenyl-1H-pyrazole-3-carboxylic acid (2-oxo-2-piperazin-1-yl-ethyl)-amide A suspension of 2.5 g 4-[2-({5-[2-((S)-2-Cyclobutylcarbamoyl-pyrrolidin-1-yl)-2-oxo-ethoxy]-1-phenyl-1H-pyrazole-3-carbonyl}-amino)-acetyl]-piperazine-1-carboxylic acid benzyl ester and 0.5 g Pd/C (10%) in 100 ml ethanol was stirred under an atmosphere of hydrogen (3 bar) for 12 h. The mixture was filtrated over a plug of Celite, washed with ethanol and the combined wash solutions concentrated to give the title compound as colourless oil. Yield: 2.3 g.

iii) 5-[2-((S)-2-Cyclobutylcarbamoyl-pyrrolidin-1-yl)-2-oxo-ethoxy]-1-phenyl-1H-pyrazole-3-carboxylic acid [2-oxo-2-(4-pentanoyl-piperazin-1-yl)-ethyl]amide To a solution of 50 mg 5-[2-((S)-2-Cyclobutylcarbamoyl-pyrrolidin-1-yl)-2-oxo-ethoxy]-1-phenyl-1H-pyrazole-3-carboxylic acid (2-oxo-2-piperazin-1-yl-ethyl)-amide in 4 ml dichloromethane were added at 0° C. 15 l pyridine, 13 l valeryl chloride and a catalytic amount of DMAP. After stirring for 12 h it was concentrated and the residue obtained was purified by preparative HPLC (C18 reverse phase column, elution with a water/MeCN gradient with 0.1% TFA) to give the title compound.
Yield: 31 mg MS (ES+): m/e=622.

Example 242

5-[2-((S)-2-Cyclobutylcarbamoyl-pyrrolidin-1-yl)-2-oxo-ethoxy]-1-phenyl-1H-pyrazole-3-carboxylic acid {2-oxo-2-[4-(3,3,3-trifluoro-propionyl)-piperazin-1-yl]-ethyl}-amide The title compound was prepared by adapting the procedures described in example 241 with the difference that 3,3,3-trifluoropropionyl chloride was used instead of valeryl chloride. Yield: 26 mg MS (ES+): m/e=648.

Example 243

5-[2-((S)-2-Cyclobutylcarbamoyl-pyrrolidin-1-yl)-2-oxo-ethoxy]-1-phenyl-1H-pyrazole-3-carboxylic acid [2-(4-cyclopropanecarbonyl-piperazin-1-yl)-2-oxo-ethyl]-amide The title compound was prepared by adapting the procedures described in example 241 with the difference that cyclopropanecarbonyl chloride was used instead of valeryl chloride. Yield: 26 mg MS (ES+): m/e=606.

Example 244

5-[2-((S)-2-Cyclobutylcarbamoyl-pyrrolidin-1-yl)-2-oxo-ethoxy]-1-phenyl-1H-pyrazole-3-carboxylic acid [2-(4-cyclobutanecarbonyl-piperazin-1-yl)-2-oxo-ethyl]-amide The title compound was prepared by adapting the procedures described in example 241 with the difference that cyclobutanecarbonyl chloride was used instead of valeryl chloride. Yield: 32 mg MS (ES+): m/e=620.

Example 245

5-[2-((S)-2-Cyclobutylcarbamoyl-pyrrolidin-1-yl)-2-oxo-ethoxy]-1-phenyl-1H-pyrazole-3-carboxylic acid {2-[4-((1R,2S)-2-fluoro-cyclopropanecarbonyl)-piperazin-1-yl]-2-oxo-ethyl}-amide The title compound was prepared by adapting the procedures described in example 241 with the difference that (1R, 2S)-2-Fluoro-cyclopropanecarbonyl chloride was used instead of valeryl chloride. Yield: 32 mg MS (ES+): m/e=624.

Example 246

5-[2-((S)-2-Cyclobutylcarbamoyl-pyrrolidin-1-yl)-2-oxo-ethoxy]-1-phenyl-1H-pyrazole-3-carboxylic acid {2-oxo-2-[4-((1R,2R)-2-phenyl-cyclopropanecarbonyl)-piperazin-1-yl]-ethyl}-amide The title compound was prepared by adapting the procedures described in example 241 with the difference that (1R, 2R)-2-phenyl-cyclopropanecarbonyl chloride was used instead of valeryl chloride. Yield: 35 mg MS (ES+): m/e=682.

Example 247

{1-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-methyl-pentanoyl]-piperidin-4-yl}-carbamic acid butyl ester The title compound was prepared by adapting the procedures described in example 215 with the difference that piperidin-4-yl-carbamic acid butyl ester was used instead of 1-ethoycarbonylpiperazine. Yield: 21 mg MS (ES+): m/e=708.

Example 248

{1-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-pentanoyl]-piperidin-4-yl}-carbamic acid butyl ester The title compound was prepared by adapting the procedures described in example 216 with the difference that piperidin-4-yl-carbamic acid butyl ester was used instead of 1-ethoycarbonylpiperazine. Yield: 24 mg MS (ES+): m/e=694.

Example 249

{1-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-3-methyl-butyryl]-piperidin-4-yl}-carbamic acid butyl ester The title compound was prepared by adapting the procedures described in example 217 with the difference that piperidin-4-yl-carbamic acid butyl ester was used instead of 1-ethoycarbonylpiperazine. Yield: 22 mg MS (ES+): m/e=694.

Example 250

{1-[(2S,3S)-2-({5-[2-((S)-2-Cyclobutylcarbamoyl-pyrrolidin-1-yl)-2-oxo-ethoxy]-1-phenyl-1H-pyrazole-3-carbonyl}-amino)-3-methyl-pentanoyl]-piperidin-4-yl}-carbamic acid butyl ester The title compound was prepared by adapting the procedures described in example 218 with the difference that piperidin-4-yl-carbamic acid butyl ester was used instead of 1-ethoycarbonylpiperazine. Yield: 26 mg MS (ES+): m/e=708.

Example 251

{1-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-2-cyclohexyl-acetyl]-piperidin-4-yl}-carbamic acid butyl ester The title compound was prepared by adapting the procedures described in example 219 with the difference that piperidin-4-yl-carbamic acid butyl ester was used instead of 1-ethoycarbonylpiperazine. Yield: 17 mg MS (ES+): m/e=734.

Example 252

{1-[2-({5-[2-((S)-2-Cyclobutylcarbamoyl-pyrrolidin-1-yl)-2-oxo-ethoxy]-1-phenyl-1H-pyrazole-3-carbonyl}-amino)-acetyl]-piperidin-4-yl}-carbamic acid butyl ester i) [1-(2-Benzyloxycarbonylamino-acetyl)-piperidin-4-yl]carbamic acid butyl ester To a solution of 150 mg Z-Gly-OH in 5 ml DMF were added 0.4 ml N-ethylmorpholine, 144 mg piperidin-4-yl-carbamic acid butyl ester and 236 mg TOTU. After stirring for 12 h it was diluted with ethyl acetate and subsequently washed with aqueous LiCl (4%), saturated NaHCO$_3$ and 0.1 M HCl. The crude product thus obtained after evaporation of the solvent was directly used in the next step. Yield: 287 mg.

ii) [1-(2-Amino-acetyl)-piperidin-4-yl]carbamic acid butyl ester

A suspension of 287 mg [1-(2-Benzyloxycarbonylamino-acetyl)-piperidin-4-yl]-carbamic acid butyl ester and 0.1 g Pd/C (10%) in 25 ml ethanol was stirred under an atmosphere of hydrogen (3 bar) for 12 h. The mixture was filtrated over a plug of Celite, washed with ethanol and the combined wash solutions concentrated to give the title compound as colourless oil. Yield: 156 mg.

iii) {1-[2-({5-[2-((S)-2-Cyclobutylcarbamoyl-pyrrolidin-1-yl)-2-oxo-ethoxy]-1-phenyl-1H-pyrazole-3-carbonyl}-amino)-acetyl]-piperidin-4-yl}-carbamic acid butyl ester To solution of 250 mg 5-[2-((S)-2-Cyclobutylcarbamoyl-pyrrolidin-1-yl)-2-oxo-ethoxy]-1-phenyl-1H-pyrazole-3-carboxylic acid in 4 ml DMF were added 231 mg HATU, 0.10 ml DIPEA and 156 mg [1-(2-Amino-acetyl)-piperidin-4-yl]-carbamic acid butyl ester. After stirring for 12 h it was concentrated and the residue dissolved in dichloromethane. It was extracted with aqueous LiCl (4% w/w), aqueous NaHCO$_3$ and 0.1 M HCl. The organic layer was dried over MgSO$_4$ and concentrated to furnish the crude coupling product which was further purified by preparative HPLC (C18 reverse phase column, elution with a water/MeCN gradient with 0.1% TFA) to give the title compound.
Yield: 176 mg MS (ES+): m/e=652.

Example 253

{1-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-3-cyclohexyl-propionyl]-piperidin-4-yl}-carbamic acid butyl ester The title compound was prepared by adapting the procedures described in example 220 with the difference that piperidin-4-yl-carbamic acid butyl ester was used instead of 1-ethoycarbonylpiperazine. Yield: 22 mg MS (ES+): m/e=748.

Example 254

4-[2-({5-[2-((S)-2-Cyclobutylcarbamoyl-pyrrolidin-1-yl)-2-oxo-ethoxy]-1-phenyl-1H-pyrazole-3-carbonyl}-amino)-acetyl]-piperazine-1-carboxylic acid 2-methoxy-ethyl ester To a solution of 100 mg 5-[2-((S)-2-Cyclobutylcarbamoyl-pyrrolidin-1-yl)-2-oxo-ethoxy]-1-phenyl-1H-pyrazole-3-carboxylic acid (2-oxo-2-piperazin-1-yl-ethyl)-amide in 5 ml dichloromethane were added at 0° C. 56 l triethylamine and 24 l chloroformic acid 2-methoxyethyl ester. After stirring for 12 h it was concentrated and the residue obtained was purified by preparative HPLC (C18 reverse phase column, elution with a water/MeCN gradient with 0.1% TFA) to give the title compound.
Yield: 25 mg MS (ES+): m/e=672.

Example 255

4-[2-({5-[2-((S)-2-Cyclobutylcarbamoyl-pyrrolidin-1-yl)-2-oxo-ethoxy]-1-phenyl-1H-pyrazole-3-carbonyl}-amino)-acetyl]-piperazine-1-carboxylic acid butylamide To a solution of 100 mg 5-[2-((S)-2-Cyclobutylcarbamoyl-pyrrolidin-1-yl)-2-oxo-ethoxy]-1-phenyl-1H-pyrazole-3-carboxylic acid (2-oxo-2-piperazin-1-yl-ethyl)-amide in 5 ml dichloromethane were added at 0° C. 56 l DIPEA and 25 l butyl isocyanate. After stirring for 12 h it was concentrated and the residue obtained was purified by preparative HPLC (C18 reverse phase column, elution with a water/MeCN gradient with 0.1% TFA) to give the title compound. Yield: 55 mg MS (ES+): m/e=637.

Example 256

4-[2-({5-[2-((S)-2-Cyclobutylcarbamoyl-pyrrolidin-1-yl)-2-oxo-ethoxy]-1-phenyl-1H-pyrazole-3-carbonyl}-amino)-acetyl]-piperazine-1-carboxylic acid 3,3,3-trifluoro-propyl ester To a solution of 22 mg triphosgene and 31 l 3,3,3-trifluoropropan-1-ol in 3 ml dichloromethane were added 37 l DIPEA dropwise at 0° C. After 2 h a solution of 93 mg 5-[2-((S)-2-Cyclobutylcarbamoyl-pyrrolidin-1-yl)-2-oxo-ethoxy]-1-phenyl-1H-pyrazole-3-carboxylic acid (2-oxo-2-piperazin-1-yl-ethyl)-amide and 37 l DIPEA in 1 ml dichloromethane were added at 0° C. The reaction mixture was allowed to warm to RT overnight. Excess triphosgene was destroyed by adding a solution of 140 mg NaOH in 5 ml water and stirring for 2 h. The layers were separated, the organic layer washed with 1 M HCl and dried over MgSO$_4$ and concentrated. The crude product was purified by preparative HPLC (C18 reverse phase column, elution with a water/MeCN gradient with 0.1% TFA) to give the title compound.
Yield: 25 mg MS (ES+): m/e=678.

Example 257

4-[2-({5-[2-((S)-2-Cyclobutylcarbamoyl-pyrrolidin-1-yl)-2-oxo-ethoxy]-1-phenyl-1H-pyrazole-3-carbonyl}-amino)-acetyl]-piperazine-1-carboxylic acid 2-ethoxy-ethyl ester The title compound was prepared by adapting the procedures described in example 256 with the difference that 2-ethoxyethanol was used instead of 3,3,3-trifluoropropan-1-ol.
Yield: 13 mg MS (ES+): m/e=654.

Example 258

4-[2-({5-[2-((S)-2-Cyclobutylcarbamoyl-pyrrolidin-1-yl)-2-oxo-ethoxy]-1-phenyl-1H-pyrazole-3-carbonyl}-amino)-acetyl]-piperazine-1-carboxylic acid (2-ethoxy-ethyl)-amide The title compound was prepared by adapting the procedures described in example 256 with the difference that 2-ethoxyethylamine was used instead of 3,3,3-trifluoropropan-1-ol. Yield: 47 mg MS (ES+): m/e=653.

Example 259

4-[2-({5-[2-((S)-2-Cyclobutylcarbamoyl-pyrrolidin-1-yl)-2-oxo-ethoxy]-1-phenyl-1H-pyrazole-3-carbonyl}-amino)-acetyl]-piperazine-1-carboxylic acid butyl-methyl-amide The title compound was prepared by adapting the procedures described in example 256 with the difference that N-methyl-butylamine was used instead of 3,3,3-trifluoropropan-1-ol. Yield: 12 mg MS (ES+): m/e=651.

Example 260

4-[2-({5-[2-((S)-2-Cyclobutylcarbamoyl-pyrrolidin-1-yl)-2-oxo-ethoxy]-1-phenyl-1H-pyrazole-3-carbonyl}-amino)-acetyl]-piperazine-1-carboxylic acid (2-methoxy-ethyl)-amide The title compound was prepared by adapting the procedures described in example 256 with the difference that 2-methoxyethylamine was used instead of 3,3,3-trifluoropropan-1-ol. Yield: 50 mg MS (ES+): m/e=639.

Example 261

4-[(R)-2-({5-[2-((S)-2-Cyclobutylcarbamoyl-pyrrolidin-1-yl)-2-oxo-ethoxy]-1-phenyl-1H-pyrazole-3-carbonyl}-amino)-3-fluoro-propionyl]-piperazine-1-carboxylic acid ethyl ester i) 4-((R)-2-Amino-3-fluoro-propionyl)-piperazine-1-carboxylic acid ethyl ester To a solution of 150 mg (R)-tert-butoxycarbonylamino-3-fluoropropionic acid in 2 ml DMF were added 115 mg 1-ethoxycarbonylpiperazine, 0.18 ml N-ethylmorpholine and 238 mg TOTU. After stirring for 12 h it was diluted with ethyl acetate and extracted with aqueous LiCl (4% w/w), aqueous NaHCO$_3$, 0.1 M HCl and brine. The organic layer was dried over MgSO$_4$ and concentrated to furnish the crude coupling product which was deprotected by using 10 equivalents TFA in dichloromethane. After stirring for 12 h it was concentrated and codistilled twice with toluene. Yield: 216 mg colorless oil.

ii) 4-[(R)-2-({5-[2-((S)-2-Cyclobutylcarbamoyl-pyrrolidin-1-yl)-2-oxo-ethoxy]-1-phenyl-1H-pyrazole-3-carbonyl}-amino)-3-fluoro-propionyl]-piperazine-1-carboxylic acid ethyl ester To a solution of 164 mg 5-[2-((S)-2-Cyclobutylcarbamoyl-pyrrolidin-1-yl)-2-oxo-ethoxy]-1-phenyl-1H-pyrazole-3-carboxylic acid in 2 ml DMF were added 152 mg HATU, 0.20 ml DIPEA and 144 mg 4-((R)-2-Amino-3-fluoro-propionyl)-piperazine-1-carboxylic acid ethyl ester. After stirring for 3 h saturated NaHCO$_3$ solution (1.5 ml) was added and the mixture passed through a Chem Elute® cartridge eluting with DCM. The crude product obtained after evaporation of the solvent was purified by preparative HPLC (C18 reverse phase column, elution with a water/MeCN gradient with 0.1% TFA) to give the title compound.
Yield: 93 mg MS (ES+): m/e=642.

Example 262

4-[(R)-2-({5-[2-((S)-2-Cyclobutylcarbamoyl-pyrrolidin-1-yl)-2-oxo-ethoxy]-1-phenyl-1H-pyrazole-3-carbonyl}-amino)-3-fluoro-propionyl]-piperazine-1-carboxylic acid butyl ester The title compound was prepared by adapting the procedures described in example 261 with the difference that 1-butoxycarbonylpiperazine was used instead of 1-ethoxycarbonylpiperazine. Yield: 118 mg MS (ES+): m/e=670.

Example 263

4-[2-({5-[2-((S)-2-Cyclobutylcarbamoyl-pyrrolidin-1-yl)-2-oxo-ethoxy]-1-phenyl-1H-pyrazole-3-carbonyl}-amino)-acetyl]-piperazine-1-carboxylic acid (2-methoxy-ethyl)-methyl-amide The title compound was prepared by adapting the procedures described in example 256 with the difference that N-(2-methoxyethyl)methylamine was used instead of 3,3,3-trifluoropropan-1-ol. Yield: 15 mg MS (ES+): m/e=653.

Example 264

4-[2-({5-[2-((S)-2-Cyclobutylcarbamoyl-pyrrolidin-1-yl)-2-oxo-ethoxy]-1-phenyl-1H-pyrazole-3-carbonyl}-amino)-acetyl]-piperazine-1-carboxylic acid benzyl-methyl-amide The title compound was prepared by adapting the procedures described in example 256 with the difference that N-benzylmethylamine was used instead of 3,3,3-trifluoropropan-1-ol. Yield: 40 mg MS (ES+): m/e=685.

Example 265

4-[2-({5-[2-((S)-2-Cyclobutylcarbamoyl-pyrrolidin-1-yl)-2-oxo-ethoxy]-1-phenyl-1H-pyrazole-3-carbonyl}-amino)-acetyl]-piperazine-1-carboxylic acid cyclopropylamide The title compound was prepared by adapting the procedures described in example 256 with the difference that cyclopropylamine was used instead of 3,3,3-trifluoropropan-1-ol.
Yield: 50 mg MS (ES+): m/e=621.

Example 266

4-[2-({5-[2-((S)-2-Cyclobutylcarbamoyl-pyrrolidin-1-yl)-2-oxo-ethoxy]-1-phenyl-1H-pyrazole-3-carbonyl}-amino)-acetyl]-piperazine-1-carboxylic acid cyclobutylamide The title compound was prepared by adapting the procedures described in example 256 with the difference that cyclobutylamine was used instead of 3,3,3-trifluoropropan-1-ol.
Yield: 50 mg MS (ES+): m/e=635.

Example 267

5-[2-((S)-2-Cyclobutylcarbamoyl-pyrrolidin-1-yl)-2-oxo-ethoxy]-1-phenyl-1H-pyrazole-3-carboxylic acid {2-oxo-2-[4-(pyrrolidine-1-carbonyl)-piperazin-1-yl]-ethyl}-amide The title compound was prepared by adapting the procedures described in example 256 with the difference that pyrrolidine was used instead of 3,3,3-trifluoropropan-1-ol.
Yield: 11 mg MS (ES+): m/e=635.

Example 268

4-[2-({5-[2-((S)-2-Cyclobutylcarbamoyl-pyrrolidin-1-yl)-2-oxo-ethoxy]-1-phenyl-1H-pyrazole-3-carbonyl}-amino)-acetyl]-piperazine-1-carboxylic acid cyclopentyl ester The title compound was prepared by adapting the procedures described in example 256 with the difference that cyclopentanol was used instead of 3,3,3-trifluoropropan-1-ol.
Yield: 11 mg MS (ES+): m/e=650.

Example 269

4-[2-({5-[(R)-2-((S)-2-Cyclobutylcarbamoyl-pyrrolidin-1-yl)-1-methyl-2-oxo-ethoxy]-1-phenyl-1H-pyrazole-3-carbonyl}-amino)-acetyl]-piperazine-1-carboxylic acid butyl ester i) (S)-2-Cyclobutylcarbamoyl-pyrrolidine-1-carboxylic acid benzyl ester To a solution of 5.00 g pyrrolidine-1,2-dicarboxylic acid 1-benzyl ester in 100 ml DMF were added 2.73 g HOAt, 3.85 g EDC, 6.9 ml DIPEA and 1.43 g cyclobutylamine. After 24 h the mixture was diluted with ethyl acetate and subsequently extracted with aqueous LiCl (4% w/w), 0.1 M HCl and saturated aqueous NaHCO$_3$. The organic layer was dried over MgSO₄ and the solvent was removed under reduced pressure to give the crude which was pure enough for the subsequent transformation. Yield: 9.00 g.

ii) (S)-Pyrrolidine-2-carboxylic acid cyclobutylamide

To a solution of 9.00 g (S)-2-Cyclobutylcarbamoyl-pyrrolidine-1-carboxylic acid benzyl ester in 120 ml ethanol were added 1.0 g Pd/C (10%) and the suspension stirred under an atmosphere of hydrogen (3 bar) for 12 h. The reaction mixture was filtrated over a plug of Celite, washed with ethanol and concentrated to give the crude product which was used in the subsequent reaction. Yield: 3.3 g.

iii) 4-(2-Benzyloxycarbonylamino-acetyl)-piperazine-1-carboxylic acid butyl ester To a solution of 5.62 g Z-Gly-OH (Benzyloxycarbonylamino-acetic acid) in 100 ml DMF were added 13.7 ml N-ethylmorpholine, 8.8 g TOTU and 5.0 g piperazine-1-carboxylic acid butyl ester. After stirring for 12 h, aqueous NaHCO₃ was added and the reaction mixture was diluted with ethyl acetate and washed with aqueous LiCl (4%) and 0.1 M HCl. The crude product obtained after evaporation of the solvent was purified by flash chromatography on silica using an ethyl acetate/heptane gradient. Yield: 6.34 g iv) 4-(2-Amino-acetyl)-piperazine-1-carboxylic acid butyl ester

To a solution of 6.34 g 4-(2-Benzyloxycarbonylamino-acetyl)-piperazine-1-carboxylic acid butyl ester in 120 ml ethanol were added 200 mg Pd/C (10%) and the suspension stirred under an atmosphere of hydrogen (3 bar) for 12 h. The reaction mixture was filtrated over a plug of Celite®, washed with ethanol and concentrated.
Yield: 4.47 g colorless solid.

v) 4-{2-[(5-Hydroxy-1-phenyl-1H-pyrazole-3-carbonyl)-amino]-acetyl}-piperazine-1-carboxylic acid butyl ester To a solution of 2.77 g of 1-phenyl-3-carboxy-5-pyrazolone and 3.3 g 4-(2-Amino-acetyl)-piperazine-1-carboxylic acid butyl ester in 70 ml DMF 2.7 g HOBT, 5.6 ml DIPEA and 3.4 g EDC were added and the reaction mixture was stirred for 12 h at RT. Then the reaction mixture was diluted with ethyl acetate and subsequently extracted with aqueous LiCl (4% w/w), 0.1 M HCl and aqueous NaHCO₃. The organic layer was dried over MgSO₄ and the solvent was removed under reduced pressure. The crude product thus obtained was used in the subsequent reaction. Yield: 5.3 g.

vi) 4-(2-{[5-((R)-1-Benzyloxycarbonyl-ethoxy)-1-phenyl-1H-pyrazole-3-carbonyl]-amino}-acetyl)-piperazine-1-carboxylic acid butyl ester To a solution of 1.75 g 4-{2-[(5-Hydroxy-1-phenyl-1H-pyrazole-3-carbonyl)-amino]-acetyl}-piperazine-1-carboxylic acid butyl ester in 10 ml DMF were added 990 mg (S)-2-bromo-propionic acid benzyl ester (prepared by standard benzylation procedure using (S)-2-bromopropionic acid and benzyl alcohol/p-TsOH) and 2.67 g cesium carbonate. After stirring at room temperature for 12 h the solution was diluted with 100 ml ethyl acetate and extracted with aqueous LiCl (4% w/w), 0.1 M HCl and aqueous NaHCO₃. The crude product obtained after evaporation of the solvent was pure enough for the following reactions. Yield: 2.1 g vii) 4-(2-{[5-((R)-1-Carboxy-ethoxy)-1-phenyl-1H-pyrazole-3-carbonyl]-amino}-acetyl)-piperazine-1-carboxylic acid butyl ester To a solution of 2.1 g 4-(2-{[5-((R)-1-Benzyloxycarbonyl-ethoxy)-1-phenyl-1H-pyrazole-3-carbonyl]-amino}-acetyl)-piperazine-1-carboxylic acid butyl ester in 60 ml ethyl acetate were added 0.4 g Pd/C (10%) and the suspension stirred under an atmosphere of hydrogen (3 bar) for 12 h. The reaction mixture was filtrated over a plug of Celite, washed with ethyl acetate and concentrated to give the crude product which was used in the subsequent reaction. Yield: 1.8 g viii) 4-[2-({5-[(R)-2-((S)-2-Cyclobutylcarbamoyl-pyrrolidin-1-yl)-1-methyl-2-oxo-ethoxy]-1-phenyl-1H-pyrazole-3-carbonyl}-amino)-acetyl]-piperazine-1-carboxylic acid butyl ester To a solution of 1.00 g 4-(2-{[5-((R)-1-Carboxy-ethoxy)-1-phenyl-1H-pyrazole-3-carbonyl]-amino}-acetyl)-piperazine-1-carboxylic acid butyl ester in 40 ml DMF were added 521 μl DIPEA and 758 mg HATU. After 20 minutes 336 mg (S)-Pyrrolidine-2-carboxylic acid cyclobutylamide were added and the reaction mixture stirred for 3 h. After evaporation of the solvent the crude product was dissolved in dichloromethane and extracted with aqueous LiCl (4% w/w), 0.1 M HCl and aqueous NaHCO₃. The crude product obtained after evaporation of the solvent was purified by preparative HPLC (C18 reverse phase column, elution with a water/MeCN gradient with 0.1% TFA). The fractions containing the product were immediately lyophilized to yield the pure product which was taken up in dichloromethane and washed once with aqueous NaHCO₃. The residue obtained after evaporation of the solvent was lyophilized again to give the title compound. Yield: 517 mg MS (ES+): m/e=652.

Example 270

4-[2-({5-[2-((2S,4R)-2-Cyclobutylcarbamoyl-4-hydroxy-pyrrolidin-1-yl)-2-oxo-ethoxy]-1-phenyl-1H-pyrazole-3-carbonyl}-amino)-acetyl]-piperazine-1-carboxylic acid butyl ester i) (2S,4R)-2-Cyclobutylcarbamoyl-4-hydroxy-pyrrolidine-1-carboxylic acid tert-butyl ester To a solution of 2.00 g (2S,4R)-4-Hydroxy-pyrrolidine-1,2-dicarboxylic acid 1-tert-butyl ester in 20 ml DMF were added 1.18 g HOAT, 615 mg cyclobutylamine and 1.66 g EDC. After stirring for 12 h saturated NaHCO₃ solution (3 ml) was added and the mixture passed through a Chem Elute® cartridge eluting with DCM. The crude product obtained after evaporation of the solvent was purified by filtering over a short plug of silica eluting with ethyl acetate. Yield: 1.22 g ii) (2S,4R)-4-Hydroxy-pyrrolidine-2-carboxylic acid cyclobutylamide hydrotrifluoroacetate To a solution of 1.22 g (2S,4R)-2-Cyclobutylcarbamoyl-4-hydroxy-pyrrolidine-1-carboxylic acid tert-butyl ester in 31 ml dichloromethane were added 3.2 ml TFA. After stirring for 4 h the reaction mixture was concentrated and the residue iii) 4-[2-({5-[2-((2S,4R)-2-Cyclobutylcarbamoyl-4-hydroxy-pyrrolidin-1-yl)-2-oxo-ethoxy]-1-phenyl-1H-pyrazole-3-carbonyl}-amino)-acetyl]-piperazine-1-carboxylic acid butyl ester To a solution of 700 mg 4-{2-[(5-Carboxymethoxy-1-phenyl-1H-pyrazole-3-carbonyl)-amino]-acetyl}-piperazine-1-carboxylic acid butyl ester in 10 ml DMF were added 317 mg pentafluorophenol and 330 mg EDC. The mixture was stirred under exclusion of moisture until LCMS indicated complete conversion to the corresponding pentafluorophenolester. (2S,4R)-4-Hydroxy-pyrrolidine-2-carboxylic acid cyclobutylamide hydrotrifluoroacetate (455 mg) was mixed with 0.55 ml N-ethylmorpholine and 5 ml DMF and this mixture added dropwise to the solution of the pentafluorophenolester. After 12 h the reaction mixture was diluted with DCM and washed with aqueous LiCl (4%), saturated aqueous $NaHCO_3$ and brine. The crude product obtained after evaporation of the solvent was purified by preparative HPLC (C18 reverse phase column, elution with a water/MeCN gradient with 0.1% TFA). The fractions containing the product were immediately lyophilized to yield the pure product which was taken up in dichloromethane and washed once with aqueous $NaHCO_3$. The residue obtained after evaporation of the solvent was lyophilized again to give the title compound. Yield: 454 mg MS (ES+): m/e=654.

Example 271

4-{2-[(5-{2-oxo-2-[(S)-2-(1H-tetrazol-5-yl)-pyrrolidin-1-yl]-ethoxy}-1-phenyl-1H-pyrazole-3-carbonyl)-amino]-acetyl}-piperazine-1-carboxylic acid butyl ester i) 4-{2-[(5-Benzyloxycarbonylmethoxy-1-phenyl-1H-pyrazole-3-carbonyl)-amino]-acetyl}-piperazine-1-carboxylic acid butyl ester To a solution of 3.5 g 4-{2-[(5-Hydroxy-1-phenyl-1H-pyrazole-3-carbonyl)-amino]-acetyl}-piperazine-1-carboxylic acid butyl ester in 23 ml DMF were added 1.87 g benzyl bromoacetate and 5.31 g cesium carbonate. After stirring at room temperature for 12 h the solution was diluted with 100 ml ethyl acetate and extracted with aqueous LiCl (4 w/w), 0.1 M HCl and aqueous $NaHCO_3$. The crude product obtained after evaporation of the solvent was pure enough for the following reactions. Yield: 3.6 g ii) 4-{2-[(5-Carboxymethoxy-1-phenyl-1H-pyrazole-3-carbonyl)-amino]-acetyl}-piperazine-1-carboxylic acid butyl ester To a solution of 3.6 g 4-{2-[(5-Benzyloxycarbonylmethoxy-1-phenyl-1H-pyrazole-3-carbonyl)-amino]-acetyl}-piperazine-1-carboxylic acid butyl ester in 80 ml THF were added 0.6 g Pd/C (10%) and the suspension stirred under an atmosphere of hydrogen (3 bar) for 12 h. The reaction mixture was filtered over a plug of Celite, washed with THF and concentrated to give the crude product which was used in the subsequent reaction.
Yield: 2.6 g iii) 4-{2-[(5-{2-oxo-2-[(S)-2-(1H-tetrazol-5-yl)-pyrrolidin-1-yl]-ethoxy}-1-phenyl-1H-pyrazole-3-carbonyl)-amino]acetyl}-piperazine-1-carboxylic acid butyl ester To a solution of 193 mg 4-{2-[(5-Carboxymethoxy-1-phenyl-1H-pyrazole-3-carbonyl)-amino]-acetyl}-piperazine-1-carboxylic acid butyl ester in 2 ml DMF were added 150 mg HATU and 69 µl DIPEA. After 10 minutes a solution of 54 mg (S)-5-Pyrrolidin-2-yl-1H-tetrazole in 1 ml DMF was added and after 36 h the reaction mixture was diluted with dichloromethane and extracted with aqueous LiCl (4%), 0.1 M HCl and brine. The crude product thus obtained after evaporation of the solvent was purified by preparative HPLC (C18 reverse phase column, elution with a water/MeCN gradient with 0.1% TFA). The fractions containing the product were immediately lyophilized to yield the title compound
Yield: 24 mg MS (ES+): m/e=609.

Example 272

4-{2-[(5-{(R)-1-Methyl-2-oxo-2-[(S)-2-(1H-tetrazol-5-yl)-pyrrolidin-1-yl]-ethoxy}-1-phenyl-1H-pyrazole-3-carbonyl)-amino]-acetyl}-piperazine-1-carboxylic acid butyl ester (i) (S)-2-Benzylcarbamoyl-pyrrolidine-1-carboxylic acid benzyl ester To a solution of 5.00 g Z-Pro-OH in 50 ml DMF were added 3.84 g EDC, 2.73 g HOAt, 7.3 ml DIPEA and 2.2 ml benzylamine at 0° C. After stirring for 2 h the reaction mixture was concentrated, the residue was dissolved in dichloromethane and subsequently extracted with aqueous LiCl (4%), 0.1 M HCl and saturated $NaHCO_3$. The crude product obtained after evaporation of the solvent was pure enough for the subsequent transformation.
Yield: 7.11 g colorless amorphous solid.

(ii) (S)-2-(1-Benzyl-1H-tetrazol-5-yl)-pyrrolidine-1-carboxylic acid benzyl ester To a suspension of 1.50 g (S)-2-Benzylcarbamoyl-pyrrolidine-1-carboxylic acid benzyl ester and 2.91 g triphenylphosphine in 30 ml acetonitrile were added dropwise at 0° C. 2.3 ml diisopropylazodicarboxylate and after 2 minutes 1.5 ml trimethylsilylazide over a period of 20 minutes. After 30 minutes the mixture was allowed to warm to RT and stirred for 12 h. The mixture was cooled to 0° C. and 1.5 ml aqueous sodium nitrite (2.9 M) were added, after 30 minutes a solution of 2.4 g ceric ammonium nitrate in 15 ml water was added and stirred for another 20 minutes. After this time the mixture was poured into ice and extracted twice with dichloromethane. The crude product thus obtained after evaporation of the solvent was purified by flash chromatography on silica eluting with ethyl acetate/heptane gradient. Yield: 494 mg colorless foam.

(iii) (S)-5-Pyrrolidin-2-yl-1H-tetrazole

To a solution of 494 mg (S)-2-(1-Benzyl-1H-tetrazol-5-yl)-pyrrolidine-1-carboxylic acid benzyl ester in 50 ml ethanol were added 100 mg $Pd(OH)_2$/C (10%) and the suspension stirred under an atmosphere of hydrogen (4 bar) for 6 h. The reaction mixture was filtered over a plug of Celite® and washed with ethanol. Yield: 173 mg colorless foam.

iv) 4-{2-[(5-{(R)-1-Methyl-2-oxo-2-[(S)-2-(1H-tetrazol-5-yl)-pyrrolidin-1-yl]-ethoxy}-1-phenyl-1H-pyrazole-3-carbonyl)-amino]-acetyl}-piperazine-1-carboxylic acid butyl ester The title compound was prepared by adapting the procedures described in example 269 with the difference that (S)-5-Pyrrolidin-2-yl-1H-tetrazole was used instead of (S)-Pyrrolidine-2-carboxylic acid cyclobutylamide. Yield: 23 mg MS (ES+): m/e=623.

Example 273

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4,4,4-trifluoro-butyryl]-piperazine-1-carboxylic acid propyl ester i) (S)-2-Benzyloxycarbonylamino-4,4,4-trifluoro-butyric acid To a solution of 250 mg (S)-2-Benzyloxycarbonylamino-4,4,4-trifluoro-butyric acid methyl ester in 2 ml THF and 0.5 ml water were added 20 mg LiOH at 0° C. The reaction mixture was brought to pH 3 by using Amberlite IR-120 ion exchange resin before being filtered and concentrated to give the crude title compound. Yield: 236 mg.

ii) piperazine-1,4-dicarboxylic acid propyl ester benzyl ester

To a solution of 15.0 g benzyl 1-piperazinecarboxylate in 100 ml dichloromethane were added 20.7 ml triethylamine. The solution was cooled to 0° C. and 8.4 ml propylchloroformate added dropwise at this temperature. After stirring for 1 h the reaction mixture was diluted with dichloromethane and washed with 0.1 M HCl and saturated NaHCO₃. The crude product obtained after evaporation of the solvent was purified by flash chromatography on silica using an ethyl acetate/heptane gradient. Yield: 19.3 g.

iii) piperazine-1-carboxylic acid propyl ester

To a solution of 19.3 g piperazine-1,4-dicarboxylic acid propyl ester benzyl ester in 200 ml ethanol were added 2.0 g Pd/C (10%) and the suspension stirred under an atmosphere of hydrogen (3 bar) for 3 h. The reaction mixture was filtrated over a plug of Celite, washed with ethanol and concentrated to give the crude product which was used in the subsequent reaction. Yield: 10.5 g.

iv) 4-((S)-2-Benzyloxycarbonylamino-4,4,4-trifluoro-butyryl)-piperazine-1-carboxylic acid propyl ester To a solution of 118 mg (S)-2-Benzyloxycarbonylamino-4,4,4-trifluoro-butyric acid in 2 ml DMF were added 70 mg 1-propoxycarbonylpiperazine, 0.18 ml N-ethylmorpholine and 238 mg TOTU. After stirring for 12 h it was diluted with ethyl acetate and extracted with aqueous LiCl (4% w/w), aqueous NaHCO₃, 0.1 M HCl and brine. The organic layer was dried over MgSO₄ and concentrated to furnish the crude coupling product which was used without further purification in the next step.

v) 4-((S)-2-Amino-4,4,4-trifluoro-butyryl)-piperazine-1-carboxylic acid propyl ester To a solution of 170 mg 4-((S)-2-Benzyloxycarbonylamino-4,4,4-trifluoro-butyryl)-piperazine-1-carboxylic acid propyl ester in 20 ml ethanol were added 0.05 g Pd/C (10%) and the suspension stirred under an atmosphere of hydrogen (3 bar) for 12 h. The reaction mixture was filtrated over a plug of Celite, washed with ethanol and concentrated to give the crude product which was used in the subsequent reaction. Yield: 106 mg.

vi) 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4,4,4-trifluoro-butyryl]-piperazine-1-carboxylic acid propyl ester To a solution of 100 mg 5-[2-((S)-2-Cyclobutylcarbamoyl-pyrrolidin-1-yl)-2-oxo-ethoxy]-1-phenyl-1H-pyrazole-3-carboxylic acid in 3 ml DMF were added 92 mg HATU, 82 l DIPEA and 75 mg 4-((S)-2-Amino-4,4,4-trifluoro-butyryl)-piperazine-1-carboxylic acid propyl ester. After stirring for 3 h saturated NaHCO₃ solution (1.5 ml) was added and the mixture passed through a Chem Elute® cartridge eluting with DCM. The crude product obtained after evaporation of the solvent was purified by preparative HPLC (C18 reverse phase column, elution with a water/MeCN gradient with 0.1% TFA) to give the title compound.
Yield: 81 mg MS (ES+): m/e=706.

Example 274

4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4,4,4-trifluoro-butyryl]-piperazine-1-carboxylic acid butyl ester The title compound was prepared by adapting the procedures described in example 273 with the difference that piperazine-1-carboxylic acid butyl ester was used instead of piperazine-1-carboxylic acid propyl ester. Yield: 85 mg MS (ES+): m/e=720.

Example 275

4-[2-({5-[2-((S)-2-Cyclobutylcarbamoyl-pyrrolidin-1-yl)-2-oxo-ethoxy]-1-phenyl-1H-pyrazole-3-carbonyl}-amino)-acetyl]-piperazine-1-carboxylic acid benzyl ester To a solution of 3.34 g ({5-[2-((S)-2-Cyclobutylcarbamoyl-pyrrolidin-1-yl)-2-oxo-ethoxy]-1-phenyl-1H-pyrazole-3-carbonyl}-amino)-acetic acid in 100 ml DMF were added 1.9 ml DIPEA, 2.7 g HATU and 1.4 ml 1-benzyloxycarbonylpiperazine. After stirring for 1 h it was diluted with ethyl acetate and extracted with aqueous LiCl (4% w/w), aqueous NaHCO₃ and 0.1 M HCl. The crude product obtained after evaporation of the solvent was purified by flash chromatography on silica using an ethyl acetate/methanol gradient.
Yield: 2.5 g colorless oil MS (ES+): m/e=672.
Pharmacological Testing The ability of the compounds of the formula I to inhibit the P2Y12 receptor can be assessed by determining the concentration of the compound of the formula I that binds to the human P2Y12 Recombinant Cell Membrane Binding Assay with 33P 2MeS-ADP.
Human P2Y12 Recombinant Cell Membrane Binding Assay The ability of a test compound to bind to the P2Y12 receptor was evaluated in a recombinant cell membrane binding assay. In this competitive binding assay, the test compound competed against a radiolabeled agonist for binding to the P2Y12 receptor, expressed on the cell membrane. Inhibition of binding of the labeled material was measured and correlated to the amount and potency of the test compound. This binding assay is a modification of the procedure described by Takasaki, J. et. al, Mol. Pharmacol., 2001, Vol. 60, pg. 432. A membrane preparation was prepared from Chinese Hamster Ovary (CHO) cells with recombinant expression of the human P2Y12 receptor according to standard procedures as a source of P2Y12.

To a 96-well microtiterplate the following were added: a) 24 μl of assay buffer (10 mM HEPES, 138 mM NaCl, 2.9 mN KCl, 12 mM NaHCO$_3$, 1 mM EDTA-Na, 0.1% BSA, pH 7.4) b) 1 μL compound in DMSO c) 50 μL P2Y12 CHO membrane (20 μg/ml) and after 15 min at RT d) 25 μL of 1.61 nM 33P 2MeS-ADP (Perkin Elmer NEN custom synthesis, specific activity ~2100 Ci/mmol) made in assay buffer.

After 20 min incubation at RT samples were transferred to 96-well microtiter filterplates (Millipore HTS GF/B), pre-wetted for 20 min with 300 μL of stop buffer (10 mM HEPES, 138 mM NaCl pH 7.4) and then filtered through completely with a Millipore plate vacuum. Next, wells were washed four times with 400 μl/well of stop buffer on a plate vacuum. The plate was disassembled and allowed to air dry overnight with the filter side up overnight. The filter plates were snapped into adapter plates and 0.1 mL of Microscint 20 Scintillation Fluid (Perkin Elmer #6013621) was added to each well. The top of the filterplate was sealed with plastic plate covers. The sealed filterplate were incubated 2 hours at RT. A Microbeta Scintillation Counter was used to measure counts. The binding of compound is expressed as a % inhibition of specific binding, defined by subtraction of the background with 1 mM ADP.

Compounds were diluted as 10 mM DMSO stocks and tested in a four-point, five-fold dilution series run in triplicate beginning at 10 μM, final concentration. Data were analyzed using a four-parameter curve fit with a fixed minimum and maximum experimentally defined as the average positive and negative controls on each plate. The IC$_{50}$ data of the above described human P2Y12 recombinant cell membrane binding assay for exemplary compounds of the present invention are shown in table 1.

TABLE 1

| Example | IC50 [mikro M] | Example | IC50 [mikro M] | Example | IC50 [mikro M] |
|---|---|---|---|---|---|
| 1 | 0.27 | 102 | 0.058 | 187 | 0.098 |
| 2 | 0.120 | 103 | 0.127 | 188 | 0.010 |
| 3 | 0.183 | 106 | 0.104 | 189 | 0.035 |
| 5 | 0.019 | 115 | 0.059 | 191 | 0.006 |
| 9 | 0.172 | 118 | 0.009 | 192 | 0.131 |
| 10 | 0.146 | 120 | 0.003 | 195 | 0.088 |
| 12 | 0.107 | 121 | 0.010 | 196 | 0.023 |
| 15 | 0.164 | 122 | 0.012 | 197 | 0.099 |
| 18 | 0.146 | 123 | 0.005 | 198 | 0.116 |
| 20 | 0.050 | 124 | 0.071 | 199 | 0.139 |
| 21 | 0.032 | 126 | 0.004 | 206 | 0.187 |
| 41 | 0.109 | 127 | 0.037 | 208 | 0.126 |
| 53 | 0.129 | 128 | 0.043 | 210 | 0.072 |
| 55 | 0.070 | 129 | 0.083 | 211 | 0.020 |
| 57 | 0.183 | 130 | 0.059 | 212 | 0.017 |
| 58 | 0.096 | 131 | 0.054 | 213 | 0.022 |
| 61 | 0.093 | 132 | 0.025 | 221 | 0.034 |
| 62 | 0.017 | 133 | 0.042 | 222 | 0.028 |
| 63 | 0.041 | 134 | 0.042 | 225 | 0.136 |
| 65 | 0.055 | 135 | 0.060 | 226 | 0.059 |
| 71 | 0.192 | 136 | 0.039 | 227 | 0.016 |
| 73 | 0.055 | 137 | 0.148 | 229 | 0.022 |
| 74 | 0.182 | 138 | 0.083 | 230 | 0.014 |
| 76 | 0.028 | 139 | 0.056 | 231 | 0.019 |
| 77 | 0.028 | 140 | 0.173 | 232 | 0.016 |
| 78 | 0.190 | 143 | 0.005 | 233 | 0.021 |
| 79 | 0.145 | 150 | 0.020 | 234 | 0.085 |
| 83 | 0.031 | 151 | 0.166 | 237 | 0.030 |
| 84 | 0.092 | 152 | 0.037 | 261 | 0.018 |
| 85 | 0.154 | 159 | 0.015 | 268 | 0.099 |
| 87 | 0.184 | 161 | 0.033 | 269 | 0.003 |
| 88 | 0.125 | 162 | 0.008 | 270 | 0.040 |
| 89 | 0.111 | 163 | 0.013 | 273 | 0.160 |
| 90 | 0.035 | 164 | 0.081 | 274 | 0.036 |
| 91 | 0.130 | 167 | 0.146 | | |
| 92 | 0.109 | 170 | 0.086 | | |
| 93 | 0.108 | 172 | 0.146 | | |
| 94 | 0.059 | 175 | 0.179 | | |
| 95 | 0.076 | 176 | 0.045 | | |
| 96 | 0.108 | 178 | 0.017 | | |
| 99 | 0.158 | 182 | 0.020 | | |
| 100 | 0.197 | 184 | 0.018 | | |
| 101 | 0.077 | 186 | 0.016 | | |
| 73 | 0.055 | 151 | 0.166 | | |

Inhibition of Human Platelet Aggregation

Alternatively to a binding assay which measures a compound's ability to bind to the P2Y12 receptor, the effect on cellular function was also determined. This ability of the compound was evaluated in two platelet aggregation assays: in 96-well plates and with the "Born"-method using single cuvettes.

96-Well Assay:

Whole blood was collected from healthy volunteers using 20 ml syringes containing 2 ml of ACD-A Aqua-Citrat-Dextrose-A, Fresenius). The anticoagulated whole blood was transferred into 15 ml polypropylene conical tubes (10 ml per tube). The tubes were centrifuged for 15 minutes at 150×g at RT without using the centrifuge brake. This procedure leads to a pellet of cellular components and a supernatant of platelet rich plasma (PRP). The PRP layer was collected from each tube and pooled for each donor. To avoid carry over of cellular components following centrifugation, approximately 5 ml of PRP was left in the tube. The platelet concentration was determined using a Coulter Counter.

The 15 ml tubes containing the pellet of cellular components were centrifuged again for 10 minutes at 1940×g. This pelleted out most particulate blood constituents remaining, leaving a layer of Platelet Poor Plasma (PPP). The PPP was collected for each donor. The PRP layer, previously set aside, was diluted with PPP to a final concentration of approximately 3×E8 platelets/ml with the PPP.

The human platelet aggregation assay is performed in 96-well plates using a microtiter plate reader (SpectraMax Plus 384 with SoftMax Pro software from Molecular Devices). In the plate 15 μl of test compound at 10× final concentration in NaCl is mixed with 120 μl fresh PRP and incubated for 5 minutes. Following that incubation period, 15 μl of 40 μM ADP is added to the reaction mix. This addition of ADP is sufficient to induce aggregation in the absence of an inhibitor. The plates are then transferred to the microplate reader and aggregation is measured over 20 minutes. The instrument settings include:

Absorbance at 650 nm, run time 20 minutes with readings in 1-minute intervals and 50 seconds shaking between readings all performed at 37° C. Results of the assay are expressed as % inhibition, and are calculated using area under curve (AUC) of the absorbance over 20 minutes.

The IC$_{50}$ data of the above described platelet aggregation 96-well assay using human platelet rich plasma for exemplary compounds of the present invention are shown in table 2.

TABLE 2

| Example | IC50 [micro M] |
|---|---|
| 1 | 0.01 |
| 5 | 0.03 |
| 7 | 1.46 |
| 8 | 0.47 |
| 9 | 0.06 |
| 10 | 0.04 |
| 11 | 0.03 |
| 12 | 0.02 |
| 13 | 0.01 |
| 15 | 0.13 |
| 17 | 0.60 |
| 18 | 0.07 |
| 19 | 0.21 |
| 20 | 0.10 |
| 21 | 0.062 |
| 22 | 0.22 |
| 27 | 0.76 |
| 40 | 0.86 |
| 41 | 0.08 |
| 53 | 0.03 |
| 55 | 0.02 |
| 56 | 0.06 |
| 58 | 0.060 |
| 59 | 0.63 |
| 61 | 0.05 |
| 62 | 0.13 |
| 64 | 0.19 |
| 66 | 0.33 |
| 67 | 0.11 |
| 68 | 0.07 |
| 70 | 0.26 |
| 71 | 0.71 |
| 73 | 0.010 |
| 74 | 0.26 |
| 76 | 0.17 |
| 77 | 0.16 |
| 83 | 0.12 |
| 84 | 0.55 |
| 87 | 1.13 |
| 92 | 1.13 |
| 93 | 0.59 |
| 94 | 0.13 |
| 95 | 0.26 |
| 96 | 0.67 |
| 98 | 1.81 |
| 101 | 0.79 |
| 103 | 0.56 |
| 104 | 1.23 |
| 106 | 1.33 |
| 108 | 1.88 |
| 115 | 0.21 |
| 118 | 0.02 |
| 119 | 0.02 |
| 120 | 0.01 |
| 121 | 0.03 |
| 122 | 0.04 |
| 123 | 0.03 |
| 126 | 0.05 |
| 127 | 0.44 |
| 128 | 0.69 |
| 131 | 0.74 |
| 135 | 0.66 |
| 136 | 0.26 |
| 138 | 1.65 |
| 139 | 0.36 |
| 143 | 0.09 |
| 150 | 0.07 |
| 153 | 0.43 |
| 156 | 1.08 |
| 159 | 0.12 |
| 161 | 0.24 |
| 162 | 0.02 |
| 163 | 0.01 |
| 164 | 0.04 |
| 165 | 0.34 |
| 166 | 0.08 |
| 170 | 0.29 |
| 172 | 0.38 |
| 173 | 0.86 |
| 174 | 0.76 |
| 180 | 0.45 |
| 181 | 0.09 |
| 182 | 0.03 |
| 184 | 0.28 |
| 187 | 0.44 |
| 188 | 0.49 |
| 189 | 0.35 |
| 190 | 0.18 |
| 191 | 0.38 |
| 192 | 0.19 |
| 193 | 0.46 |
| 198 | 0.72 |
| 199 | 0.92 |
| 200 | 0.42 |
| 201 | 0.57 |
| 202 | 0.84 |
| 203 | 0.49 |
| 204 | 0.72 |
| 205 | 0.46 |
| 206 | 0.41 |
| 208 | 0.39 |
| 210 | 0.12 |
| 211 | 0.28 |
| 213 | 0.33 |
| 215 | 0.95 |
| 221 | 0.26 |
| 222 | 0.26 |
| 227 | 0.13 |
| 230 | 0.21 |
| 231 | 0.07 |
| 232 | 0.41 |
| 233 | 0.20 |
| 245 | 0.80 |
| 246 | 0.56 |
| 254 | 0.75 |
| 256 | 0.13 |
| 257 | 0.24 |
| 261 | 0.06 |
| 262 | 0.03 |
| 268 | 0.02 |
| 270 | 0.017 |
| 273 | 0.38 |
| 275 | 0.49 |

"Born"-Method:

Whole blood was collected from healthy volunteers using 20 ml syringes containing 2 ml of buffered Citrate. The anticoagulated whole blood was transferred into 15 ml polypropylene conical tubes (10 ml per tube). The tubes were centrifuged for 15 minutes at 340×g at RT without using the centrifuge brake. This procedure leads to a pellet of cellular components and a supernatant of platelet rich plasma (PRP). The PRP layer was collected from each tube and pooled for each donor. To avoid carry over of cellular components following centrifugation, approximately 5 ml of PRP was left in the tube. The platelet concentration was determined using a Coulter Counter.

The 15 ml tubes containing the pellet of cellular components were centrifuged again for 10 minutes at 1940×g. This pelleted out most particulate blood constituents remaining, leaving a layer of Platelet Poor Plasma (PPP). The PPP was collected for each donor. The PRP layer, previously set aside, was diluted with PPP to a final concentration of approximately 3×E8 platelets/ml with the PPP.

The human platelet aggregation assay is performed in single use cuvettes using the platelet aggregation profiler (PAP-4 or -8, Bio/Data corporation).

In the assay cuvette 4 μl of test compound at 100× final concentration in DMSO is mixed with 392 μl fresh PRP and incubated for 2 minutes at 37° C. with 1.200 rpm stirring. Following that incubation period, 4 μl of 250 μM ADP is added to the reaction mix. This addition of ADP is sufficient to induce aggregation in the absence of an inhibitor. After that aggregation is measured over 6 minutes at 37° C. with 1.200 rpm stirring. Results of the assay are expressed as % inhibition, and are calculated using maximum aggregation ($T_{max}$) or area under curve (AUC) of the absorbance over 6 minutes.

The $IC_{50}$ data of the above described platelet aggregation assay using human platelet rich plasma for exemplary compounds of the present invention are shown in table 3.

TABLE 3

| Example | IC50 [micro M] |
|---|---|
| 1 | 0.21 |
| 2 | 0.011 |
| 9 | 0.091 |
| 10 | 0.34 |
| 11 | 0.12 |
| 12 | 0.070 |
| 13 | 0.038 |
| 15 | 0.12 |
| 16 | 0.046 |
| 20 | 0.072 |
| 53 | 0.039 |
| 55 | 0.06 |
| 61 | 0.18 |
| 62 | 0.058 |
| 63 | 0.020 |
| 65 | 0.12 |
| 67 | 0.95 |
| 73 | 0.21 |
| 103 | 0.12 |
| 115 | 0.12 |
| 117 | 0.22 |
| 118 | 0.025 |
| 119 | 0.013 |
| 120 | 0.021 |
| 121 | 0.0058 |
| 122 | 0.081 |
| 123 | 0.0026 |
| 124 | 0.020 |
| 126 | 0.079 |
| 143 | 0.15 |
| 150 | 0.021 |
| 162 | 0.033 |
| 163 | 0.042 |
| 172 | 0.53 |
| 173 | 0.94 |
| 174 | 2.22 |
| 178 | 0.070 |
| 181 | 0.10 |
| 182 | 0.046 |
| 184 | 0.08 |
| 185 | 0.09 |
| 210 | 0.030 |
| 227 | 0.13 |
| 230 | 0.08 |
| 231 | 0.03 |
| 233 | 0.06 |
| 256 | 0.19 |
| 262 | 0.04 |
| 269 | 0.050 |

What is claimed is:

1. A compound of Formula (I),

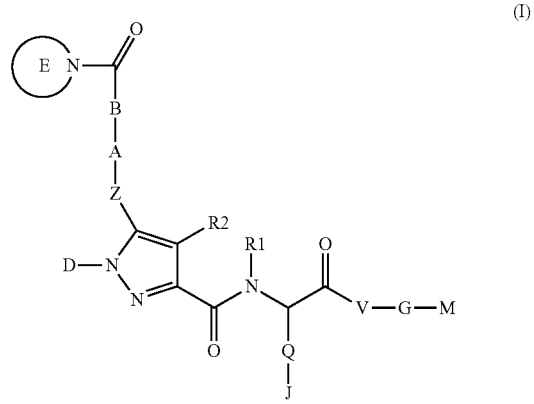

wherein

E is 3- to 10-membered heterocyclic residue selected from azetidine, piperazine, piperidine or pyrrolidine, wherein said heterocyclic residue is bond by its nitrogen atom to the carbonyl carbon atom and wherein said heterocyclic residue is unsubstituted or mono- or disubstituted independently of one another by R3, D is phenyl, wherein phenyl is unsubstituted or substituted 1 or 2 times by R4, Q is 1) a covalent bond,
  2) —($C_0$-$C_4$)-alkylene-O—,
  3) —($C_0$-$C_4$)-alkylene-C(O)—O—($C_0$-$C_4$)-alkylene-,
  4) —($C_0$-$C_4$)-alkylene-NH—C(O)—($C_0$-$C_2$)-alkylene-,
  5) —($C_0$-$C_4$)-alkylene-NH—C(O)—O—($C_0$-$C_2$)-alkylene-,
  6) —($C_0$-$C_4$)-alkylene-NH—$SO_2$—($C_0$-$C_2$)-alkylene- or
  7) —($C_3$-$C_{15}$)-heterocyclyl-, wherein said heterocyclyl is selected from azetidinyl, furanyl, imidazolyl, indolyl, isoxazolyl, oxadiazolyl, oxazolyl, piperazinyl, piperidinyl, pyrrolidinyl, tetrazolyl or thienyl, and is unsubstituted or mono-, di- or trisubstituted independently of one another by R14;

J is 1) hydrogen atom,
  2) —($C_1$-$C_6$)-alkyl, wherein alkyl is unsubstituted or mono-, di- or trisubstituted independently of one another by R13,
  3) —($C_0$-$C_4$)-alkylene-C(O)—O—R11, or
  4) —($C_0$-$C_4$)-alkylene-phenyl, wherein phenyl is unsubstituted or mono-, di- or trisubstituted independently of one another by R13, Z-A-B together with the carbonyl carbon atom form a residue selected from —O—$CH_2$—C(O)—, —O—CH($CH_3$)—C(O)— or —O—C($CH_3$)$_2$—C(O)—, wherein said residue is bond via oxygen atom to pyrazole residue and by the carbonyl carbon atom to the nitrogen atom of E, V is heterocyclyl selected from azetidinyl, piperazinyl, piperidinyl or pyrrolidinyl, and is unsubstituted or mono- or di-substituted independently of one another by R14, G is 1) a covalent bond,
  2) —($C_0$-$C_2$)-alkylene-C(O)—,
  3) —($C_0$-$C_2$)-alkylene-C(O)—O—($C_0$-$C_4$)-alkylene-, or 4) —($C_0$-$C_2$)-alkylene-N(R10)-C(O)—O—($C_0$-$C_4$)-alkylene-, M is 1) hydrogen atom,
2) —($C_1$-$C_4$)-alkyl, wherein alkyl is unsubstituted or mono-, di- or trisubstituted independently of one another by R14,
3) —($C_3$-$C_6$)-cycloalkyl, wherein said cycloalkyl is unsubstituted or mono-, di- or trisubstituted independently of one another by R14, or
4) -phenyl, wherein phenyl is unsubstituted or mono-, di- or trisubstituted independently of one another by R14, R1 and R2 are each hydrogen atom, R3 is 1) hydrogen atom,
2) halogen,
3) —($C_1$-$C_6$)-alkyl, wherein alkyl is unsubstituted or mono-, di- or trisubstituted independently of one another by R13,
4) =O,
5) —($C_1$-$C_3$)-fluoroalkyl,
6) —($C_0$-$C_4$)-alkylene-OH,
7) —($C_0$-$C_4$)-alkylene-C(O)—R11,
8) —($C_0$-$C_4$)-alkylene-C(O)—O—R11,
9) —($C_0$-$C_4$)-alkylene-C(O)—N(R11)-R12,
10) —($C_0$-$C_4$)-alkylene-C(O)—N(R11)-R13,
11) —($C_0$-$C_4$)-alkylene-N(R11)-R13,
12) —($C_0$-$C_4$)-alkylene-$SO_s$—R11, wherein s is 1 or 2,
13) —($C_0$-$C_4$)-alkylene-phenyl, wherein phenyl is unsubstituted or mono-, di- or trisubstituted independently of one another by R13, or
14) —($C_0$-$C_4$)-alkylene—($C_3$-$C_{15}$)-heterocyclyl, wherein heterocyclyl is as defined above and is unsubstituted or mono-, di- or trisubstituted independently of one another by R13, R4 is hydrogen atom or halogen, R10 is hydrogen atom or —($C_1$-$C_4$)-alkyl, R11 and R12 are independently of one another identical or different and are
1) hydrogen atom,
2) —($C_1$-$C_4$)-alkyl, wherein alkyl is unsubstituted or mono- or disubstituted independently of one another by R13,
3) —($C_1$-$C_3$)-fluoroalkyl,
4) —($C_0$-$C_6$)-alkylene—($C_3$-$C_8$)-cycloalkyl, wherein alkylene and cycloalkyl independently from one another are unsubstituted or mono-, di- or trisubstituted independently of one another by R13, or R11 and R12 form together with the nitrogen atom to which they are attached a heterocyclic ring selected from azetidine, piperidine or pyrrolidine, and wherein said ring is unsubstituted or substituted depending on the number of ring atoms one, two, three or four times by R13, R13 is halogen, —OH, —($C_3$-$C_6$)-cycloalkyl, —S—R10, —C(O)-R10, —($C_1$-$C_6$)-alkyl, —($C_1$-$C_6$)-alkoxy or —($C_1$-$C_3$)-fluoroalkyl, and R14 is —($C_1$-$C_4$)-alkyl or —($C_1$-$C_4$)-alkoxy, in all its stereoisomeric forms and mixtures thereof in any ratio, and its physiologically tolerable salts.

2. The compound as claimed in claim 1, wherein the compound of formula I is

4-[(S)-4-Carboxy-2-({5-[2-((S)-2-cyclopropylcarbamoyl-pyrrolidin-1-yl)-2-oxo-ethoxy]-1-phenyl-1H-pyrazole-3-carbonyl}-amino)-butyryl]-piperazine-1-carboxylic acid ethyl ester, 4-{(S)-4-Carboxy-2-[(5-{2-oxo-2-[(S)-2-(2,2,2-trifluoro-ethyl-carbamoyl)pyrrolidin-1-yl]-ethoxy}-1-phenyl-1H-pyrazole-3-carbonyl)-amino]-butyryl}-piperazine-1-carboxylic acid ethyl ester, 4-{(S)-4-Carboxy-2-[(5-{2-[(S)-2-(2-methylsulfanyl-ethylcarbamoyl)-pyrrolidin-1-yl]-2-oxo-ethoxy}-1-phenyl-1H-pyrazole-3-carbonyl)-amino]-butyryl}-piperazine-1-carboxylic acid ethyl ester, 4-{(S)-4-Carboxy-2-[(5-{2-[(S)-2-dimethylcarbamoyl)-pyrrolidin-1-yl]-2-oxo-ethoxy}-1-phenyl-1H-pyrazole-3-carbonyl)-amino]-butyryl}-piperazine-1-carboxylic acid ethyl ester, 4-{(S)-4-Carboxy-2-[(5-{2-[(S)-2-cyclobutylcarbamoyl)-pyrrolidin-1-yl]-2-oxo-ethoxy}-1-phenyl-1H-pyrazole-3-carbonyl)-amino]-butyryl}- 1-piperazine-1-carboxylic acid ethyl ester, 4-{(S)-4-Carboxy-2-[(5-{2-[(S)-2-(2-fluoro-ethylcarbamoyl)-pyrrolidin-1-yl]-2-oxo-ethoxy}-1-phenyl-1H-pyrazole-3-carbonyl)-amino]-butyryl}-piperazine-1-carboxylic acid ethyl ester, 4-{(S)-4-Carboxy-2-[(5-{2-[(S)-2-(2-methylcarbamoyl)-pyrrolidin-1-yl]-2-oxo-ethoxy}-1-phenyl-1H-pyrazole-3-carbonyl)-amino]-butyryl}-piperazine-1-carboxylic acid ethyl ester, 4-{(S)-4-Carboxy-2-[(5-{2-[(S)-2-ethylcarbamoyl-pyrrolidin-1-yl]-2-oxo-ethoxy}-1-phenyl-1H-pyrazole-3-carbonyl)-amino]-butyryl}-piperazine-1-carboxylic acid ethyl ester, 4-{(S)-4-Carboxy-2-[(5-{2-[(S)-2-propylcarbamoyl-pyrrolidin-1-yl]-2-oxo-ethoxy}-1-phenyl-1H-pyrazole-3-carbonyl)-amino]-butyryl}-piperazine-1-carboxylic acid ethyl ester, 4-{(S)-4-Carboxy-2-[(5-{2-[(S)-2-isopropylcarbamoyl-pyrrolidin-1-yl]-2-oxo-ethoxy}-1-phenyl-1H-pyrazole-3-carbonyl)-amino]-butyryl}-piperazine-1-carboxylic acid ethyl ester, 4-{(S)-4-Carboxy-2-[(5-{2-[(S)-2-butylcarbamoyl-pyrrolidin-1-yl]-2-oxo-ethoxy}-1-phenyl-1H-pyrazole-3-carbonyl-amino]-butyryl}-piperazine-1-carboxylic acid ethyl ester, 4-{(S)-4-Carboxy-2-[(5-{2-[(S)-2-tert-butylcarbamoyl-pyrrolidin-1-yl]-2-oxo-ethoxy}-1-phenyl-1H-pyrazole-3-carbonyl)-amino]-butyryl}-piperazine-1-carboxylic acid ethyl ester, 4-{(S)-4-Carboxy-2-[(5-{2-[(S)-2-cyclopentylcarbamoyl-pyrrolidin-1-yl]-2-oxo-ethoxy}-1-phenyl-1H-pyrazole-3-carbonyl)-amino]-butyryl}-piperazine-1-carboxylic acid ethyl ester, 4-{(S)-2-[(5-{2-[(S)-2-(Azetidine-1-carbonyl)-pyrrolidin-1-yl]-2-oxo-ethoxyl}-1-phenyl-1H-pyrazole-3-carbonyl)-amino]-4-carboxy-butyryl}-piperazine-1-carboxylic acid ethyl ester, 4-{(S)-4-Carboxy-2-[(5-{2-[(S)-2-(2,2-difluoro-ethylcarbamoyl)-pyrrolidin-1-yl]-2-oxo-ethoxy}-1-phenyl-1H-pyrazole-3-carbonyl)-amino]-butyryl}-piperazine-1-carboxylic acid ethyl ester, 4-{(S)-4-Carboxy-2-[(5-{2-[(S)-2-(cyclopropylmethyl-carbamoyl)-pyrrolidin-1-yl]-2-oxo-ethoxy}-1-phenyl-1H-pyrazole-3-carbonyl)-amino]-butyryl}-piperazine-1-carboxylic acid ethyl ester, 4-{(S)-4-Carboxy-2-[(5-{2-oxo-2-[(S)-2-(pyrrolidine-1-carbonyl)-pyrrolidin-1-yl]-ethoxy}-1-phenyl-1H-pyrazole-3-carbonyl)-amino]-butyryl}-piperazine-1-carboxylic acid ethyl ester, 4-{(S)-4-Carboxy-2-[(5-{2-oxo-2-[(S)-2-(piperidine-1-carbonyl)-pyrrolidin-1-yl]-ethoxy}-1-phenyl-1H-pyrazole-3-carbonyl)-amino]-butyryl}-piperazine-1-carboxylic acid ethyl ester, 4-{(S)-4-Carboxy-2-[(5-{2-[(S)-2-(4,4-difluoro-piperidine-1-carbonyl)-pyrrolidin-1-yl]-2-oxo-ethoxy}-1-phenyl-1H-pyrazole-3-carbonyl-amino]-butyryl}-piperazine-1-carboxylic acid ethyl ester, 4-{(S)-4-Carboxy-2-[(5-{2-[(S)-2-(cyclobutylmethyl-carbamoyl)-pyrrolidin-1-yl]-2-oxo-ethoxy}-1-phenyl-1H-pyrazole-3-carbonyl)-amino]-butyryl}-piperazine-1-carboxylic acid ethyl ester, 4-{(S)-4-Carboxy-2-[(5-{2-[(S)-2-(2,2-difluoro-cyclopropylcarbamoyl)-pyrrolidin-1-yl]-2-oxo-ethoxy}-1-phenyl-1H-pyrazole-3-carbonyl-amino]-butyryl}-piperazine-1-carboxylic acid ethyl ester, 4-{(S)-4-Carboxy-2-[(5-{2-[(S)-2-(cyclobutyl-methyl-carbamoyl)-pyrrolidin-1-yl]-2-oxo-ethoxy}-1-phenyl-1H-pyrazole-3-carbonyl)-amino]-butyryl}-piperazine-1-carboxylic acid ethyl ester, 4-[(S)-4-Carboxy-2-({5-[2-((R)-3-hydroxy-pyrrolidin-1-yl)-2-oxo-ethoxy]-1-phenyl-1H-pyrazole-3-carbonyl}-amino)-butyryl]-piperazine-1-carboxylic acid ethyl ester, 4-[(S)-4-Carboxy-2-({5-[2-((2S,4R)-2-ethoxycarbonyl-4-hydroxy-pyrrolidin-1-yl)-2-oxo-ethoxy]-1-phenyl-1H-pyrazole-3-carbonyl}-amino)-butyryl]-piperazine-1-carboxylic acid ethyl ester, 4-[(S)-4-Carboxy-2-({5-[2-((S)-2-carboxy-azetidin-1-yl)-2-oxo-ethoxy]-1-phenyl-1H-pyrazole-3-carbonyl}-amino)-butyryl]-piperazine-1-carboxylic acid ethyl ester, 4-[(S)-4-Carboxy-2-({5-[2-((2R,4R)-2-carboxy-4-hydroxy-pyrrolidin-1-yl)-2-oxo-ethoxy]-1-phenyl-1H-pyrazole-3-carbonyl}-amino)-butyryl]-piperazine-1-carboxylic acid ethyl ester, 4-[(S)-2-({5-[2-(4-Acetyl-piperazin-1-yl)-2-oxo-ethoxy]-1-phenyl-1H-pyrazole-3-carbonyl}-amino)-4-carboxy-butyryl]-piperazine-1-carboxylic acid ethyl ester, 4-[(S)-4-Carboxy-2-({5-[2-(4-ethyl-piperazin-1-yl)-2-oxo-ethoxy]-1-phenyl-1H-pyrazole-3-carbonyl}-amino)-butyryl]-piperazine-1-carboxylic acid ethyl ester, 4-[(S)-2-({5-[2-(3-Acetylamino-pyrrolidin-1-yl)-2-oxo-ethoxy]-1-phenyl-1H-pyrazole-3-carbonyl}-amino)-4-carboxy-butyryl]-piperazine-1-carboxylic acid ethyl ester, 4-[(S)-4-Carboxy-2-({5-[2-oxo-2-(3-oxo-piperazin-1-yl)-ethoxy]-1-phenyl-1H-pyrazole-3-carbonyl}-amino)-butyryl]-piperazine-1-carboxylic acid ethyl ester, 4-((S)-4-Carboxy-2-{[5-(2-oxo-2-pyrrolidin-1-yl-ethoxy)-1-phenyl-1H-pyrazole-3-carbonyl]-amino}-butyryl)-piperazine-1-carboxylic acid ethyl ester, 4-[(S)-4-Carboxy-2-({5-[2-((S)-2-carboxy-pyrrolidin-1-yl)-2-oxo-ethoxy]-1-phenyl-1H-pyrazole-3-carbonyl}-amino)-butyryl]-piperazine-1-carboxylic acid ethyl ester, 4-[(S)-4-Carboxy-2-({5-[2-((2S,4R)-2-carboxy-4-hydroxy-pyrrolidin-1-yl)-2-oxo-ethoxy]-1-phenyl-1H-pyrazole-3-carbonyl}-amino)-butyryl]-piperazine-1-carboxylic acid ethyl ester, 4-[(S)-4-Carboxy-2-({5-[2-(3-methanesulfonyl-pyrrolidin-1-yl)-2-oxo-ethoxy]-1-phenyl-1H-pyrazole-3-carbonyl}-amino)-butyryl]-piperazine-1-carboxylic acid ethyl ester, 4-[(S)-4-Carboxy-2-({5-[2-((2S,4S)-4-hydroxy-2-methoxycarbonyl-pyrrolidin-1-yl)-2-oxo-ethoxy]-1-phenyl-1H-pyrazole-3-carbonyl}-amino)-butyryl]-piperazine-1-carboxylic acid ethyl ester, 4-{(S)-4-Carboxy-2-[(5-{2-[4-(2-hydroxy-ethyl)-piperazin-1-yl]-2-oxo-ethoxy}-1-phenyl-1H-pyrazole-3-carbonyl)-amino]-butyryl}-piperazine-1-carboxylic acid ethyl ester, 4-[(S)-4-Carboxy-2-({5-[2-(4-hydroxy-piperidin-1-yl)-2-oxo-ethoxyl]-1-phenyl-1H-pyrazole-3-carbonyl}-amino)-butyryl]-piperazine-1-carboxylic acid ethyl ester, 4-[(S)-4-Carboxy-2-({5-[2-oxo-2-((S)-2-trifluoromethyl-pyrrolidin-1-yl)-ethoxy]-1-phenyl-1H-pyrazole-3-carbonyl}-amino)-butyryl]-piperazine-1-carboxylic acid ethyl ester, 4-[(S)-2-({5-[2-((S)-2-Carbamoyl-pyrrolidin-1-yl)-2-oxo-ethoxy]-1-phenyl-1H-pyrazole-3-carbonyl}-amino)-4-carboxy-butyryl]-piperazine-1-carboxylic acid ethyl ester, 4-[(S)-4-Carboxy-2-({5-[2-((S)-2-cyclopropylcarbamoyl-azetidin-1-yl)-2-oxo-ethoxy]-1-phenyl-1H-pyrazole-3-carbonyl}-amino)-butyryl]-piperazine-1-carboxylic acid ethyl ester, 4-[(S)-4-Carboxy-2-({5-[2-((S)-2-cyclobutylcarbamoyl-azetidin-1-yl)-2-oxo-ethoxy]-1-phenyl-1H-pyrazole-3-carbonyl}-amino)-butyryl]-piperazine-1-carboxylic acid ethyl ester, 4-[(S)-4-Carboxy-2-({5-[2-(3-cyclopropylcarbamoyl-azetidin-1-yl)-2-oxo-ethoxy]-1-phenyl-1H-pyrazole-3-carbonyl}-amino)-butyryl]-piperazine-1-carboxylic acid ethyl ester, 4-[(S)-4-Carboxy-2-({5-[2-(3-cyclobutylcarbamoyl-azetidin-1-yl)-2-oxo-ethoxy]-1-phenyl-1H-pyrazole-3-carbonyl}-amino)-butyryl]-piperazine-1-carboxylic acid ethyl ester, 4-[(S)-4-Carboxy-2-({5-[2-((S)-2-cyclopropylcarbamoyl-pyrrolidin-1-yl)-1,1-dimethyl-2-oxo-ethoxy]-1-phenyl-1H-pyrazole-3-carbonyl}-amino)-butyryl]-piperazine-1-carboxylic acid ethyl ester, 4-[(S)-4-Carboxy-2-({5-[2-((2S,4R)-4-hydroxy-2-methoxycarbonyl-pyrrolidin-1-yl)-1,1-dimethyl-2-oxo-ethoxy]-1-phenyl-1H-pyrazole-3-carbonyl}-amino)-butyryl]-piperazine-1-carboxylic acid ethyl ester, 4-[(S)-4-Carboxy-2-({5-[2-((3S,4S)-3,4-dihydroxy-pyrrolidin-1-yl)-1,1-dimethyl-2-oxo-ethoxy]-1-phenyl-1H-pyrazole-3-carbonyl}-amino)-butyryl]-piperazine-1-carboxylic acid ethyl ester, 4-[(S)-4-Carboxy-2-({5-[2-((R)-2-cyclopropylcarbamoyl-pyrrolidin-1-yl)-1,1-dimethyl-2-oxo-ethoxy]-1-phenyl-1H-pyrazole-3-carbonyl}-amino)-butyryl]-piperazine-1-carboxylic acid ethyl ester, 4-[(S)-4-Carboxy-2-({5-[2-((2S,4R)-4-hydroxy-2-methoxycarbonyl-pyrrolidin-1-yl)-1-methyl-2-oxo-ethoxy]-1-phenyl-1H-pyrazole-3-carbonyl}-amino)-butyryl] piperazine-1-carboxylicacid ethyl ester, 4-[(S)-4-Carboxy-2-({5-[2-((3S,4S)-3,4-dihydroxy-pyrrolidin-1-yl)-1-methyl-2-oxo-ethoxy]-1-phenyl-1H-pyrazole-3-carbonyl}-amino)-butyryl]-piperazine-1-carboxylicacid ethyl ester, 4-[(S)-4-Carboxy-2-({5-[2-((S)-2-cyclopropylcarbamoyl-pyrrolidin-1-yl)-1-methyl-2-oxo-ethoxy]-1-phenyl-1H-pyrazole-3-carbonyl}-amino)-butyryl]-piperazine-1-carboxylic acid ethyl ester, 4-[(S)-4-Carboxy-2-({5-[2-((S)-2-cyclopropylcarbamoyl-azetidin-1-yl)-1-methyl-2-oxo-ethoxy]-1-phenyl-1H-pyrazole-3-carbonyl}-amino)-butyryl]-piperazine-1-carboxylic acid ethyl ester, 4-[(S)-4-Carboxy-2-({5-[2-((S)-2-carboxy-pyrrolidin-1-yl)-1-methyl-2-oxo-ethoxy]-1-phenyl-1H-pyrazole-3-carbonyl}-amino)-butyryl]-piperazine-1-carboxylic acid ethyl ester, 4-{(S)-4-Carboxy-2-[(5-{1-methyl-2-oxo-2-[(S)-2-(2,2,2-trifluoro-ethylcarbamoyl)-pyrrolidin-1-yl]-ethoxy}-1-phenyl-1H-pyrazole-3-carbonyl)-amino]-butyryl}-piperazine-1-carboxylic acid ethyl ester, 4-[(S)-4-Carboxy-2-({5-[2-((S)-2-dimethylcarbamoyl-pyrrolidin-1-yl)-1-methyl-2-oxo-ethoxy]-1-phenyl-1H-pyrazole-3-carbonyl}-amino)-butyryl]-piperazine-1-carboxylic acid ethyl ester, 4-{(S)-3-Carboxy-2-[(5-{2-[(S)-2-(cyclopropylmethyl-carbamoyl)-pyrrolidin-1-yl]-2-oxo-ethoxy}-1-phenyl-1H-pyrazole-3-carbonyl)-amino]-propionyl}-piperazine-1-carboxylic acid ethyl ester, 4-[(S)-3-Carboxy-2-({5-[2-((S)-2-cyclopropylcarbamoyl-pyrrolidin-1-yl)-2-oxo-ethoxy]-1-phenyl-1H-pyrazole-3-carbonyl}-amino)-propionyl]-piperazine-1-carboxylic acid ethyl ester, 4-{(S)-3-Carboxy-2-[(5-{2-[(S)-2-(2,2-difluoro-ethylcarbamoyl-pyrrolidin-1-yl]-2-oxo-ethoxy}-1-phenyl-1H-pyrazole-3-carbonyl)-amino]-propionyl}-piperazine-1-carboxylic acid ethyl ester, 4-{(S)-3-Carboxy-2-[(5-{2-[(S)-2-(2,2,2-trifluoro-ethylcarbamoyl)-pyrrolidin-1-yl]-2-oxo-ethoxy}-1-phenyl-1H-pyrazole-3-carbonyl)-amino]-propionyl}-piperazine-1-carboxylic acid ethyl ester, 4-{(S)-3-Carboxy-2-[(5-{2-[(S)-2-(2-fluoro-ethylcarbamoyl)-pyrrolidin-1-yl]-2-oxo-ethoxy}-1-phenyl-1H-pyrazole-3-carbonyl)-amino]-propionyl}-piperazine-1-carboxylic acid ethyl ester, 4-[(S)-3-Carboxy-2-({5-[2-oxo-2-(2-oxo-pyrrolidin-1-yl)-ethoxy]-1-phenyl-1H-pyrazole-3-carbonyl}-amino)-butyryl]-piperazine-1-carboxylic acid ethyl ester, 4-[(S)-4-Carboxy-2-({5-[(R)-2-((S)-2-cyclopropylcarbamoyl-pyrrolidin-1-yl)-1-methyl-2-oxo-ethoxy]-1-phenyl-1H-pyrazole-3-carbonyl}-amino)-butyryl]-piperazine-1-carboxylic acid ethyl ester, 4-[(S)-4-Carboxy-2-({5-[(R)-2-((S)-2-cyclobutylcarbamoyl-pyrrolidin-1-yl)-1-methyl-2-oxo-ethoxy]-1-phenyl-1H-pyrazole-3-carbonyl}-amino)-butyryl]-piperazine-1-carboxylic acid ethyl ester, 4-[(S)-4-Carboxy-2-({5-[(R)-2-((S)-2-cyclopropylmethylcarbamoyl-pyrrolidin-1-yl)-1-methyl-2-oxo-ethoxy]-1-phenyl-1H-pyrazole-3-carbonyl}-amino)-butyryl]-piperazine-1-carboxylic acid ethyl ester, 4-{(S)-4-Carboxy-2-[(5-{(R)-1-methyl-2-oxo-2-[(S)-2-(pyrrolidine-1-carbonyl)-pyrrolidin-1-yl]-ethoxy}-1-phenyl-1H-pyrazole-3-carbonyl)-amino]-butyryl}-piperazine-1-carboxylic acid ethyl ester, 4-[(S)-4-Carboxy-2-({5-[(R)-2-((S)-2-(2,2,2-trifluoroethylcarbamoyl)-pyrrolidin-1-yl)-1-methyl-2-oxo-ethoxy]-1-phenyl-1H-pyrazole-3-carbonyl}-amino)-butyryl]-piperazine-1-carboxylic acid ethyl ester, 4-[(S)-4-Carboxy-2-({5-[(S)-2-((S)-2-cyclopropylcarbamoyl-pyrrolidin-1-yl)-1-methyl-2-oxo-ethoxy]-1-phenyl-1H-pyrazole-3-carbonyl}-amino)-butyryl]-piperazine-1-carboxylic acid ethyl ester, 4-[(S)-4-Carboxy-2-({5-[(S)-2-((S)-2-cyclobutylcarbamoyl-pyrrolidin-1-yl)-1-methyl-2-oxo-ethoxy]-1-phenyl-1H-pyrazole-3-carbonyl}-amino)-butyryl]-piperazine-1-carboxylic acid ethyl ester, 4-[(S)-4-Carboxy-2-({5-[(S)-2-((S)-2-cyclopropylmethylcarbamoyl-pyrrolidin-1-yl)-1-methyl-2-oxo-ethoxy]-1-phenyl-1H-pyrazole-3-carbonyl}-amino)-butyryl]-piperazine-1-carboxylic acid ethyl ester, 4-{(S)-4-Carboxy-2-[(5-{(S)-1-methyl-2-oxo-2-[(S)-2-(pyrrolidine-1-carbonyl)-pyrrolidin-1-yl]-ethoxy}-1-phenyl-1H-pyrazole-3-carbonyl)-amino]-butyryl}-piperazine-1-carboxylic acid ethyl ester, 4-[(S)-4-Carboxy-2-({5-[(S)-2-((S)-2-(2,2,2-trifluoroethylcarbamoyl)-pyrrolidin-1-yl)-1-methyl-2-oxo-ethoxy]-1-phenyl-1H-pyrazole-3-carbonyl}-amino)-butyryl]-piperazine-1-carboxylic acid ethyl ester, 4-((S)-4-Carboxy-2-{[5-[2-((S)-2-cyclopropylcarbamoyl-pyrrolidin-1-yl)-2-oxo-ethoxy]-1-(3-fluoro-phenyl)-1H-pyrazole-3-carbonyl]-amino}-butyryl)-piperazine-1-carboxylic acid ethyl ester, 4-((S)-4-Carboxy-2-{[5-[2-((S)-2-(2-fluoroethylcarbamoyl)-pyrrolidin-1-yl)-2-oxo-ethoxy]-1-(3-fluoro-phenyl)-1H-pyrazole-3-carbonyl]-amino}-butyryl)-piperazine-1-carboxylic acid ethyl ester, 4-((S)-4-Carboxy-2-{[5-[2-((S)-2-cyclobutylcarbamoyl-pyrrolidin-1-yl)-2-oxo-ethoxy]-1-(3-fluoro-phenyl)-1H-pyrazole-3-carbonyl]-amino}-butyryl)-piperazine-1-carboxylic acid ethyl ester, 4-((S)-4-Carboxy-2-{[5-[2-((S)-2-cyclopropylmethylcarbamoyl-pyrrolidin-1-yl)-2-oxo-ethoxy]-1-(3-fluoro-phenyl)-1H-pyrazole-3-carbonyl]-amino}-butyryl)-piperazine-1-carboxylic acid ethyl ester, 4-((S)-4-Carboxy-2-{[5-[2-((S)-2-(2,2,2-trifluoroethylcarbamoyl)-pyrrolidin-1-yl)-2-oxo-ethoxy]-1-(3-fluoro-phenyl)-1H-pyrazole-3-carbonyl]-amino}-butyryl)-piperazine-1-carboxylic acid ethyl ester, 4-((S)-4-Carboxy-2-{[5-[2-((S)-2-(2,2-difluoroethylcarbamoyl)-pyrrolidin-1-yl)-2-oxo-ethoxy]-1-(3-fluoro-phenyl)-1H-pyrazole-3-carbonyl]-amino}-butyryl)-piperazine-1-carboxylic acid ethyl ester, 4-((S)-3-Carboxy-2-{[5-[2-((S)-2-cyclopropylmethylcarbamoyl-pyrrolidin-1-yl)-2-oxo-ethoxy]-1-(3-fluoro-phenyl)-1H-pyrazole-3-carbonyl]-amino}-propionyl)-piperazine-1-carboxylic acid ethyl ester, 4-((S)-3-Carboxy-2-{[5-[2-((S)-2-(2-fluoroethylcarbamoyl)-pyrrolidin-1-yl)-2-oxo-ethoxy]-1-(3-fluoro-phenyl)-1H-pyrazole-3-carbonyl]-amino}-propionyl)-piperazine-1-carboxylic acid ethyl ester, 4-((S)-3-Carboxy-2-{[5-[2-((S)-2-(2,2-difluoroethylcarbamoyl)-pyrrolidin-1-yl)-2-oxo-ethoxy]-1-(3-fluoro-phenyl)-1H-pyrazole-3-carbonyl]-amino}-propionyl)-piperazine-1-carboxylic acid ethyl ester, 4-((S)-3-Carboxy-2-{[5-[2-((S)-2-cyclopropyl-carbamoyl-pyrrolidin-1-yl)-2-oxo-ethoxyl]-1-(3-fluoro-phenyl)-1H-pyrazole-3-carbonyl]-amino}-propionyl)-piperazine-1-carboxylic acid ethyl ester, 4-((S)-4-Carboxy-2-{[5-[2-((S)-2-cyclopropylcarbamoyl-pyrrolidin-1-yl)-2-oxo-ethoxy]-1-(3,4-difluoro-phenyl)-1H-pyrazole-3-carbonyl]-amino}-butyryl)-piperazine-1-carboxylic acid ethyl ester, 4-((S)-4-Carboxy-2-{[5-[2-((S)-2-(2-fluoroethylcarbamoyl)-pyrrolidin-1-yl)-2-oxo-ethoxy]-1-(3,4-difluoro-phenyl)-1H-pyrazole-3-carbonyl]-amino}-butyryl)-piperazine-1-carboxylic acid ethyl ester, 4-((S)-4-Carboxy-2-{[5-[2-((S)-2-cyclobutylcarbamoyl-pyrrolidin-1-yl)-2-oxo-ethoxy]-1-(3,4-difluoro-phenyl)-1H-pyrazole-3-carbonyl]-amino}-butyryl)-piperazine-1-carboxylic acid ethyl ester, 4-((S)-4-Carboxy-2-{[5-[2-((S)-2-cyclopropylmethylcarbamoyl-pyrrolidin-1-yl)-2-oxo-ethoxy]-1-(3,4-difluoro-phenyl)-1H-pyrazole-3-carbonyl]-amino}-butyryl)-piperazine-1-carboxylic acid ethyl ester, 4-((S)-4-Carboxy-2-{[5-[2-((S)-2-(2,2,2-trifluoroethyl-carbamoyl)-pyrrolidin-1-yl)-2-oxo-ethoxy]-1-(3,4-difluoro-phenyl)-1H-pyrazole-3-carbonyl]-amino}-butyryl)-piperazine-1-carboxylic acid ethyl ester, 4-((S)-4-Carboxy-2-{[5-[2-((S)-2-(2,2-difluoroethylcarbamoyl)-pyrrolidin-1-yl)-2-oxo-ethoxy]-1-(3,4-difluoro-phenyl)-1H-pyrazole-3-carbonyl]-amino}-butyryl)-piperazine-1-carboxylic acid ethyl ester, 4-[(S)-3-Acetylamino-2-({5-[2-((S)-2-cyclobutylcarbamoyl-pyrrolidin-1-yl)-2-oxo-ethoxy]-1-phenyl-1H-pyrazole-3-carbonyl}-amino)-propionyl]-piperazine-1-carboxylic acid ethyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-3-methanesulfonylamino-propionyl]-piperazine-1-carboxylic acid ethyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-3-methoxycarbonylamino-propionyl]-piperazine-1-carboxylic acid ethyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-3-(ethoxyoxalyl-amino)-propionyl]-piperazine-1-carboxylic acid ethyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-3-(cyclopropanecarbonyl-amino)-propionyl]-piperazine-1-carboxylic acid ethyl ester, 4-[(S)-4-Acetylamino-2-({5-[2-((S)-2-cyclobutylcarbamoyl-pyrrolidin-1-yl)-2-oxo-ethoxy]-1-phenyl-1H-pyrazole-3-carbonyl}-amino)-butyryl]-piperazine-1-carboxylic acid ethyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-methoxycarbonylamino-butyryl]-piperazine-1-carboxylic acid ethyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-methanesulfonylamino-butyryl]-piperazine-1-carboxylic acid ethyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-(cyclopropanecarbonyl-amino)-butyryl]-piperazine-1-carboxylic acid ethyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-(ethoxyoxalyl-amino)-butyryl]-piperazine-1-carboxylic acid ethyl ester, 4-[(S)-4-(Cyclobutanecarbonyl-amino)-2-({5-[2-((S)-2-cyclobutylcarbamoyl-pyrrolidin-1-yl)-2-oxo-ethoxy]-1-phenyl-1H-pyrazole-3-carbonyl}-amino)-butyryl]-piperazine-1-carboxylic acid ethyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-(2,2,2-trifluoro-acetylamino)-butyryl]-piperazine-1-carboxylic acid ethyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-(2,2-dimethyl-propionylamino)-butyryl]-piperazine-1-carboxylic acid ethyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-isobutyrylamino-butyryl]-piperazine-1-carboxylic acid ethyl ester, (S)-4-({5-[2-((S)-2-Cyclobutylcarbamoyl-pyrrolidin-1-yl)-2-oxo-ethoxy]-1-phenyl-1H-pyrazole-3-carbonyl}-amino)-5-[4-(3-methoxy-phenyl)-piperazin-1-yl]-5-oxo-pentanoic acid, (S)-5-(4-Butoxycarbonylamino-piperidin-1-yl)-4-({5-[2-((S)-2-cyclobutylcarbamoyl-pyrrolidin-1-yl)-2-oxo-ethoxy]-1-phenyl-1H-pyrazole-3-carbonyl}-amino)-5-oxo-pentanoic acid, (S)-5-[4-(3-Chloro-benzoyl)-piperidin-1-yl]-4-({5-[2-((S)-2-cyclobutylcarbamoyl-pyrrolidin-1-yl)-2-oxo-ethoxy]-1-phenyl-1H-pyrazole-3-carbonyl}-amino)-5-oxo-pentanoic acid, (S)-5-(4-Benzoyl-piperidin-1-yl)-4-({5-[2-((S)-2-cyclobutylcarbamoyl-pyrrolidin-1-yl)-2-oxo-ethoxy]-1-phenyl-1H-pyrazole-3-carbonyl}-amino)-5-oxo-pentanoic acid, 4-[(S)-4-Carboxy-2-({5-[2-((S)-2-cyclobutylcarbamoyl-pyrrolidin-1-yl)-2-oxo-ethoxy]-1-phenyl-1H-pyrazole-3-carbonyl}-amino)-butyrylamino]-piperidine-1-carboxylic acid ethyl ester, (S)-5-(4-Benzoyl-piperidin-1-yl)-4-({5-[2-((S)-2-cyclobutylcarbamoyl-pyrrolidin-1-yl)-2-oxo-ethoxy]-1-phenyl-1H-pyrazole-3-carbonyl}-amino)-5-oxo-pentanoic acid, 3-[(S)-4-Carboxy-2-({5-[2-((S)-2-cyclobutylcarbamoyl-pyrrolidin-1-yl)-2-oxo-ethoxy]-1-phenyl-1H-pyrazole-3-carbonyl}-amino)-butyrylamino]-pyrrolidine-1-carboxylic acid butyl ester, (S)-5-(3-Butoxycarbonylamino-pyrrolidin-1-yl)-4-({5-[2-((S)-2-cyclobutylcarbamoyl-pyrrolidin-1-yl)-2-oxo-ethoxy]-1-phenyl-1H-pyrazole-3-carbonyl}-amino)-5-oxo-pentanoic acid, 4-[(S)-4-Carboxy-2-({5-[2-(3-cyclopropylcarbamoyl-pyrrolidin-1-yl)-2-oxo-ethoxy]-1-phenyl-1H-pyrazole-3-carbonyl}-amino)-butyryl]-piperazine-1-carboxylic acid ethyl ester, 4-{(S)-4-Carboxy-2-[(5-{2-[3-(cyclopropylmethyl-carbamoyl)-pyrrolidin-1-yl]-2-oxo-ethoxy}-1-phenyl-1H-pyrazole-3-carbonyl)-amino]-butyryl}-piperazine-1-carboxylic acid ethyl ester, 4-[(S)-4-Carboxy-2-({5-[2-(3-cyclobutylcarbamoyl-pyrrolidin-1-yl)-2-oxo-ethoxy]-1-phenyl-1H-pyrazole-3-carbonyl}-amino)-butyryl]-piperazine-1-carboxylic acid ethyl ester, 4-{(S)-4-Carboxy-2-[(5-{2-[3-(2,2-difluoro-ethylcarbamoyl)-pyrrolidin-1-yl]-2-oxo-ethoxy}-1-phenyl-1H-pyrazole-3-carbonyl)-amino]-butyryl}-piperazine-1-carboxylic acid ethyl ester, 4-{(S)-4-Carboxy-2-[(5-{2-[3-(2,2,2-trifluoro-ethylcarbamoyl)-pyrrolidin-1-yl]-2-oxo-ethoxy}-1-phenyl-1H-pyrazole-3-carbonyl)-amino]-butyryl}-piperazine-1-carboxylic acid ethyl ester, 4-{(S)-4-Carboxy-2-[(5-{2-[3-(2-fluoro-ethylcarbamoyl)-pyrrolidin-1-yl]-2-oxo-ethoxy}-1-phenyl-1H-pyrazole-3-carbonyl-amino]-butyryl}-piperazine-1-carboxylic acid ethyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-hydroxy-butyryl]-piperazine-1-carboxylic acid ethyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-5-hydroxy-pentanoyl]-piperazine-1-carboxylic acid butyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4,5-dihydroxy-pentanoyl]-piperazine-1-carboxylic acid ethyl ester, 4-[(S)-4-Carboxy-2-({5-[2-((S)-2-cyclopropylcarbamoyl-pyrrolidin-1-yl)-2-oxo-ethoxy]-1-phenyl-1H-pyrazole-3-carbonyl}-amino)-butyryl]-piperazine-1-carboxylic acid butyl ester, 4-[(S)-4-Carboxy-2-({5-[2-((S)-2-cyclobutylcarbamoyl-pyrrolidin-1-yl)-2-oxo-ethoxy]-1-phenyl-1H-pyrazole-3-carbonyl}-amino)-butyryl]-piperazine-1-carboxylic acid butyl ester, 4-[(S)-4-Carboxy-2-({5-[2-((S)-2-cyclopropylmethylcarbamoyl-pyrrolidin-1-yl)-2-oxo-ethoxy]-1-phenyl-1H-pyrazole-3-carbonyl}-amino)-butyryl]-piperazine-1-carboxylic acid butyl ester, 4-{(S)-4-Carboxy-2-[(5-{2-[(S)-2-(2,2-difluoro-ethylcarbamoyl)-pyrrolidin-1-yl]-2-oxo-ethoxy}-1-phenyl-1H-pyrazole-3-carbonyl)-amino]-butyryl}-piperazine-1-carboxylic acid butyl ester, 4-{(S)-4-Carboxy-2-[(5-{2-[(S)-2-(2-fluoro-ethylcarbamoyl)-pyrrolidin-1-yl]-2-oxo-ethoxy}-1-phenyl-1H-pyrazole-3-carbonyl)-amino]-butyryl}-piperazine-1-carboxylic acid butyl ester, 4-{(S)-4-Carboxy-2-[(5-{2-[(S)-2-(2,2,2-trifluoro-ethylcarbamoyl)-pyrrolidin-1-yl]-2-oxo-ethoxy}-1-phenyl-1H-pyrazole-3-carbonyl)-amino]-butyryl}-piperazine-1-carboxylic acid butyl ester, 4-{(S)-4-Carboxy-2-[(5-{2-[(S)-2-(cyclobutyl-methyl-carbamoyl)-pyrrolidin-1-yl]-2-oxo-ethoxy}-1-phenyl-1H-pyrazole-3-carbonyl)-amino]-butyryl}-piperazine-1-carboxylic acid butyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-(2H-tetrazol-5-yl)-butyryl]-piperazine-1-carboxylic acid ethyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-(2H-tetrazol-5-yl)-butyryl]-piperazine-1-carboxylic acid butyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-ethoxycarbonyl-butyryl]-piperazine-1-carboxylic acid ethyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-cyclopropylmethoxycarbonyl-butyryl]-piperazine-1-carboxylic acid ethyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-cyclohexyloxycarbonyl-butyryl]-piperazine-1-carboxylic acid ethyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-cyclopentyloxycarbonyl-butyryl]-piperazine-1-carboxylic acid ethyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-cyclobutoxycarbonyl-butyryl]-piperazine-1-carboxylic acid ethyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-benzyloxycarbonyl-butyryl]-piperazine-1-carboxylic acid ethyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-propoxycarbonyl-butyryl]-piperazine-1-carboxylic acid ethyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-butoxycarbonyl-butyryl]-piperazine-1-carboxylic acid ethyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-isobutoxycarbonyl-butyryl]piperazine-1-carboxylic acid ethyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-methoxycarbonyl-butyryl]-piperazine-1-carboxylic acid ethyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-isopropoxycarbonyl-butyryl]-piperazine-1-carboxylic acid ethyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-cyclopentylmethoxycarbonyl-butyryl]-piperazine-1-carboxylic acid ethyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-(2,2-dimethyl-propionyloxymethoxycarbonyl)-butyryl]-piperazine-1-carboxylic acid ethyl ester, 4-((S)-2-{[5-[2-((S)-2-Cyclobutylcarbamoyl-pyrrolidin-1-yl)-2-oxo-ethoxy]-1-(3-fluoro-phenyl)-1H-pyrazole-3-carbonyl]-amino}-4-ethoxyoxycarbonyl-butyryl)-piperazine-1-carboxylic acid ethyl ester, 4-((S)-2-{[5-[2-((S)-2-Cyclobutylcarbamoyl-pyrrolidin-1-yl)-2-oxo-ethoxy]-1-(3-fluoro-phenyl)-1H-pyrazole-3-carbonyl]-amino}-4-isopropoxycarbonyl-butyryl)-piperazine-1-carboxylic acid ethyl ester, 4-((S)-2-{[5-[2-((S)-2-Cyclobutylcarbamoyl-pyrrolidin-1-yl)-2-oxo-ethoxy]-1-(3,4-difluoro-phenyl)-1H-pyrazole-3-carbonyl]-amino}-4-ethoxycarbonyl-butyryl)-piperazine-1-carboxylic acid ethyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-ethoxycarbonyl-butyryl]-piperazine-1-carboxylic acid butyl ester, (R)-4-[(S)-4-Carboxy-2-({5-[2-((S)-2-cyclobutylcarbamoyl-pyrrolidin-1-yl)-2-oxo-ethoxy]-1-phenyl-1H-pyrazole-3-carbonyl}-amino)-butyryl]-2-methyl-piperazine-1-carboxylic acid ethyl ester, (R)-4-{(S)-4-Carboxy-2-[(5-{2-[(S)-2-(2-fluoro-ethylcarbamoyl)-pyrrolidin-1-yl]-2-oxo-ethoxy}-1-phenyl-1H-pyrazole-3-carbonyl)-amino]-butyryl}-2-methyl-piperazine-1-carboxylic acid ethyl ester, (R)-4-{(S)-4-Carboxy-2-[(5-{2-[(S)-2-(cyclopropylmethyl-carbamoyl)-pyrrolidin-1-yl]-2-oxo-ethoxy}-1-phenyl-1H-pyrazole-3-carbonyl)-amino]-butyryl}-2-methyl-piperazine-1-carboxylic acid ethyl ester, (S)-4-[(S)-4-Carboxy-2-({5-[2-((S)-2-cyclobutylcarbamoyl-pyrrolidin-1-yl)-2-oxo-ethoxy]-1-phenyl-1H-pyrazole-3-carbonyl}-amino)-butyryl]-2-methyl-piperazine-1-carboxylic acid ethyl ester, (S)-4-{(S)-4-Carboxy-2-[(5-{2-[(S)-2-(2-fluoro-ethylcarbamoyl)-pyrrolidin-1-yl]-2-oxo-ethoxy}-1-phenyl-1H-pyrazole-3-carbonyl)-amino]-butyryl}-2-methyl-piperazine-1-carboxylic acid ethyl ester, (S)-4-{(S)-4-Carboxy-2-[(5-{2-[(S)-2-(cyclopropylmethyl-carbamoyl)-pyrrolidin-1-yl]-2-oxo-ethoxy}-1-phenyl-1H-pyrazole-3-carbonyl)-amino]-butyryl}-2-methyl-piperazine-1-carboxylic acid ethyl ester, (R)-4-[(S)-4-Carboxy-2-({5-[2-((S)-2-cyclobutylcarbamoyl-pyrrolidin-1-yl)-2-oxo-ethoxy]-1-phenyl-1H-pyrazole-3-carbonyl}-amino)-butyryl]-3-methyl-piperazine-1-carboxylic acid ethyl ester, (R)-4-[(S)-4-Carboxy-2-({5-[2-((S)-2-(2-fluoroethyl-carbamoyl)-pyrrolidin-1-yl)-2-oxo-ethoxy]-1-phenyl-1H-pyrazole-3-carbonyl}-amino)-butyryl]-3-methyl-piperazine-1-carboxylic acid ethyl ester, (R)-4-[(S)-4-Carboxy-2-({5-[2-((S)-2-(cyclopropylmethyl-carbamoyl)-pyrrolidin-1-yl)-2-oxo-ethoxy]-1-phenyl-1H-pyrazole-3-carbonyl}-amino)-butyryl]-3-methyl-piperazine-1-carboxylic acid ethyl ester, (S)-4-[(S)-4-Carboxy-2-({5-[2-((S)-2-cyclobutylcarbamoyl-pyrrolidin-1-yl)-2-oxo-ethoxy]-1-phenyl-1H-pyrazole-3-carbonyl}-amino)-butyryl]-3-methyl-piperazine-1-carboxylic acid ethyl ester, (S)-4-[(S)-4-Carboxy-2-({5-[2-((S)-2-(2-fluoro-ethyl-carbamoyl-pyrrolidin-1-yl)-2-oxo-ethoxy]-1-phenyl-1H-pyrazole-3-carbonyl}-amino)-butyryl]-3-methyl-piperazine-1-carboxylic acid ethyl ester, (S)-4-[(S)-4-Carboxy-2-({5-[2-((S)-2-(cyclopropylmethyl-carbamoyl)-pyrrolidin-1-yl)-2-oxo-ethoxy]-1-phenyl-1H-pyrazole-3-carbonyl}-amino)-butyryl]-3-methyl-piperazine-1-carboxylic acid ethyl ester, 4-[(S)-4-Carboxy-2-({5-[2-((S)-2-cyclobutylcarbamoyl-pyrrolidin-1-yl)-2-oxo-ethoxy]-1-phenyl-1H-pyrazole-3-carbonyl}-amino)-butyryl]-piperazine-1-carboxylic acid phenyl ester, 4-[(S)-4-Carboxy-2-({5-[2-((S)-2-(2-fluoroethyl-carbamoyl)-pyrrolidin-1-yl)-2-oxo-ethoxy]-1-phenyl-1H-pyrazole-3-carbonyl}-amino)-butyryl]-piperazine-1-carboxylic acid phenyl ester, 4-[(S)-4-Carboxy-2-({5-[2-((S)-2-(cyclopropylmethyl-carbamoyl)-pyrrolidin-1-yl)-2-oxo-ethoxy]-1-phenyl-1H-pyrazole-3-carbonyl}-amino)-butyryl]-piperazine-1-carboxylic acid phenyl ester, 4-[(S)-4-Carboxy-2-({5-[2-((S)-2-cyclobutylcarbamoyl-pyrrolidin-1-yl)-2-oxo-ethoxy]-1-phenyl-1H-pyrazole-3-carbonyl}-amino)-butyryl]-piperazine-1-carboxylic acid benzyl ester, 4-[(S)-4-Carboxy-2-({5-[2-((S)-2-(2-fluoroethyl-carbamoyl)-pyrrolidin-1-yl)-2-oxo-ethoxy]-1-phenyl-1H-pyrazole-3-carbonyl}-amino)-butyryl]-piperazine-1-carboxylic acid benzyl ester, 4-[(S)-4-Carboxy-2-({5-[2-((S)-2-(cyclopropylmethyl-carbamoyl)-pyrrolidin-1-yl)-2-oxo-ethoxy]-1-phenyl-1H-pyrazole-3-carbonyl}-amino)-butyryl]-piperazine-1-carboxylic acid benzyl ester, 4-[(S)-4-Carboxy-2-({5-[2-((S)-2-cyclobutylcarbamoyl-pyrrolidin-1-yl)-2-oxo-ethoxy]-1-phenyl-1H-pyrazole-3-carbonyl}-amino)-butyryl]-piperazine-1-carboxylic acid propyl ester, 4-[(S)-4-Carboxy-2-({5-[2-((S)-2-cyclobutylcarbamoyl-pyrrolidin-1-yl)-2-oxo-ethoxy]-1-phenyl-1H-pyrazole-3-carbonyl}-amino)-butyryl]-piperazine-1-carboxylic acid cyclobutyl ester, 4-[(S)-4-Carboxy-2-({5-[2-((S)-2-cyclobutylcarbamoyl-4,4-difluoro-pyrrolidin-1-yl)-2-oxo-ethoxy]-1-phenyl-1H-pyrazole-3-carbonyl}-amino)-butyryl]-piperazine-1-carboxylic acid ethyl ester, 4-[(S)-4-Carboxy-2-({5-[2-((S)-2-cyproylcarbamoyl-4,4-difluoro-pyrrolidin-1-yl)-2-oxo-ethoxy]-1-phenyl-1H-pyrazole-3-carbonyl}-amino)-butyryl]-piperazine-1-carboxylic acid ethyl ester, 4-[(S)-4-Carboxy-2-({5-[2-((S)-2-(cyproylmethyl-carbamoyl)-4,4-difluoro-pyrrolidin-1-yl)-2-oxo-ethoxy]-1-phenyl-1H-pyrazole-3-carbonyl}-amino)-butyryl]-piperazine-1-carboxylic acid ethyl ester, 4-[(S)-4-Carboxy-2-({5-[2-oxo-2-(2-thiophen-2-yl-pyrrolidin-1-yl)-ethoxy]-1-phenyl-1H-pyrazole-3-carbonyl}-amino)-butyryl]-piperazine-1-carboxylic acid ethyl ester, 4-[(S)-4-Carboxy-2-({5-[2-(2-furan-2-yl-pyrrolidin-1-yl)-2-oxo-ethoxy]-1-phenyl-1H-pyrazole-3-carbonyl}-amino)-butyryl]-piperazine-1-carboxylic acid ethyl ester, 4-{(S)-4-Carboxy-2-[(5-{2-[2-(5-methyl-furan-2-yl)-pyrrolidin-1-yl]-2-oxo-ethoxy}-1-phenyl-1H-pyrazole-3-carbonyl)-amino]-butyryl}-piperazine-1-carboxylic acid ethyl ester, 4-[(S)-4-Carboxy-2-({5-[2-oxo-2-((S)-2-phenyl-pyrrolidin-1-yl)-ethoxy]-1-phenyl-1H-pyrazole-3-carbonyl}-amino)-butyryl]-piperazine-1-carboxylic acid ethyl ester, 4-{(S)-4-Carboxy-2-[(5-{2-[(S)-2-(4-methyl-oxazol-2-yl)-pyrrolidin-1-yl]-2-oxo-ethoxy}-1-phenyl-1H-pyrazole-3-carbonyl)-amino]-butyryl}-piperazine-1-carboxylic acid ethyl ester, 4-{(S)-4-Carboxy-2-[(5-{2-[(S)-2-(4-methyl-1H-imidazol-2-yl)-pyrrolidin-1-yl]-2-oxo-ethoxy}-1-phenyl-1H-pyrazole-3-carbonyl)-amino]-butyryl}-piperazine-1-carboxylic acid ethyl ester, 4-{(S)-4-Carboxy-2-[(5-{2-[(S)-2-(3-methyl-isoxazol-5-yl)-pyrrolidin-1-yl]-2-oxo-ethoxy}-1-phenyl-1H-pyrazole-3-carbonyl)-amino]-butyryl}-piperazine-1-carboxylic acid ethyl ester, 4-{(S)-4-Carboxy-2-[(5-{2-[(S)-2-(3-methyl-[1,2,4]oxadiazol-5-yl)-pyrrolidin-1-yl]-2-oxo-ethoxy}-1-phenyl-1H-pyrazole-3-carbonyl)-amino]-butyryl}-piperazine-1-carboxylic acid ethyl ester, 4-[2-({5-[2-((S)-2-Cyclobutylcarbamoyl-pyrrolidin-1-yl)-2-oxo-ethoxy]-1-phenyl-1H-pyrazole-3-carbonyl}-amino)-3-fluoro-butyryl]-piperazine-1-carboxylic acid propyl ester, 4-[2-({5-[2-((S)-2-Cyclobutylcarbamoyl-pyrrolidin-1-yl)-2-oxo-ethoxy]-1-phenyl-1H-pyrazole-3-carbonyl}-amino)-3-fluoro-butyryl]-piperazine-1-carboxylic acid butyl ester, 4-[(S)-4-Carboxy-2-({5-[2-((S)-2-carboxy-4,4-difluoro-pyrrolidin-1-yl)-2-oxo-ethoxy]-1-phenyl-1H-pyrazole-3-carbonyl}-amino)-butyryl]-piperazine-1-carboxylic acid ethyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-5-hydroxy-pentanoyl]-piperazine-1-carboxylic acid butyl ester, 4-((S)-4-Carboxy-2-{[5-[2-((S)-2-cyclobutylcarbamoyl-pyrrolidin-1-yl)-2-oxo-ethoxy]-1-(4-trifluoromethyl-phenyl)-1H-pyrazole-3-carbonyl]-amino}-butyryl)-piperazine-1-carboxylic acid ethyl ester, 4-{(S)-4-Carboxy-2-[(5-{2-[(S)-2-(3-cyclopropyl-[1,2,4]oxadiazol-5-yl)-pyrrolidin-1-yl]-2-oxo-ethoxy}-1-phenyl-1H-pyrazole-3-carbonyl)-amino]-butyryl}-piperazine-1-carboxylic acid ethyl ester, 4-[2-({5-[2-((S)-2-Cyclobutylcarbamoyl-pyrrolidin-1-yl)-2-oxo-ethoxy]-1-phenyl-1H-pyrazole-3-carbonyl}-amino)-acetyl]-piperazine-1-carboxylic acid ethyl ester, 4-[2-({5-[2-((S)-2-Cyclobutylcarbamoyl-pyrrolidin-1-yl)-2-oxo-ethoxy]-1-phenyl-1H-pyrazole-3-carbonyl}-amino)-acetyl]-piperazine-1-carboxylic acid butyl ester, 4-[(R)-2-({5-[2-((S)-2-Cyclobutylcarbamoyl-pyrrolidin-1-yl)-2-oxo-ethoxy]-1-phenyl-1H-pyrazole-3-carbonyl}-amino)-propionyl]-piperazine-1-carboxylic acid ethyl ester, 4-[(R)-2-({5-[2-((S)-2-Cyclobutylcarbamoyl-pyrrolidin-1-yl)-2-oxo-ethoxy]-1-phenyl-1H-pyrazole-3-carbonyl}-amino)-propionyl]-piperazine-1-carboxylic acid butyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-propionyl]-piperazine-1-carboxylic acid ethyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-propionyl]-piperazine-1-carboxylic acid butyl ester, 4-{(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-[(2,2-difluoro-cyclopropanecarbonyl)-amino]-butyryl}-piperazine-1-carboxylic acid ethyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-trifluoromethanesulfonylamino-butyryl]-piperazine-1-carboxylic acid ethyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-methoxycarbonyl-butyryl]-piperazine-1-carboxylic acid cyclobutyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-methoxycarbonyl-butyryl]-piperazine-1-carboxylic acid propyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-methoxycarbonyl-butyryl]-piperazine-1-carboxylic acid butyl ester, 4-[2-({5-[2-((S)-2-Cyclobutylcarbamoyl-pyrrolidin-1-yl)-2-oxo-ethoxy]-1-phenyl-1H-pyrazole-3-carbonyl}-amino)-acetyl]-piperazine-1-carboxylic acid cyclobutyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-propionyl]-piperazine-1-carboxylic acid cyclobutyl ester, 4-[(R)-2-({5-[2-((S)-2-Cyclobutylcarbamoyl-pyrrolidin-1-yl)-2-oxo-ethoxy]-1-phenyl-1H-pyrazole-3-carbonyl}-amino)-propionyl]-piperazine-1-carboxylic acid cyclobutyl ester, 4-[(S)-6-Benzyloxy-2-({5-[2-((S)-2-cyclobutylcarbamoyl-pyrrolidin-1-yl)-2-oxo-ethoxy]-1-phenyl-1H-pyrazole-3-carbonyl}-amino)-hexanoyl]-piperazine-1-carboxylic acid ethyl ester, 4-[(S)-6-Benzyloxy-2-({5-[2-((S)-2-cyclobutylcarbamoyl-pyrrolidin-1-yl)-2-oxo-ethoxy]-1-phenyl-1H-pyrazole-3-carbonyl}-amino)-hexanoyl]-piperazine-1-carboxylic acid butyl ester, 4-[(S)-6-Benzyloxy-2-({5-[2-((S)-2-cyclobutylcarbamoyl-pyrrolidin-1-yl)-2-oxo-ethoxy]-1-phenyl-1H-pyrazole-3-carbonyl}-amino)-hexanoyl]-piperazine-1-carboxylic acid cyclobutyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-(2-ethoxy-ethoxycarbonyl)-butyryl]-piperazine-1-carboxylic acid ethyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-(tetrahydro-furan-2-ylmethoxycarbonyl)-butyryl]-piperazine-1-carboxylic acid ethyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-(3-methoxy-propoxycarbonyl)-butyryl]-piperazine-1-carboxylic acid ethyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-(2-morpholin-4-yl-ethoxycarbonyl)-butyryl]-piperazine-1-carboxylic acid ethyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-(tetrahydro-furan-3-ylmethoxycarbonyl)-butyryl]-piperazine-1-carboxylic acid ethyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-(3-methyl-oxetan-3-ylmethoxycarbonyl)-butyryl]piperazine-1-carboxylic acid ethyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-(3-ethyl-oxetan-3-ylmethoxycarbonyl)-butyryl]-piperazine-1-carboxylic acid ethyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-(3-methoxy-butoxycarbonyl-butyryl]-piperazine-1-carboxylic acid ethyl ester, 4-[(R)-2-({5-[2-((S)-2-Cyclobutylcarbamoyl-pyrrolidin-1-yl)-2-oxo-ethoxy]-1-phenyl-1H-pyrazole-3-carbonyl}-amino)-propionyl]-piperazine-1-carboxylic acid propyl ester, 5-[2-((S)-2-Cyclobutylcarbamoyl-pyrrolidin-1-yl)-2-oxo-ethoxy]-1-phenyl-1H-pyrazole-3-carboxylic acid{(R)-2-[4-(3-methoxy-phenyl)-piperazin-1-yl]-1-methyl-2-oxo-ethyl}-amide, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-propionyl]-piperazine-1-carboxylic acid propyl ester, 5-[2-((S)-2-Cyclobutylcarbamoyl-pyrrolidin-1-yl)-2-oxo-ethoxy]-1-phenyl-1H-pyrazole-3-carboxylic acid {(S)-2-[4-(3-methoxy-phenyl)-piperazin-1-yl]-1-methyl-2-oxo-ethyl}-amide, 4-[2-({5-[2-((S)-2-Cyclobutylcarbamoyl-pyrrolidin-1-yl)-2-oxo-ethoxy]-1-phenyl-1H-pyrazole-3-carbonyl}-amino)-acetyl]-piperazine-1-carboxylic acid propyl ester, 4-[(S)-5-Acetoxy-2-({5-[2-((S)-2-cyclobutylcarbamoyl-pyrrolidin-1-yl)-2-oxo-ethoxy]-1-phenyl-1H-pyrazole-3-carbonyl}-amino)-pentanoyl]-piperazine-1-carboxylic acid butyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-5-isobutyryloxy-pentanoyl]-piperazine-1-carboxylic acid butyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-6-hydroxy-hexanoyl]-piperazine-1-carboxylic acid butyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-6-hydroxy-hexanoyl]-piperazine-1-carboxylic acid cyclobutyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-methyl-pentanoyl]-piperazine-1-carboxylic acid ethyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-pentanoyl]-piperazine-1-carboxylic acid ethyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-3-methyl-butyryl]-piperazine-1-carboxylic acid ethyl ester, 4-[(2S,3S)-2-({5-[2-((S)-2-Cyclobutylcarbamoyl-pyrrolidin-1-yl)-2-oxo-ethoxy]-1-phenyl-1H-pyrazole-3-carbonyl}-amino)-3-methyl-pentanoyl]-piperazine-1-carboxylic acid ethyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-2-cyclohexyl-acetyl]-piperazine-1-carboxylic acid ethyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-3-cyclohexyl-propionyl]-piperazine-1-carboxylic acid ethyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-pentanoyl]-piperazine-1-carboxylic acid butyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-3-methyl-butyryl]-piperazine-1-carboxylic acid butyl ester, 4-[(2S,3S)-2-({5-[2-((S)-2-Cyclobutylcarbamoyl-pyrrolidin-1-yl)-2-oxo-ethoxy]-1-phenyl-1H-pyrazole-3-carbonyl}-amino)-3-methyl-pentanoyl]-piperazine-1-carboxylic acid butyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-2-cyclohexyl-acetyl]-piperazine-1-carboxylic acid butyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-3-cyclohexyl-propionyl]-piperazine-1-carboxylic acid butyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-methyl-pentanoyl]-piperazine-1-carboxylic acid butyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-3-ethoxy-propionyl]-piperazine-1-carboxylic acid butyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-3-hydroxy-3-methyl-butyryl]-piperazine-1-carboxylic acid butyl ester, 4-[(2S,3R)-2-({5-[2-((S)-2-Cyclobutylcarbamoyl-pyrrolidin-1-yl)-2-oxo-ethoxy]-1-phenyl-1H-pyrazole-3-carbonyl}-amino)-3-methyl-pentanoyl]-piperazine-1-carboxylic acid butyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-2-cyclopropyl-acetyl]-piperazine-1-carboxylic acid butyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-methoxy-butyryl]-piperazine-1-carboxylic acid butyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-3-methoxy-propionyl]-piperazine-1-carboxylic acid butyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-butyryl]-piperazine-1-carboxylic acid butyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-3-cyclopropyl-propionyl]-piperazine-1-carboxylic acid butyl ester, 4-[(S)-3-Cyclobutyl-2-({5-[2-((S)-2-cyclobutylcarbamoyl-pyrrolidin-1-yl)-2-oxo-ethoxy]-1-phenyl-1H-pyrazole-3-carbonyl}-amino)-propionyl]-piperazine-1-carboxylic acid butyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-6-hydroxy-hexanoyl]-piperazine-1-carboxylic acid ethyl ester, 4-[(S)-6-Acetoxy-2-({5-[2-((S)-2-cyclobutylcarbamoyl-pyrrolidin-1-yl)-2-oxo-ethoxy]-1-phenyl-1H-pyrazole-3-carbonyl}-amino)-hexanoyl]-piperazine-1-carboxylic acid ethyl ester, 4-[(S)-6-Acetoxy-2-({5-[2-((S)-2-cyclobutylcarbamoyl-pyrrolidin-1-yl)-2-oxo-ethoxy]-1-phenyl-1H-pyrazole-3-carbonyl}-amino)-hexanoyl]-piperazine-1-carboxylic acid butyl ester, 4-[(S)-6-Acetoxy-2-({5-[2-((S)-2-cyclobutylcarbamoyl-pyrrolidin-1-yl)-2-oxo-ethoxy]-1-phenyl-1H-pyrazole-3-carbonyl}-amino)-hexanoyl]-piperazine-1-carboxylic acid cyclobutyl ester, 4-{(S)-2-[(5-{2-[(S)-2-(Cyclobutyl-methyl-carbamoyl)-pyrrolidin-1-yl]-2-oxo-ethoxy}-1-phenyl-1H-pyrazole-3-carbonyl)-amino]-6-hydroxy-hexanoyl}-piperazine-1-carboxylic acid cyclobutyl ester, 5-[2-((S)-2-Cyclobutylcarbamoyl-pyrrolidin-1-yl)-2-oxo-ethoxy]-1-phenyl-1H-pyrazole-3-carboxylic acid [2-oxo-2-(4-pentanoyl-piperazin-1-yl)-ethyl]-amide, 5-[2-((S)-2-Cyclobutylcarbamoyl-pyrrolidin-1-yl)-2-oxo-ethoxy]-1-phenyl-1H-pyrazole-3-carboxylic acid {2-oxo-2-[4-(3,3,3-trifluoro-propionyl)-piperazin-1-yl]-ethyl}-amide, 5-[2-((S)-2-Cyclobutylcarbamoyl-pyrrolidin-1-yl)-2-oxo-ethoxy]-1-phenyl-1H-pyrazole-3-carboxylic acid [2-(4-cyclopropanecarbonyl-piperazin-1-yl)-2-oxo-ethyl]-amide, 5-[2-((S)-2-Cyclobutylcarbamoyl-pyrrolidin-1-yl)-2-oxo-ethoxy]-1-phenyl-1H-pyrazole-3-carboxylic acid [2-(4-cyclobutanecarbonyl-piperazin-1-yl)-2-oxo-ethyl]-amide, 5-[2-((S)-2-Cyclobutylcarbamoyl-pyrrolidin-1-yl)-2-oxo-ethoxy]-1-phenyl-1H-pyrazole-3-carboxylic acid {2-[4-((1R,2S)-2-fluoro-cyclopropanecarbonyl)-piperazin-1-yl]-2-oxo-ethyl}-amide, 5-[2-((S)-2-Cyclobutylcarbamoyl-pyrrolidin-1-yl)-2-oxo-ethoxy]-1-phenyl-1H-pyrazole-3-carboxylic acid {2-oxo-2-[4-((1R,2R)-2-phenyl-cyclopropanecarbonyl)-piperazin-1-yl]-ethyl}-amide, {1-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4-methyl-pentanoyl]-piperidin-4-yl}-carbamic acid butyl ester, {1-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-pentanoyl]-piperidin-4-yl}-carbamic acid butyl ester, {1-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-3-methyl-butyryl]-piperidin-4-yl}-carbamic acid butyl ester, {1-[(2S,3S)-2-({5-[2-((S)-2-Cyclobutylcarbamoyl-pyrrolidin-1-yl)-2-oxo-ethoxy]-1-phenyl-1H-pyrazole-3-carbonyl}-amino)-3-methyl-pentanoyl]-piperidin-4-yl}-carbamic acid butyl ester, {1-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-2-cyclohexyl-acetyl]-piperidin-4-yl}-carbamic acid butyl ester, {1-[2-({5-[2-((S)-2-Cyclobutylcarbamoyl-pyrrolidin-1-yl)-2-oxo-ethoxy]-1-phenyl-1H-pyrazole-3-carbonyl}-amino)-acetyl]-piperidin-4-yl}-carbamic acid butyl ester, {1-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-3-cyclohexyl-propionyl]-piperidin-4-yl}-carbamic acid butyl ester, 4-[2-({5-[2-((S)-2-Cyclobutylcarbamoyl-pyrrolidin-1-yl)-2-oxo-ethoxy]-1-phenyl-1H-pyrazole-3-carbonyl}-amino)-acetyl]-piperazine-1-carboxylic acid 2-methoxy-ethyl ester, 4-[2-({5-[2-((S)-2-Cyclobutylcarbamoyl-pyrrolidin-1-yl)-2-oxo-ethoxy]-1-phenyl-1H-pyrazole-3-carbonyl}-amino)-acetyl]-piperazine-1-carboxylic acid butylamide, 4-[2-({5-[2-((S)-2-Cyclobutylcarbamoyl-pyrrolidin-1-yl)-2-oxo-ethoxy]-1-phenyl-1H-pyrazole-3-carbonyl}-amino)-acetyl]-piperazine-1-carboxylic acid 3,3,3-trifluoro-propyl ester, 4-[2-({5-[2-((S)-2-Cyclobutylcarbamoyl-pyrrolidin-1-yl)-2-oxo-ethoxy]-1-phenyl-1H-pyrazole-3-carbonyl}-amino)-acetyl]-piperazine-1-carboxylic acid 2-ethoxy-ethyl ester, 4-[2-({5-[2-((S)-2-Cyclobutylcarbamoyl-pyrrolidin-1-yl)-2-oxo-ethoxy]-1-phenyl-1H-pyrazole-3-carbonyl}-amino)-acetyl]-piperazine-1-carboxylic acid (2-ethoxy-ethyl)-amide, 4-[2-({5-[2-((S)-2-Cyclobutylcarbamoyl-pyrrolidin-1-yl)-2-oxo-ethoxy]-1-phenyl-1H-pyrazole-3-carbonyl}-amino)-acetyl]-piperazine-1-carboxylic acid butyl-methyl-amide, 4-[2-({5-[2-((S)-2-Cyclobutylcarbamoyl-pyrrolidin-1-yl)-2-oxo-ethoxy]-1-phenyl-1H-pyrazole-3-carbonyl}-amino)-acetyl]-piperazine-1-carboxylic acid (2-methoxy-ethyl)-amide, 4-[(R)-2-({5-[2-((S)-2-Cyclobutylcarbamoyl-pyrrolidin-1-yl)-2-oxo-ethoxy]-1-phenyl-1H-pyrazole-3-carbonyl}-amino)-3-fluoro-propionyl]-piperazine-1-carboxylic acid ethyl ester, 4-[(R)-2-({5-[2-((S)-2-Cyclobutylcarbamoyl-pyrrolidin-1-yl)-2-oxo-ethoxy]-1-phenyl-1H-pyrazole-3-carbonyl}-amino)-3-fluoro-propionyl]-piperazine-1-carboxylic acid butyl ester, 4-[2-({5-[2-((S)-2-Cyclobutylcarbamoyl-pyrrolidin-1-yl)-2-oxo-ethoxy]-1-phenyl-1H-pyrazole-3-carbonyl}-amino)-acetyl]-piperazine-1-carboxylic acid (2-methoxy-ethyl)-methyl-amide, 4-[2-({5-[2-((S)-2-Cyclobutylcarbamoyl-pyrrolidin-1-yl)-2-oxo-ethoxy]-1-phenyl-1H-pyrazole-3-carbonyl}-amino)-acetyl]-piperazine-1-carboxylic acid benzyl-methyl-amide, 4-[2-({5-[2-((S)-2-Cyclobutylcarbamoyl-pyrrolidin-1-yl)-2-oxo-ethoxy]-1-phenyl-1H-pyrazole-3-carbonyl}-amino)-acetyl]-piperazine-1-carboxylic acid cyclopropylamide, 4-[2-({5-[2-((S)-2-Cyclobutylcarbamoyl-pyrrolidin-1-yl)-2-oxo-ethoxy]-1-phenyl-1H-pyrazole-3-carbonyl}-amino)-acetyl]-piperazine-1-carboxylic acid cyclobutylamide, 5-[2-((S)-2-Cyclobutylcarbamoyl-pyrrolidin-1-yl)-2-oxo-ethoxy]-1-phenyl-1H-pyrazole-3-carboxylic acid {2-oxo-2-[4-(pyrrolidine-1-carbonyl)-piperazin-1-yl]-ethyl}-amide, 4-[2-({5-[2-((S)-2-Cyclobutylcarbamoyl-pyrrolidin-1-yl)-2-oxo-ethoxy]-1-phenyl-1H-pyrazole-3-carbonyl}-amino)-acetyl]-piperazine-1-carboxylic acid cyclopentyl ester, 4-[2-({5-[(R)-2-((S)-2-Cyclobutylcarbamoyl-pyrrolidin-1-yl)-1-methyl-2-oxo-ethoxy]-1-phenyl-1H-pyrazole-3-carbonyl}-amino)-acetyl]-piperazine-1-carboxylic acid butyl ester, 4-[2-({5-[2-((2S,4R)-2-Cyclobutylcarbamoyl-4-hydroxy-pyrrolidin-1-yl)-2-oxo-ethoxy]-1-phenyl-1H-pyrazole-3-carbonyl}-amino)-acetyl]-piperazine-1-carboxylic acid butyl ester, 4-{2-[(5-{2-Oxo-2-[(S)-2-(1H-tetrazol-5-yl)-pyrrolidin-1-yl]-ethoxy}-1-phenyl-1H-pyrazole-3-carbonyl-amino]-acetyl}-piperazine-1-carboxylic acid butyl ester, 4-{2-[(5-{(R)-1-Methyl-2-oxo-2-[(S)-2-(1H-tetrazol-5-yl)-pyrrolidin-1-yl]-ethoxy}-1-phenyl-1H-pyrazole-3-carbonyl)-amino]-acetyl}-piperazine-1-carboxylic acid butyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4,4,4-trifluoro-butyryl]-piperazine-1-carboxylic acid propyl ester, 4-[(S)-2-({5-[2-((S)-2-Cyclobutylcarbamoyl-pyrrolidin-1-yl)-2-oxo-ethoxy]-1-phenyl-1H-pyrazole-3-carbonyl}-amino)-4,4,4-trifluoro-butyryl]-piperazine-1-carboxylic acid butyl ester, or 4-[2-({5-[2-((S)-2-Cyclobutylcarbamoyl-pyrrolidin-1-yl)-2-oxo-ethoxy]-1-phenyl-1H-pyrazole-3-carbonyl}-amino)-acetyl]-piperazine-1-carboxylic acid benzyl ester.

3. A pharmaceutical preparation, comprising at least one compound as claimed in claim 1 in all its stereoisomeric forms and mixtures thereof in any ratio or its physiologically tolerable salts and a pharmaceutically acceptable carrier.

* * * * *